(12) United States Patent
Han et al.

(10) Patent No.: US 7,199,149 B2
(45) Date of Patent: Apr. 3, 2007

(54) MONOCYCLIC AND BICYCLIC LACTAMS AS FACTOR XA INHIBITORS

(75) Inventors: Wei Han, Yardley, PA (US); Jennifer X. Qiao, Princeton, NJ (US); Zilun Hu, Jamison, PA (US)

(73) Assignee: Bristol Myers Squibb Company, Princeton, NJ (US)

( * ) Notice: Subject to any disclaimer, the term of this patent is extended or adjusted under 35 U.S.C. 154(b) by 70 days.

(21) Appl. No.: 10/952,397

(22) Filed: Sep. 28, 2004

(65) Prior Publication Data

US 2005/0107361 A1 May 19, 2005

Related U.S. Application Data

(60) Provisional application No. 60/507,533, filed on Oct. 1, 2003.

(51) Int. Cl.
*A61K 31/4025* (2006.01)
*C07D 207/24* (2006.01)
*C07D 409/12* (2006.01)

(52) U.S. Cl. ........................ 514/422; 548/518; 548/527

(58) Field of Classification Search ................ 548/527; 514/422
See application file for complete search history.

(56) References Cited

U.S. PATENT DOCUMENTS

| | | | |
|---|---|---|---|
| 6,034,093 A * | 3/2000 | Ewing et al. ................ | 514/301 |
| 6,271,342 B1 | 8/2001 | Lerchen et al. | |
| 6,710,058 B2 | 3/2004 | Jacobson et al. | |
| 2003/0212054 A1 | 11/2003 | Quan et al. | |
| 2003/0232804 A1 | 12/2003 | Pinto et al. | |
| 2004/0254158 A1 | 12/2004 | Pinto et al. | |

FOREIGN PATENT DOCUMENTS

| WO | WO9405668 | 3/1994 |
|---|---|---|
| WO | WO9932477 | 7/1999 |
| WO | WO0208227 | 1/2002 |

OTHER PUBLICATIONS

Wang et al., "Inhibition of Factor Xa Reduces Ischemic Brain Damage After Thromboembolic Stroke in Rats," Stroke, vol. 34, p. 468-474 (2003).*
Wong et al., Nonpeptide Factor Xa Inhibitors III: Effects of DPC423, an Orally Active Pyrazole Antithrombotic Agent, on Arterial Thrombosis in Rabbits, J. Pharmacology & Experimental Therapeutics, vol. 303, No. 3 (2002).*
U.S. Appl. No. 10/952,204, filed Sep. 28, 2004, Shi et al.
U.S. Appl. No. 10/952,396, filed Sep. 28, 2004, Han et al.
U.S. Appl. No. 10/801,518, filed Mar. 16, 2004, Pinto et al.
U.S. Appl. No. 10/850,587, filed May 20, 2004, Pinto et al.
U.S. Appl. No. 10/970,781, filed Oct. 21, 2004, Pinto et al.
U.S. Appl. No. 10/970,807, filed Oct. 21, 2004, Pinto et al.
U.S. Appl. No. 10/730,170, filed Dec. 8, 2003, Jacobson et al.

* cited by examiner

*Primary Examiner*—Joseph K. McKane
*Assistant Examiner*—Andrew B. Freistein
(74) *Attorney, Agent, or Firm*—Jing G. Sun; David H. Vance

(57) ABSTRACT

The present application describes monocyclic and bicyclic lactams and derivatives thereof of Formulae Ia–e:

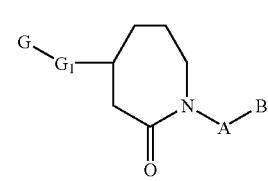

Ia

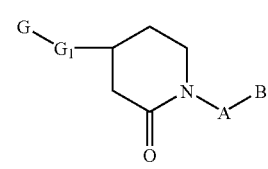

Ib

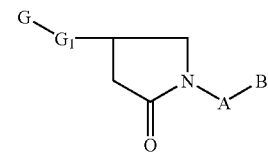

Ic

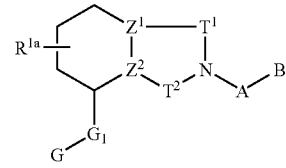

Id

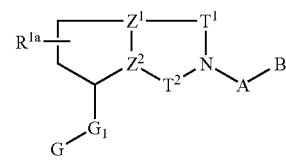

Ie wherein one of one of $T^1$ and $T^2$ is carbonyl, thiocarbonyl, or sulfonyl or pharmaceutically acceptable salt forms thereof. Compounds of the present invention are useful as inhibitors of trypsin-like serine proteases, specifically factor Xa.

26 Claims, No Drawings

MONOCYCLIC AND BICYCLIC LACTAMS AS FACTOR Xa INHIBITORS

CROSS-REFERENCE TO RELATED APPLICATIONS

The present application claims the priority benefit of U.S. Provisional Application No. 60/507,533, filed Oct. 1, 2003, which is expressly incorporated fully herein by reference.

FIELD OF THE INVENTION

This invention relates generally to monocyclic and bicyclic lactams and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

Accordingly, the present invention provides novel monocyclic and bicyclic lactams and derivatives thereof that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a mammal in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder.

The present invention provides a novel method, comprising: administering a compound of the present invention or a pharmaceutically acceptable salt form thereof in an amount effective to treat a thromboembolic disorder.

The present invention provides novel lactam-containing compounds and derivatives thereof for use in therapy.

The present invention provides the use of novel lactam-containing compounds for the manufacture of a medicament for the treatment of a thromboembolic disorder.

These and other objects, which will become apparent during the following detailed description, have been achieved by the inventors' discovery that monocyclic and bicyclic lactams of Formulae Ia–e:

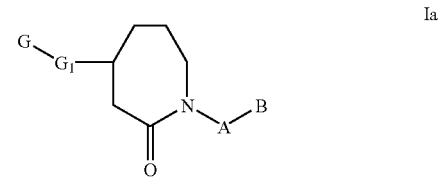

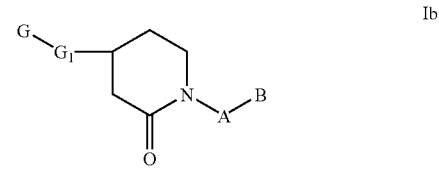

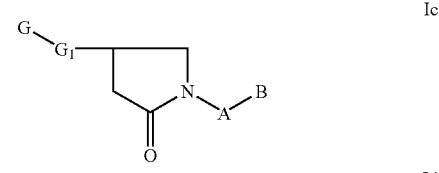

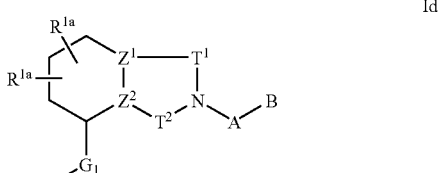

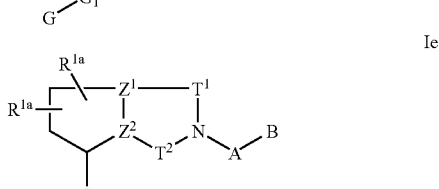

wherein one of one of $T^1$ and $T^2$ is carbonyl, thiocarbonyl, or sulfonyl and G, $G_1$, A, B, $R^{1a}$, $Z^1$, and $Z^2$ are defined below or pharmaceutically acceptable salt or prodrug forms thereof, are effective factor Xa inhibitors.

DETAILED DESCRIPTION OF PREFERRED EMBODIMENTS

In a first embodiment, the present invention provides a novel compound of formula Ia, Ib, Ic, Id, or Ie:

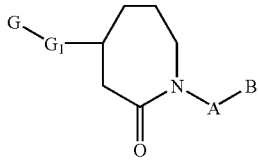

Ia

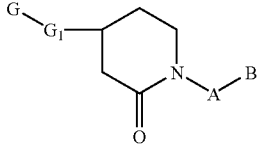

Ib

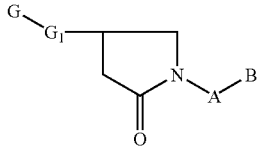

Ic

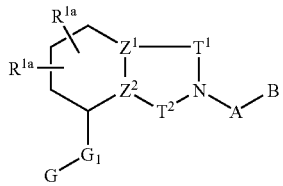

Id

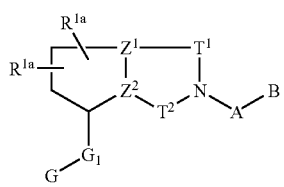

Ie or a stereoisomer or pharmaceutically acceptable salt thereof, wherein;

the central lactam ring of Ia, Ib, and Ic is substituted with 0–2 $R^{1a}$;

one of $T^1$ and $T^2$ is selected from C(O), C(S), and $S(O)_2$ and the other is selected from C(O), C(S), $S(O)_2$, $CH_2$, and CHOH;

one of $Z^1$ and $Z^2$ is N and the other is C;

G is a group of formula IIa or IIb:

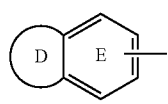

IIa

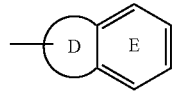

IIb ring D, including the two atoms of Ring E to which it is attached, is a 5–6 membered ring consisting of carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–3 R and there are 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, $NH_2$, $NH(C_{1-3}$ alkyl), $N(C_{1-3}$ alkyl)$_2$, C(=NH)$NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, C(=NR$^8$)NR$^7$R$^9$, NHC(=NR$^8$)NR$^7$R$^9$, ONHC(=NR$^8$)NR$^7$R$^9$, $NR^8CH(=NR^7)$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rNR^7C(O)R^7$, $(CR^8R^9)_rOR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$, provided that $S(O)_pR^7$ and $S(O)_2R^3$ form other than $S(O)_2H$ or S(O)H;

alternatively, when 2 R groups are attached to adjacent atoms, they combine to form methylenedioxy or ethylenedioxy;

$G_1$ is selected from $(CR^3R^{3a})_{1-5}$, $(CR^3R^{3a})_{0-2}CR^3$=$CR^3(CR^3R^{3a})_{0-2}$, $(CR^3R^{3a})_{0-2}C$≡$C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uOC(O)NR^{3b}(CR^3R^{3a})_w$, $(CR^3R^{3a})_uNR^{3b}C(O)O(CR^3R^{3a})_w$, $(CR^3R^{3a})_uNR^{3b}C(O)NR^{3b}(CR^3R^{3a})_w$, $(CR^3R^{3a})_uNR^{3b}C(S)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uNR^{3b}S(O)_2NR^{3b}(CR^3R^{3a})_w$, $(CR^3R^{3a})_uNRR^{3e}(CR^3R^{3a})_w$, $(CR^3R^{3a})_uC(O)(CR^3R^{3a})_uC(O)(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(O)(CR^3R^{3a})_w$, $(CR^3R^{3a})_uC(O)(CR^3R^{3a})_uC(O)NR^{3b}(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uNR^{3b}C(O)(CR^3R^{3a})_uC(S)NR^{3b}(CR^3R^{3a})_w$, $(CR^3R^{3a})_uNR^{3b}C(S)(CR^3R^{3a})_uC(O)NR^{3b}(CR^3R^{3a})_w$, $(CR^3R^{3a})_uS(O)_2NR^{3b}C(O)(CR^3R^{3a})_w$, $(CR^3R^{3a})_uC(O)NR^{3b}S(O)_2(CR^3R^{3a})_w$, and $(CR^3R^{3a})_uS(O)_2NR^{3b}C(O)NR^{3b}CR^3R^{3a})_w$, wherein u+w total 0, 1, 2, 3, or 4 and the right side of $G_1$ is attached to ring G, provided that $G_1$ does not form an N—S, NCH₂N, NCH₂O, or NCH₂S bond with either group to which it is attached;

A is selected from: $C_{3-10}$ carbocycle substituted with 0–2 $R^4$, and 5–12 membered heterocycle consisting of: carbon atoms and 1–4 heteroatoms selected from the group consisting of N, O, and $S(O)_p$ and substituted with 0–2 $R^4$;

B is selected from Y, X—Y, $N(B^1)C(O)C(R^3R^{3g})_{1-4}$ $NB^2B^3$, $C(B^5)=NB^4$, and

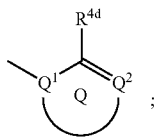

provided that lactam nitrogen and B are attached to different atoms on A and that the $R^{4d}$ shown is other than OH;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-2}$—$C_{3-7}$ carbocycle substituted with 0–2 $R^{4b}$, and —$(CH_2)_{0-2}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $C_{1-6}$ alkyl substituted with 0–2 $R^{4c}$, $C(O)R^{2e}$, $C(O)OR^{2d}$, $C(O)NR^{2d}R^{2d}$, $C(O)NH(CH_2)_2NR^{2d}R^{2d}$, $SO_2NR^{2d}R^{2d}$, $C(O)NHSO_2$—$C_{1-4}$ alkyl, and $S(O)_pR^{5a}$;

$B^3$ is selected from H, $C_{1-6}$ alkyl substituted with 0–2 $R^{4c}$, —$(CH_2)_{0-2}$-3–6 membered carbocycle substituted with 0–2 $R^5$, and a —$(CH_2)_{0-2}$-4–6 membered heterocycle consisting of: carbon atoms and 1–4 heteroatoms selected from the group consisting of N, O, and $S(O)_p$ and substituted with 0–2 $R^5$;

$B^4$ is selected from H, $SO_2R^{3b}$, $C(O)R^{3b}$, $SO_2NR^3R^{3b}$, $C(O)NR^3R^{3b}$, $OR^2$, $SR^2$, —CN, and $NO_2$;

$B^5$ is $NR^2R^{2f}$ or $CR^3R^2R^{2f}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

ring Q is a 5–8 membered ring consisting of, in addition to the $Q^1$—$CR^{4d}$=$Q^2$ group shown, carbon atoms and 0–2 heteroatoms selected from N, O, and $S(O)_p$, and the ring is substituted with an additional 0–2 $R^{4d}$;

X is absent or is selected from —$(CR^2R^{2a})_{1-4}$—, —$CR^2(CR^2R^{2b})(CH_2)_t$—, —C(O)—, —C(=$NR^{1b}$)—, —$CR^2(NR^{1b}R^2)$—, —$CR^2(OR^2)$—, —$CR^2(SR^2)$—, —C(O) $CR^2R^{2a}$—, —$CR^2R^{2a}C(O)$—, —S(O)—, —$S(O)_2$—, —$SCR^2R^{2a}$—, —$S(O)CR^2R^{2a}$—, —$S(O)_2CR^2R^{2a}$—, —$CR^2R^{2a}S(O)$—, —$CR^2R^{2a}S(O)_2$—, —$S(O)_2NR^2CR^2R^{2a}$—, —$NR^2S(O)_2$—, —$CR^2R^{2a}NR^2S(O)_2$—, —$NR^2S(O)_2CR^2R^{2a}$—, —$NR^2C(O)$—, —C(O) $NR^2CR^2R^{2a}$—, —$NR^2C(O)CR^2R^{2a}$—, —$CR^2R^{2a}NR^2C(O)$—, —$NR^2CR^2R^{2a}$—, and —$OCR^2R^{2a}$—;

Y is selected from: $CY^1Y^2R^{4a}$, $NR^3R^{3a}$, $C(O)NR^3R^{3a}$, $SO_2R^3$, $SO_2NR^3R^{3a}$, $C_{3-10}$ carbocycle substituted 0–2 $R^4$ and 0–1 $R^{4a}$, and, 3-10 membered heterocycle consisting of: carbon atoms and 1–4 heteroatoms selected from the group consisting of N, O, and $S(O)_p$ and substituted with 0–2 $R^4$ and 0–1 $R^{4a}$;

when ring A has 0–1 ring double bonds, then Y is additionally selected from $C_{1-6}$ alkyl, $C_{1-4}$ haloalkyl, —CN, $C(O)R^3$, $C(O)OR^3$, $S(O)_pR^3$, $S(O)_2NR^3R^3$, $OR^3$, $NR^3C(O)R^3$, $C(O)NR^3SO_2R^3$, $NR^3C(O)NR^3R^3$, $NR^3R^3$, $C(S)R^3$, $NR^3C(S)NR^3R^3$, $C(S)OR^3$, and $NR^3C(O)R^3$;

$Y^1$ and $Y^2$ are independently $C_{1-4}$ alkyl substituted with 0–2 $R^4$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$(CR^3R^{3a})_r$—$NR^2$—$(CR^3R^{3a})_r$—$R^{1b}$, —$(CR^3R^{3a})_r$—$S(O)_p$—$(CR^3R^{3a})_r$—$R^{1b}$, —$(CR^3R^{3a})_r$—$CO_2$—$(CR^3R^{3a})_r$—$R^{1b}$, —$(CR^3R^{3a})_r$—$C(O)NR^2$—$(CR^3R^{3a})_r$—$R^{1b}$, —$(CR^3R^{3a})_r$—C(O)—$(CR^3R^{3a})_r$—$R^{1b}$, —$C_{2-6}$ alkenylene-$R^{1b}$, —$C_{2-6}$ alkynylene-$R^{1b}$, and —$(CR^3R^{3a})_r$—C(=$NR^{1b}$)$NR^3R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, C(O) $R^{2b}$, $CO_2R^{2b}$, $OC(O)R^2$, $CH(CH_2OR^2)_2$, $(CF_2)_rCO_2R^{2a}$, $S(O)_pR^{2b}$, $NR^2(CH_2)_rOR^2$, C(=$NR^{2c}$)$NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_4$-5–10 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_4$-5–10 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_4$-5–10 membered heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_4$-5–10 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, S(O)$_p$-halo, O-halo, N—S, S—N, S(O)$_p$—S(O)$_p$, S—O, O—N, O—S, or O—O moiety;

alternatively, NR$^{2d}$R$^{2d}$ forms a 5–10 membered saturated, partially saturated or unsaturated ring substituted with 0–2 R$^{4b}$ and consisting of: 0–1 additional heteroatoms selected from the group consisting of N, O, and S(O)$_p$;

R$^{2e}$, at each occurrence, is selected from H, R$^{4c}$, C$_{1-6}$ alkyl substituted with 0–2 R$^{4c}$, —(CR$^3$R$^{3a}$)$_r$—C$_{3-10}$ carbocycle substituted with 0–2 R$^{4c}$, and —(CR$^3$R$^{3a}$)$_4$-5–10 membered heterocycle substituted with 0–2 R$^{4c}$ and consisting of: carbon atoms and 1–4 heteroatoms selected from the group consisting of N, O, and S(O)$_p$, provided that R$^{2e}$ forms other than a C(O)-halo or C(O)—S(O)$_p$ moiety;

R$^{2f}$ at each occurrence, is selected from H, CF$_3$, C$_{1-4}$ alkoxy substituted with 0–2 R$^{4b}$, C$_{1-6}$ alkyl substituted with 0–2 R$^{4b}$, —(CH$_2$)$_r$—C$_{3-10}$ carbocycle substituted with 0–2 R$^{4b}$, and —(CH$_2$)$_4$-5–10 membered heterocycle consisting of: carbon atoms and 1–4 heteroatoms selected from the group consisting of N, O, and S(O)$_p$ and substituted with 0–2 R$^{4b}$;

alternatively, CR$^2$R$^{2f}$ forms a 5–8 membered ring consisting of: carbon atoms and 0–2 heteroatoms selected from N, O, and S(O)$_p$, and this ring is substituted with 0–2 R$^{4b}$;

alternatively, NR$^2$R$^{2f}$ forms a 5–8 membered ring consisting of: carbon atoms and 0–2 additional heteroatoms selected from N, O, and S(O)$_p$, and this ring is substituted with 0–2 R$^{4b}$;

alternatively, when B$^4$ is SO$_2$R$^{3b}$ and B$^5$ is NR$^2$R$^{2f}$, R$^{3b}$ and R$^{2f}$ combine to form a 5–8 membered ring consisting of: carbon atoms and 0–2 additional heteroatoms selected from N, O, and S(O)$_p$, and this ring is substituted with 0–2 R$^{4b}$;

alternatively, when B$^4$ is C(O)R$^{3b}$ and B$^5$ is NR$^2$R$^{2f}$, R$^{3b}$ and R$^{2f}$ combine to form a 5–8 membered ring consisting of: carbon atoms and 0–2 additional heteroatoms selected from N, O, and S(O)$_p$, and this ring is substituted with 0–2 R$^{4b}$;

alternatively, when B$^5$ is NR$^2$R$^{2f}$, B$^4$ and R$^{2f}$ combine to form a 5–8 membered ring consisting of: carbon atoms and 0–2 additional heteroatoms selected from N, O, and S(O)$_p$, and this ring is substituted with 0–2 R$^{4b}$ and the R$^2$ group of NR$^2$R$^{2f}$, in addition to the groups recited below, is selected from SO$_2$R$^{3b}$, C(O)R$^{3b}$, and —CN;

R$^3$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

alternatively, R$^3$ and R$^{3a}$, together with the nitrogen atom to which they are attached, combine to form a 5 or 6 membered saturated, partially unsaturated, or unsaturated ring consisting of: carbon atoms, the nitrogen atom to which R$^3$ and R$^{3a}$ are attached, and 0–1 additional heteroatoms selected from the group consisting of N, O, and S(O)$_p$;

R$^{3b}$, at each occurrence, is selected from H, C$_{1-6}$ alkyl substituted with 0–2 R$^{1a}$, C$_{2-6}$ alkenyl substituted with 0–2 R$^{1a}$, C$_{2-6}$ alkynyl substituted with 0-2 R$^{1a}$, —(C$_{0-4}$ alkyl)-5–10 membered carbocycle substituted with 0–3 R$^{1a}$, and —(C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

R$^{3c}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH (CH$_3$)$_2$, CH(CH$_3$)CH$_2$CH$_3$, C(CH$_3$)$_3$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C$_{1-4}$ alkyl-phenyl, and C(=O)R$^{3c}$;

R$^{3e}$, at each occurrence, is selected from H, SO$_2$NHR$^3$, SO$_2$NR$^3$R$^3$, C(O)R$^3$, C(O)NHR$^3$, C(O)OR$^{3f}$, S(O)R$^{3f}$, S(O)$_2$R$^{3f}$, C$_{1-6}$ alkyl substituted with 0–2 R$^{1a}$, C$_{2-6}$ alkenyl substituted with 0–2 R$^{1a}$, C$_{2-6}$ alkynyl substituted with 0–2 R$^{1a}$, —(C$_{0-4}$ alkyl)-5–10 membered carbocycle substituted with 0–3 R$^{1a}$, and —(C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

R$^{3f}$, at each occurrence, is selected from: C$_{1-6}$ alkyl substituted with 0–2 R$^{1a}$, C$_{2-6}$ alkenyl substituted with 0–2 R$^{1a}$, C$_{2-6}$ alkynyl substituted with 0-2R$^{1a}$, —(C$_{0-4}$ alkyl)-5–10 membered carbocycle substituted with 0–3 R$^{1a}$, and —(C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

R$^{3g}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —(CH$_2$)$_r$-3–6 membered carbocycle, and —(CH$_2$)$_4$-5–6 membered heterocycle consisting of: carbon atoms and 1–4 heteroatoms selected from the group consisting of N, O, and S(O)$_p$;

alternatively, CR$^3$R$^{3g}$ forms a cyclopropyl group;

R$^4$, at each occurrence, is selected from =O, CHO, (CR$^3$R$^{3a}$)$_r$OR$^2$, (CR$^3$R$^{3a}$)$_r$F, (CR$^3$R$^{3a}$)$_r$Cl, (CR$^3$R$^{3a}$)$_r$Br, (CR$^3$R$^{3a}$)$_r$I, C$_{1-4}$ alkyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$C(O)R$^{2c}$, (CR$^3$R$^{3a}$)$_r$NR$^2$C(O) R$^{2b}$, (CR$^3$R$^{3a}$)$_r$C(O)NR$^2$R$^{2a}$, (CR$^3$R$^{3a}$)$_r$NR$^2$C(O)NR$^2$R$^{2a}$, (CR$^3$R$^{3a}$)$_r$C(=NR$^2$)NR$^2$R$^{2a}$, (CR$^3$R$^{3a}$)$_r$C(=NS(O)$_2$R$^5$) NR$^2$R$^{2a}$, (CR$^3$R$^{3a}$)$_r$NR$^2$C(=NR$^2$)NR$^2$R$^{2a}$, (CR$^3$R$^{3a}$)$_r$C(O) NR$^2$C(=NR$^2$)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$—C$_{1-4}$ alkyl, (CR$^3$R$^{3a}$)$_r$ NR$^2$SO$_2$R$^5$, (CR$^3$R$^{3a}$)$_r$S(O)$_p$R$^{5a}$, (CR$^3$R$^{3a}$)$_r$ (CF$_2$)$_r$ CF$_3$, NHCH$_2$R$^{1b}$, OCH$_2$R$^{1b}$, SCH$_2$R$^{1b}$, NH(CH$_2$)$_2$ (CH$_2$)$_t$ R$^{1b}$, O(CH$_2$)$_2$(CH$_2$)$_r$R$^{1b}$, S(CH$_2$)$_2$(CH$_2$)$_r$R$^{1b}$, (CR$^3$R$^{3a}$)$_4$-5–6 membered carbocycle substituted with 0–1 R$^5$, and a (CR$^3$R$^{3a}$)$_4$-5–6 membered heterocycle consisting of: carbon atoms and 1–4 heteroatoms selected from the group consisting of N, O, and S(O)$_p$ and substituted with 0–1 R$^5$;

R$^{4a}$ is selected from C$_{1-6}$ alkyl substituted with 0–2 R$^{4c}$, C$_{2-6}$ alkenyl substituted with 0–2 R$^{4c}$, C$_{2-6}$ alkynyl substituted with 0–2 R$^{4c}$, —(CR$^3$R$^{3g}$)$_r$—C$_{5-10}$ membered carbocycle substituted with 0–3 R$^{4c}$, —(CR$^3$R$^{3g}$)$_4$-5–10 membered heterocycle substituted with 0–3 R$^{4c}$ and consisting of: carbon atoms and 1–4 heteroatoms selected from the group consisting of N, O, and S(O)$_p$, (CR$^3$R$^{3g}$)$_r$CN, (CR$^3$R$^{3g}$)$_r$C (=NR$^{2d}$)NR$^{2d}$R$^{2d}$, (CR$^3$R$^{3g}$)$_r$NR$^{2d}$C(=NR$^{2d}$)NR$^{2d}$R$^{2d}$, (CR$^3$R$^{3g}$)$_r$NR$^{2d}$C(R$^{2e}$)(=NR$^{2d}$), (CR$^3$R$^{3g}$)$_r$NR$^{2d}$R$^{2d}$, (CR$^3$R$^{3g}$)$_r$N(→O)R$^{2d}$R$^{2d}$, (CR$^3$R$^{3g}$)$_r$OR$^{2d}$, (CR$^3$R$^{3g}$)$_r$—NR$^{2d}$C(O)R$^{2e}$, (CR$^3$R$^{3g}$)$_r$—C(O)R$^{2e}$, (CR$^3$R$^{3g}$)$_r$—OC(O) R$^{2e}$, (CR$^3$R$^{3g}$)$_r$—C(O)NR$^{2d}$R$^{2d}$, (CR$^3$R$^{3g}$)$_r$—C(O)OR$^{2d}$, (CR$^3$R$^{3g}$)$_r$—NR$^{2d}$C(O)NR$^{2d}$R$^{2d}$, (CR$^3$R$^{3g}$)$_r$—OC(O) NR$^{2d}$R$^{2d}$, (CR$^3$R$^{3g}$)$_r$—NR$^{2d}$C(O)OR$^{2d}$, (CR$^3$R$^{3g}$)$_r$—SO$_2$NR$^{2d}$R$^{2d}$, (CR$^3$R$^{3g}$)$_r$—NR$^{2d}$SO$_2$NR$^{2d}$R$^{2d}$, (CR$^3$R$^{3g}$)$_r$—C(O)NR$^{2d}$SO$_2$R$^{2d}$, (CR$^3$R$^{3g}$)$_r$—NR$^{2d}$SO$_2$R$^{2d}$, and (CR$^3$R$^{3g}$)$_r$—S(O)$_p$R$^{2d}$, provided that S(O)$_p$R$^{2d}$ forms other than S(O)$_2$H or S(O)H and further provided that R$^{4a}$ is other than a hydroxamic acid;

R$^{4b}$, at each occurrence, is selected from H, =O, (CH$_2$)$_r$ OR$^3$, (CH$_2$)$_r$F, (CH$_2$)$_r$Cl, (CH$_2$)$_r$Br, (CH$_2$)$_r$I, C$_{1-4}$ alkyl, (CH$_2$)$_r$CN, (CH$_2$)$_r$NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$—C(O)

NR³R³ᵃ, (CH₂)ᵣNR³C(O)NR³R³ᵃ, (CH₂)ᵣ—C(=NR³) NR³R³ᵃ, (CH₂)ᵣNR³C(=NR³)NR³R³ᵃ, (CH₂)ᵣSO₂NR³R³ᵃ, (CH₂)ᵣNR³SO₂NR³R³ᵃ, (CH₂)ᵣNR³SO₂—C₁₋₄ alkyl, (CH₂)ᵣ NR³SO₂CF₃, (CH₂)ᵣNR³SO₂-phenyl, (CH₂)ᵣS(O)ₚCF₃, (CH₂)ᵣS(O)ₚ—C₁₋₄ alkyl, (CH₂)ᵣS(O)ₚ-phenyl, and (CH₂)ᵣ(CF₂)ᵣCF₃;

R⁴ᶜ, at each occurrence, is selected from =O, (CR³R³ᵃ)ᵣOR², (CR³R³ᵃ)ᵣF, (CR³R³ᵃ)ᵣBr, (CR³R³ᵃ)ᵣCl, (CR³R³ᵃ)ᵣCF₃, C₁₋₄ alkyl, C₂₋₆ alkenyl, C₂₋₆ alkynyl, (CR³R³ᵃ)ᵣCN, (CR³R³ᵃ)ᵣNO₂, (CR³R³ᵃ)ᵣNR²R²ᵃ, (CR³R³ᵃ)ᵣN(→O)R²R²ᵃ, (CR³R³ᵃ)ᵣC(O)R²ᶜ, (CR³R³ᵃ)ᵣNR²C(O)R²ᵇ, (CR³R³ᵃ)ᵣC(O)NR²R²ᵃ, (CR³R³ᵃ)ᵣN=CHOR³, (CR³R³ᵃ)ᵣC(O)NR²(CH₂)₂NR²R²ᵃ, (CR³R³ᵃ)ᵣNR²C(O)NR²R²ᵃ, (CR³R³ᵃ)ᵣC(=NR²)NR²R²ᵃ, (CR³R³ᵃ)ᵣNR²C(=NR²)NR²R²ᵃ, (CR³R³ᵃ)ᵣSO₂NR²R²ᵃ, (CR³R³ᵃ)ᵣNR²SO₂NR²R²ᵃ, (CR³R³ᵃ)ᵣC(O)NR²SO₂—C₁₋₄ alkyl, (CR³R³ᵃ)ᵣNR²SO₂R⁵ᵃ, (CR³R³ᵃ)ᵣC(O)NR²SO₂R⁵ᵃ, (CR³R³ᵃ)ᵣS(O)ₚR⁵ᵃ, (CF₂)ᵣCF₃, (CR³R³ᵃ)ᵣC₃₋₁₀ carbocycle substituted with 0–2 R⁴ᵇ, and (CR³R³ᵃ)ᵣ-4–10 membered heterocycle substituted with 0–2 R⁴ᵇ and consisting of carbon atoms and from 1–4 heteroatoms selected from the group consisting of N, O, and S(O)ₚ;

R⁴ᵈ, at each occurrence, is selected from H, (CR³R³ᵃ)ᵣOR², (CR³R³ᵃ)ᵣF, (CR³R³ᵃ)ᵣBr, (CR³R³ᵃ)ᵣCl, C₁₋₄ alkyl, (CR³R³ᵃ)ᵣCN, (CR³R³ᵃ)ᵣNO₂, (CR³R³ᵃ)ᵣNR²R²ᵃ, (CR³R³ᵃ)ᵣC(O)R²ᶜ, (CR³R³ᵃ)ᵣNR²C(O)R²ᵇ, (CR³R³ᵃ)ᵣC(O)NR²R²ᵃ, (CR³R³ᵃ)ᵣN=CHOR³, (CR³R³ᵃ)ᵣC(O)NH(CH₂)₂NR²R²ᵃ, (CR³R³ᵃ)ᵣNR²C(O)NR²R²ᵃ, (CR³R³ᵃ)ᵣC(=NR²)NR²R²ᵃ, (CR³R³ᵃ)ᵣNHC(=NR²)NR²R²ᵃ, (CR³R³ᵃ)ᵣSO₂NR²R²ᵃ, (CR³R³ᵃ)ᵣNR²SO₂NR²R²ᵃ, (CR³R³ᵃ)ᵣNR²SO₂—C₁₋₄ alkyl, (CR³R³ᵃ)ᵣC(O)NHSO₂—C₁₋₄ alkyl, (CR³R³ᵃ)NR²SO₂R⁵, (CR³R³ᵃ)ᵣS(O)ₚR⁵ᵃ, (CR³R³ᵃ)ᵣ(CF₂)ᵣCF₃, (CR³R³ᵃ)₄-5–6 membered carbocycle substituted with 0–1 R⁵, and a (CR³R³ᵃ)₄-5–6 membered heterocycle consisting of: carbon atoms and 1–4 heteroatoms selected from the group consisting of N, O, and S(O)ₚ and substituted with 0–1 R⁵;

R⁵, at each occurrence, is selected from H, C₁₋₆ alkyl, =O, (CH₂)ᵣOR³, F, Cl, Br, I, —CN, NO₂, (CH₂)ᵣNR³R³ᵃ, (CH₂)ᵣC(O)R³, (CH₂)ᵣC(O)OR³ᶜ, (CH₂)ᵣNR³C(O)R³ᵃ, (CH₂)ᵣC(O)NR³R³ᵃ, (CH₂)ᵣNR³C(O)NR³R³ᵃ, (CH₂)ᵣCH(=NOR³ᵈ), (CH₂)ᵣC(=NR³)NR³R³ᵃ, (CH₂)ᵣNR³C(=NR³)NR³R³ᵃ, (CH₂)ᵣSO₂NR³R³ᵃ, (CH₂)ᵣNR³SO₂NR³R³ᵃ, (CH₂)ᵣNR³SO₂—C₁₋₄ alkyl, (CH₂)ᵣNR³SO₂CF₃, (CH₂)ᵣNR³SO₂-phenyl, (CH₂)ᵣS(O)ₚCF₃, (CH₂)ᵣS(O)ₚ—C₁₋₄ alkyl, (CH₂)ᵣS(O)ₚ-phenyl, (CF₂)ᵣCF₃, phenyl substituted with 0–2 R⁶, naphthyl substituted with 0–2 R⁶, and benzyl substituted with 0–2 R⁶;

R⁵ᵃ, at each occurrence, is selected from C₁₋₆ alkyl, (CH₂)ᵣOR³, (CH₂)ᵣNR³R³ᵃ, (CH₂)ᵣC(O)R³, (CH₂)ᵣC(O)OR³C, (CH₂)ᵣNR³C(O)R³ᵃ, (CH₂)ᵣC(O)NR³R³ᵃ, (CF₂)ᵣCF₃, phenyl substituted with 0–2 R⁶, naphthyl substituted with 0–2 R⁶, and benzyl substituted with 0–2 R⁶, provided that R⁵ᵃ does not form a S—N or S(O)ₚ—C(O) bond;

R⁶, at each occurrence, is selected from H, OH, (CH₂)ᵣOR², halo, C₁₋₄ alkyl, CN, NO₂, (CH₂)ᵣNR²R²ᵃ, (CH₂)ᵣC(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂C₁₋₄ alkyl;

R⁷, at each occurrence, is selected from H, OH, C₁₋₆ alkyl, C₁₋₆ alkyl-C(O)—, C₁₋₆ alkyl-O—, (CH₂)ₙ-phenyl, C₁₋₄ alkyl-OC(O)—, C₆₋₁₀ aryl-O—, C₆₋₁₀ aryl-OC(O)—, C₆₋₁₀ aryl-CH₂—C(O)—, C₁₋₄ alkyl-C(O)O—C₁₋₄ alkyl-OC(O)—, C₆₋₁₀ aryl-C(O)O—C₁₋₄ alkyl-OC(O)—, C₁₋₆ alkyl-NH₂—C(O)—, phenyl-NH₂—C(O)—, and phenyl-C₁₋₄ alkyl-C(O)—;

R⁸, at each occurrence, is selected from H, C₁₋₆ alkyl, and (CH₂)ₙ-phenyl;

alternatively, R⁷ and R⁸, when attached to the same nitrogen, combine to form a 5–10 membered heterocyclic ring consisting of carbon atoms and 0–2 additional heteroatoms selected from the group consisting of N, O, and S(O)ₚ;

R⁹, at each occurrence, is selected from H, C₁₋₆ alkyl, and (CH₂)ₙ-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and t, at each occurrence, is selected from 0, 1, 2, and 3.

In a second embodiment, the present invention provides a novel compound selected from formula Ia, Ib, and Ic, wherein:

G is a group of formula IIa or IIb:

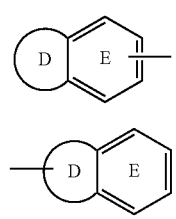

ring D, including the two atoms of ring E to which it is attached, is a 5–6 membered ring consisting of: carbon atoms and 0–2 heteroatoms selected from the group consisting of N, O, and S(O)ₚ;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with a 5 membered heterocycle consisting of: carbon atoms and 1–4 heteroatoms selected from the group consisting of N, O, and S(O)ₚ, wherein the 5 membered heterocycle is substituted with 0–1 carbonyls and 1–2 R and has 0–3 ring double bonds;

R is selected from H, C₁₋₄ alkyl, F, Cl, OH, OCH₃, OCH₂CH₃, OCH(CH₃)₂, CN, C(=NH)NH₂, NH₂, NH(C₁₋₃ alkyl), N(C₁₋₃ alkyl)₂, C(=NH)NH₂, CH₂NH₂, CH₂NH(C₁₋₃ alkyl), CH₂N(C₁₋₃ alkyl)₂, (CR⁸R⁹)ᵣNR⁷R⁸, C(O)NR⁷R⁸, CH₂C(O)NR⁷R⁸, S(O)ₚNR⁷R⁸, CH₂S(O)ₚNR⁷R⁸, and OCF₃;

alternatively, when 2 R groups are attached to adjacent atoms, they combine to form methylenedioxy or ethylenedioxy;

G₁ is selected from (CR³R³ᵃ)₂₋₄, (CR³R³ᵃ)ᵤC(O)(CR³R³ᵃ)ᵥᵥ, (CR³R³ᵃ)ᵤC(O)O(CR³R³ᵃ)ᵥᵥ, (CR³R³ᵃ)ᵤOC(O)(CR³R³ᵃ)ᵥᵥ, (CR³R³ᵃ)ᵤO(CR³R³ᵃ)ᵥᵥ, (CR³R³ᵃ)ᵤNR³ᵇ(CR³R³ᵃ)ᵥᵥ, (CR³R³ᵃ)ᵤC(O)NR³ᵇ(CR³R³ᵃ)ᵥᵥ, (CR³R³ᵃ)ᵤNR³ᵇC(O)(CR³R³ᵃ)ᵥᵥ, (CR³R³ᵃ)ᵤC(O)NR³ᵇ(CR³R³ᵃ)ᵥᵥ, (CR³R³ᵃ)ᵤS(CR³R³ᵃ)ᵥᵥ, (CR³R³ᵃ)ᵤS(O)(CR³R³ᵃ)ᵥᵥ, (CR³R³ᵃ)ᵤS(O)₂(CR³R³ᵃ)ᵥᵥ, (CR³R³ᵃ)ᵤS(O)NR³ᵇ(CR³R³ᵃ)ᵥᵥ, (CR³R³ᵃ)ᵤNR³ᵇS(O)₂(CR³R³ᵃ)ᵥᵥ, (CR³R³ᵃ)ᵤS(O)₂NR³ᵇ(CR³R³ᵃ)ᵥᵥ, and (CR³R³ᵃ)ᵤNR³ᵉ(CR³R³ᵃ)ᵥᵥ, wherein u+w total 1, 2, or 3 and the right side of G₁ is attached to ring G, provided that G₁ does not form an N—S, NCH₂N, NCH₂O, or NCH₂S bond with either group to which it is attached;

A is selected from: $C_{5-10}$ carbocycle substituted with 0–2 $R^4$, and 5–10 membered heterocycle consisting of: carbon atoms and 1–4 heteroatoms selected from the group consisting of N, O, and $S(O)_p$ and substituted with 0–2 $R^4$;

B is selected from Y, X—Y, $N(B^1)C(O)C(R^3R^{3g})NB^2B^3$, $N(B^1)C(O)C(R^3R^{3g})C(R^3R^{3g})NB^2B^3$,

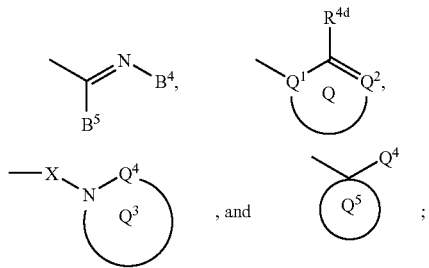

, and provided that the lactam nitrogen and B are attached to different atoms on A, the $R^{4d}$ shown is other than OH, and that the A—X—N moiety forms other than a N—N—N group;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-1}$—$C_{3-7}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$, $C(O)R^{3b}$, $SO_2NR^3R^{3b}$, $C(O)NR^3R^{3b}$, $OR^2$, and —CN;

$B^5$ is $NR^2R^{2f}$ or $CR^3R^2R^{2f}$;

ring Q is a 5–6 membered ring consisting of, in addition to the $Q^1$—$CR^4$=$Q^2$ group shown, carbon atoms and 0–2 heteroatoms selected from N, O, and $S(O)_p$, and the ring is substituted with an additional 0–2 $R^{4d}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

$Q^4$ is selected from C=O and $SO_2$;

ring $Q^3$ is a 4–7 membered monocyclic or tricyclic ring consisting of, in addition to the N—$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 4–7 membered ring to which another ring is fused, wherein: the 4–7 membered ring consists of, in addition to the shown amide group, carbon atoms and 0–2 heteroatoms selected from $NR^{4c}$, O, S, S(O), and $S(O)_2$ and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 4–7 membered ring and the fusion ring, is substituted with 0–3 $R^4$;

ring $Q^5$ is a $C_{3-7}$ monocyclic carbocycle or 3–7 membered monocyclic heterocycle, wherein the carbocycle or heterocycle consists of: carbon atoms and 0–2 heteroatoms selected from N, O, and $S(O)_p$, the carbocycle or heterocycle further comprises 0–2 double bonds and 0–2 carbonyl groups, and the carbocycle or heterocycle is substituted with 0–2 $R^4$;

X is selected from —$(CR^2R^{2a})_{1-4}$—, —$C(O)$—, —$C(=NR^{1c})$—, —$CR^2(NR^{1b}R^2)$—, —$C(O)CR^2R^{2a}$—, —$CR^2R^{2a}C(O)$—, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, —$S(O)_2$—, —$NR^2S(O)_2$—, O, —$CR^2R^{2a}O$—, and —$OCR^2R^{2a}$—;

Y is selected from: $CY^1Y^2R^{4a}$, $NR^3R^{3a}$, $SO_2NR^3R^{3a}$, and $C(O)NR^3R^{3a}$;

$Y^1$ and $Y^2$ are independently $C_{1-3}$ alkyl substituted with 0–2 $R^4$;

alternatively, Y is selected from one of the following carbocyclic and heterocycles that are substituted with 1 $R^{4a}$ and 0–2 $R^4$: cyclopropyl, cyclopentyl, cyclohexyl, phenyl, piperidinyl, piperazinyl, pyridyl, pyrimidyl, furanyl, morpholinyl, tetrahydropyranyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, when A is selected from one of the following carbocyclic and heterocyclic groups, which are substituted with 0–2 $R^{4c}$,cyclohexyl, cyclopentyl, azetidinyl, oxazolinyl, isoxazolinyl, thiazolinyl, isothiazolinyl, piperidinyl, piperazinyl, hexahydropyrimidyl, morpholinyl, and pyrrolidinyl;

then Y is additionally selected from methyl, ethyl, 1-propyl, 2-propyl, 1-butyl, 2-butyl, 2-methyl-1-propyl, 1,1-dimethyl-1-ethyl, 1-pentyl, 2-pentyl, 3-pentyl, 3-hexyl, cyclopropyl, cyclobutyl, cyclopentyl, 2,5-dimethyl-cyclopentyl, cyclohexyl, 2,6-dimethyl-cyclohexyl, $CH(CF_3)_2$, $CH(CHF_2)$, $CH(CH_2F)$, $CH_2CF_3$, $CH(CF_2CF_3)_2$, $CH(Cl)CF_3$, —CN, $C(O)CH_2CH_3$, $C(O)CH(CH_3)_2$, $C(O)CH_2CH_2CH_3$, $C(O)NHCH_2CH_3$, $C(O)N(CH_3)_2$, $C(O)N(CH_3)(CH_2CH_3)$, $C(O)OCH_2CH_3$, $C(O)C(CH_3)_3$, $SO_2CH_3$, $SO_2CH_2CH_3$, $SO_2CH_2CH_2CH_3$, $SO_2CH(CH_3)_2$, $SO_2CH(CH_3)CH_2CH_3$, $SO_2N(CH_3)_2$, $SO_2N(CH_3)CH_2CH_3$, $OCH_3$, $OCH_2CH_3$, $OCH(CH_3)_2$, $OCH(CH_3)CH_2CH_3$, $SCH_3$, $SCH_2CH_3$, $SCH(CH_3)_2$, $SCH(CH_3)CH_2CH_3$, $SCH(CH_2CH_3)_2$, $N(CH_3)_2$, $N(CH_2CH_3)_2$, $N(CH_3)CH_2CH_3$, $N(CH_2CH_3)CH_2CH_2CH_3$, $NHC(O)CH_3$, $NHC(O)CH_2CH_3$, $NHC(O)CH(CH_3)_2$, $NHC(O)CH(CH_3)CH_2CH_3$, $C(O)NHSO_2CH_3$, $C(O)NHSO_2CH_2CH_3$, $NHC(O)N(CH_3)_2$, $NHC(O)N(CH_3)CH_2CH_3$, $C(S)CH_3$, $C(S)CH_2CH_3$, $NHC(S)N(CH_3)_2$, $NHC(S)N(CH_3)CH_2CH_3$, $C(S)OCH_3$, and $NHC(O)CH_3$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, a $C_{5-6}$ carbocyclic-$CH_2$-group substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{56}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–1 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

alternatively, $CR^2R^{2f}$ forms a 5–6 membered ring consisting of: carbon atoms and 0–2 heteroatoms selected from N, O, and $S(O)_p$, and this ring is substituted with 0–2 $R^{4b}$;

alternatively, $NR^2R^{2f}$ forms a 5–6 membered ring consisting of: carbon atoms and 0–2 additional heteroatoms selected from N, O, and $S(O)_p$, and this ring is substituted with 0–2 $R^{4b}$;

alternatively, when $B^5$ is $NR^2R^{2f}$, $B^4$ and $R^{2f}$ combine to form a 5–6 membered ring consisting of: carbon atoms and 0–2 additional heteroatoms selected from N, O, and $S(O)_p$, and this ring is substituted with 0–2 $R^{4b}$ and the $R^2$ group of $NR^2R^{2f}$, in addition to the groups recited below, is selected from $SO_2R^{3b}$ and $C(O)R^{3b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3b}$, at each occurrence, is selected from H, $CF_3$, $CH_3$, $CH_2CH_3$, $CH_2CH_2CH_3$, $CH(CH_3)_2$, —$(C_{0-1}$ alkyl)-5–6 membered carbocycle substituted with 0–1 $R^{1a}$, and —$(C_{0-1}$ alkyl)-5–6 membered heterocycle substituted with 0–1 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and C(=O)$R^{3c}$;

$R^4$, at each occurrence, is selected from =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $NR^2SO_2NR^2R^{2a}$, $S(O)_pR^{5a}$, $NR^2SO_2$—$C_{1-4}$ alkyl, $NR^2SO_2R^5$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$, and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C$ (=NR³)NR³R³ᵃ, SO₂NR³R³ᵃ, CH₂SO₂NR³R³ᵃ, NR³SO₂NR³R³ᵃ, CH₂NR³SO₂NR³R³ᵃ, NR³SO₂—C₁₋₄ alkyl, CH₂NR³SO₂—C₁₋₄ alkyl, NR³SO₂CF₃, CH₂NR³SO₂CF₃, NR³SO₂-phenyl, CH₂NR³SO₂-phenyl, S(O)$_p$CF₃, CH₂S(O)$_p$CF₃, S(O)$_p$—C₁₋₄ alkyl, CH₂S(O)$_p$—C₁₋₄ alkyl, S(O)$_p$-phenyl, CH₂S(O)$_p$-phenyl, CF₃, and CH₂—CF₃;

R$^{4c}$, at each occurrence, is selected from =O, (CR³R³ᵃ)$_r$OR², (CR³R³ᵃ)$_r$F, (CR³R³ᵃ)$_r$Br, (CR³R³ᵃ)$_r$Cl, (CR³R³ᵃ)$_r$CF₃, C₁₋₄ alkyl, C₂₋₃ alkenyl, C₂₋₃ alkynyl, (CR³R³ᵃ)$_r$CN, (CR³R³ᵃ)$_r$NO₂, (CR³R³ᵃ)$_r$NR²R²ᵃ, (CR³R³ᵃ)$_r$N(→O)R²R²ᵃ, (CR³R³ᵃ)$_r$C(O)R²ᶜ, (CR³R³ᵃ)$_r$NR²C(O)R²ᵇ, (CR³R³ᵃ)$_r$C(O)NR²R²ᵃ, (CR³R³ᵃ)$_r$NR²C(O)NR²R²ᵃ, (CR³R³ᵃ)$_r$SO₂NR²R²ᵃ, (CR³R³ᵃ)$_r$NR²SO₂NR²R²ᵃ, (CR³R³ᵃ)$_r$NR²SO₂R⁵ᵃ, (CR³R³ᵃ)$_r$C(O)NR²SO₂R⁵ᵃ, (CR³R³ᵃ)$_r$S(O)$_p$R⁵ᵃ, (CF₂)$_r$CF₃, (CR³R³ᵃ)$_r$—C₃₋₁₀ carbocycle substituted with 0–2 R⁴ᵇ, and (CR³R³ᵃ)$_r$5-10 membered heterocycle consisting of carbon atoms and from 1–4 heteroatoms selected from the group consisting of N, O, and S(O)$_p$ and substituted with 0–2 R⁴ᵇ;

R$^{4d}$, at each occurrence, is selected from H, CH₂OR², OR², C₁₋₄ alkyl, CH₂—CN, —CN, CH₂NO₂, NO₂, CH₂NR²R²ᵃ, NR²R²ᵃ, CH₂—C(O)R²ᶜ, C(O)R²ᶜ, NR²C(O)R²ᵇ, (CH₂)$_r$C(O)NR²R²ᵃ, NR²C(O)NR²R²ᵃ, (CH₂)$_r$SO₂NR²R²ᵃ, NR²SO₂NR²R²ᵃ, NR²SO₂R⁵, (CH₂)$_r$S(O)$_p$R⁵ᵃ, CH₂CF₃, CF₃, CH₂-5–6 membered carbocycle substituted with 0–1 R⁵, 5–6 membered carbocycle substituted with 0–1 R⁵, a CH₂-5–6 membered heterocycle consisting of: carbon atoms and 1–4 heteroatoms selected from the group consisting of N, O, and S(O)$_p$ and substituted with 0–1 R⁵, and a 5–6 membered heterocycle consisting of: carbon atoms and 1–4 heteroatoms selected from the group consisting of N, O, and S(O)$_p$ and substituted with 0–1 R⁵;

R⁵, at each occurrence, is selected from H, =O, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, OR³, CH₂OR³, F, Cl, —CN, NO₂, NR³R³ᵃ, CH₂NR³R³ᵃ, C(O)R³, CH₂C(O)R³, C(O)OR³ᶜ, CH₂C(O)OR³ᶜ, NR³C(O)R³ᵃ, C(O)NR³R³ᵃ, NR³C(O)NR³R³ᵃ, CH(=NOR³ᵈ), C(=NR³)NR³R³ᵃ, NR³C(=NR³)NR³R³ᵃ, SO₂NR³R³ᵃ, NR³SO₂NR³R³ᵃ, NR³SO₂—C₁₋₄ alkyl, NR³SO₂CF₃, NR³SO₂-phenyl, S(O)$_p$CF₃, S(O)$_p$—C₁₋₄ alkyl, S(O)$_p$-phenyl, CF₃, phenyl substituted with 0–2 R⁶, naphthyl substituted with 0–2 R⁶, and benzyl substituted with 0–2 R⁶; and, R$^{5a}$, at each occurrence, is selected from CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, OR³, CH₂OR³, NR³R³ᵃ, CH₂NR³R³ᵃ, C(O)R³, CH₂C(O)R³, C(O)OR³ᶜ, CH₂C(O)OR³ᶜ, NR³C(O)R³ᵃ, CH₂NR³C(O)R³ᵃ, C(O)NR³R³ᵃ, CH₂C(O)NR³R³ᵃ, CF₃, CF₂CF₃, phenyl substituted with 0–2 R⁶, naphthyl substituted with 0–2 R⁶, and benzyl substituted with 0–2 R⁶, provided that R⁵ᵃ does not form a S—N or S(O)$_p$—C(O) bond; and R⁶, at each occurrence, is selected from H, OH, OR², F, Cl, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, CN, NO₂, NR²R²ᵃ, CH₂NR²R²ᵃ, C(O)R²ᵇ, CH₂C(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂C₁₋₄ alkyl.

In a third embodiment, the present invention provides a novel compound selected from formula Ib and Ic, wherein:

the central lactam ring is substituted with 0–1 R$^{1a}$;

G is selected from:

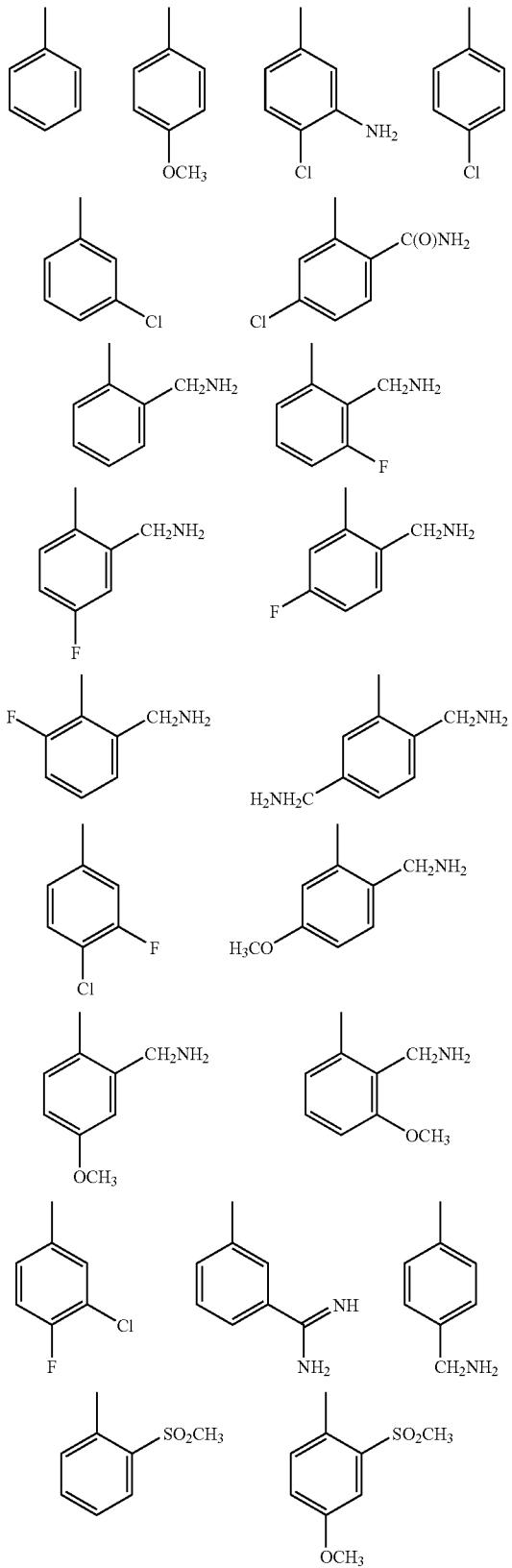

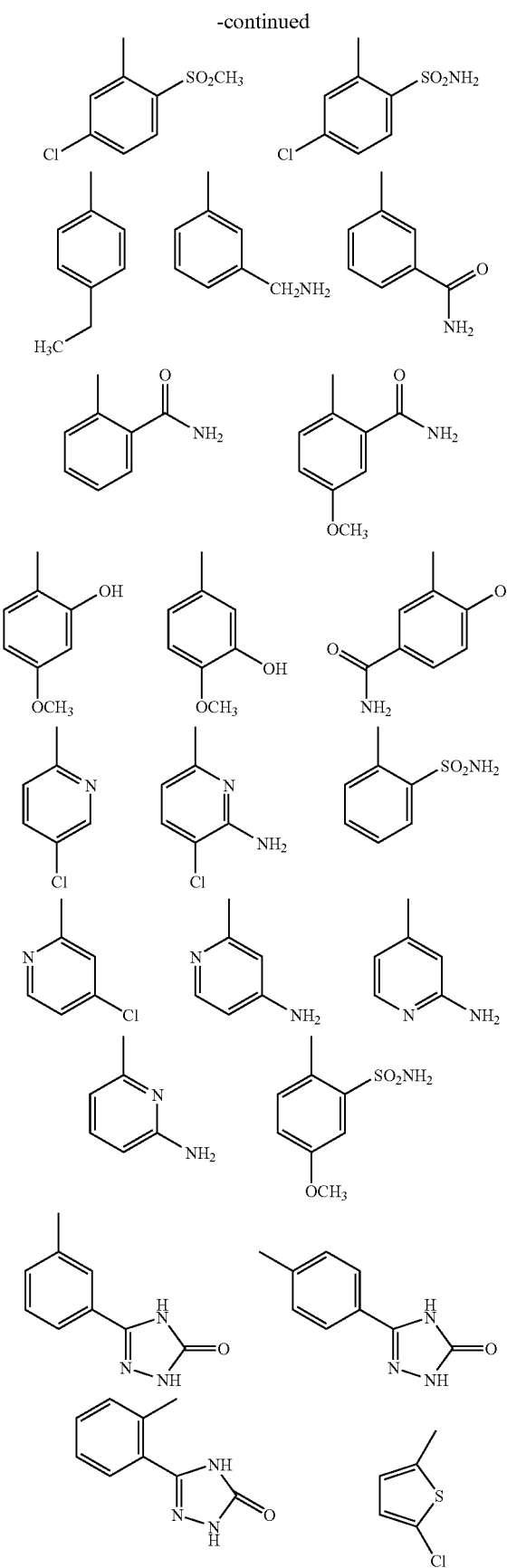
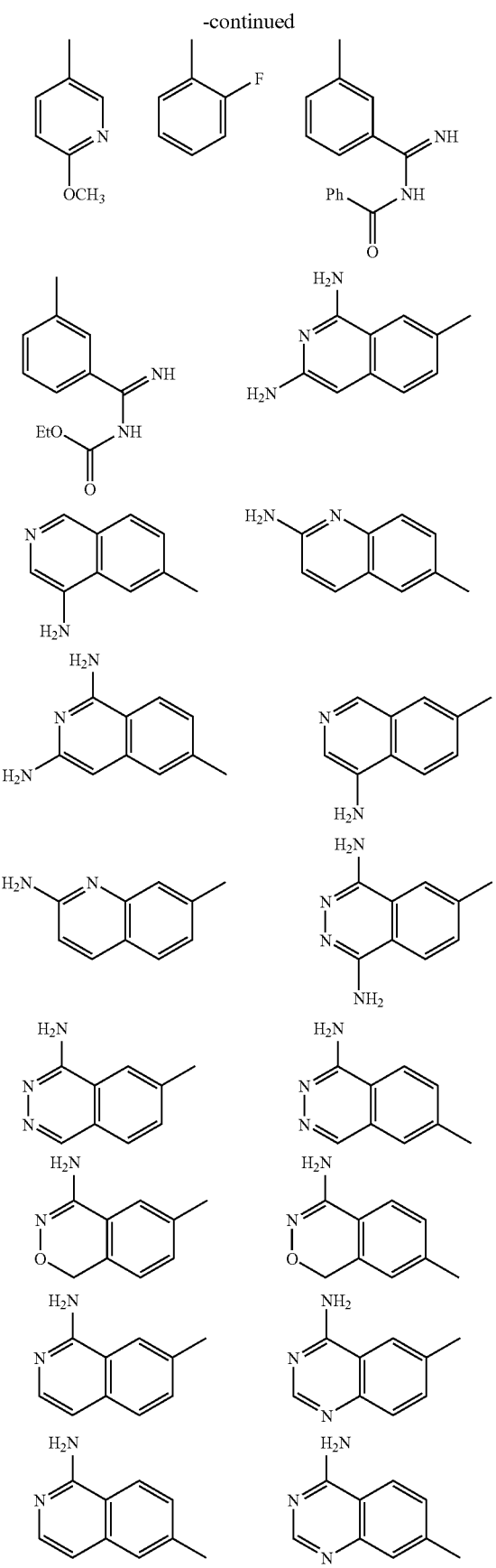

-continued
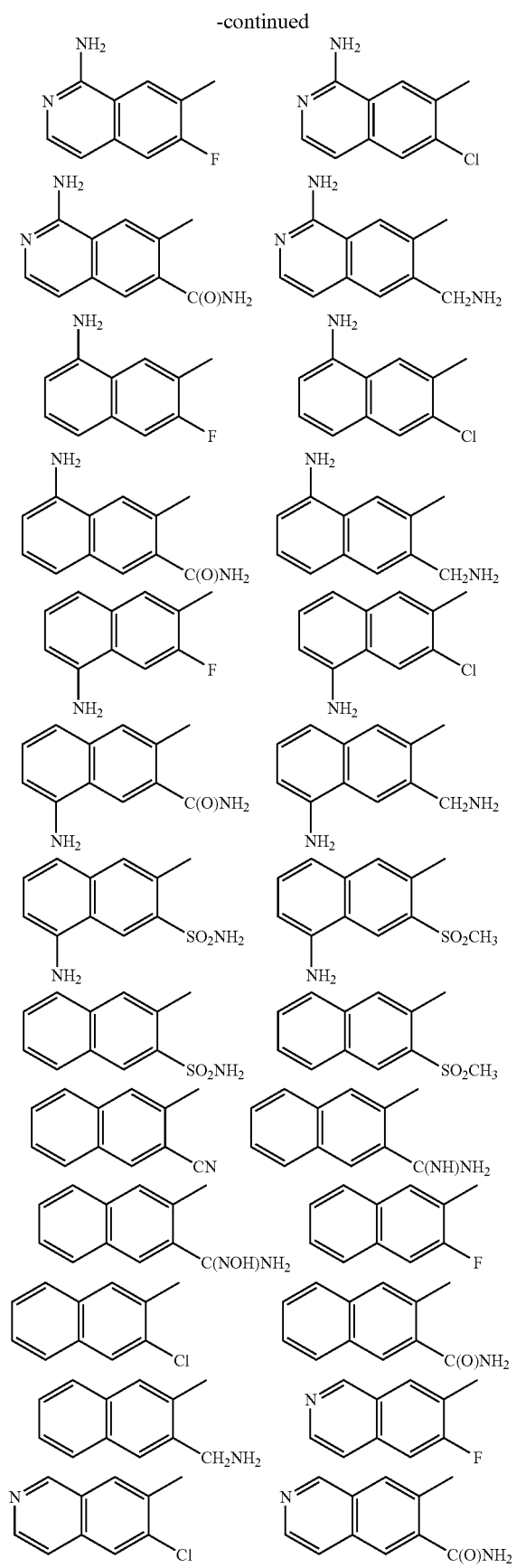
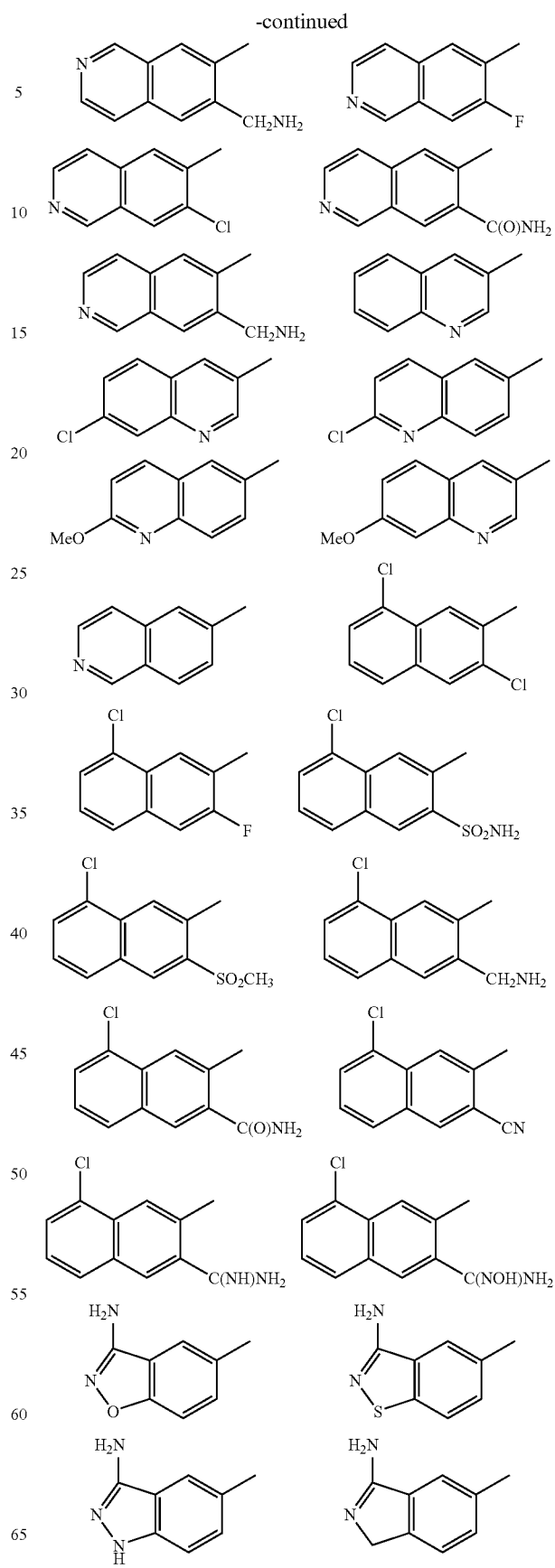

-continued
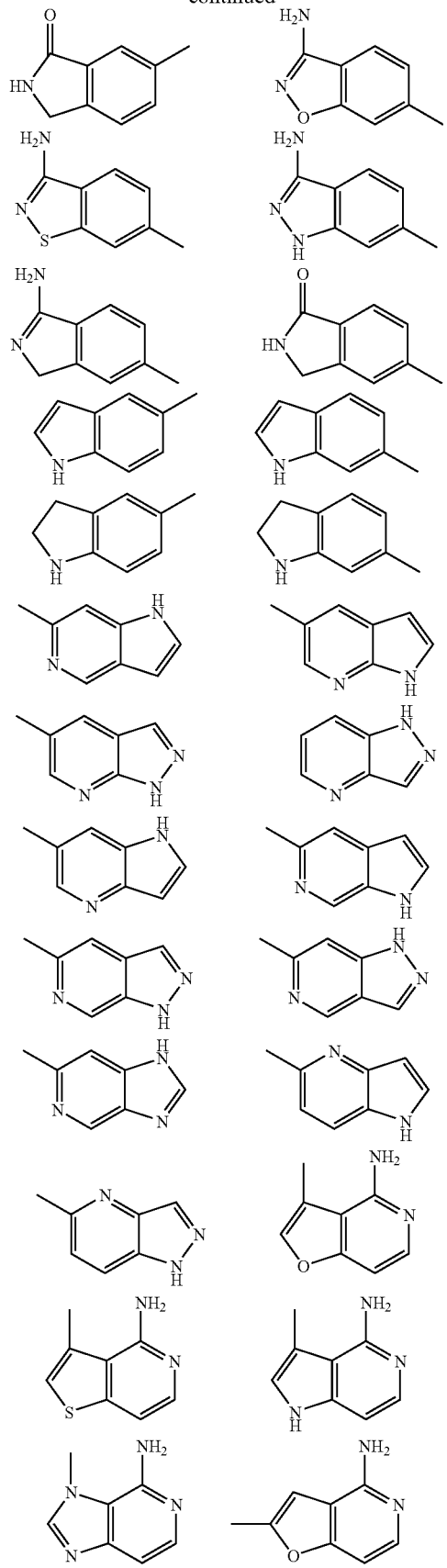
-continued
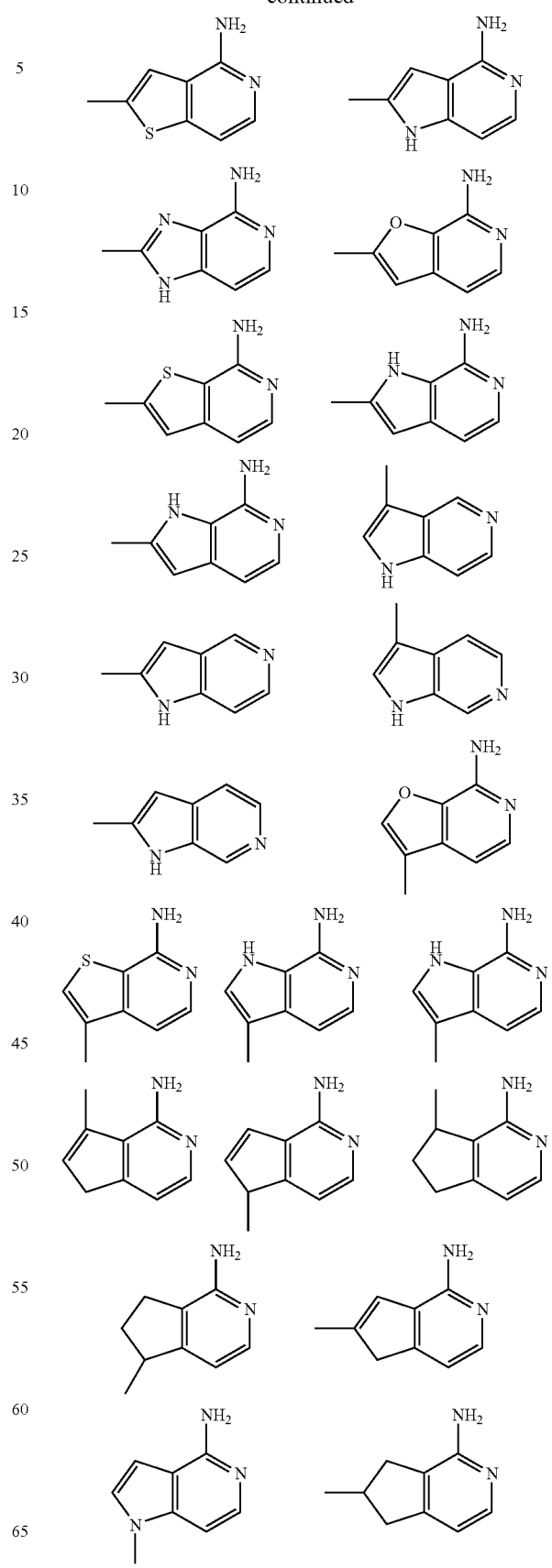

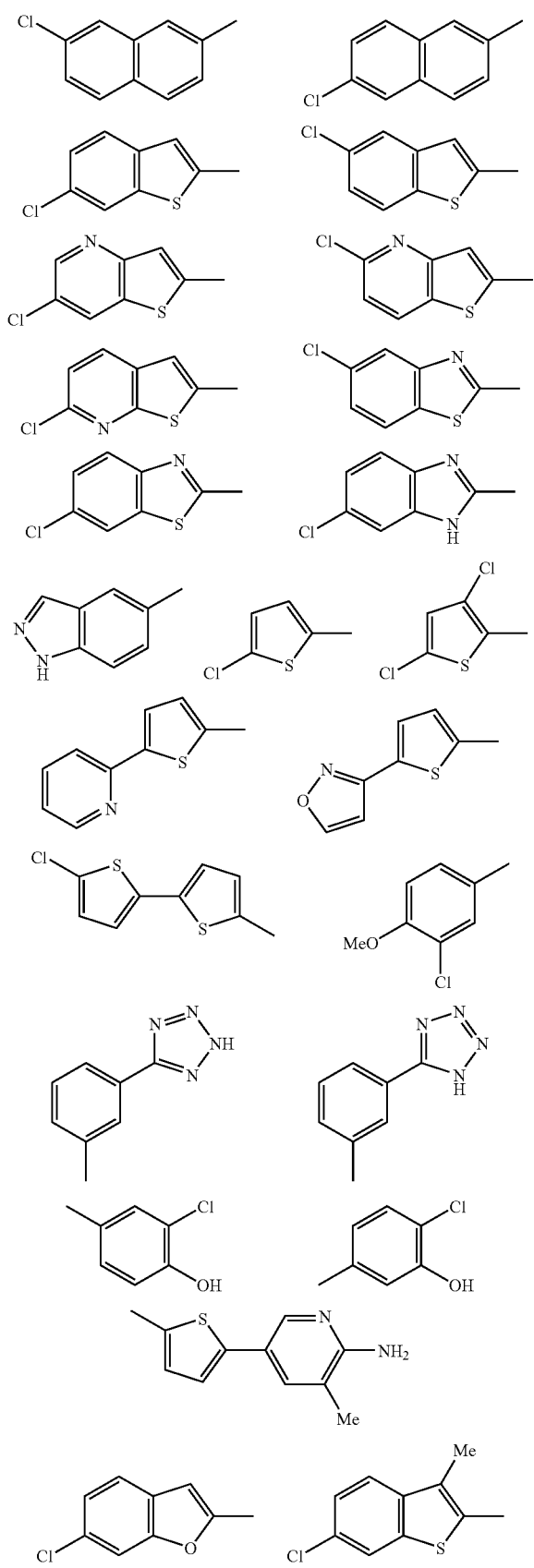
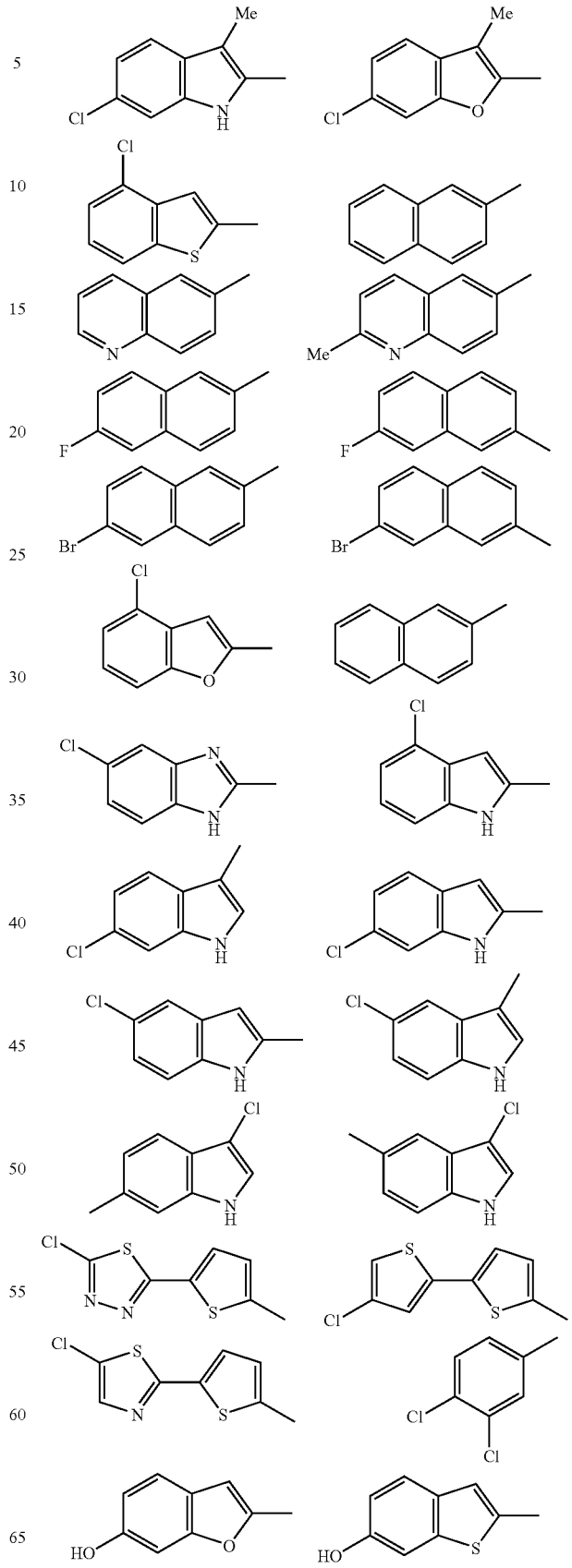

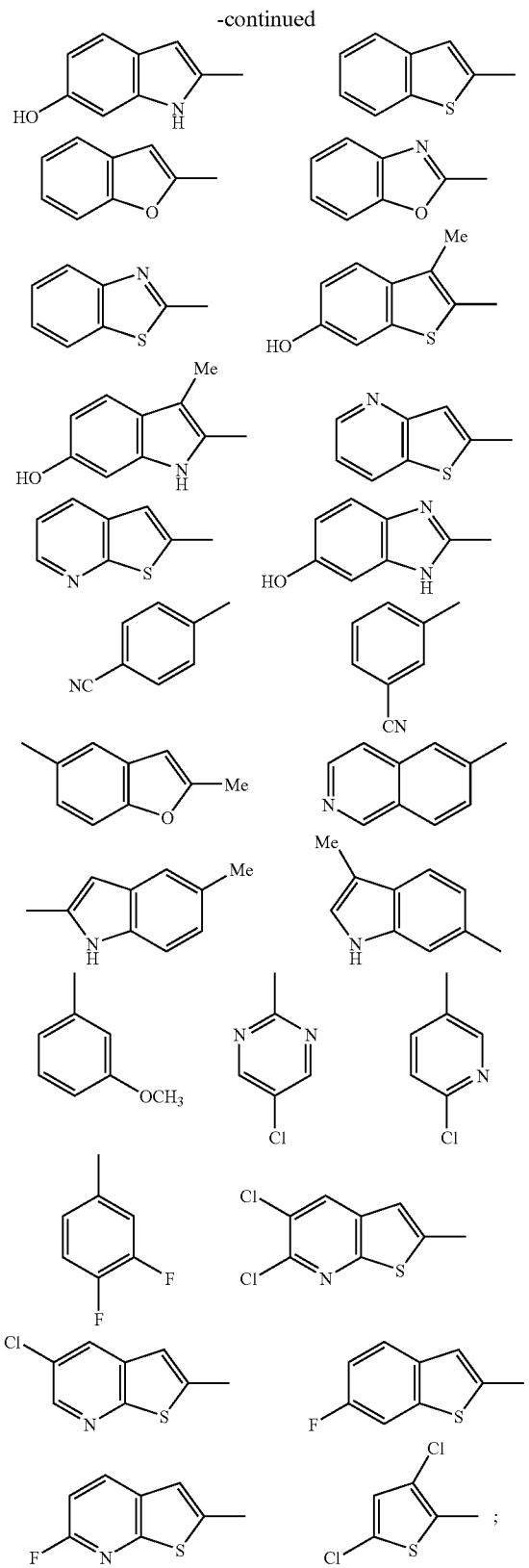

$(CH_2)_uNR^{3b}C(O)(CH_2)_w$, $(CH_2)_uOC(O)NR^{3b}(CH_2)_w$, $(CH_2)_uS(CH_2)_w$, $(CH_2)_uS(O)(CH_2)_w$, $(CH_2)_uS(O)_2(CH_2)_w$, $(CH_2)_uS(O)NR^{3b}(CH_2)_w$, $(CH_2)_uNR^{3b}S(O)_2(CH_2)_w$, $(CH_2)_uS(O)_2NR^{3b}(CH_2)_w$, and $(CH_2)_uNR^{3e}(CH_2)_w$, wherein u+w total 1, 2, or 3 and the right side of $G_1$ is attached to ring G, provided that $G_1$ does not form an N—S, $NCH_2N$, $NCH_2O$, or $NCH_2S$ bond with either group to which it is attached;

A is selected from one of the following carbocyclic and heterocyclic groups, which are substituted with 0–2 $R^4$, cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

$B^1$ is selected from H, $CH_3$, $CH_2CH_3$, $CH_2CH_2CH_3$, $CH(CH_3)_2$, —$(CH_2)_{0-1}$—$C_{5-6}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$ and $OR^2$;

$B^5$ is $NR^2R^{2f}$;

ring Q is a 5–6 membered ring consisting of, in addition to the N—$CR^{4d}$=N group shown, carbon atoms and 0–2 heteroatoms selected from N, O, and $S(O)_p$, and the ring is substituted with an additional 0–2 $R^{4d}$;

$Q^4$ is selected from C=O and $SO_2$;

ring $Q^3$ is a 5–7 membered ring consisting of, in addition to the N—$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^{4a}$;

alternatively, ring $Q^3$ is a 5–7 membered ring to which another ring is fused, wherein: the 5–7 membered ring consists of, in addition to the shown amide group, carbon atoms and 0–2 heteroatoms selected from $NR^{4c}$, O, S, S(O), and $S(O)_2$, and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 5–7 membered ring and the fusion ring, is substituted with 0–3 $R^{4a}$;

ring $Q^5$, is a $C_{3-6}$ monocyclic carbocycle or 5–6 membered monocyclic heterocycle, wherein the carobocycle or heterocycle consists of carbon atoms and 0–2 heteroatoms selected from N, O, and $S(O)_p$, the carbocycle or heterocycle further comprises 0–1 double bonds and 0–1 carbonyl groups, and the carbocycle or heterocycle is substituted with 0–2 $R^4$;

X is selected from —$(CR^2R^{2a})_{1-2}$—, —C(=$NR^{1b}$)—, —C(O)—, —S(O)_2—, —$NR^2S(O)_2$—, —$NR^2S(O)_2$—, —$NR^2C(O)$—, —C(O)$NR^2$—, —$NR^2C(O)CR^2R^{2a}$—, $G_1$ is selected from $(CH_2)_{2-4}$, $(CH_2)_uC(O)(CH_2)_w$, $(CH_2)_uC(O)O(CH_2)_w$, $(CH_2)_uOC(O)(CH_2)_w$, $(CH_2)_uO(CH_2)_w$, $(CH_2)_w(CH_2)_uNR^{3b}(CH_2)_w$, $(CH_2)_uC(O)NR^{3b}(CH_2)_w$, —NR²C(O)NR²—, NR², —NR²CR²R²ᵃ—, —CR²R²ᵃNR²—, O, —OCR²R²ᵃ—, and —CR²R²ᵃO—;

Y is selected from: CY¹Y²R⁴ᵃ, NR³R³ᵃ, SO₂NR³R³ᵃ, and C(O)NR³R³ᵃ;

Y¹ and Y² are independently C$_{1-2}$ alkyl substituted with 0–2 R⁴;

alternatively, Y is selected from one of the following carbocyclic and heterocycles that are substituted with 1 R⁴ᵃ and 0–1 R⁴: cyclopentyl, cyclohexyl, phenyl, piperidinyl, piperazinyl, pyridyl, pyrimidyl, furanyl, morpholinyl, tetrahydropyranyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, and isoindazole;

alternatively, when A is selected from one of the following carbocyclic and heterocyclic groups, which are substituted with 0–2 R⁴ᶜ, cyclopentyl, cyclohexyl, azetidinyl, piperidinyl, hexahydropyrimidyl, pyrrolidinyl, morpholinyl, and piperazinyl;

then Y is additionally selected from methyl, ethyl, 1-propyl, 2-propyl, 1-butyl, 2-butyl, 2-methyl-1-propyl, 1,1-dimethyl-1-ethyl, 1-pentyl, 2-pentyl, 3-pentyl, cyclopropyl, cyclobutyl, cyclopentyl, cyclohexyl, CH(CF₃)₂, CH(CHF₂), CH(CH₂F), CH₂CF₃, CH(CF₂CF₃)₂, —CN, C(O)NHCH₂CH₃, C(O)N(CH₃)₂, C(O)CH₂CH₂CH₃, C(O)C(CH₃)₃, N(CH₃)₂, N(CH₂CH₃)₂, NHC(O)CH₂CH₃, NHC(O)CH(CH₃)₂, SO₂CH₃, C(O)NHSO₂CH₃, C(O)NHSO₂CH₂CH₃, NHC(O)N(CH₃)₂, NHC(O)N(CH₃)CH₂CH₃, C(S)CH₃, C(S)CH₂CH₃, NHC(S)N(CH₃)₂, NHC(S)N(CH₃)CH₂CH₃, C(S)OCH₃, and NHC(O)CH₃;

R¹ᵃ is selected from H, R¹ᵇ, CH(CH₃)R¹ᵇ, C(CH₃)₂R¹ᵇ, CH₂R¹ᵇ, and CH₂CH₂R¹ᵇ, provided that R¹ᵃ forms other than an N-halo, N—S, or N—CN bond;

alternatively, when two R¹ᵃ groups are attached to adjacent atoms, together with the atoms to which they are attached they form a 5–6 membered ring consisting of: carbon atoms and 0–2 heteroatoms selected from the group consisting of N, O, and S(O)$_p$, this ring being substituted with 0–2 R⁴ᵇ and 0–3 ring double bonds;

R¹ᵇ is selected from H, CH₃, CH₂CH₃, F, Cl, Br, —CN, —CHO, CF₃, OR², NR²R²ᵃ, C(O)R²ᵇ, CO₂R²ᵇ, OC(O)R², CO₂R²ᵃ, S(O)$_p$R², NR²(CH₂)$_r$OR², NR²C(O)R²ᵇ, C(O)NR²R²ᵃ, SO₂NR²R²ᵃ, NR²SO₂R², phenyl substituted with 0–2 R⁴ᵇ, and 5–6 membered aromatic heterocycle consisting of carbon atoms and from 1–4 heteroatoms selected from the group consisting of N, O, and S(O)$_p$, and substituted with 0–2 R⁴ᵇ, provided that R¹ᵇ forms other than an O—O, N-halo, N—S, or N—CN bond;

R², at each occurrence, is selected from H, CF₃, CH₃, CH₂CH₃, CH₂CH₂CH₃, CH(CH₃)₂, phenyl substituted with 0–2 R⁴ᵇ, a benzyl substituted with 0–2 R⁴ᵇ, and a 5–6 membered aromatic heterocycle consisting of: carbon atoms and 1–4 heteroatoms selected from the group consisting of N, O, and S(O)$_p$, and substituted with 0–2 R⁴ᵇ;

R²ᵃ, at each occurrence, is selected from H, CF₃, CH₃, CH₂CH₃, CH₂CH₂CH₃, CH(CH₃)₂, benzyl substituted with 0–2 R⁴ᵇ, phenyl substituted with 0–2 R⁴ᵇ, and 5–6 membered aromatic heterocycle consisting of: carbon atoms and 1–4 heteroatoms selected from the group consisting of N, O, and S(O)$_p$, and substituted with 0–2 R⁴ᵇ;

alternatively, NR²R²ᵃ forms a 5 or 6 membered saturated, partially saturated or unsaturated ring substituted with 0–2 R⁴ᵇ and consisting of: 0–1 additional heteroatoms selected from the group consisting of N, O, and S(O)$_p$;

R²ᵇ, at each occurrence, is selected from CF₃, C$_{1-4}$ alkoxy, CH₃, CH₂CH₃, CH₂CH₂CH₃, CH(CH₃)₂, benzyl substituted with 0–2 R⁴ᵇ, phenyl substituted with 0–2 R⁴ᵇ, and 5–6 membered aromatic heterocycle consisting of: carbon atoms and 1–4 heteroatoms selected from the group consisting of N, O, and S(O)$_p$, and substituted with 0–2 R⁴ᵇ;

R²ᶜ, at each occurrence, is selected from CF₃, OH, OCH₃, OCH₂CH₃, OCH₂CH₂CH₃, OCH(CH₃)₂, CH₃, CH₂CH₃, CH₂CH₂CH₃, CH(CH₃)₂, benzyl substituted with 0–2 R⁴ᵇ, phenyl substituted with 0–2 R⁴ᵇ, and 5–6 membered aromatic heterocycle containing from 1–4 heteroatoms selected from the group consisting of N, O, and S(O)$_p$, and substituted with 0–2 R⁴ᵇ;

R²ᵈ, at each occurrence, is selected from H, R⁴ᶜ, C$_{1-4}$ alkyl substituted with 0–2 R⁴ᶜ, C$_{3-6}$ carbocycle substituted with 0–2 R⁴ᶜ, —(CR³R³ᵃ)—C$_{3-6}$ carbocycle substituted with 0–2 R⁴ᶜ, 5–6 membered heterocycle substituted with 0–2 R⁴ᶜ and consisting of: carbon atoms and 1–4 heteroatoms selected from the group consisting of N, O, and S(O)$_p$, and —(CR³R³ᵃ)-5–6 membered heterocycle substituted with 0–2 R⁴ᶜ and consisting of: carbon atoms and 1–4 heteroatoms selected from the group consisting of N, O, and S(O)$_p$, provided that R²ᵈ forms other than a N-halo, N—C-halo, S(O)$_p$-halo, O-halo, N—S, S—N, S(O)$_p$—S(O)$_p$, S—O, O—N, O—S, or O—O moiety;

R²ᵉ, at each occurrence, is selected from H, R⁴ᶜ, C$_{1-4}$ alkyl substituted with 0–2 R⁴ᶜ, C$_{3-6}$ carbocycle substituted with 0–2 R⁴ᶜ, —(CR³R³ᵃ)—C$_{3-6}$ carbocycle substituted with 0–2 R⁴ᶜ, 5–6 membered heterocycle substituted with 0–2 R⁴ᶜ and consisting of: carbon atoms and 1–4 heteroatoms selected from the group consisting of N, O, and S(O)$_p$, and —(CR³R³ᵃ)-5–6 membered heterocycle substituted with 0–2 R⁴ᶜ and consisting of: carbon atoms and 1–4 heteroatoms selected from the group consisting of N, O, and S(O)$_p$, provided that R²ᵉ forms other than a C(O)-halo or C(O)—S(O)$_p$ moiety;

R²ᶠ, at each occurrence, is selected from H, CF₃, CH₃, CH₂CH₃, CH₂CH₂CH₃, CH(CH₃)₂, OCH₃, and benzyl;

alternatively, NR²R²ᶠ forms a 5–6 membered ring consisting of: carbon atoms and 0–2 additional heteroatoms selected from N, O, and S(O)$_p$, and this ring is substituted with 0–2 R⁴ᵇ;

alternatively, B⁴ and R²ᶠ combine to form a 5–6 membered ring consisting of: carbon atoms and 0–1 additional heteroatoms selected from N, O, and S(O)$_p$, and this ring is substituted with 0–2 R⁴ᵇ and the R² group of NR²R²ᶠ, in addition to the groups recited below, can be SO₂R³ᵇ;

R³ᵇ, at each occurrence, is selected from H, CF₃, CH₃, CH₂CH₃, CH₂CH₂CH₃, and CH(CH₃)₂;

R⁴, at each occurrence, is selected from H, =O, CH₂OR², (CH₂)₂OR², OR², F, Cl, Br, I, CH₃, CH₂CH₃, CH₂CH₂CH₃, CH(CH₃)₂, CH₂CH₂CH₃, CH₂CH(CH₃)₂, CH(CH₃)CH₂CH₃, C(CH₃)₃, —CN, NO₂, NR²R²ᵃ, CH₂NR²R²ᵃ, (CH₂)₂NR²R²ᵃ, C(O)R²ᶜ, NR²C(O)R²ᵇ, C(O)NR²R²ᵃ, NR²C(O)NR²R²ᵃ, SO₂NR²R²ᵃ, CF₃, and CF₂CF₃;

R⁴ᵃ is selected from —(CR³R³ᵍ)$_r$-5–6 membered carbocycle substituted with 0–3 R⁴ᶜ, —(CR³R³ᵍ)$_r$-5–6 membered heterocycle substituted with 0–3 R⁴ᶜ and consisting of: carbon atoms and 1–4 heteroatoms selected from the group consisting of N, O, and S(O)$_p$, (CR³R³ᵍ)$_r$NR²ᵈR²ᵈ, (CR³R³ᵍ)$_r$N(→O)R²ᵈR²ᵈ, (CR³R³ᵍ)$_r$OR²ᵈ, (CR³R³ᵍ)$_r$—NR²ᵈC(O)R²ᵉ, (CR³R³ᵍ)$_r$—C(O)R²ᵉ, (CR³R³ᵍ)$_r$—OC(O)R²ᵉ, (CR³R³ᵍ)$_r$—C(O)NR²ᵈR²ᵈ, (CR³R³ᵍ)$_r$—C(O)OR²ᵈ, (CR³R³ᵍ)$_r$—NR²ᵈC(O)NR²ᵈR²ᵈ, (CR³R³ᵍ)$_r$—NR²ᵈC(O)OR²ᵈ, (CR³R³ᵍ)$_r$—SO₂NR²ᵈR²ᵈ, (CR³R³ᵍ)$_r$—

NR$^{2d}$SO$_2$R$^{2d}$, and (CR$^3$R$^{3g}$)$_r$—S(O)$_p$R$^{2d}$, provided that S(O)$_p$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, CH$_2$—C(O)R$^3$, C(O)OR$^{3c}$, CH$_2$—C(O)OR$^{3c}$, NR$^3$C(O)R$^{3a}$, CH$_2$NR$^3$C(O)R$^{3a}$, C(O)NR$^3$R$^{3a}$, CH$_2$—C(O)NR$^3$R$^{3a}$, SO$_2$NR$^3$R$^{3a}$, CH$_2$SO$_2$NR$^3$R$^{3a}$, NR$^3$SO$_2$—C$_{1-4}$ alkyl, CH$_2$NR$^3$SO$_2$—C$_{1-4}$ alkyl, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, and CF$_3$;

R$^{4c}$, at each occurrence, is selected from =O, OR$^2$, (CR$^3$R$^{3a}$)OR$^2$, F, (CR$^3$R$^{3a}$)F, Br, (CR$^3$R$^{3a}$)Br, Cl, (CR$^3$R$^{3a}$)Cl, CF$_3$, (CR$^3$R$^{3a}$)CF$_3$, C$_{2-3}$ alkenyl, C$_{2-3}$ alkynyl, C$_{1-4}$ alkyl, —CN, (CR$^3$R$^{3a}$)CN, NO$_2$, (CR$^3$R$^{3a}$)NO$_2$, NR$^2$R$^{2a}$, (CR$^3$R$^{3a}$)NR$^2$R$^{2a}$, N(→O)R$^2$R$^{2a}$, (CR$^3$R$^{3a}$)N(→O)R$^2$R$^{2a}$, C(O)R$^{2c}$, (CR$^3$R$^{3a}$)C(O)R$^{2c}$, NR$^2$C(O)R$^{2b}$, (CR$^3$R$^{3a}$)NR$^2$C(O)R$^{2b}$, C(O)NR$^2$R$^{2a}$, (CR$^3$R$^{3a}$)C(O)NR$^2$R$^{2a}$, NR$^2$C(O)NR$^2$R$^{2a}$, (CR$^3$R$^{3a}$)NR$^2$C(O)NR$^2$R$^{2a}$, SO$_2$NR$^2$R$^{2a}$, (CR$^3$R$^{3a}$)SO$_2$NR$^2$R$^{2a}$, NR$^2$SO$_2$NR$^2$R$^{2a}$, (CR$^3$R$^{3a}$)NR$^2$SO$_2$NR$^2$R$^{2a}$, NR$^2$SO$_2$R$^{5a}$, (CR$^3$R$^{3a}$)NR$^2$SO$_2$R$^{5a}$, S(O)$_p$R$^{5a}$, (CR$^3$R$^{3a}$)S(O)$_p$R$^{5a}$, CF$_3$, CF$_2$CF$_3$, C$_{3-10}$ carbocycle substituted with 0–2 R$^{4b}$, (CR$^3$R$^{3a}$)C$_{3-10}$ carbocycle substituted with 0–2 R$^{4b}$, 5–10 membered heterocycle consisting of carbon atoms and from 1–4 heteroatoms selected from the group consisting of N, O, and S(O)$_p$ and substituted with 0–2 R$^{4b}$, and (CR$^3$R$^{3a}$)-5–10 membered heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, CH$_2$OR$^2$, OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, CH$_2$NR$^2$R$^{2a}$, NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, NR$^2$SO$_2$R$^5$, SO$_2$NR$^2$R$^{2a}$, 6 membered carbocycle substituted with 0–1 R$^5$, and a 5–6 membered heterocycle consisting of: carbon atoms and 1–2 heteroatoms selected from the group consisting of N, O, and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and, R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, SO$_2$NR$^2$R$^{2a}$, and NR$^2$SO$_2$C$_{1-4}$ alkyl.

In a fourth embodiment, the present invention provides a novel compound of formula Ic:

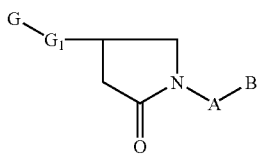

Ic or a stereoisomer or pharmaceutically acceptable salt thereof, wherein;

the central lactam ring is substituted with 0–1 R$^{1a}$;

G is selected from:

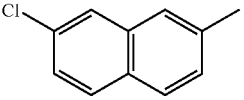
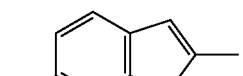
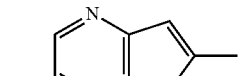
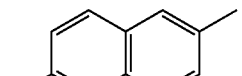
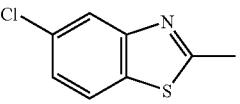
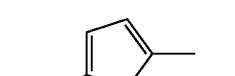
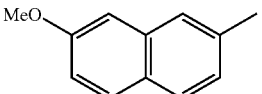
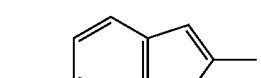
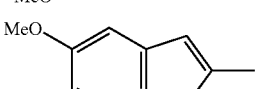
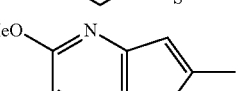
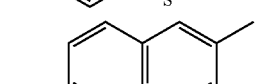
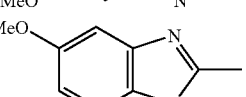
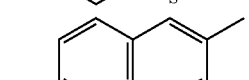
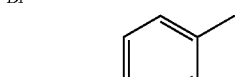
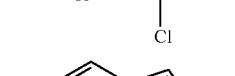
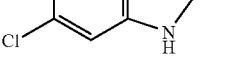
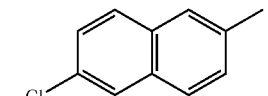
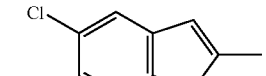
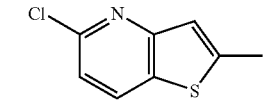
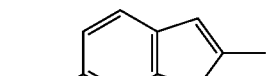
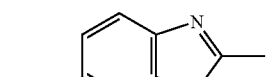
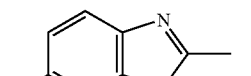
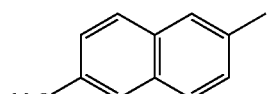
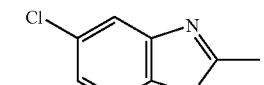
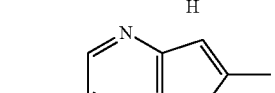
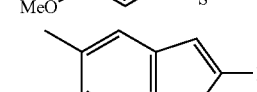
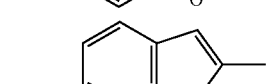
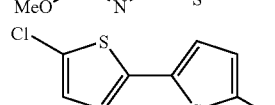
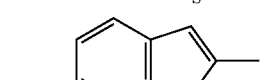
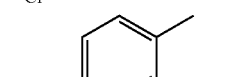
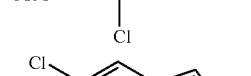
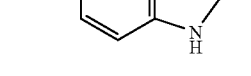

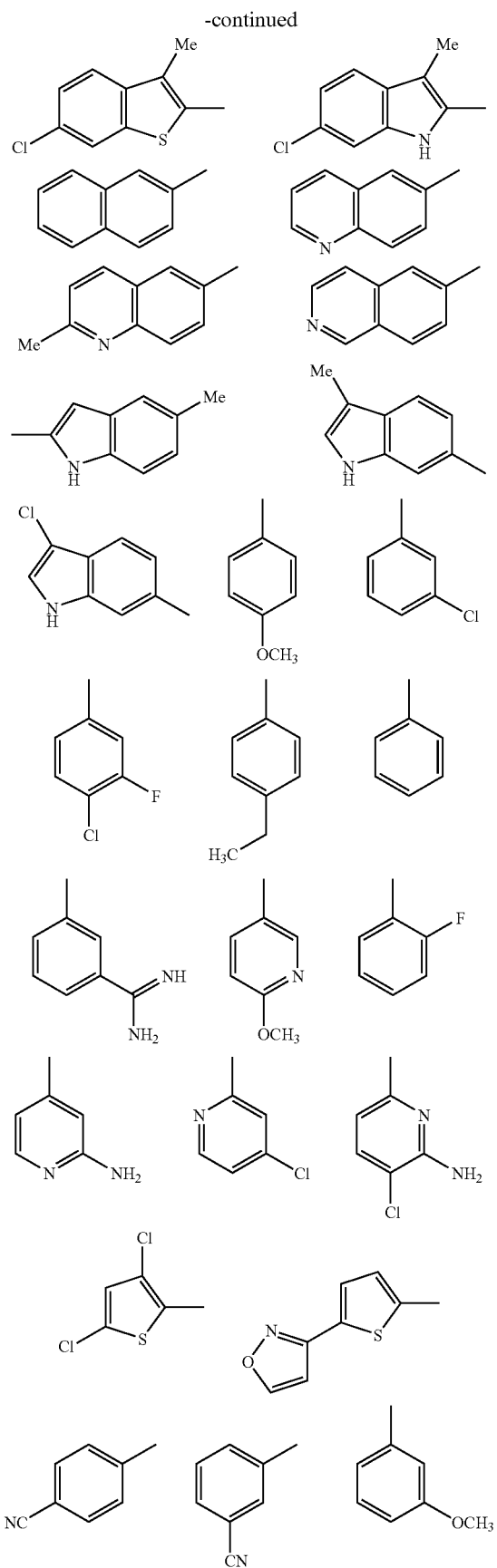

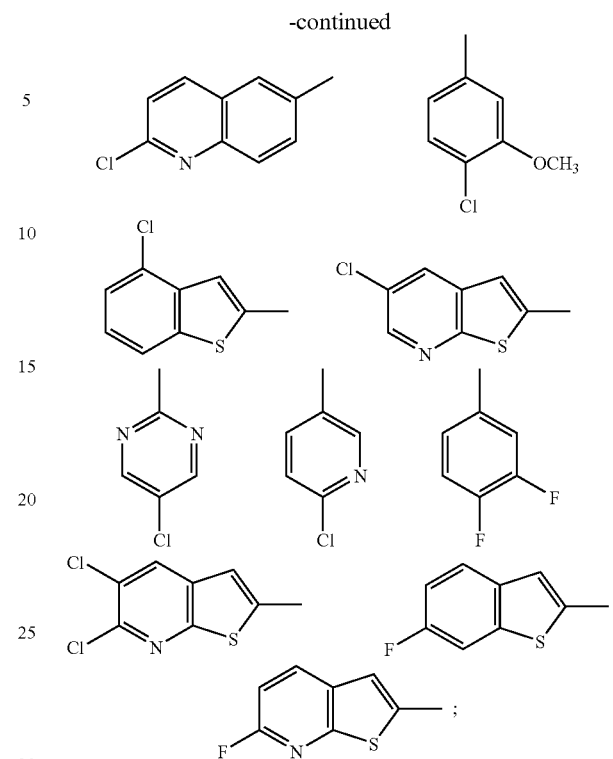

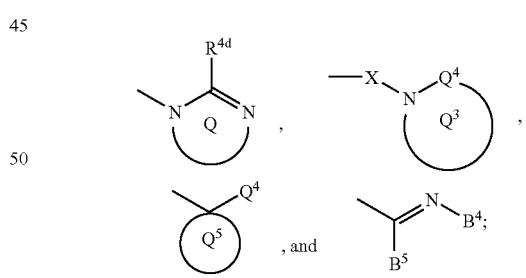

$G_1$ is selected from $(CH_2)_3$, $CH_2C(O)CH_2$, $CH_2C(O)O$, $CH_2OC(O)$, $CH_2OCH_2$, $CH_2NR^{3b}CH_2$, $CH_2C(O)NR^{3b}$, $CH_2NR^{3b}C(O)$, $CH_2SCH_2$, $CH_2S(O)CH_2$, $CH_2S(O)_2CH_2$, $CH_2S(O)NR^{3b}$, $CH_2NR^{3b}S(O)_2$, and $CH_2S(O)_2NR^{3b}$, wherein u+w total 1, 2, or 3 and the right side of $G_1$ is attached to ring G, provided that $G_1$ does not form an N—S, $NCH_2N$, $NCH_2O$, or $NCH_2S$ bond with either group to which it is attached;

A is selected from cyclohexyl, piperidinyl, piperazinyl, phenyl, pyridyl, and pyrimidyl, and is substituted with 0–2 $R^4$;

B is selected from Y, $N(B^1)C(O)C(R^3R^{3g})NB^2B^3$, provided that the lactam nitrogen and B are attached to different atoms on A, the $R^{4d}$ shown is other than OH, and that the A—X—N moiety forms other than a N—N—N group;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$, and $OR^2$;

$B^5$ is $NR^2R^{2f}$;

ring Q is a 5–6 membered ring consisting of, in addition to the N—$CR^{4d}$=N group shown, carbon atoms and 0–1 heteroatoms selected from N, O, and $S(O)_p$, and the ring is substituted with an additional 0–2 $R^{4d}$;

$Q^4$ is selected from C=O and $SO_2$;

ring $Q^3$ is a 6–7 membered ring consisting of, in addition to the N—$Q^4$ group shown, carbon atoms and 0–1 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 5–7 membered ring to which another ring is fused, wherein: the 5–7 membered ring consists of, in addition to the shown amide group, carbon atoms and 0–1 heteroatoms selected from $NR^{4c}$, O, S, S(O), and $S(O)_2$, and 0–1 double bonds are present within the ring; the fusion ring is phenyl;

ring $Q^3$, which includes the 5–7 membered ring and the fusion ring, is substituted with 0–2 $R^4$;

ring $Q^5$ is substituted with 0–1 $R^4$ and is selected from cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl;

X is selected from $CH_2$, C(O), —$S(Q)_2$—, —NHC(O)—, —N($CH_3$)C(O)$CH_2$—, —C(O)NH—, —$CH_2$NH—, O, and —$CH_2$O—;

Y is selected from N($CH_3$)$_2$, C(O)($CH_3$)$_2$, C($CH_3$)$_2R^{4a}$, ($CH_2CH_3$)$_2R^{4a}$, C(O)N($CH_3$)$_2$, and $SO_2N(CH_3)_2$;

alternatively, Y is selected from phenyl, pyridyl, pyrrolidino, N-pyrrolidino-carbonyl, morpholino, tetrahydropyranyl, N-morpholino-carbonyl, 1,2,3-triazolyl, imidazolyl, and benzimidazolyl, and is substituted with 1 $R^{4a}$ and 0–1 $R^4$;

alternatively, when A is selected from cyclopentyl, cyclohexyl, piperidinyl, and piperazinyl, then Y is additionally selected from methyl, 1-propyl, 2-propyl, 2-methyl-1-propyl, 2-butyl, 1,1-dimethyl-1-ethyl, 3-pentyl, cyclopropyl, cyclobutyl, cyclopentyl, tetrahydropyranyl, —CN, CH($CF_3$)$_2$, CH($CHF_2$), CH($CH_2F$), $CH_2CF_3$, CH($CF_2CF_3$)$_2$, C(O)N($CH_3$)$_2$, N($CH_3$)$_2$, and $SO_2CH_3$;

$R^{1a}$, at each occurrence, is selected from H, $R^{1b}$, CH($CH_3$)$R^{1b}$, C($CH_3$)$_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, C(O)$R^{2b}$, $CO_2R^{2b}$, $CO_2R^{2a}$, $S(O)_pR^2$, C(O)$NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, CH($CH_3$)$_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, $CH_2CH_3$, $CH_2CH_2CH_3$, CH($CH_3$)$_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

alternatively, $NR^2R^{2a}$ forms a 5 or 6 membered saturated, partially saturated or unsaturated ring substituted with 0–1 $R^{4b}$ and consisting o,f: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, OCH($CH_3$)$_2$, $CH_3$, $CH_2CH_3$, $CH_2CH_2CH_3$, CH($CH_3$)$_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2c}$, at each occurrence, is selected from OH, $OCH_3$, $OCH_2CH_3$, $OCH_2CH_2CH_3$, OCH($CH_3$)$_2$, $CH_3$, $CH_2CH_3$, $CH_2CH_2CH_3$, CH($CH_3$)$_2$, benzyl substituted with 0–1 $R^{4b}$, phenyl substituted with 0–1 $R^{4b}$, and 5–6 membered aromatic heterocycle containing from 1–4 heteroatoms selected from the group consisting of N, O, and $S(O)_p$, and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —($CH_2$)—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —($CH_2$)—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CH_3$, $CH_2CH_3$, $OCH_3$, and benzyl;

alternatively, $NR^2R^{2f}$ forms a 5–6 membered ring consisting of: carbon atoms and 0–1 additional heteroatoms selected from N, O, and $S(O)_p$, and this ring is substituted with 0–1 $R^{4b}$;

alternatively, $B^4$ and $R^{2f}$ combine to form a 5 membered ring consisting of: carbon atoms and 0–1 additional heteroatoms selected from N, O, and $S(O)_p$, and this ring is substituted with 0–2 $R^{4b}$ and the $R^2$ group of $NR^2R^{2f}$ in addition to the groups recited below, can be $SO_2R^{3b}$;

$R^{3b}$, at each occurrence, is selected from H and $CH_3$;

$R^4$, at each occurrence, is selected from H, =O, OH, $OR^2$, $CH_2OR^2$, ($CH_2$)$_2OR^2$, F, Br, Cl, I, $CH_3$, $CH_2CH_3$, $CH_2CH_2CH_3$, CH($CH_3$)$_2$, $CH_2CH_2CH_2CH_3$, $CH_2$CH($CH_3$)$_2$, CH($CH_3$)$CH_2CH_3$, C($CH_3$)$_3$, $NR^2R^{2a}$, $CH_2NR^2R^{2a}$, ($CH_2$)$_2NR^2R^{2a}$, C(O)$R^{2c}$, $NR^2C(O)R^{2b}$, C(O)$NR^2R^{2a}$, $SO_2NR^2R^{2a}$, $CF_3$, and $CF_2CF_3$;

$R^{4a}$ is selected from —($CR^3R^{3g}$)$_r$-5–6 membered carbocycle substituted with 0–3 $R^{4c}$, —($CR^3R^{3g}$)$_r$-5–6 membered heterocycle substituted with 0–3 $R^{4c}$ and consisting of: carbon atoms and 1–4 heteroatoms selected from the group consisting of N, O, and $S(O)_p$, ($CR^3R^{3g}$)$_r$$NR^{2d}R^{2d}$, ($CR^3R^{3g}$)$_r$N(→O)$R^{2d}R^{2d}$, ($CR^3R^{3g}$)$_r$$OR^{2d}$, ($CR^3R^{3g}$)$_r$—C(O)$NR^{2d}R^{2d}$, ($CR^3R^{3g}$)$_r$—$NR^{2d}C(O)R^{2e}$, ($CR^3R^{3g}$)$_r$—C(O)

R$^{2e}$, (CR$^3$R$^{3g}$)$_r$—NR$^{2d}$C(O)NR$^{2d}$R$^{2d}$, (CR$^3$R$^{3g}$)$_r$—NR$^{2d}$C(O)OR$^{2d}$, (CR$^3$R$^{3g}$)$_r$—NR$^{2d}$SO$_2$R$^{2d}$, and (CR$^3$R$^{3g}$)$_r$—S(O)$_p$R$^{2d}$, provided that S(O)$_p$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, and CF$_3$;

R$^{4c}$, at each occurrence, is selected from =O, OR$^2$, CH$_2$OR$^2$, F, Br, Cl, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, C$_{2-3}$ alkenyl, C$_{2-3}$ alkynyl, —CN, NO$_2$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, CF$_2$CF$_3$, C$_{3-6}$ carbocycle substituted with 0–2 R$^{4b}$, (CH$_2$)C$_{3-6}$ carbocycle substituted with 0–2 R$^{4b}$, 5–6 membered heterocycle consisting of carbon atoms and from 1–4 heteroatoms selected from the group consisting of N, O, and S(O)$_p$ and substituted with 0–2 R$^{4b}$, and (CH$_2$)-5–6 membered heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, CH$_2$OR$^2$, OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, CH$_2$NR$^2$R$^{2a}$, NR$^2$R$^{2a}$, C(O)R$^{2c}$, NR$^2$C(O)R$^{2b}$, C(O)NR$^2$R$^{2a}$, SO$_2$NR$^2$R$^{2a}$, NR$^2$SO$_2$R$^5$, phenyl substituted with 0–1 R$^5$, and a 5–6 membered heterocycle consisting of: carbon atoms and 1 heteroatom selected from the group consisting of N, O and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, and SO$_2$NR$^2$R$^{2a}$.

In a fifth embodiment, the present invention provides a novel compound of formula Ic, wherein:

G is selected from:

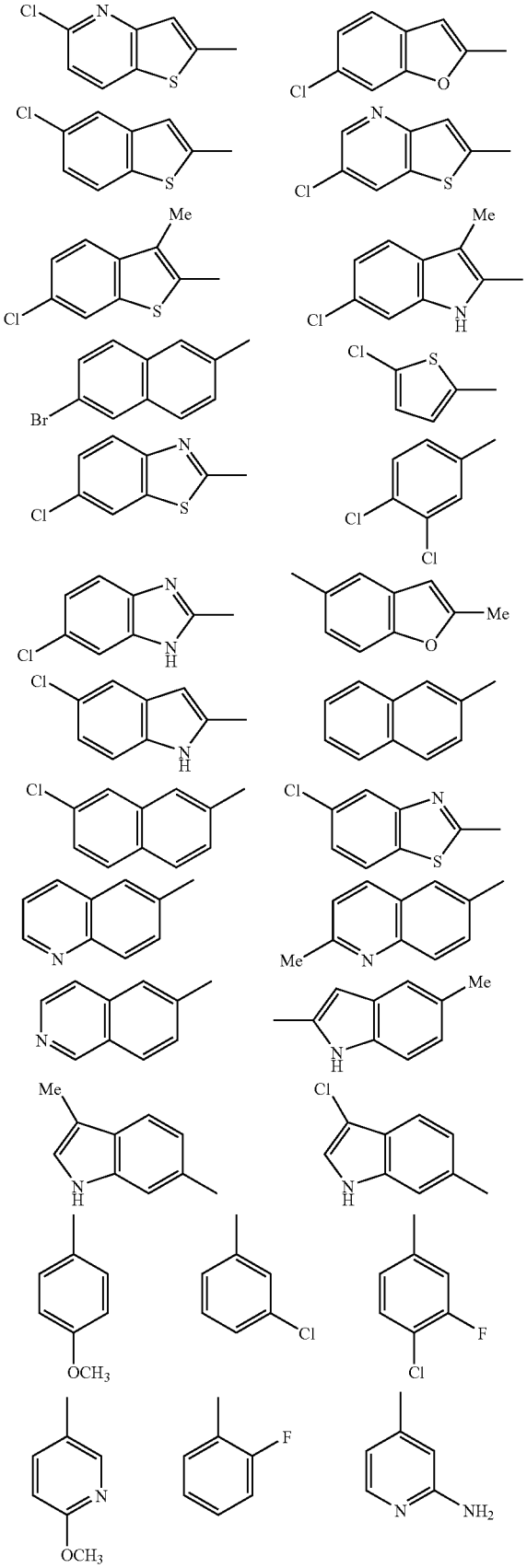

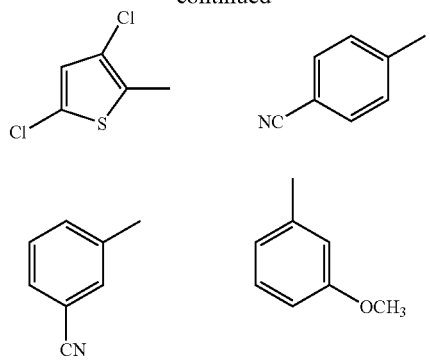

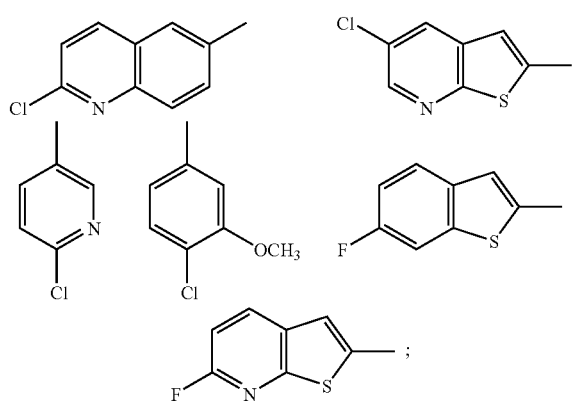

G₁ is selected from CH₂NHC(O), and CH₂S(O)₂NH, wherein the right side of G₁ is attached to ring G, provided that G₁ does not form an N—S, NCH₂N, NCH₂O, or NCH₂S bond with either group to which it is attached;

A is selected from the group: cyclohexyl, piperidinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from Y, $N(B^1)C(O)C(R^3R^{3g})NB^2B^3$,

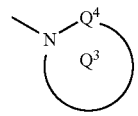

provided that the lactam nitrogen and B are attached to different atoms on A and that the $R^{4d}$ shown is other than OH;

$B^1$ is selected from H, CH₃, CH₂CH₃, and CH₂CH₂CH₃;
$B^2$ is selected from H, CH₃, and CH₂CH₃;
$B^3$ is selected from CH₃, CH₂CH₃, CH₂CH₂CH₃, CH(CH₃)₂, CH₂CH₂CH₂CH₃, C(CH₃)₃, CH(CH₃)CH₂CH (CH₃)₂, CH₂CH₂OH, CH(CH₃)CH₂OH, CH(phenyl)CH₂CH₃, cyclopropyl, cyclobutyl, cyclopentyl, cyclohexyl, and CH₂-cyclopropyl;

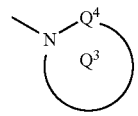

is attached to a different atom on A than M and is selected from the group:

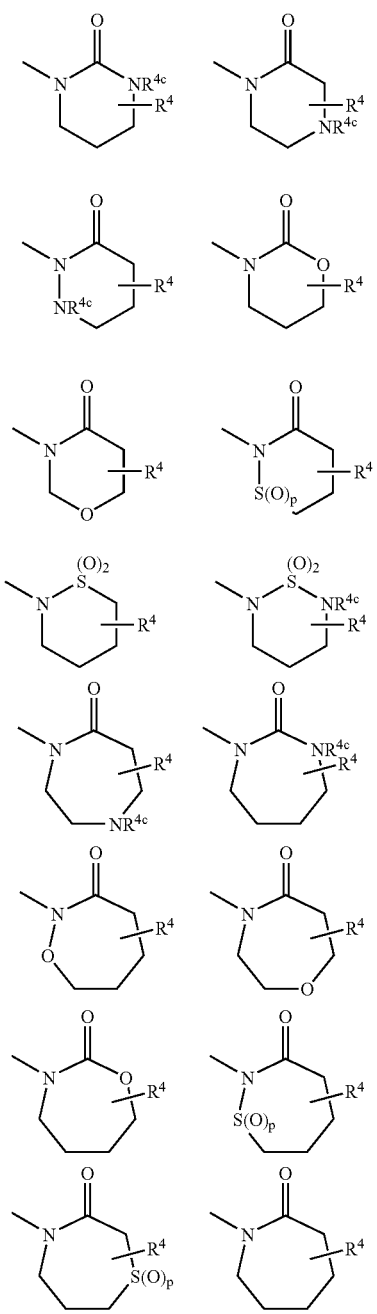

-continued

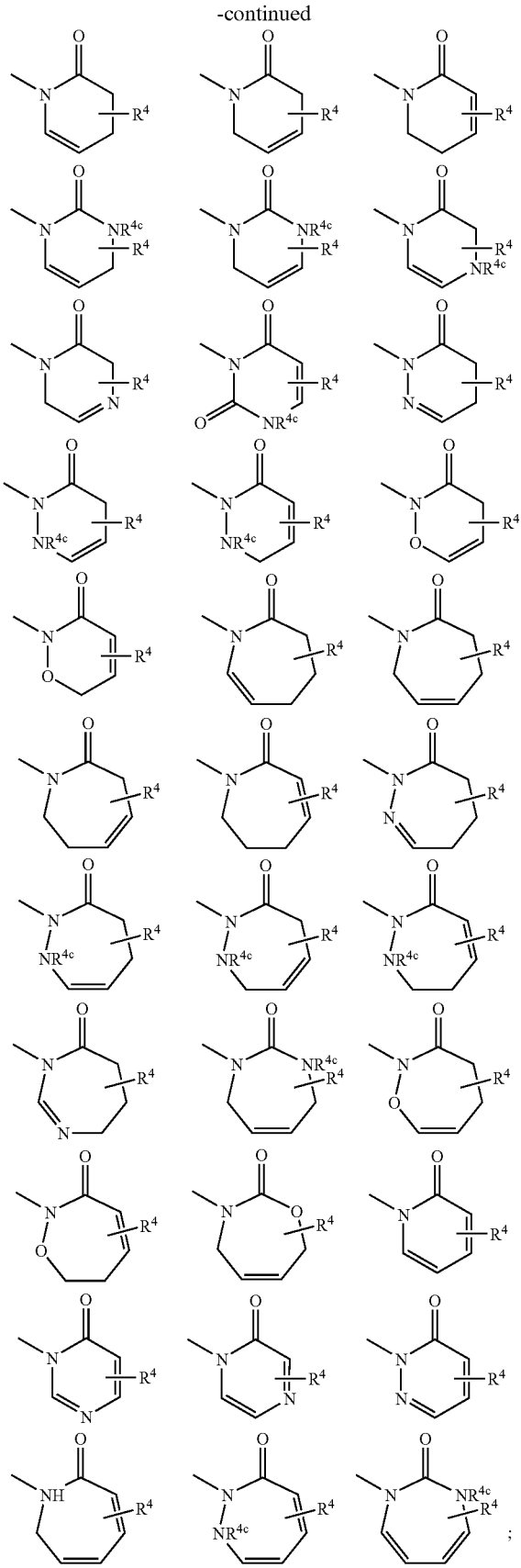

ring $Q^5$ is selected from cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$ at the 3-position), piperidinyl (attached to A and $R^{4a}$ at the 4-position), 4-piperidinonyl (attached to A and $R^{4a}$ at the 3-position), tetrahydrofuranyl, and tetrahydropyranyl (attached to A and $R^{4a}$ at the 4-position);

Y is selected from $N(CH_3)_2$, $C(O)(CH_3)_2$, $C(CH_3)_2R^{4a}$, $C(CH_2CH_3)_2R^{4a}$, $C(O)N(CH_3)_2$, and $SO_2N(CH_3)_2$;

alternatively, Y is selected from phenyl, pyridyl, 1,2,3-triazolyl, imidazolyl, morpholino, and benzimidazolyl, and is substituted with 1 $R^{4a}$;

alternatively, A–B is selected from 4-(2-propyl)-cyclohexyl, 4-(2-propyl)-piperazinyl, 4-(2-propyl)-piperidinyl, 4-(N,N-dimethylamino)-cyclohexyl, 4-(N,N-dimethylamino)-piperazinyl, 4-(N,N-dimethylamino)-piperidinyl, N-methyl-piperdin-4-yl, N-ethyl-piperdin-4-yl, N-(1-propyl)-piperdin-4-yl, N-(2-butyl)-piperdin-4-yl, N-(1,1-dimethyl-ethyl)-piperdin-4-yl, N-(2-methyl-1-propyl)-piperdin-4-yl, N-(N,N-dimethylamido)-piperdin-4-yl, N-(methylsulfonyl)-piperdin-4-yl, N-(cyclopropyl)-piperdin-4-yl, N-(cyclobutyl)-piperdin-4-yl, N-(cyclopentyl)-piperdin-4-yl, N-(tetrahydropyranyl)-piperdin-5-yl, N-(1,3-difluoro-2-propyl)-piperdin-4-yl, N-(cyano)-piperdin-4-yl, N-(di-trifluoromethyl-methyl)-piperdin-4-yl, N-(3-pentyl)-piperdin-4-yl, 4-(($CH_3)_2NCH_2C(O)N(CH_3)$)-phenyl, and 4-((N-pyrrolidinyl)$CH_2C(O)N(CH_3)$)-phenyl;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CH_3$, $CH_2CH_3$, and $OCH_3$;

alternatively, $NR^2R^{2f}$ forms a ring selected from morpholine, piperazine, piperidine, and pyrrolidine;

$R^4$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^{4a}$ is selected from —$(CH_2)_r$-5–6 membered carbocycle substituted with 0–3 $R^{4c}$, —$(CH_2)_r$-5–6 membered heterocycle substituted with 0–3 $R^{4c}$ and consisting of: carbon atoms and 1–4 heteroatoms selected from the group consisting of N, O, and $S(O)_p$, $(CH_2)_rNR^{2d}R^{2d}$, $(CH_2)_rN(\to O)R^{2d}R^{2d}$, $(CH_2)_rOR^{2d}$, $(CH_2)_r$—$C(O)NR^{2d}R^{2d}$, $(CH_2)_r$—$NR^{2d}C(O)R^{2e}$, $(CH_2)_r$—$C(O)R^{2e}$, $(CH_2)_r$—$NR^{2d}C(O)NR^{2d}R^{2d}$, $(CH_2)_r$—$NR^{2d}C(O)OR^{2d}$, $(CH_2)_r$—$NR^{2d}SO_2R^{2d}$, and $(CH_2)_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $C_{2-3}$ alkenyl, $C_{2-3}$ alkynyl, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(\to O)R^2R^{2a}$, $CH_2N(\to O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, —$CH_2$-cyclopropyl substituted with 0–1 $R^{4b}$, —$CH_2$-cyclobutyl substituted with 0–1 $R^{4b}$, —$CH_2$-cyclopentyl substituted with 0–1 $R^{4b}$, benzyl substituted with 0–2 $R^{4b}$, 5–6 membered aromatic heterocycle consisting of carbon atoms and from 1–4 heteroatoms selected from the group consisting of N, O, and $S(O)_p$ and substituted with 0–2 $R^{4b}$, and $(CH_2)$-5–6 membered aromatic heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $OCH_3$, $CH_3$, $CH_2CH_3$, $CH_2CH_2CH_3$, $CH(CH_3)_2$, $NR^2R^{2a}$, $NR^2C(O)R^{2b}$, $NR^2SO_2R^5$, phenyl, 2-oxo-pyrrolidinyl, and 2-oxo-piperidinyl;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR_3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

In a sixth embodiment, the present invention provides a novel compound, wherein:

A is selected from the group: piperidinyl, phenyl, 2-pyridyl, 2-pyrimidyl, and 2-F-phenyl, wherein B is substituted at the 4-position of A;

B is selected from:

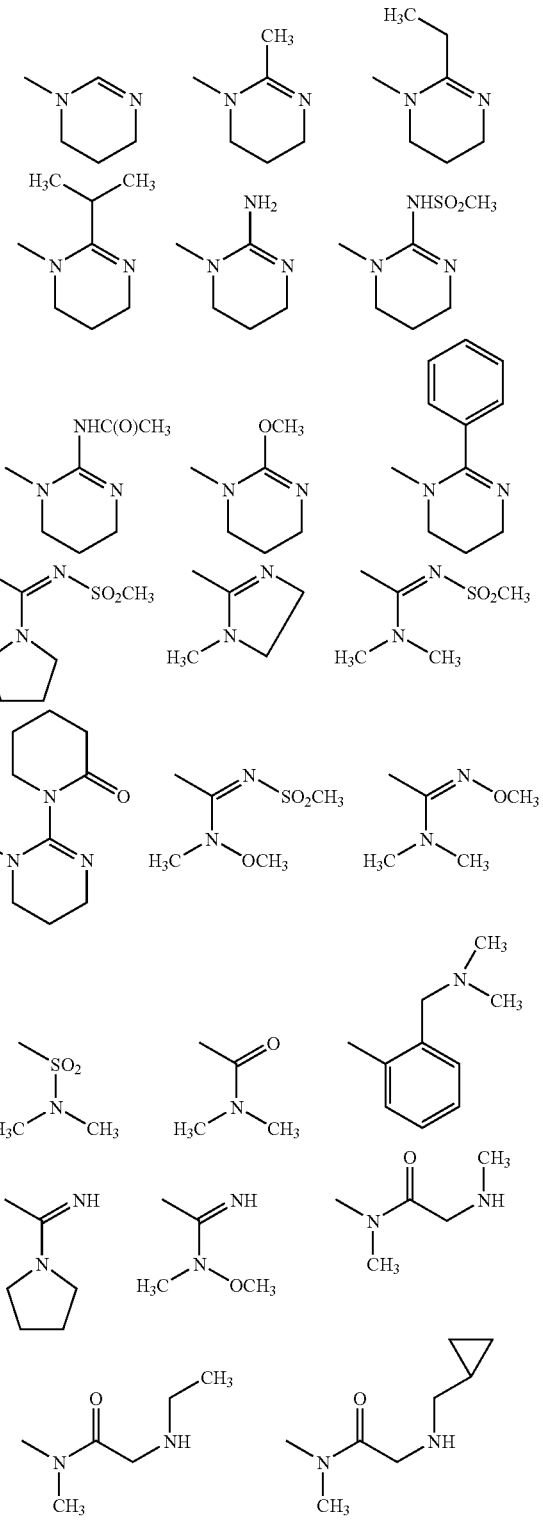

yl, N-(tetrahydropyranyl)-piperdin-5-yl, N-(1,3-difluoro-2-propyl)-piperdin-4-yl, N-(di-trifluoromethyl-methyl)-piperdin-4-yl, N-(cyano)-piperdin-4-yl, N-(3-pentyl)-piperdin-4-yl, N-(2-pyridyl)-piperdin-4-yl, and 4-((N-pyrrolidinyl)$CH_2C(O)N(CH_3)$)-phenyl;

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, —($CH_2$)-5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle substituted with 0–2 $R^{4c}$ and consisting of: carbon atoms and 1–4 heteroatoms selected from the group consisting of N, O, and $S(O)_p$ provided that $S(O)_pR^{2d}$ forms other than $S(O)_2H$ or $S(O)H$; and $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

In a seventh embodiment, the present invention provides a novel compound, wherein:

A–B is selected from:

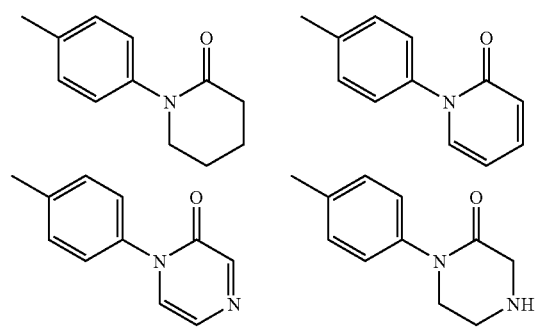

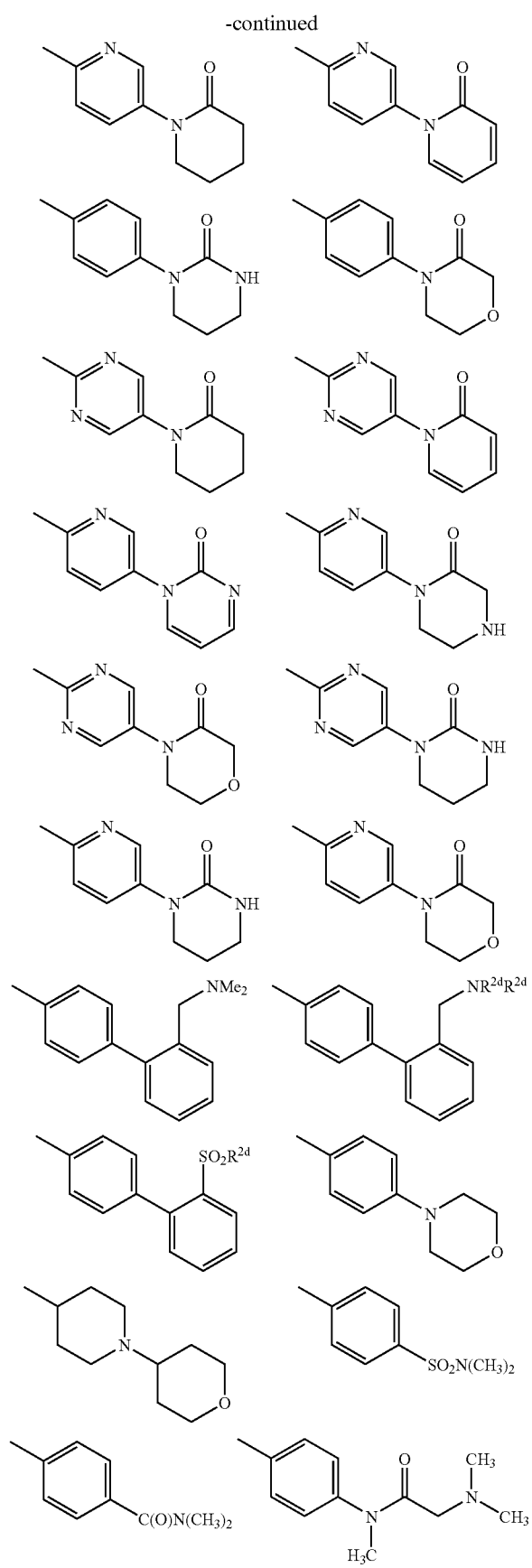
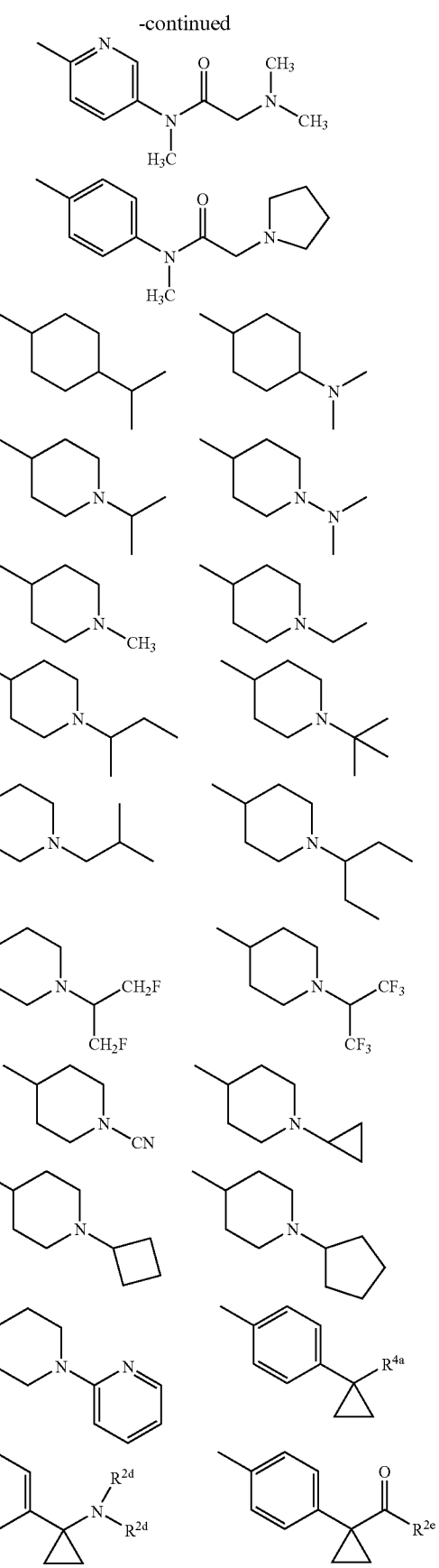

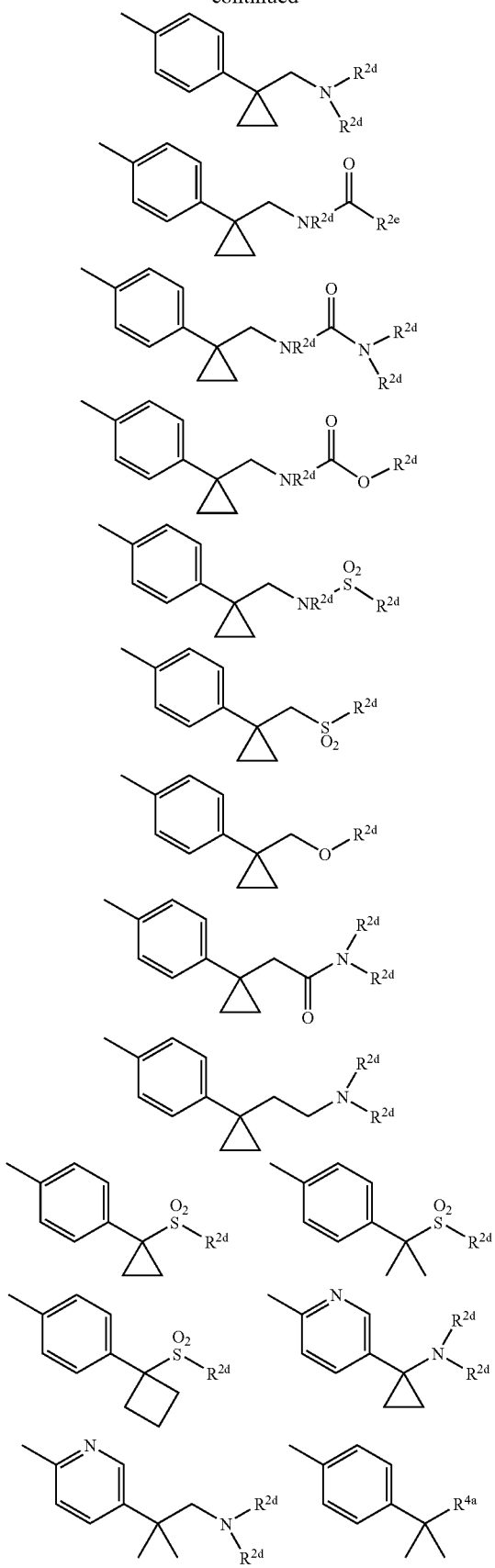
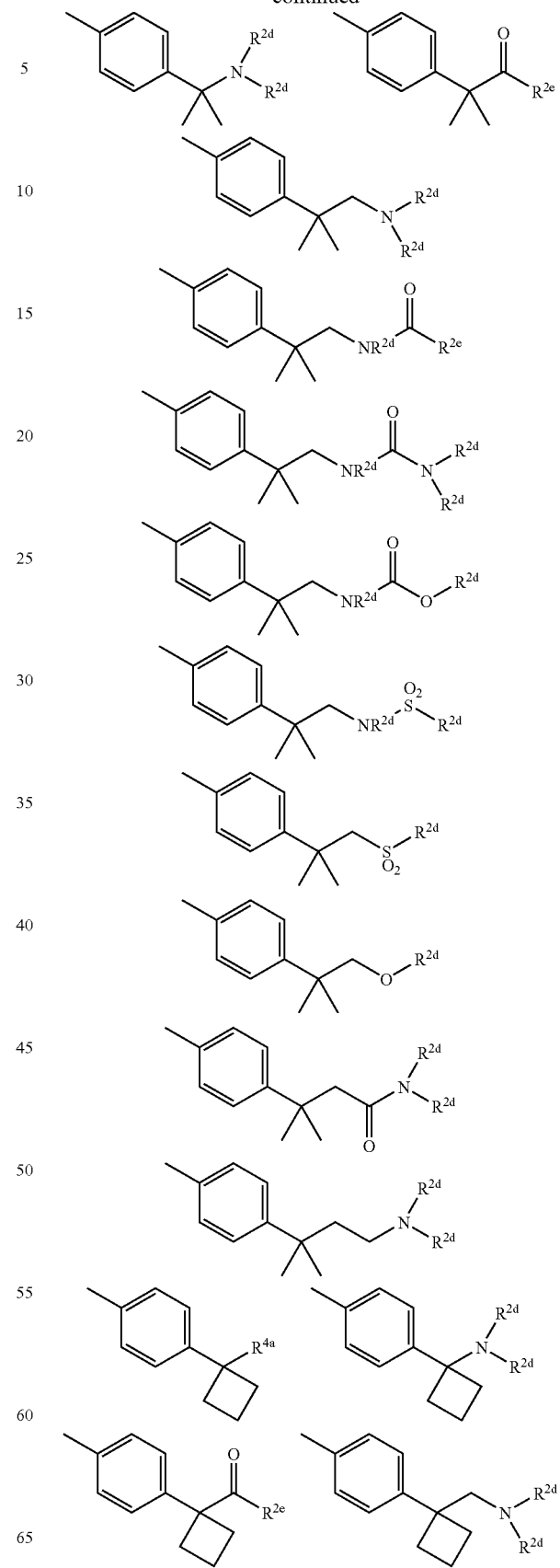

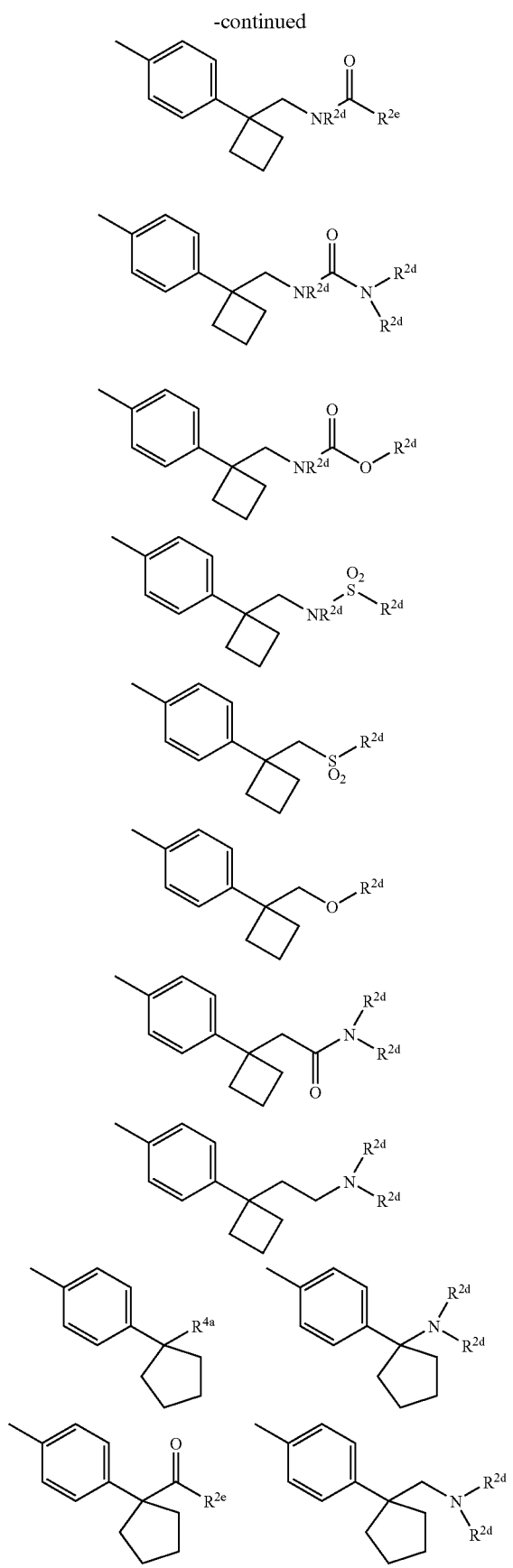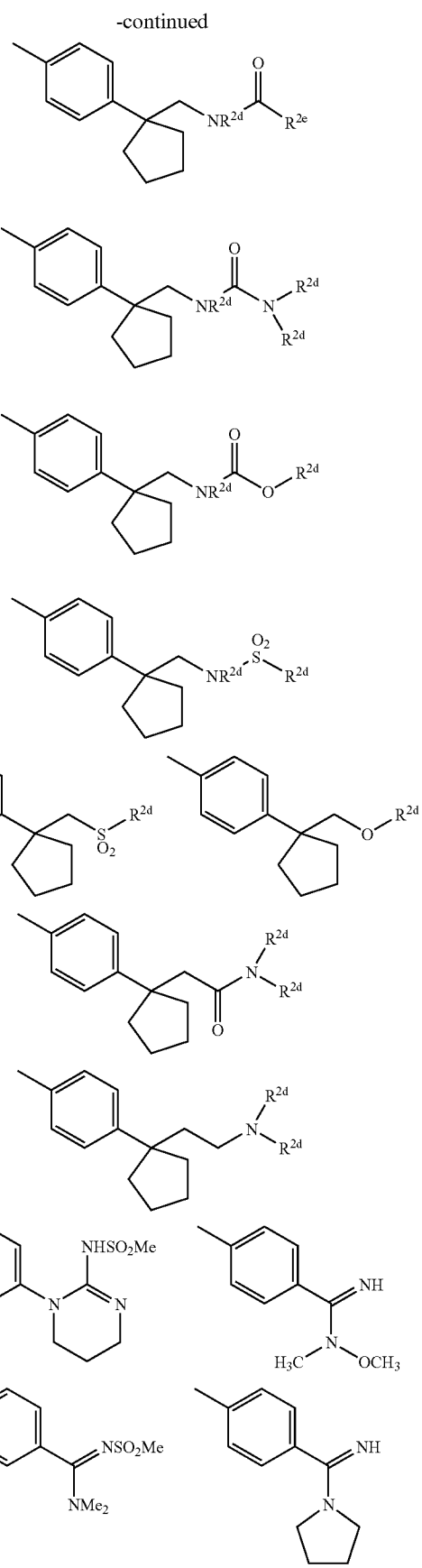

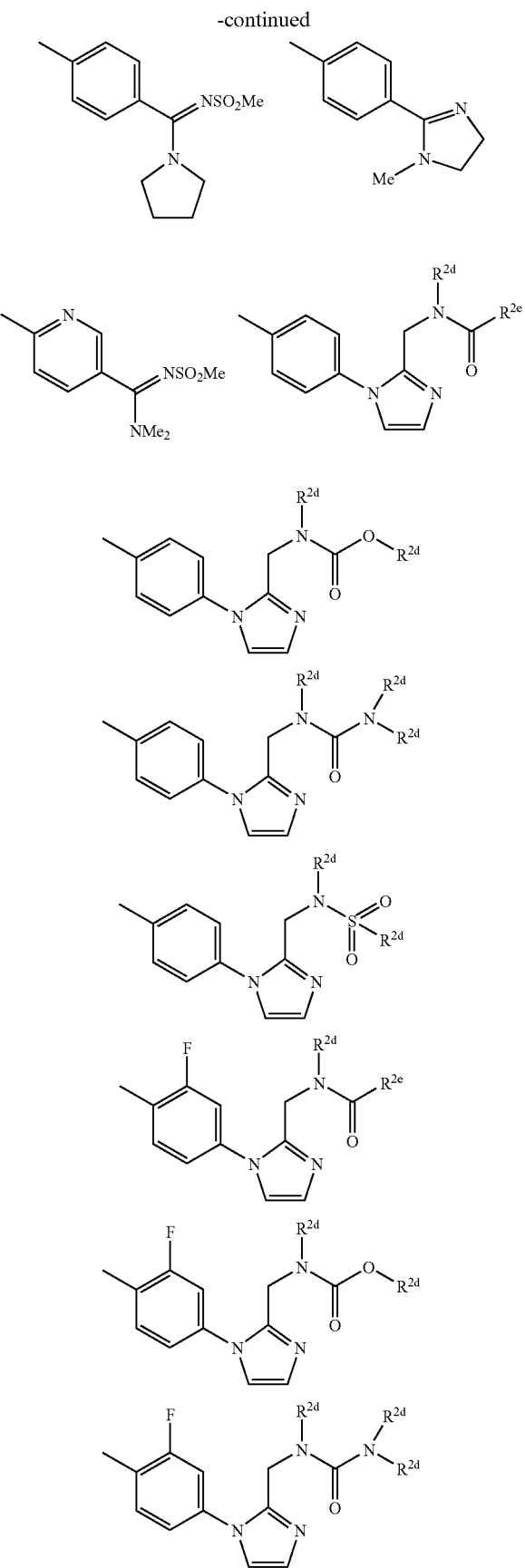

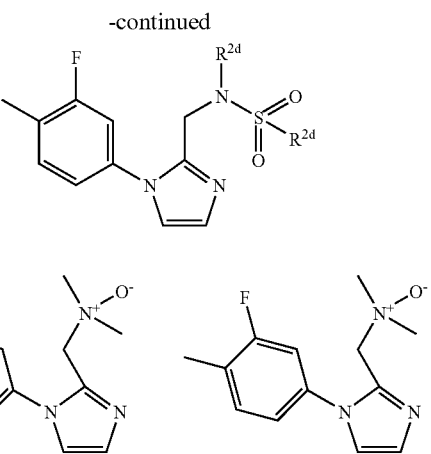

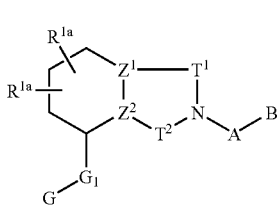

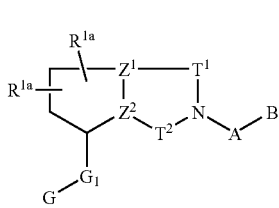

$R^{2d}$, at each occurrence, is selected from H, CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$CCH, CH$_2$CH$_2$OH, CH$_2$C(O)NH$_2$, cyclopropyl, CH$_2$-cyclopropyl, cyclobutyl, cyclopentyl, and thiazolyl;

$R^{2e}$, at each occurrence, is selected from CH$_3$, CR$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$-cyclopropyl, cyclopropyl, and cyclopentyl;

$R^{4a}$ is substituted with 0–2 $R^{4c}$ and selected from morpholine, 1,1-dioxo-thiomorpholine, dihydropyridine, piperidine, piperazine, pyrrolidine, imidazole, imidazoline, imidazolidine, oxazoline, and thiazoline; and $R^{4c}$ is selected from =O, OH, OCH$_3$, and CH$_3$.

In an eighth embodiment, the present invention provides a novel compound selected from: Examples 1–2 or a pharmaceutically acceptable salt form thereof.

In a ninth embodiment, the present invention provides a novel compound selected from formula Id and Ie:

or a stereoisomer or pharmaceutically acceptable salt thereof, wherein;

one of T$^1$ and T$^2$ is selected from C(O) and S(O)$_2$ and the other is selected from C(O), S(O)$_2$, CH$_2$ and CHOH;

one of Z$^1$ and Z$^2$ is N and the other is C;

G is a group of formula IIa or IIb:

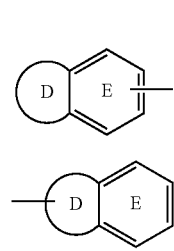

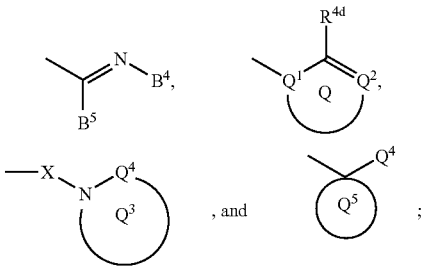

ring D, including the two atoms of ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with a 5 membered heterocycle consisting of: carbon atoms and 1–4 heteroatoms selected from the group consisting of N, O, and $S(O)_p$, wherein the 5 membered heterocycle is substituted with 0–1 carbonyls and 1–2 R and has 0–3 ring double bonds;

R is selected from H, $C_{1-4}$ alkyl, F, Cl, OH, $OCH_3$, $OCH_2CH_3$, $OCH(CH_3)_2$, CN, C(=NH)$NH_2$, $NH_2$, $NH(C_{1-3}$ alkyl), $N(C_{1-3}$ alkyl$)_2$, C(=NH)$NH_2$, $CH_2NH_2$, $CH_2NH(C_{1-3}$ alkyl), $CH_2N(C_{1-3}$ alkyl$)_2$, $(CR^8R^9)_rNR^7R^8$, $C(O)NR^7R^8$, $CH_2C(O)NR^7R^8$, $S(O)_pNR^7R^8$, $CH_2S(O)_pNR^7R^8$, and $OCF_3$;

alternatively, when 2 R groups are attached to adjacent atoms, they combine to form methylenedioxy or ethylenedioxy;

$G_1$ is selected from $(CR^3R^{3a})_{1-3}$, $CR^3$=$CR^3$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uC(O)NR^{3b}S(O)_2(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(S)NR^{3b}(CR^3R^{3a})_w$, and $(CR^3R^{3a})_uNR^{3b}C(S)(CR^3R^{3a})_uC(O)NR^{3b}(CR^3R^{3a})_w$, wherein u+w or u+u+w total 0, 1, or 2 and the right side of $G_1$ is attached to ring G, provided that $G_1$ does not form a N—S, $NCH_2N$, $NCH_2O$, or $NCH_2S$ bond with either group to which it is attached;

A is selected from: $C_{5-10}$ carbocycle substituted with 0–2 $R^4$, and 5–10 membered heterocycle consisting of: carbon atoms and 1–4 heteroatoms selected from the group consisting of N, O, and $S(O)_p$ and substituted with 0–2 $R^4$;

B is selected from Y, X—Y, $N(B^1)C(O)C(R^3R^{3g})NB^2B^3$, $N(B^1)C(O)C(R^3R^{3g})C(R^3R^{3g})NB^2B^3$, provided that the lactam nitrogen and B are attached to different atoms on A, the $R^{4d}$ shown is other than OH, and that the A—X—N moiety forms other than a N—N—N group;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-1}$—$C_{3-7}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$, $C(O)R^{3b}$, $SO_2NR^3R^{3b}$, $C(O)NR^3R^{3b}$, $OR^2$, and —CN;

$B^5$ is $NR^2R^{2f}$ or $CR^3R^2R^{2f}$;

ring Q is a 5–6 membered ring consisting of, in addition to the $Q^1$—$CR^{4c}$=$Q^2$ group shown, carbon atoms and 0–2 heteroatoms selected from N, O, and $S(O)_p$, and the ring is substituted with an additional 0–2 $R^{4d}$;

$Q^1$ and $Q^2$ are each N;

alternatively, $Q^1$ is $CR^3$ and $R^{4d}$ is $NR^2R^{2a}$ or $NR^{3a}B^4$, provided that when $Q^1$ is $CR^3$, then this $R^3$ group optionally forms a ring with the $R^2$ group of $R^{4d}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

$Q^4$ is selected from C=O and $SO_2$;

ring $Q^3$ is a 4–7 membered monocyclic or tricyclic ring consisting of, in addition to the N—$Q^4$ group shown, carbon atoms and 0–2 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 4–7 membered ring to which another ring is fused, wherein: the 4–7 membered ring consists of, in addition to the shown amide group, carbon atoms and 0–2 heteroatoms selected from $NR^{4c}$, O, S, S(O), and $S(O)_2$ and 0–1 double bonds are present within the ring; the fusion ring is phenyl or a 5–6 membered heteroaromatic consisting of carbon atoms and 1–2 heteroatoms selected from $NR^{4c}$, O, and S;

ring $Q^3$, which includes the 4–7 membered ring and the fusion ring, is substituted with 0–3 $R^4$;

ring $Q^5$ is a $C_{3-7}$ monocyclic carbocycle or 3–7 membered monocyclic heterocycle, wherein the carbocycle or heterocycle consists of: carbon atoms and 0–2 heteroatoms selected from N, O, and $S(O)_p$, the carbocycle or heterocycle further comprises 0–2 double bonds and 0–2 carbonyl groups, and the carbocycle or heterocycle is substituted with 0–2 $R^4$;

X is selected from —$(CR^2R^{2a})_{1-4}$—, —C(O)—, —C(=$NR^{1c}$)—, —$CR^2(NR^{1b}R^2)$—, —C(O)$CR^2R^{2a}$—, —$CR^2R^{2a}$C(O)—, —C(O)$NR^2$—, —$NR^2$C(O)—, —C(O)$NR^2CR^2R^{2a}$—, —$NR^2$C(O)$CR^2R^{2a}$—, —$CR^2R^{2a}$C(O)$NR^2$—, —$CR^2R^{2a}NR^2$C(O)—, —$NR^2$C(O)$NR^2$—, —$NR^2$—, —$NR^2CR^2R^{2a}$—, —$CR^2R^{2a}NR^2$—, —$S(O)_2$—, —$NR^2S(O)_2$—, O, —$CR^2R^{2a}$O—, and —$OCR^2R^{2a}$—;

Y is selected from: $CY^1Y^2R^{4a}$, $NR^3R^{3a}$, $SO_2R^3$, and $C(O)NR^3R^{3a}$;

$Y^1$ and $Y^2$ are independently $C_{13}$ alkyl substituted with 0–2 $R^4$;

alternatively, Y is selected from one of the following carbocyclic and heterocycles that are substituted with 1 $R^{4a}$ and 0–2 $R^4$: cyclopropyl, cyclobutyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, isoindazolyl, 4,5-dihydroimidazolyl, 1,4,5,6-tetrahydropyrimidinyl, and, [1,4]diazepanyl;

alternatively, when A is selected from one of the following carbocyclic and heterocyclic groups, which are substituted with 0–2 $R^{4c}$, cyclohexyl, cyclopentyl, azetidinyl, oxazolinyl, isoxazolinyl, thiazolinyl, isothiazolinyl, piperidinyl, piperazinyl, hexahydropyrimidyl, morpholinyl, and pyrrolidinyl;

then Y is additionally selected from methyl, ethyl, 2-propyl, 1-butyl, 2-methyl-1-propyl, 1,1-dimethyl-1-ethyl, 1-pentyl, 2-pentyl, 3-pentyl, 3-hexyl, $CH(CF_3)_2$, $CH(CHF_2)$ $CH_3$, $CH_2CF_3$, $CH(CF_2CF_3)_2$, $CH(Cl)CF_3$, $C(O)OCH_2CH_3$, $C(O)CH(CH_3)_2$, $C(O)CH_2CH_2CH_3$, $C(O)NHCH_2CH_3$, $C(O)N(CH_3)_2$, $C(O)N(CH_3)(CH_2CH_3)$, $C(O)OCH_2CH_3$, $C(O)C(CH_3)_3$, $SO_2CH_3$, $SO_2CH_2CH_3$, $SO_2CH_2CH_2CH_3$, $SO_2CH(CH_3)_2$, $SO_2CH(CH_3)CH_2CH_3$, $SO_2N(CH_3)_2$, $SO_2N(CH_3)CH_2CH_3$, $OCH_3$, $OCH_2CH_3$, $OCH(CH_3)_2$, $OCH(CH_3)CH_2CH_3$, $SCH_3$, $SCH_2CH_3$, $SCH(CH_3)_2$, $SCH(CH_3)CH_2CH_3$, $SCH(CH_2CH_3)_2$, $N(CH_3)_2$, $N(CH_2CH_3)_2$, $N(CH_3)CH_2CH_3$, $N(CH_2CH_3)CH_2CH_2CH_3$, $NHC(O)CH_3$, $NHC(O)CH_2CH_3$, $NHC(O)CH(CH_3)_2$, and $NHC(O)CH(CH_3)CH_2CH_3$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, a $C_{5-6}$ carbocyclic-$CH_2$-group substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$ at each occurrence, is selected from H, $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–1 $R^{4b}$, $C_{5-6}$ carbocycle substituted with 0–2 $R^{4b}$, and 5–6 membered heterocycle containing from 1–4 heteroatoms selected from the group consisting of N, O, and S(O)$_p$ and substituted with 0–2 R$^{4b}$;

alternatively, CR$^2$R$^{2f}$ forms a 5–6 membered ring consisting of: carbon atoms and 0–2 heteroatoms selected from N, O, and S(O)$_p$, and this ring is substituted with 0–2 R$^{4b}$;

alternatively, NR$^2$R$^{2f}$ forms a 5–6 membered ring consisting of: carbon atoms and 0–2 additional heteroatoms selected from N, O, and S(O)$_p$, and this ring is substituted with 0–2 R$^{4b}$;

alternatively, when B$^5$ is NR$^2$R$^{2f}$, B$^4$ and R$^{2f}$ combine to form a 5–6 membered ring consisting of: carbon atoms and 0–2 additional heteroatoms selected from N, O, and S(O)$_p$, and this ring is substituted with 0–2 R$^{4b}$ and the R$^2$ group of NR$^2$R$^{2f}$, in addition to the groups recited below, is selected from SO$_2$R$^{3b}$ and C(O)R$^{3b}$;

R$^3$, at each occurrence, is selected from H, CH$_3$, CH$_2$CH$_3$, CH$_2$CH$_2$CH$_3$, CH(CH$_3$)$_2$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, benzyl, and phenyl;

alternatively, R$^3$ and R$^{3a}$, together with the nitrogen atom to which they are attached, combine to form a 5 or 6 membered saturated, partially unsaturated, or unsaturated ring consisting of: carbon atoms and the nitrogen atom to which R$^3$ and R$^{3a}$ are attached;

R$^{3b}$, at each occurrence, is selected from H, CF$_3$, CH$_3$, CH$_2$CH$_3$, CH$_2$CH$_2$CH$_3$, CH(CH$_3$)$_2$, —(C$_{0-1}$ alkyl)-5–6 membered carbocycle substituted with 0–1 R$^{1a}$, and —(C$_{0-1}$ alkyl)-5–6 membered heterocycle substituted with 0–1 R$^{1a}$ and consisting of: carbon atoms and 1–4 heteroatoms selected from the group consisting of N, O, and S(O)$_p$;

R$^{3c}$, at each occurrence, is selected from CH$_3$, CH$_2$CH$_3$, CH$_2$CH$_2$CH$_3$, CH(CH$_3$)$_2$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$-phenyl, CH$_2$CH$_2$-phenyl, and C(=O)R$^{3c}$;

R$^4$, at each occurrence, is selected from =O, OR$^2$, CH$_2$OR$^2$, (CH$_2$)$_2$OR$^2$, F, Cl, Br, I, C$_{1-4}$ alkyl, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, SO$_2$NR$^2$R$^{2a}$, NR$^2$SO$_2$NR$^2$R$^{2a}$, S(O)$_p$R$^{5a}$, NR$^2$SO$_2$—C$_{1-4}$ alkyl, NR$^2$SO$_2$R$^5$, CF$_3$, CF$_2$CF$_3$, 5–6 membered carbocycle substituted with 0–1 R$^5$, and a 5–6 membered heterocycle consisting of: carbon atoms and 1–4 heteroatoms selected from the group consisting of N, O, and S(O)$_p$, and substituted with 0–1 R$^5$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^3$R$^{3a}$, CH$_2$NR$^3$R$^{3a}$, C(O)R$^3$, CH$_2$—C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, NR$^3$C(O)NR$^3$R$^{3a}$, CH$_2$NR$^3$C(O)NR$^3$R$^{3a}$, C(=NR$^3$)NR$^3$R$^{3a}$, CH$_2$C(=NR$^3$)NR$^3$R$^{3a}$, NR$^3$C(=NR$^3$)NR$^3$R$^{3a}$, CH$_2$NR$^3$C(=NR$^3$)NR$^3$R$^{3a}$, SO$_2$NR$^3$R$^{3a}$, CH$_2$SO$_2$NR$^3$R$^{3a}$, NR$^3$SO$_2$NR$^3$R$^{3a}$, CH$_2$NR$^3$SO$_2$NR$^3$R$^{3a}$, NR$^3$SO$_2$—C$_{1-4}$ alkyl, CH$_2$NR$^3$SO$_2$—C$_{1-4}$ alkyl, NR$^3$SO$_2$CF$_3$, CH$_2$NR$^3$SO$_2$CF$_3$, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, CF$_3$, and CH$_2$—CF$_3$;

R$^{4c}$, at each occurrence, is selected from =O, (CR$^3$R$^{3a}$)$_r$OR$^2$, (CR$^3$R$^{3a}$)$_r$F, (CR$^3$R$^{3a}$)$_r$Br, (CR$^3$R$^{3a}$)$_r$Cl, (CR$^3$R$^{3a}$)$_r$CF$_3$, C$_{1-4}$ alkyl, C$_{2-3}$ alkenyl, C$_{2-3}$ alkynyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$N(→O)R$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$NR$^2$C(O)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$R$^{5a}$, (CR$^3$R$^{3a}$)$_r$C(O)NR$^2$SO$_2$R$^{5a}$, (CR$^3$R$^{3a}$)$_r$S(O)$_p$R$^{5a}$, (CF$_2$)$_r$CF$_3$, (CR$^3$R$^{3a}$)$_r$C$_3$ $_{10}$ carbocycle substituted with 0–2 R$^{4b}$, and (CR$^3$R$^{3a}$)$_r$5–10 membered heterocycle consisting of carbon atoms and from 1–4 heteroatoms selected from the group consisting of N, O, and S(O)$_p$, and substituted with 0–2 R$^{4b}$;

R$^{4d}$, at each occurrence, is selected from H, CH$_2$OR$^2$, OR$^2$, C$_{1-4}$ alkyl, CH$_2$—CN, —CN, CH$_2$NO$_2$, NO$_2$, CH$_2$NR$^2$R$^{2a}$, NR$^2$R$^{2a}$, CH$_2$—C(O)R$^{2c}$, C(O)R$^{2c}$, NR$^2$C(O)R$^{2b}$, (CH$_2$)$_r$C(O)NR$^2$R$^{2a}$, NR$^2$C(O)NR$^2$R$^{2a}$, (CH$_2$)$_r$SO$_2$NR$^2$R$^{2a}$, NR$^2$SO$_2$NR$^2$R$^{2a}$, NR$^2$SO$_2$R$^5$, (CH$_2$)$_r$S(O)$_p$R$^{5a}$, CH$_2$CF$_3$, CF$_3$, CH$_{2-5-6}$ membered carbocycle substituted with 0–1 R$^5$, 5–6 membered carbocycle substituted with 0–1 R$^5$, a CH$_{2-5-6}$ membered heterocycle consisting of: carbon atoms and 1–4 heteroatoms selected from the group consisting of N, O, and S(O)$_p$ and substituted with 0–1 R$^5$, and a 5–6 membered heterocycle consisting of: carbon atoms and 1–4 heteroatoms selected from the group consisting of N, O, and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$;

R$^{5a}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, CF$_3$, CF$_2$CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl.

In a tenth embodiment, the present invention provides a novel compound selected from formula Id$_{1-8}$ and Ie$_{1-8}$:

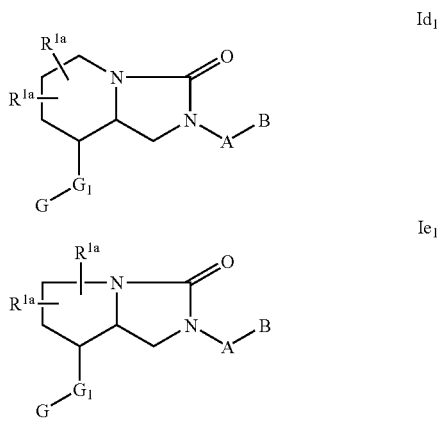

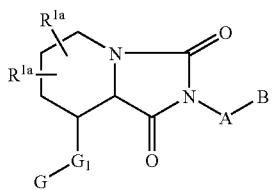 Id₂

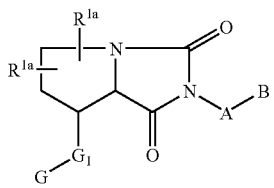 Ie₂

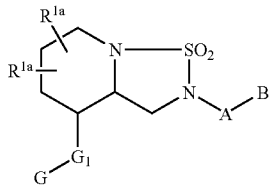 Id₃

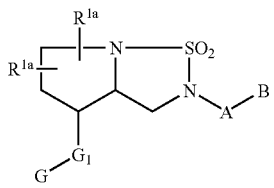 Ie₃

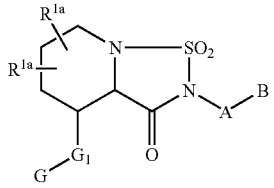 Id₄

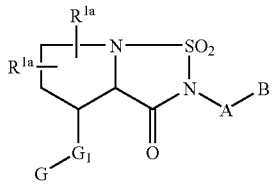 Ie₄

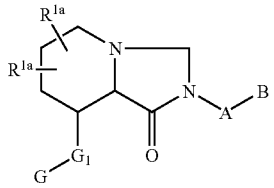 Id₅

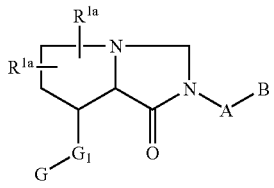 Ie₅

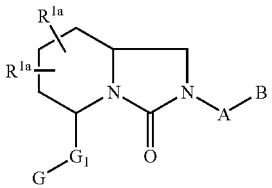 Id₆

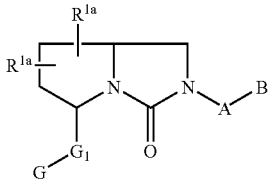 Ie₆

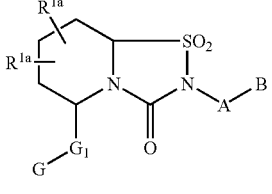 Id₇

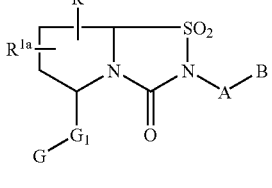 Ie₇

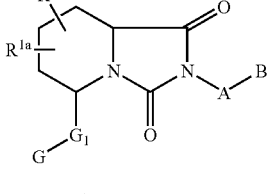 Id₈

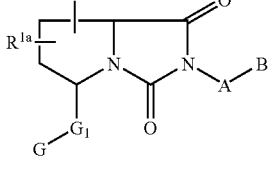 Ie₈ or a stereoisomer or pharmaceutically acceptable salt thereof, wherein;

G is selected from: 2-aminomethyl-4-chloro-phenyl, 2-aminosulfonyl-4-chloro-phenyl, 2-amido-4-chloro-phenyl, 4-chloro-2-methylsulfonyl-phenyl, 2-aminosulfonyl-4-fluoro-phenyl, 2-amido-4-fluoro-phenyl, 4-fluoro-2-methylsulfonyl-phenyl, 2-aminomethyl-4-bromo-phenyl, 2-aminosulfonyl-4-bromo-phenyl, 2-amido-4-bromo-phenyl, 4-bromo-2-methylsulfonyl-phenyl, 2-aminomethyl-4-methyl-phenyl, 2-aminosulfonyl-4-methyl-phenyl, 2-amido-4-methyl-phenyl, 2-methylsulfonyl-4-methyl-phenyl, 4-fluoro-pyrid-2-yl, 4-bromo-pyrid-2-yl, 4-methyl-pyrid-2-yl, 5-fluoro-thien-2-yl, 5-bromo-thien-2-yl, 5-methyl-thien-2-yl, 2-amido-4-methoxy-phenyl, 2-amido-phenyl, 2-aminomethyl-3-fluoro-phenyl, 2-aminomethyl-4-fluoro-phenyl, 2-aminomethyl-4-methoxy-phenyl, 2-aminomethyl- 5-fluoro-phenyl, 2-aminomethyl-5-methoxy-phenyl, 2-aminomethyl-6-fluoro-phenyl, 2-aminomethyl-phenyl, 2-amino-pyrid-4-yl, 2-aminosulfonyl-4-methoxy-phenyl, 2-aminosulfonyl-phenyl, 2-methylsulfonyl-phenyl, 3-(N,N-dimethylamino)-4-chloro-phenyl, 3-(N,N-dimethylamino)-phenyl, 3-(N-methylamino)-4-chloro-phenyl, 3-(N-methylamino)-phenyl, 3-amido-phenyl, 3-amino-4-chloro-phenyl, 3-aminomethyl-phenyl, 3-amino-phenyl, 3-chloro-phenyl, 4-(N,N-dimethylamino)-5-chloro-thien-2-yl, 4-(N-methylamino)-5-chloro-thien-2-yl, 4-amino-5-chloro-thien-2-yl, 4-chloro-phenyl, 4-methoxy-2-methylsulfonyl-phenyl, 4-methoxy-phenyl, 2-methoxy-pyrid-5-yl, 5-(N,N-dimethylamino)-4-chloro-thien-2-yl, 5-(N-methylamino)-4-chloro-thien-2-yl, 5-amino-4-chloro-thien-2-yl, 5-chloro-pyrid-2-yl; 5-chloro-thien-2-yl, 6-amino-5-chloro-pyrid-2-yl, 6-amino-pyrid-2-yl, 2-cyano-4-chloro-phenyl, 2-methoxy-4-chloro-phenyl, 2-fluoro-4-chloro-phenyl, phenyl; 4-ethyl-phenyl, 3-chloro-4-methyl-phenyl, 4-fluoro-phenyl, 3-fluoro-4-chloro-phenyl, 3-methyl-4-chloro-phenyl, 3-fluoro-4-methyl-phenyl, 3,4-dimethyl-phenyl, 3-chloro-4-fluoro-phenyl, 3-methyl-4-fluoro-phenyl, 4-methylsulfanyl-phenyl, 2-chlorothiazol-5-yl, 5-chlorothiazol-2-yl,

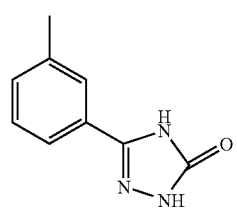
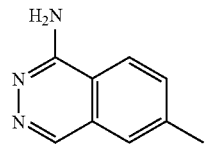
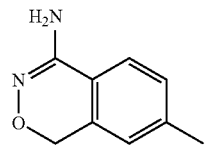
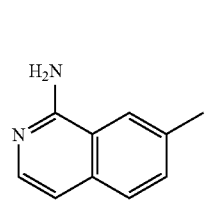
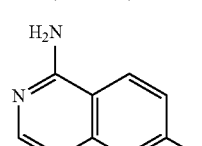
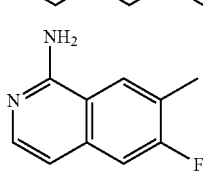
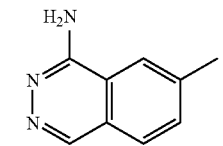
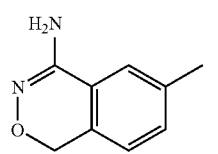
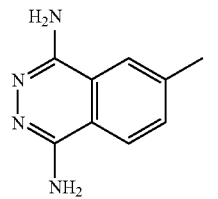
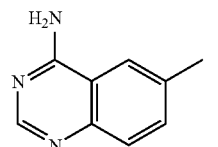
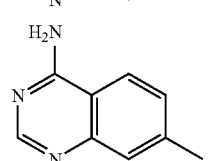
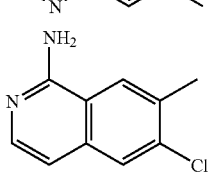

-continued

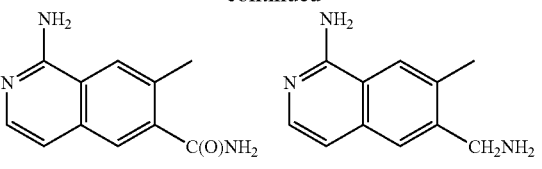
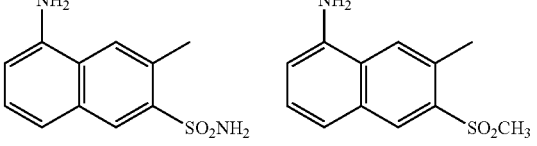
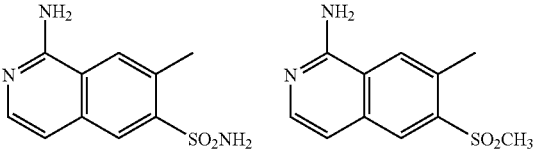
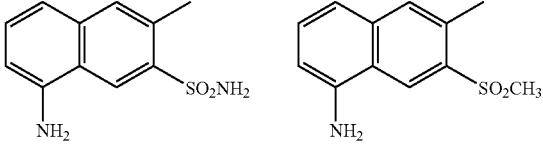
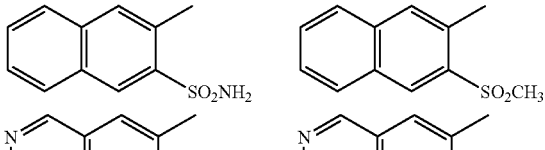
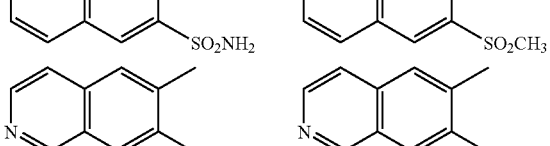
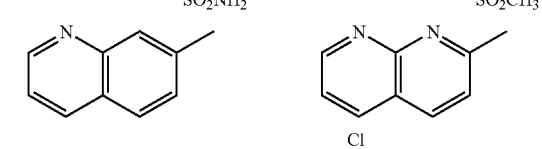
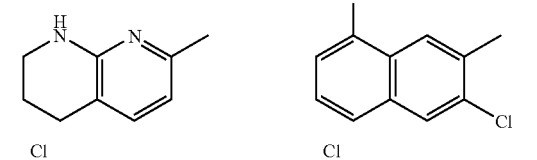
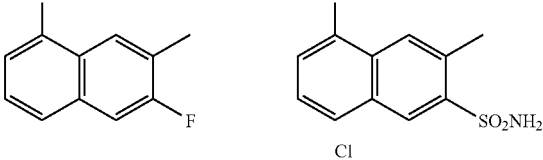
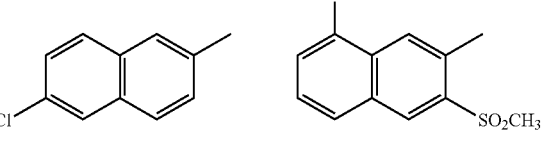
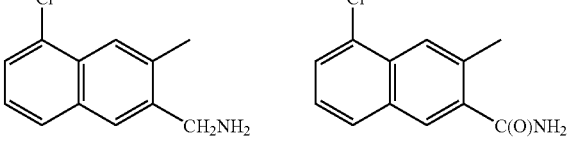

-continued
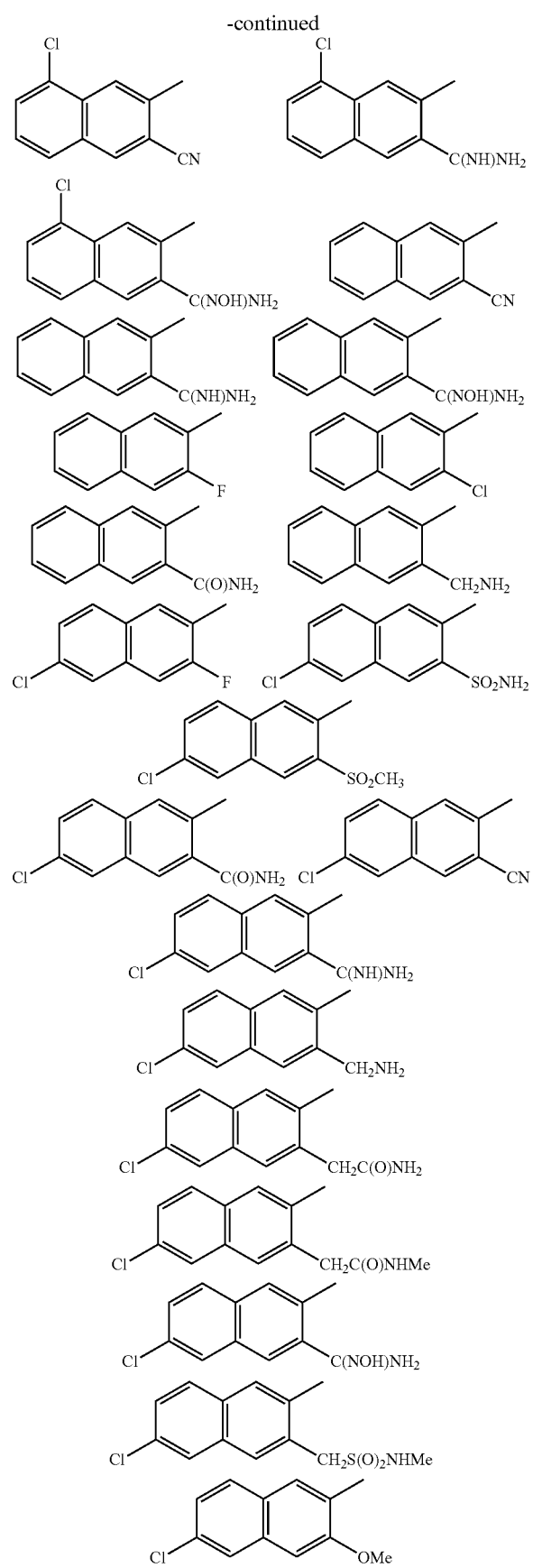
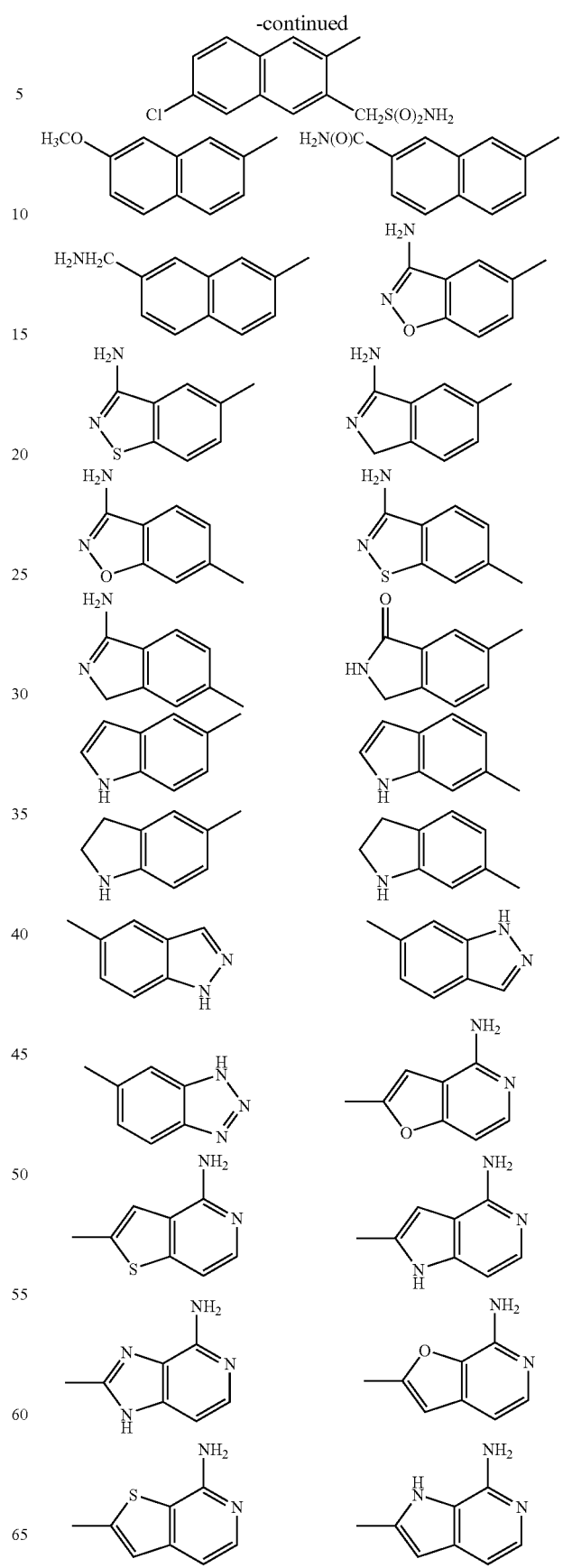

-continued
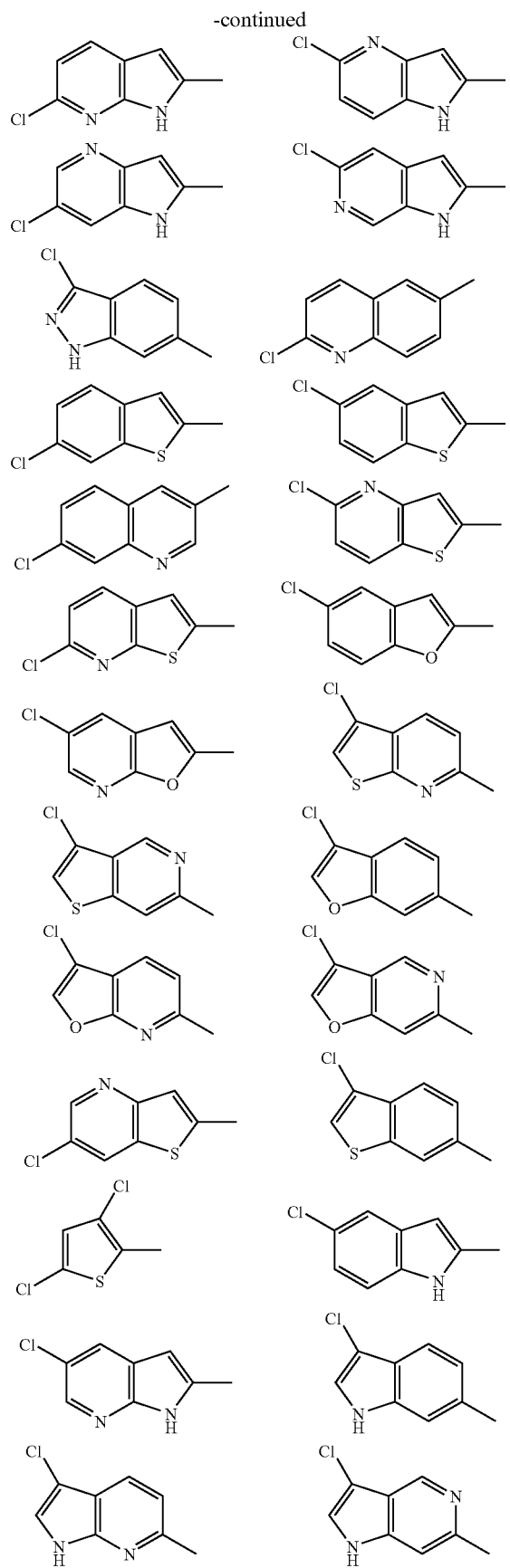
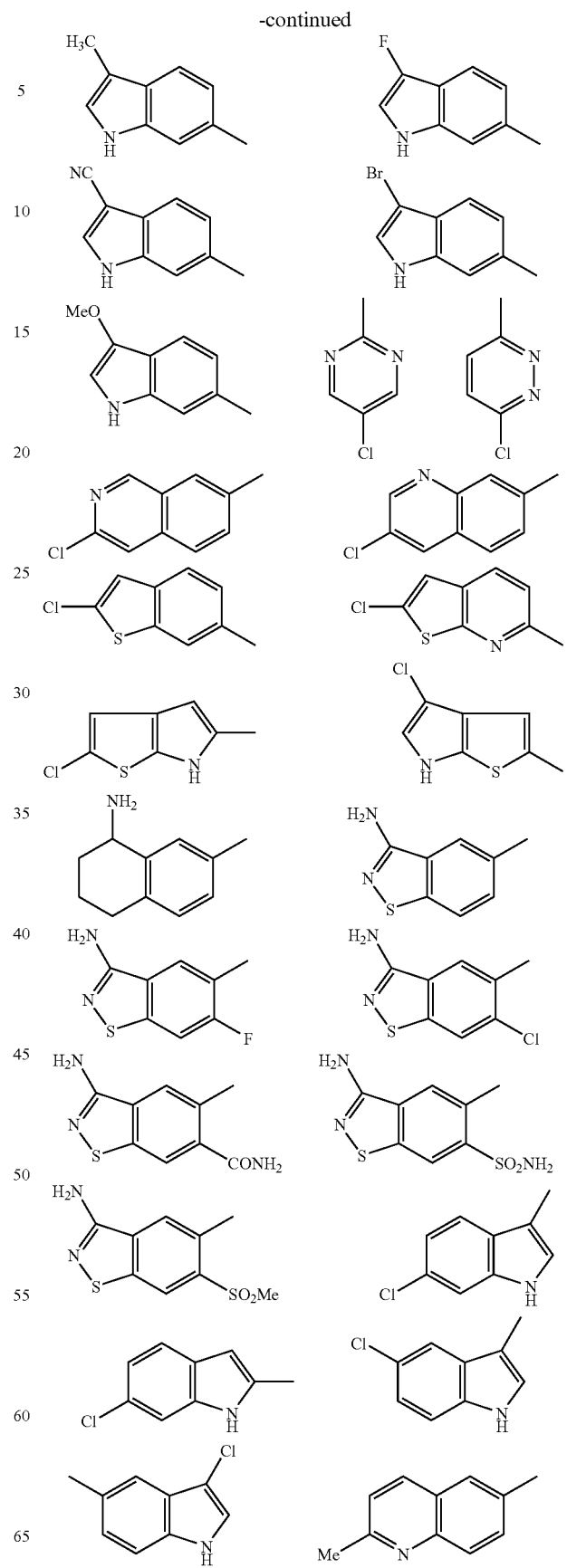

-continued

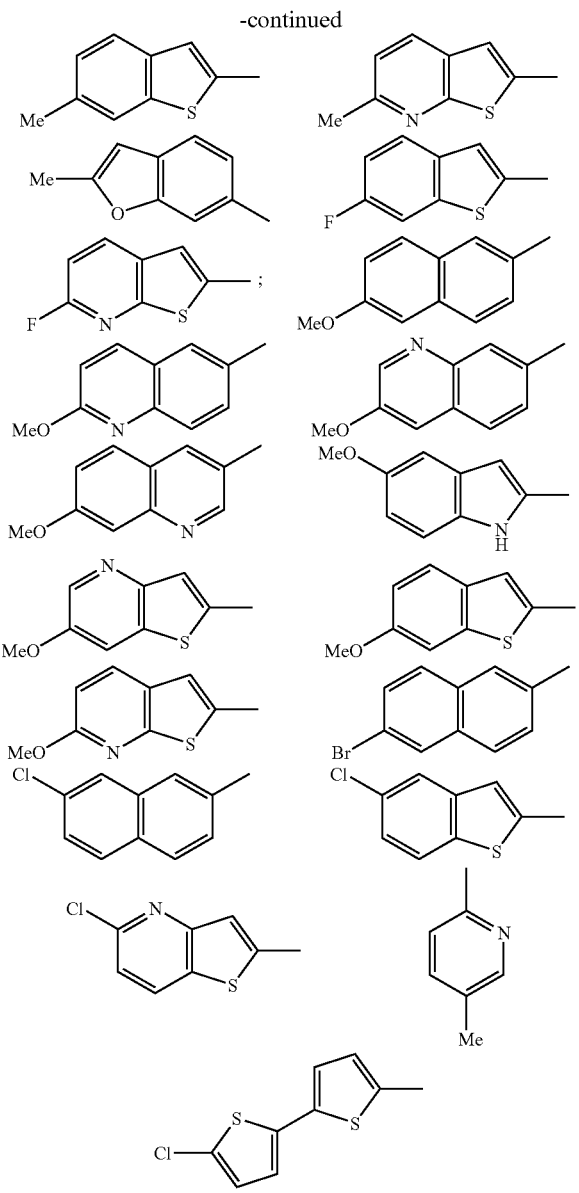

G₁ is selected from CH₂, CH₂CH₂, CH=CH, CH₂O, OCH₂, C(O), NH, CH₂NH, NHCH₂, CH₂C(O), C(O)CH₂, C(O)NH, NHC(O), NHC(O)NH, NHC(O)CH₂C(O)NH, C(O)NHS(O)₂, CH₂S, SCH₂, CH₂S(O), S(O)₂, CH₂S(O)₂, S(O)₂(CH₂), SO₂NH, NHSO₂, NHCH₂C(O)NH, NHC(O)C(O)NH, NHC(O)C(S)NH, and NHC(S)C(O)NH and the right side of G₁ is attached to ring G, provided that G₁ does not form a N—S, NCH₂N, NCH₂O, or NCH₂S bond with either group to which it is attached;

A is selected from one of the following carbocyclic and heterocyclic groups, which are substituted with 0–2 R⁴, cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

B¹ is selected from H, CH₃, CH₂CH₃, CH₂CH₂CH₃, CH(CH₃)₂, —(CH₂)₀₋₁—C₅₋₆ carbocycle substituted with 0–2 R⁴ᵇ, and —(CH₂)₀₋₁-5–6 membered heterocycle consisting of: carbon atoms and 1–4 heteroatoms selected from the group consisting of N, O, and S(O)ₚ and substituted with 0–2 R⁴ᵇ;

B² is selected from H, CH₃, CH₂CH₃, CH₂CH₂CH₃, CH(CH₃)₂, C(O)R²ᵉ, C(O)NR²ᵈR²ᵈ', SO₂NR²ᵈR²ᵈ', and S(O)ₚR⁵ᵃ;

B³ is selected from H, C₁₋₆ alkyl substituted with 0–1 R⁴ᶜ, —(CH₂)₀₋₁-3–6 membered carbocycle substituted with 0–1 R⁵, and a —(CH₂)₀₋₁-5–6 membered heterocycle consisting of: carbon atoms and 1–4 heteroatoms selected from the group consisting of N, O, and S(O)ₚ and substituted with 0–1 R⁵;

B⁴ is selected from H, SO₂R³ᵇ and OR²;

B⁵ is NR²R²ᶠ;

ring Q is a 5–6 membered ring consisting of, in addition to the N—CR⁴ᵈ=N group shown, carbon atoms and 0–2 heteroatoms selected from N, O, and S(O)ₚ, and the ring is substituted with an additional 0–2 R⁴ᵈ;

Q⁴ is selected from C=O and SO₂;

ring Q³ is a 5–7 membered ring consisting of, in addition to the N—Q⁴ group shown, carbon atoms and 0–2 heteroatoms selected from NR⁴ᶜ, O, S, S(O), and S(O)₂, wherein: 0–2 double bonds are present within the ring and the ring is substituted with 0–2 R⁴ᵃ;

alternatively, ring Q³ is a 5–7 membered ring to which another ring is fused, wherein: the 5–7 membered ring consists of, in addition to the shown amide group, carbon atoms and 0–2 heteroatoms selected from NR⁴ᶜ, O, S, S(O), and S(O)₂, and 0–1 double bonds are present within the ring; the fusion ring is phenyl or a 5–6 membered heteroaromatic consisting of carbon atoms and 1–2 heteroatoms selected from NR⁴ᶜ, O, and S;

ring Q³, which includes the 5–7 membered ring and the fusion ring, is substituted with 0–3 R⁴ᵃ;

ring Q⁵, is a C₃₋₆ monocyclic carbocycle or 5–6 membered monocyclic heterocycle, wherein the carobocycle or heterocycle consists of carbon atoms and 0–2 heteroatoms selected from N, O, and S(O)ₚ, the carbocycle or heterocycle further comprises 0–1 double bonds and 0–1 carbonyl groups, and the carbocycle or heterocycle is substituted with 0–2 R⁴;

X is selected from —(CR²R²ᵃ)₁₋₂—, —C(=NR¹ᵇ)—, —C(O)—, —S(O)₂—, —NR²S(O)₂—, —NR²S(O)₂—, —NR²C(O)—, —C(O)NR²—, —NR²C(O)CR²R²ᵃ—, —NR²C(O)NR²—, NR², —NR²CR²R²ᵃ—, —CR²R²ᵃNR²—, O, —OCR²R²ᵃ—, and —CR²R²ᵃO—;

Y is selected from: CY¹Y²R⁴ᵃ, NR³R³ᵃ, SO₂R³, and C(O)NR³R³ᵃ;

Y¹ and Y² are independently C₁₋₂ alkyl substituted with 0–2 R⁴;

alternatively, Y is selected from one of the following carbocyclic and heterocycles that are substituted with 1 R⁴ᵃ and 0–1 R⁴: cyclopropyl, cyclobutyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, isoindazole, 4,5-dihydro-2-imidazolyl, 1,4,5,6-tetrahydro-2-pyrimidinyl, and, [1,4]diazepanyl;

alternatively, when A is selected from one of the following carbocyclic and heterocyclic groups, which are substituted with 0–2 $R^{4c}$, cyclopentyl, cyclohexyl, piperidinyl, hexahydropyrimidyl, pyrrolidinyl, and piperazinyl;

then Y is additionally selected from methyl, ethyl, 2-propyl, 1-butyl, 2-methyl-1-propyl, 1-pentyl, $CH(CF_3)_2$, $CH(CHF_2)CH_3$, $CH_2CF_3$, $CH(CF_2CF_3)_2$, $C(O)NHCH_2CH_3$, $C(O)N(CH_3)_2$, $C(O)CH_2CH_2CH_3$, $C(O)C(CH_3)_3$, $N(CH_3)_2$, $N(CH_2CH_3)_2$, $NHC(O)CH_2CH_3$, $NHC(O)CH(CH_3)_2$, and $SO_2CH_3$;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and a 5–6 membered aromatic heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle containing from 1–4 heteroatoms selected from the group consisting of N, O, and $S(Q)_p$, and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CF_3$, $CH_3$, $CH_2CH_3$, $CH_2CH_2CH_3$, $CH(CH_3)_2$, $OCH_3$, and benzyl;

alternatively, $NR^2R^{2f}$ forms a 5–6 membered ring consisting of: carbon atoms and 0–2 additional heteroatoms selected from N, O, and $S(O)_p$, and this ring is substituted with 0–2 $R^{4b}$;

alternatively, $B^4$ and $R^{2f}$ combine to form a 5–6 membered ring consisting of: carbon atoms and 0–1 additional heteroatoms selected from N, O, and $S(O)_p$, and this ring is substituted with 0–2 $R^{4b}$ and the $R^2$ group of $NR^2R^{2f}$, in addition to the groups recited below, can be $SO_2R^{3b}$;

$R^{3b}$, at each occurrence, is selected from H, $CF_3$, $CH_3$, $CH_2CH_3$, $CH_2CH_2CH_3$, and $CH(CH_3)_2$;

$R^4$, at each occurrence, is selected from H, =O, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of: carbon atoms and 1–4 heteroatoms selected from the group consisting of N, O, and $S(O)_p$, $(CR^3R^{3g})_rNR^{2d}R^{2d}$, $(CR^3R^{3g})_rN(→O)R^{2d}R^{2d}$, $(CR^3R^{3g})_rOR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$OC(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$NR^{2d}C(O)OR^{2d}$, $(CR^3R^{3g})_r$—$SO_2NR^{2d}R^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{2-3}$ alkenyl, $C_{2-3}$ alkynyl, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(→O)R^2R^{2a}$, $(CR^3R^{3a})N(→O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)$ $NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})$ $NR^2SO_2NR^2R^{2a}$, $NR^2SO_2R^{5a}$, $(CR^3R^{3a})NR^2SO_2R^{5a}$, $S(O)_p R^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$-5–10 membered heterocycle consisting of carbon atoms and from 1–4 heteroatoms selected from the group consisting of N, O, and $S(O)_p$ and substituted with 0–2 $R^{4b}$;

$R^{4d}$, at each occurrence, is selected from H, $CH_2OR^2$, $OR^2$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $CH_2NR^2R^{2a}$, $NR^2R^{2a}$, $C(O)R^{2c}$, $NR^2C(O)R^{2b}$, $C(O)NR^2R^{2a}$, $NR^2C(O)NR^2R^{2a}$, $NR^2SO_2R^5$, $SO_2NR^2R^{2a}$, 6 membered carbocycle substituted with 0–1 $R^5$, and a 5–6 membered heterocycle consisting of: carbon atoms and 1–2 heteroatoms selected from the group consisting of N, O, and $S(O)_p$ and substituted with 0–1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

In an eleventh embodiment, the present invention provides a novel compound selected from formula $Id_{1.1-8.1}$ and $Ie_{1.1-8.1}$:

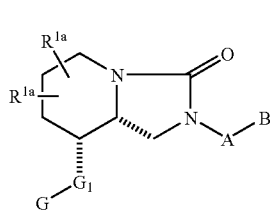

Id$_{1.1}$

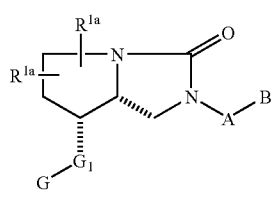

Ie$_{1.1}$

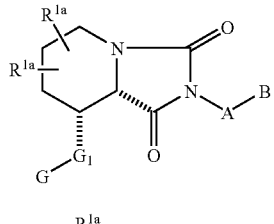

Id$_{2.1}$

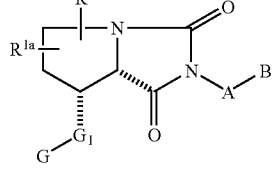

Ie$_{2.1}$

-continued

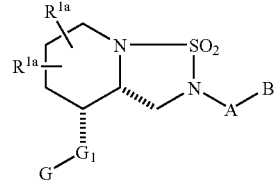

Id$_{3.1}$

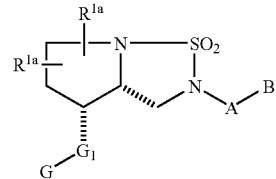

Ie$_{3.1}$

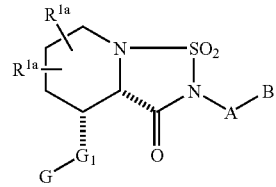

Id$_{4.1}$

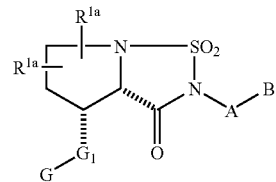

Ie$_{4.1}$

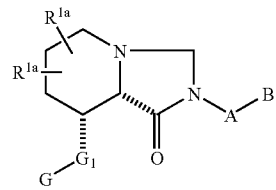

Id$_{5.1}$

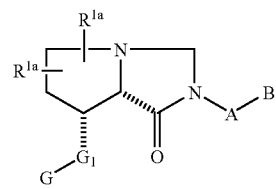

Ie$_{5.1}$

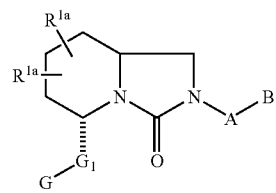

Id$_{6.1}$

Ie$_{6.1}$

-continued

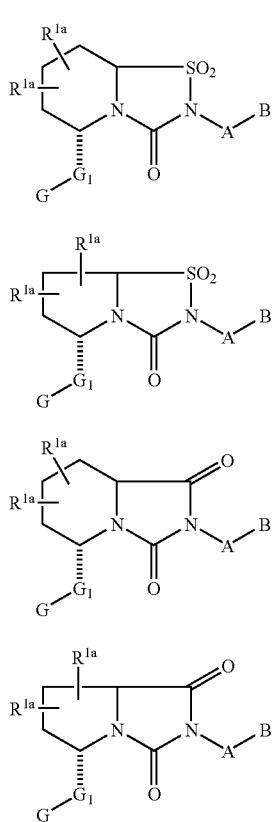

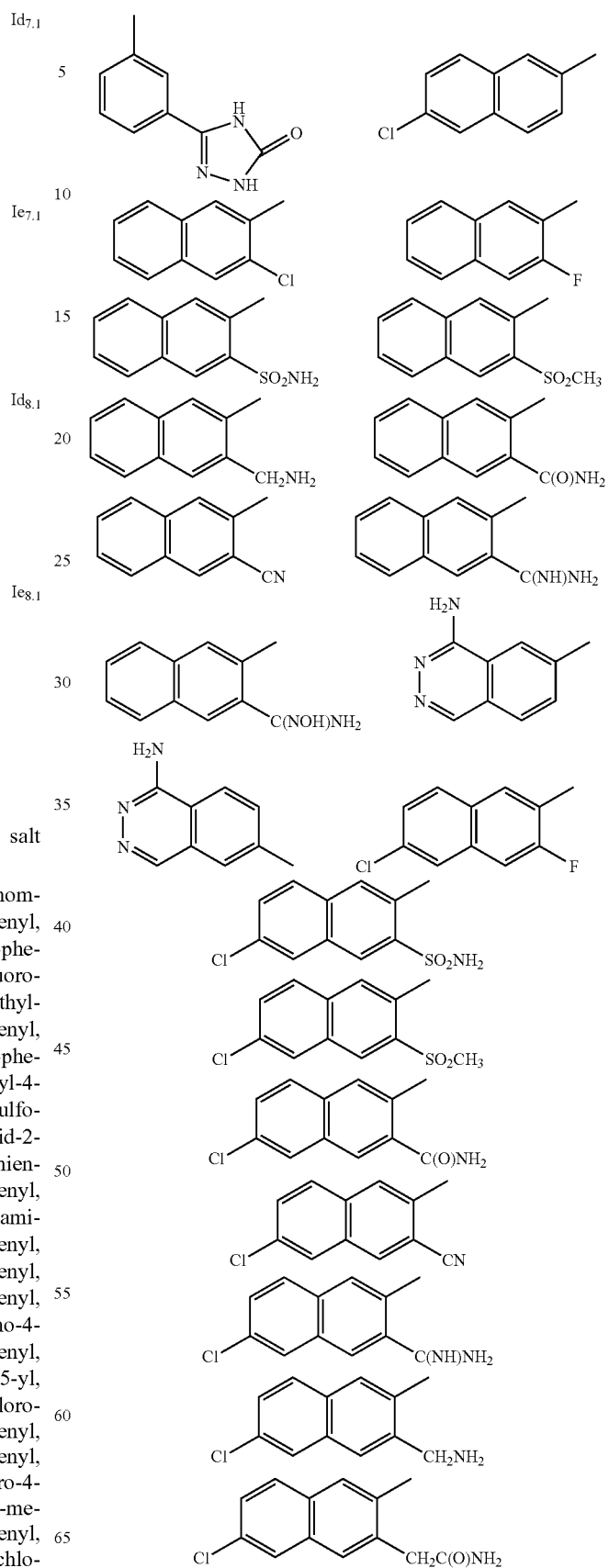

or a stereoisomer or pharmaceutically acceptable salt thereof, wherein;

G is selected from: phenyl, 4-ethyl-phenyl, 2-aminomethyl-4-chloro-phenyl, 2-aminosulfonyl-4-chloro-phenyl, 2-amido-4-chloro-phenyl, 4-chloro-2-methylsulfonyl-phenyl, 2-aminosulfonyl-4-fluoro-phenyl, 2-amido-4-fluoro-phenyl, 4-fluoro-2-methylsulfonyl-phenyl, 2-aminomethyl-4-bromo-phenyl, 2-aminosulfonyl-4-bromo-phenyl, 2-amido-4-bromo-phenyl, 4-bromo-2-methylsulfonyl-phenyl, 2-aminomethyl-4-methyl-phenyl, 2-aminosulfonyl-4-methyl-phenyl, 2-amido-4-methyl-phenyl, 2-methylsulfonyl-4-methyl-phenyl, 4-fluoro-pyrid-2-yl, 4-bromo-pyrid-2-yl, 4-methyl-pyrid-2-yl, 5-fluoro-thien-2-yl, 5-bromo-thien-2-yl, 5-methyl-thien-2-yl, 2-amido-4-methoxy-phenyl, 2-amido-phenyl, 2-aminomethyl-3-fluoro-phenyl, 2-aminomethyl-4-fluoro-phenyl, 2-aminomethyl-5-fluoro-phenyl, 2-aminomethyl-6-fluoro-phenyl, 2-aminomethyl-phenyl, 2-amino-pyrid-4-yl, 2-aminosulfonyl-4-methoxy-phenyl, 2-aminosulfonyl-phenyl, 3-amido-phenyl, 3-amino-4-chloro-phenyl, 3-aminomethyl-phenyl, 3-chloro-phenyl, 4-chloro-phenyl, 4-methoxy-phenyl, 2-methoxy-pyrid-5-yl, 5-chloro-pyrid-2-yl, 5-chloro-thien-2-yl, 6-amino-5-chloro-pyrid-2-yl, 6-amino-pyrid-2-yl, 2-cyano-4-chloro-phenyl, 2-methoxy-4-chloro-phenyl, 2-fluoro-4-chloro-phenyl, 3-chloro-4-methyl-phenyl, 4-fluoro-phenyl, 3-fluoro-4-chloro-phenyl, 3-methyl-4-chloro-phenyl, 3-fluoro-4-methyl-phenyl, 3,4-dimethyl-phenyl, 3-chloro-4-fluoro-phenyl, 3-methyl-4-fluoro-phenyl, 4-methylsulfanyl-phenyl, 2-chlorothiazol-5-yl, 5-chlorothiazol-2-yl, -continued

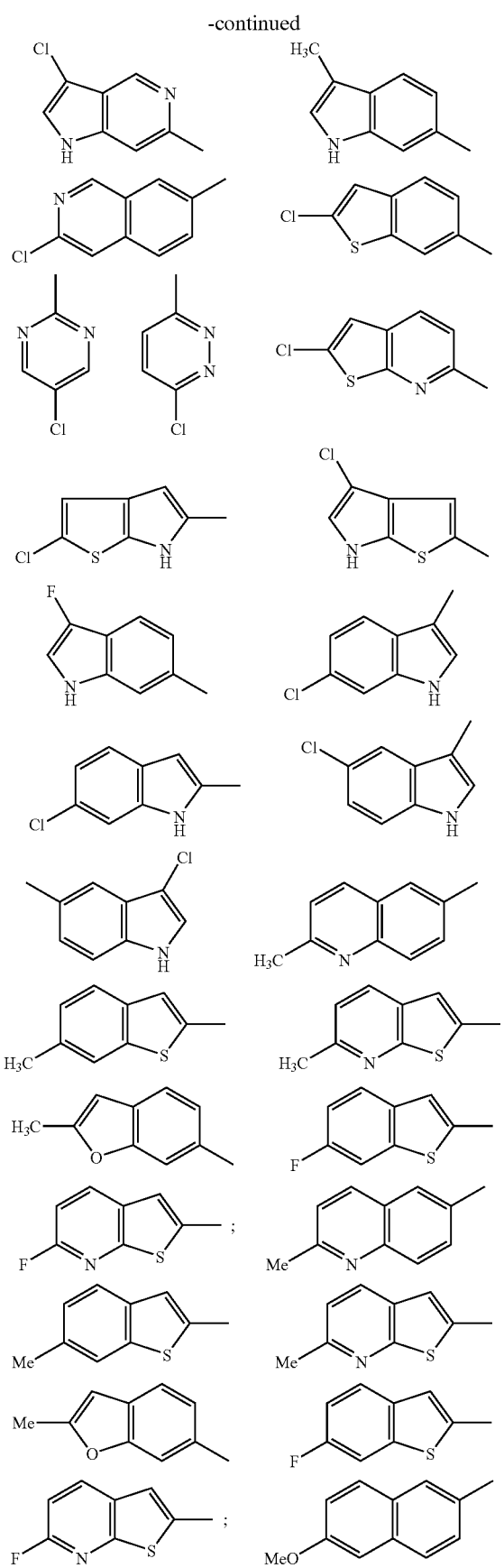

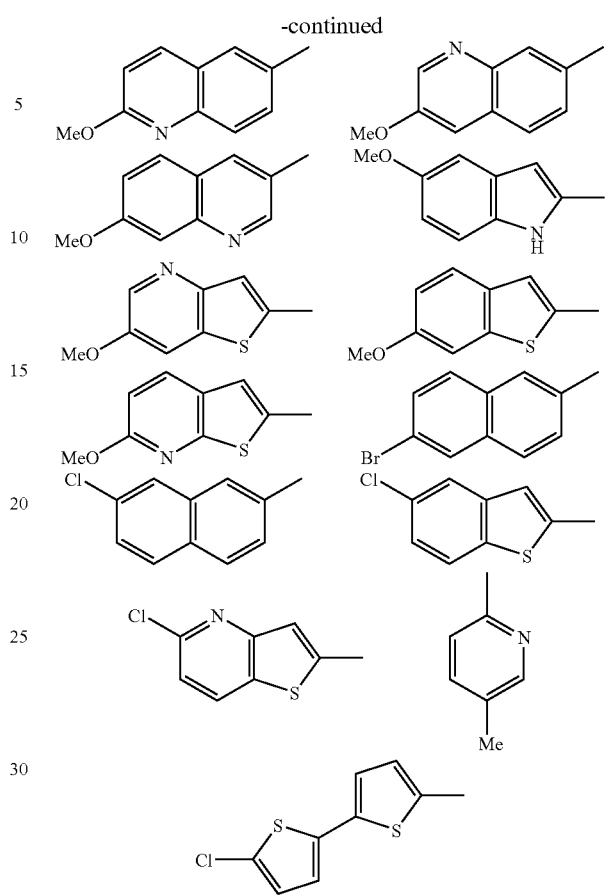

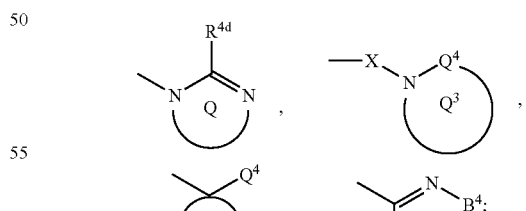

$G_1$ is selected from CH=CH, $CH_2C(O)$, $C(O)CH_2$, NH, C(O)NH, NHC(O), $CH_2S$, $SCH_2$, $CH_2S(O)$, $CH_2SO_2$, $SO_2NH$, $NHSO_2$ $NHCH_2C(O)NH$, NHC(O)C(O)NH, NHC(O)C(S)NH, and NHC(S)C(O)NH and the right side of $G_1$ is attached to ring G, provided that $G_1$ does not form a N—S, $NCH_2N$, $NCH_2O$, or $NCH_2S$ bond with either group to which it is attached;

A is selected from cyclohexyl, piperidinyl, piperazinyl, phenyl, pyridyl, and pyrimidyl, and is substituted with 0–2 $R^4$;

B is selected from Y, $N(B^1)C(O)C(R^3R^{3g})NB^2B^3$, provided that the lactam nitrogen and B are attached to different atoms on A, the $R^{4d}$ shown is other than OH, and that the A—X—N moiety forms other than a N—N—N group;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

$B^4$ is selected from H, $SO_2R^{3b}$, and $OR^2$;

$B^5$ is $NR^2R^{2f}$;

ring Q is a 5–6 membered ring consisting of, in addition to the N—$CR^{4d}$=N group shown, carbon atoms and 0–1 heteroatoms selected from N, O, and $S(O)_p$, and the ring is substituted with an additional 0–2 $R^{4d}$;

$Q^4$ is selected from C=O and $SO_2$;

ring $Q^3$ is a 5–7 membered ring consisting of, in addition to the N—$Q^4$ group shown, carbon atoms and 0–1 heteroatoms selected from $NR^{4c}$, O, S, S(O), and $S(O)_2$, wherein: 0–2 double bonds are present within the ring and the ring is substituted with 0–2 $R^4$;

alternatively, ring $Q^3$ is a 5–7 membered ring to which another ring is fused, wherein: the 5–7 membered ring consists of, in addition to the shown amide group, carbon atoms and 0–1 heteroatoms selected from $NR^{4c}$, O, S, S(O), and $S(O)_2$, and 0–1 double bonds are present within the ring; the fusion ring is phenyl;

ring $Q^3$, which includes the 5–7 membered ring and the fusion ring, is substituted with 0–2 $R^4$;

ring $Q^5$ is substituted with 0–1 $R^4$ and is selected from cyclopropyl, cyclobutyl, cyclopentyl, cyclopentanonyl, cyclohexyl, cyclohexanonyl, pyrrolidinyl, pyrrolidinonyl, piperidinyl, piperidinonyl, tetrahydrofuranyl, and tetrahydropyranyl;

X is selected from $CH_2$, C(O), —$S(O)_2$—, —NHC(O)—, —C(O)NH—, —$CH_2$NH—, O, and —$CH_2$O—;

Y is selected from $N(CH_3)_2$, $SO_2(CH_3)$, $SO_2(CH_2CH_3)$, $C(O)N(CH_3)_2$, $C(CH_3)_2R^{4a}$ and $C(CH_2CH_3)_2R^{4a}$;

alternatively, Y is selected from cyclopropyl, cyclobutyl, cyclopentyl, cyclohexyl, phenyl, pyridyl, pyrrolidino, N-pyrrolidino-carbonyl, morpholino, N-morpholino-carbonyl, 1,2,3-triazolyl, imidazolyl, benzimidazolyl, 4,5-dihydro-2-imidazolyl, 2-pyrrolidin-1-yl-methyleneamine, 2-piperidin-1-yl-methyleneamine, 2-morpholin-4-yl-methyleneamine, 1,4,5,6-tetrahydro-2-pyrimidinyl, [1,4] diazepanyl, piperdinyl, pyrrolidinyl, and morpholinyl, and is substituted with 1 $R^{4a}$ and 0–1 $R^4$;

alternatively, when A is selected from and piperidinyl, then Y is additionally 2-propyl;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

alternatively, $NR^2R^{2a}$ forms a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle containing from 1–4 heteroatoms selected from the group consisting of N, O, and $S(O)_p$, and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$-5–6 membered heterocycle and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{2f}$, at each occurrence, is selected from H, $CH_3$, $CH_2CH_3$, $OCH_3$, and benzyl;

alternatively, $NR^2R^{2f}$ forms a 5–6 membered ring consisting of: carbon atoms and 0–1 additional heteroatoms selected from N, O, and $S(O)_p$, and this ring is substituted with 0–1 $R^{4b}$;

alternatively, $B^4$ and $R^{2f}$ combine to form a 5 membered ring consisting of: carbon atoms and 0–1 additional heteroatoms selected from N, O, and $S(O)_p$, and this ring is substituted with 0–2 $R^{4b}$ and the $R^2$ group of $NR^2R^{2f}$, in addition to the groups recited below, can be $SO_2R^{3b}$;

$R^{3b}$, at each occurrence, is selected from H and $CH_3$;

$R^4$, at each occurrence, is selected from H, =O, OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$-5–6 membered heterocycle substituted with 0–3 $R^{4c}$ and consisting of:

carbon atoms and 1–4 heteroatoms selected from the group consisting of N, O, and S(O)$_p$, (CR$^3$R$^{3g}$)$_r$NR$^{2d}$R$^{2d}$, (CR$^3$R$^{3g}$)$_r$N(→O)R$^{2d}$R$^{2d}$, (CR$^3$R$^{3g}$)$_r$OR$^{2d}$, (CR$^3$R$^{3g}$)$_r$—C(O)NR$^{2d}$R$^{2d}$, (CR$^3$R$^{3g}$)$_r$—NR$^{2d}$C(O)R$^{2e}$, (CR$^3$R$^{3g}$)$_r$—C(O)R$^{2e}$, (CR$^3$R$^{3g}$)$_r$—NR$^{2d}$C(O)NR$^{2d}$R$^{2d}$, (CR$^3$R$^{3g}$)$_r$—NR$^{2d}$C(O)OR$^{2d}$, (CR$^3$R$^{3g}$)$_r$—NR$^{2d}$SO$_2$R$^{2d}$, (CR$^3$R$^{3g}$)$_r$—SO$_2$NR$^{2d}$R$^{2d}$, and (CR$^3$R$^{3g}$)$_r$—S(O)$_p$R$^{2d}$, provided that S(O)$^y$R$^{2d}$ forms other than S(O)$_2$H or S(O)H;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, and CF$_3$;

R$^{4c}$, at each occurrence, is selected from =O, OR$^2$, CH$_2$OR$^2$, F, Br, Cl, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, C$_{2-3}$ alkenyl, C$_{2-3}$ alkynyl, —CN, NO$_2$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, CF$_2$CF$_3$, C$_{3-6}$ carbocycle substituted with 0–2 R$^{4b}$, (CH$_2$)C$_{3-6}$ carbocycle substituted with 0–2 R$^{4b}$, 5–6 membered heterocycle consisting of carbon atoms and from 1–4 heteroatoms selected from the group consisting of N, O, and S(O)$_p$ and substituted with 0–2 R$^{4b}$, and (CH$_2$)-5–6 membered heterocycle consisting of carbon atoms and from 1–4 heteroatoms selected from the group consisting of N, O, and S(O)$_p$ and substituted with 0–2 R$^{4b}$;

R$^{4d}$, at each occurrence, is selected from H, CH$_2$OR$^2$, OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, CH$_2$NR$^2$R$^{2a}$, NR$^2$R$^{2a}$, C(O)R$^{2c}$, NR$^2$C(O)R$^{2b}$, C(O)NR$^2$R$^{2a}$, SO$_2$NR$^2$R$^{2a}$, NR$^2$SO$_2$R$^5$, phenyl substituted with 0–1 R$^5$, and a 5–6 membered heterocycle consisting of: carbon atoms and 1 heteroatom selected from the group consisting of N, O, and S(O)$_p$ and substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, and SO$_2$NR$^2$R$^{2a}$.

In a twelfth embodiment, the present invention provides a novel compound, wherein:

G is selected from:

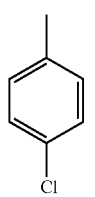
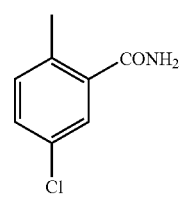
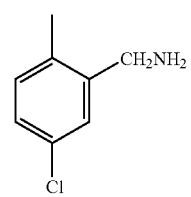

-continued

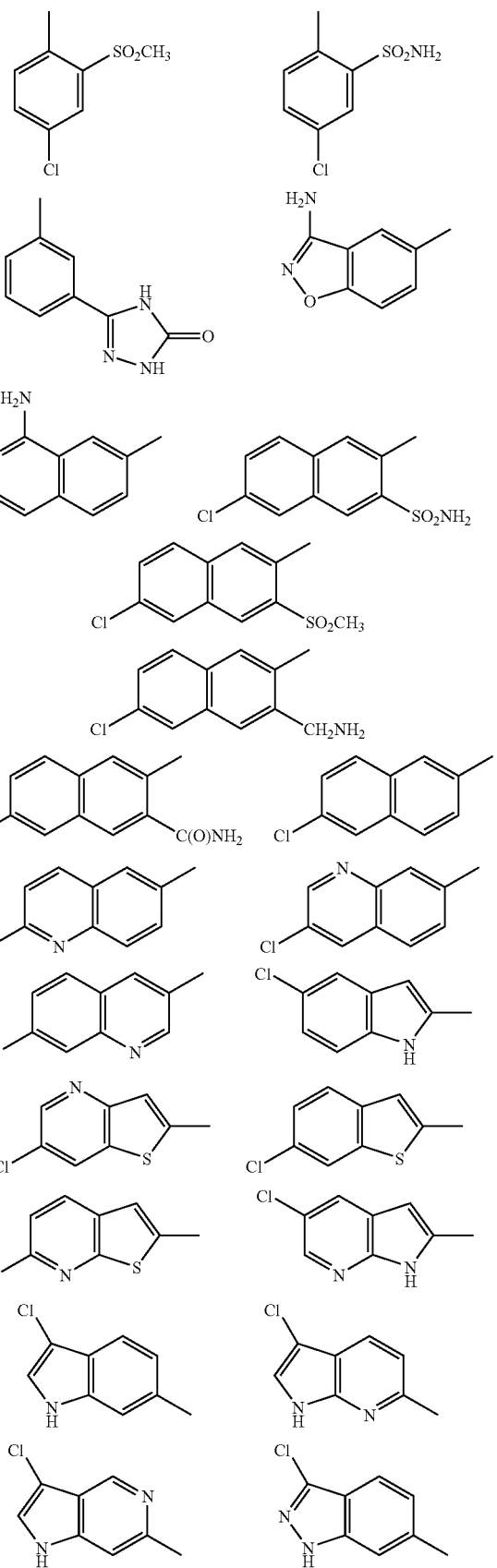

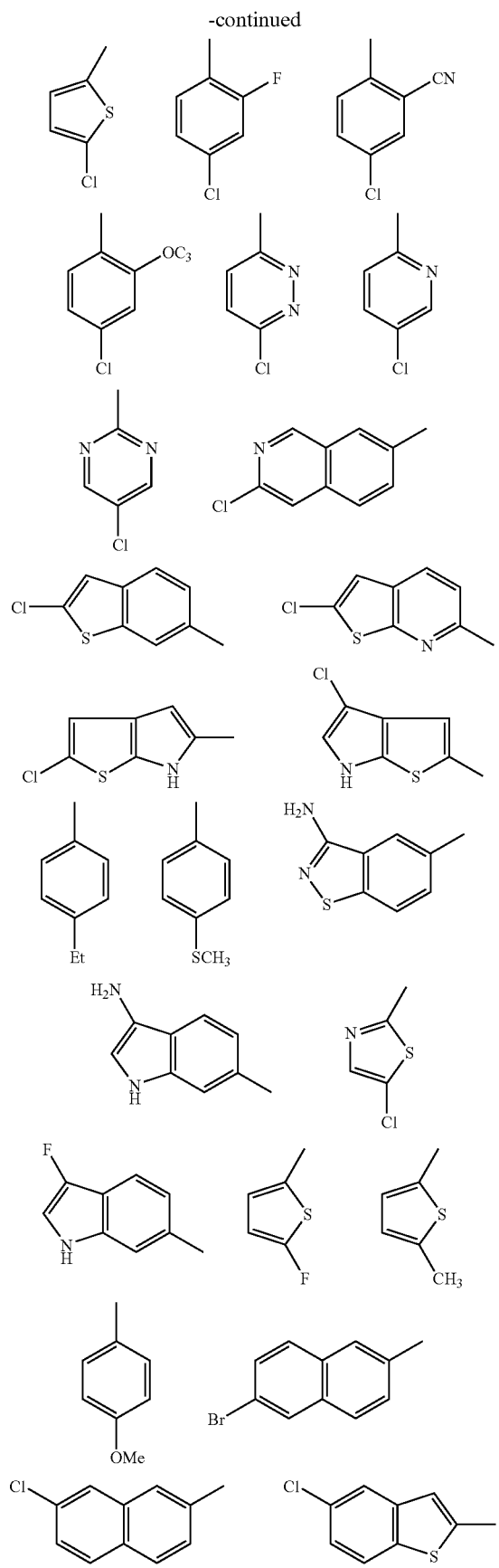

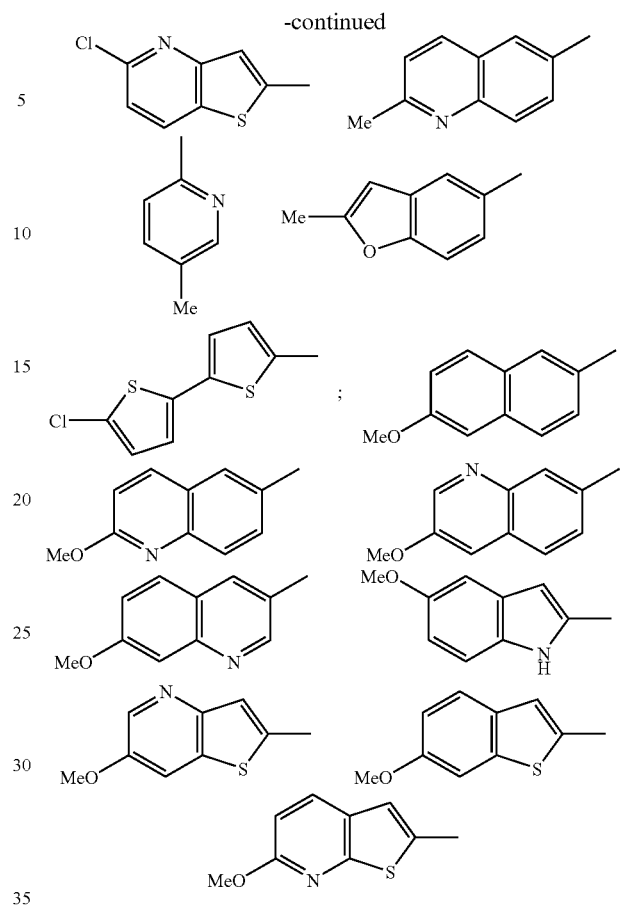

$G_1$ is selected from $CH_2NH$, $C(O)NH$, $NHC(O)$, $CH_2S$, $CH_2S(O)$, $CH_2SO_2$, $NHCH_2C(O)NH$, $NHC(O)C(O)NH$, and the right side of $G_1$ is attached to ring G, provided that $G_1$ does not form a N—S, $NCH_2N$, $NCH_2O$, or $NCH_2S$ bond with either group to which it is attached;

A is selected from the group: cyclohexyl, 4-piperdinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from Y, $N(B^1)C(O)C(R^3R^{3g})NB^2B^3$,

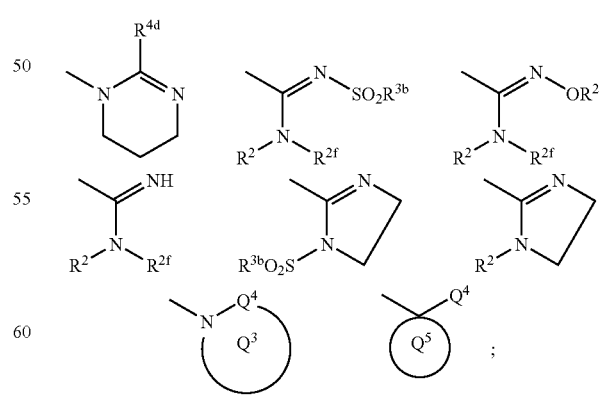

provided that the lactam nitrogen and B are attached to different atoms on A and that the $R^{4d}$ shown is other than OH;

$B^1$ is selected from H, $CH_3$, $CH_2CH_3$, and $CH_2CH_2CH_3$;

$B^2$ is selected from H, $CH_3$, and $CH_2CH_3$;

$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, cyclohexyl, and $CH_2$-cyclopropyl;

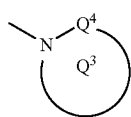

is attached to a different atom on A than M and is selected from the group:

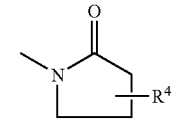 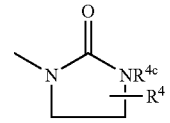 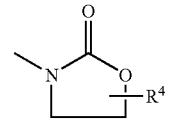

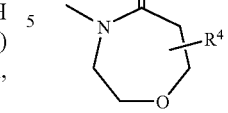 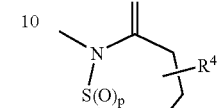 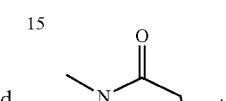 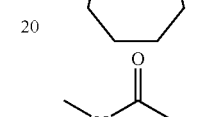 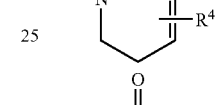 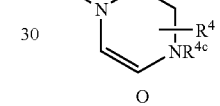 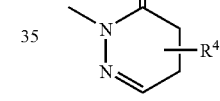 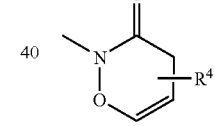 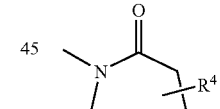 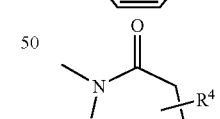 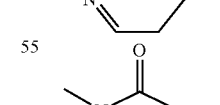 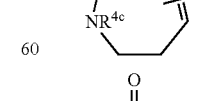 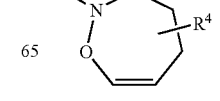

-continued

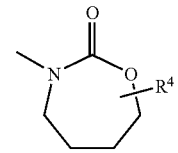 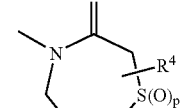 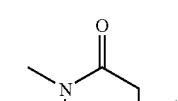 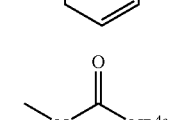 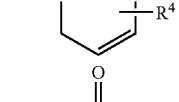 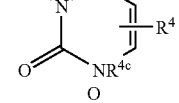 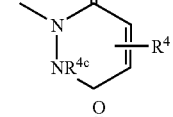 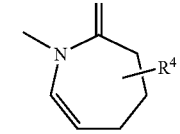 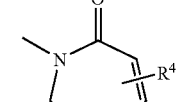 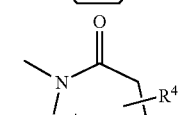 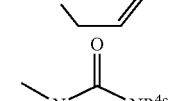 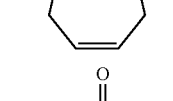

-continued

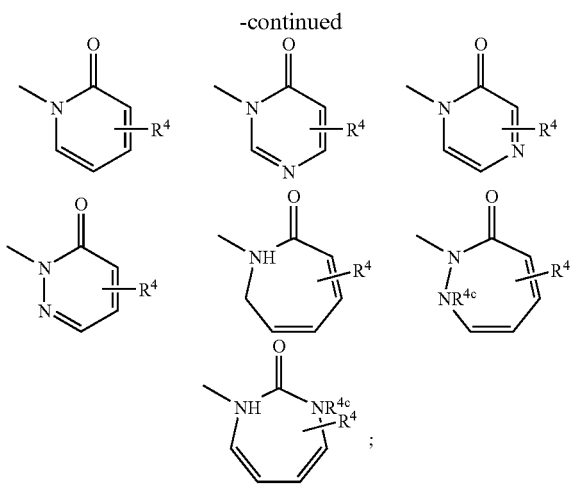

ring Q⁵ is selected from cyclopropyl, cyclobutyl, cyclopentyl, 2-cyclopentanonyl, cyclohexyl, 2-cyclohexanonyl, pyrrolidinyl (attached to A and R⁴ᵃ at the 2-position), pyrrolidinyl (attached to A and R⁴ᵃ at the 3-position), 2-pyrrolidinonyl (attached to A and R⁴ᵃ at the 3-position), piperidinyl (attached to A and R⁴ᵃ at the 4-position), 4-piperdinonyl (attached to A and R⁴ᵃ at the 3-position), tetrahydrofuranyl, and tetrahydropyranyl (attached to A and R⁴ᵃ at the 4-position);

Y is selected from N(CH₃)₂, C(O)N(CH₃)₂, C(CH₃)₂R⁴ᵃ and C(CH₂CH₃)₂R⁴ᵃ;

alternatively, Y is selected from phenyl, pyridyl, 1,2,3-triazolyl, imidazolyl, N-pyrrolidino-carbonyl, N-morpholino-carbonyl, benzimidazolyl, 4,5-dihydro-2-imidazolyl, 2-pyrrolidin-1-yl-methyleneamine, 2-piperidin-1-yl-methyleneamine, 2-morpholin-4-yl-methyleneamine, 1,4,5,6-tetrahydro-2-pyrimidinyl, [1,4]diazepanyl, pyrrolidinyl, and morpholinyl, and is substituted with 1 R⁴ᵃ;

alternatively, A-B is selected from 4-(2-propyl)-piperidinyl and 4-(N,N-dimethylamino)-piperidinyl;

R¹ᵃ, at each occurrence, is selected from H, CH₃, CH₂CH₃, CH₂CH₂CH₃, CH₂F, CH₂Cl, Br, CH₂Br, —CN, CH₂CN, CF₃, CH₂CF₃, OCH₃, CH₂OH, C(CH₃)₂OH, CH₂OCH₃, NH₂, CH₂NH₂, NHCH₃, CH₂NHCH₃, N(CH₃)₂, CH₂N(CH₃)₂, CO₂H, COCH₃, CO₂CH₃, CH₂CO₂CH₃, SCH₃, CH₂SCH₃, S(O)CH₃, CH₂S(O)CH₃, S(O)₂CH₃, CH₂S(O)₂CH₃, C(O)NH₂, CH₂C(O)NH₂, SO₂NH₂, CH₂SO₂NH₂, NHSO₂CH₃, CH₂NHSO₂CH₃, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH₂-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, CH₂-1,2,3,4-tetrazol-1-yl, and CH₂-1,2,3,4-tetrazol-5-yl, provided that R¹ᵃ forms other than an N-halo, N—S, or N—CN bond;

R², at each occurrence, is selected from H, CH₃, CH₂CH₃, CH₂CH₂CH₃, CH(CH₃)₂, phenyl substituted with 0–1 R⁴ᵇ, benzyl substituted with 0–1 R⁴ᵇ, and 5 membered aromatic heterocycle consisting of: carbon atoms and 1–4 heteroatoms selected from the group consisting of N, O, and S(O)ₚ, and substituted with 0–1 R⁴ᵇ;

R²ᵃ, at each occurrence, is selected from H, CH₃, and CH₂CH₃;

alternatively, NR²R²ᵃ forms a 5 or 6 membered saturated, partially saturated or unsaturated ring substituted with 0–1 R⁴ᵇ and consisting of: 0–1 additional heteroatoms selected from the group consisting of N, O, and S(O)ₚ;

R²ᵇ, at each occurrence, is selected from OCH₃, OCH₂CH₃, CH₃, and CH₂CH₃;

R²ᶜ, at each occurrence, is selected from OH, OCH₃, OCH₂CH₃, CH₃, and CH₂CH₃;

R²ᵈ, at each occurrence, is selected from H, R⁴ᶜ, C₁₋₄ alkyl substituted with 0–2 R⁴ᶜ, C₃₋₆ cycloalkyl substituted with 0–2 R⁴ᶜ, phenyl substituted with 0–2 R⁴ᶜ, and 5–6 membered aromatic heterocycle substituted with 0–2 R⁴ᶜ and consisting of: carbon atoms and 1–4 heteroatoms selected from the group consisting of N, O, and S(O)ₚ, provided that R²ᵈ forms other than a N-halo, N—C-halo, S(O)ₚ-halo, O-halo, N—S, S—N, S(O)ₚ—S(O)ₚ, S—O, O—N, O—S, or O—O moiety;

R²ᵉ, at each occurrence, is selected from H, R⁴ᶜ, C₁₋₄ alkyl substituted with 0–2 R⁴ᶜ, C₃₋₆ cycloalkyl substituted with 0–2 R⁴ᶜ, phenyl substituted with 0–2 R⁴ᶜ, and 5–6 membered aromatic heterocycle substituted with 0–2 R⁴ᶜ and consisting of: carbon atoms and 1–4 heteroatoms selected from the group consisting of N, O, and S(O)ₚ, provided that R²ᵉ forms other than a C(O)-halo or C(O)—S(O)ₚ moiety;

R²ᶠ, at each occurrence, is selected from H, CH₃, CH₂CH₃, and OCH₃;

alternatively, NR²R²ᶠ forms a ring selected from morpholine, piperazine, piperidine, and pyrrolidine;

R⁴, at each occurrence, is selected from H, =O, CH₃, CH₂CH₃, CH₂CH₂CH₃, CH(CH₃)₂, CH₂CH₂CH₂CH₃, CH₂CH(CH₃)₂, CH(CH₃)CH₂CH₃, and C(CH₃)₃;

R⁴ᵃ is selected from —(CH₂)ᵣ-5–6 membered carbocycle substituted with 0–3 R⁴ᶜ, —(CH₂)ᵣ-5–6 membered heterocycle substituted with 0–3 R⁴ᶜ and consisting of: carbon atoms and 1–4 heteroatoms selected from the group consisting of N, O, and S(O)ₚ, (CH₂)ᵣNR²ᵈR²ᵈ, (CH₂)ᵣN(→O) R²ᵈR²ᵈ, (CH₂)ᵣOR²ᵈ, (CH₂)ᵣ—C(O)NR²ᵈR²ᵈ, (CH₂)ᵣ—NR²ᵈC(O)R²ᵉ, (CH₂)ᵣ—C(O)R²ᵉ, (CH₂)ᵣ—NR²ᵈC(O) NR²ᵈR²ᵈ, (CH₂)ᵣ—NR²ᵈC(O)OR²ᵈ, (CH₂)ᵣ—NR²ᵈSO₂R²ᵈ, (CH₂)ᵣ—SO₂NR²ᵈR²ᵈ, and (CH₂)ᵣ—S(O)ₚR²ᵈ, provided that S(O)ₚR²ᵈ forms other than S(O)₂H or S(O)H;

R⁴ᵇ, at each occurrence, is selected from H, =O, OR³, CH₂OR³, F, Cl, CH₃, CH₂CH₃, NR³R³ᵃ, CH₂NR³R³ᵃ, C(O) R³, C(O)OR³ᶜ, NR³C(O)R³ᵃ, C(O)NR³R³ᵃ, SO₂NR³R³ᵃ, NR³SO₂-phenyl, S(O)₂CH₃, S(O)₂-phenyl, and CF₃;

R⁴ᶜ, at each occurrence, is selected from =O, OH, OCH₃, OCH₂CH₃, OCH₂CH₂CH₃, OCH(CH₃)₂, CH₃, CH₂CH₃, CH₂CH₂CH₃, CH(CH₃)₂, C₂₋₃ alkenyl, C₂₋₃ alkynyl, CH₂OH, CH₂OCH₃, CH₂OCH₂CH₃, CH₂OCH₂CH₂CH₃, CH₂OCH(CH₃)₂, F, Br, Cl, CF₃, NR²R²ᵃ, CH₂NR²R²ᵃ, N(→O)R²R²ᵃ, CH₂N(→O)R²R²ᵃ, C(O)R²ᶜ, CH₂C(O)R²ᶜ, NR²C(O)R²ᵇ, CH₂NR²C(O)R²ᵇ, C(O)NR²R²ᵃ, CH₂C(O) NR²R²ᵃ, SO₂NR²R²ᵃ, CH₂SO₂NR²R²ᵃ, NR²SO₂R⁵ᵃ, CH₂NR²SO₂R⁵ᵃ, S(O)ₚR⁵ᵃ, CH₂S(O)ₚR⁵ᵃ, CF₃, cyclopropyl substituted with 0–1 R⁴ᵇ, cyclobutyl substituted with 0–1 R⁴ᵇ, cyclopentyl substituted with 0–1 R⁴ᵇ, phenyl substituted with 0–1 R⁴ᵇ, —CH₂-cyclopropyl substituted with 0–1 R⁴ᵇ, —CH₂-cyclobutyl substituted with 0–1 R⁴ᵇ, —CH₂-cyclopentyl substituted with 0–1 R⁴ᵇ, benzyl substituted with 0–2 R⁴ᵇ, 5–6 membered aromatic heterocycle consisting of carbon atoms and from 1–4 heteroatoms selected from the group consisting of N, O, and S(O)ₚ and substituted with 0–2 R⁴ᵇ, and (CH₂)- 5–6 membered aromatic heterocycle consisting of carbon atoms and from 1–4 heteroatoms selected from the group consisting of N, O, and S(O)ₚ and substituted with 0–2 R⁴ᵇ;

$R^{4d}$, at each occurrence, is selected from H, $OCH_3$, $CH_3$, $CH_2CH_3$, $CH_2CH_2CH_3$, $CH(CH_3)_2$, $NR^2R^{2a}$, $NR^2C(O)R^{2b}$, $NR^2SO_2R^5$, phenyl, 2-oxo-pyrrolidinyl, and 2-oxo-piperidinyl;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR_3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

In a thirteenth embodiment, the present invention provides a novel compound selected from formula $Id_{1.1-3.1}$ and $Ie_{1.1-3.1}$:

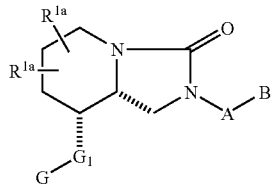

$Id_{1.1}$

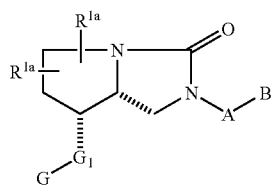

$Ie_{1.1}$

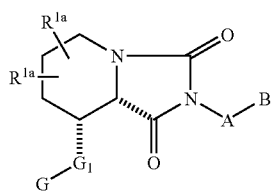

$Id_{2.1}$

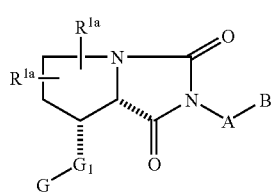

$Ie_{2.1}$

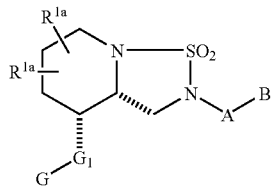

$Id_{3.1}$

-continued

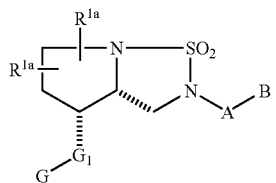

$Ie_{3.1}$ wherein:
G is selected from:

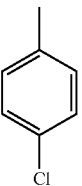 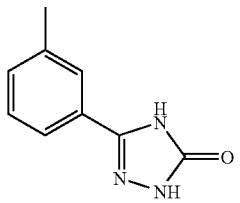

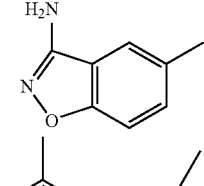 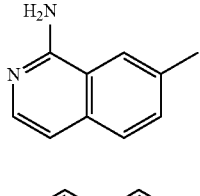

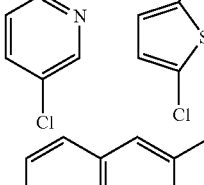 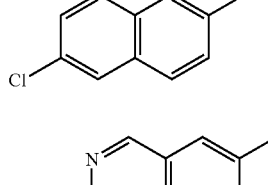

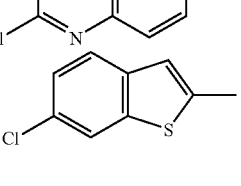 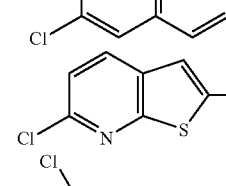

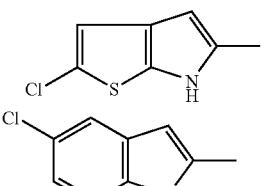 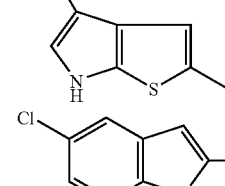

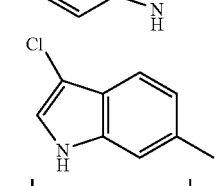 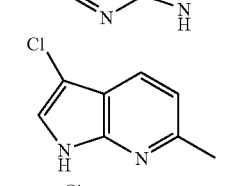

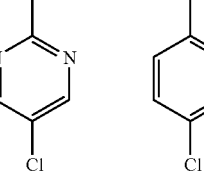 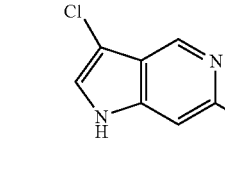

-continued
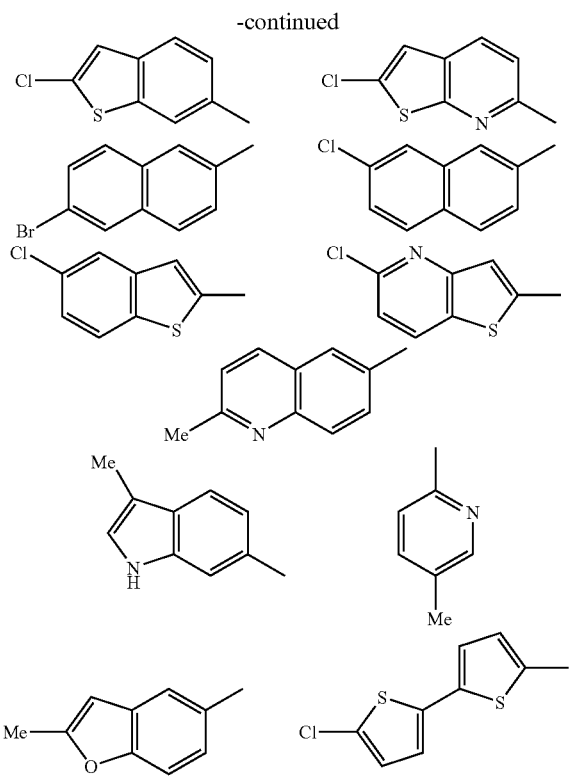
G₁ is CH₂NH, C(O)NH, NHC(O), NHC(O)C(O)NH, and the right side of G₁ is attached to ring G;
A is selected from the group: phenyl, 2-pyridyl, 2-pyrimidyl, and 2-F-phenyl, wherein B is substituted at the 4-position of A;
B is selected from:
-continued
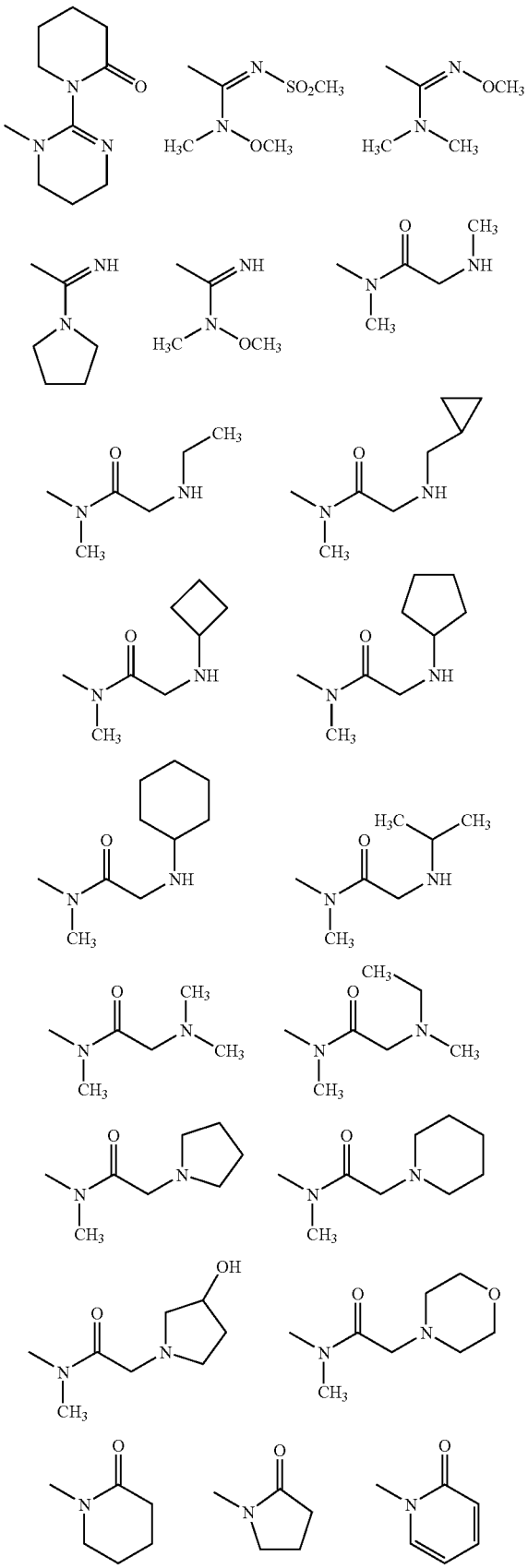

-continued

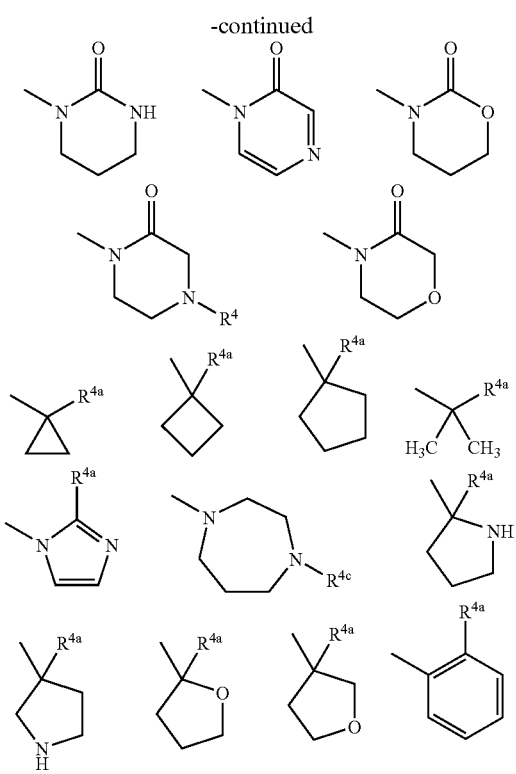

alternatively, A—B is selected from 4-(2-propyl)-piperidinyl and 4-(N,N-dimethylamino)-piperidinyl;

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or $C(O)$—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^2e$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $SO_2NR^{2d}R^{2d}$, $CH_2SO_2NR^{2d}R^{2d}$, $S(O)_pR^{2d}$, $CH_2S(O)_pR^{2d}$, 5–6 membered carbocycle substituted with 0–2 $R^{4c}$, —$(CH_2)$- 5–6 membered carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CH_2)$- 5–6 membered heterocycle substituted with 0–2 $R^{4c}$ and consisting of: carbon atoms and 1–4 heteroatoms selected from the group consisting of N, O, and $S(O)_p$ provided that $S(O)_pR^{2d}$ forms other than $S(O)_2H$ or $S(O)H$; and $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

In a fourteenth embodiment, the present invention provides a novel compound selected from formula $Id_{1.1}$ and $Ie_{1.1}$:

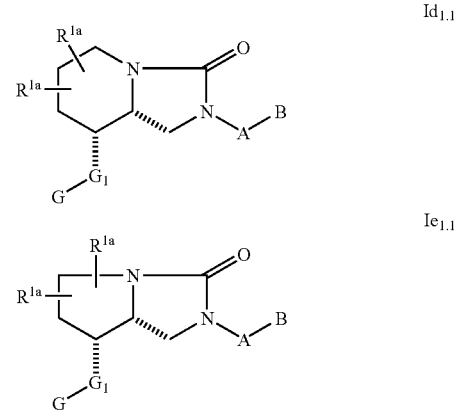

wherein:

A—B is selected from:

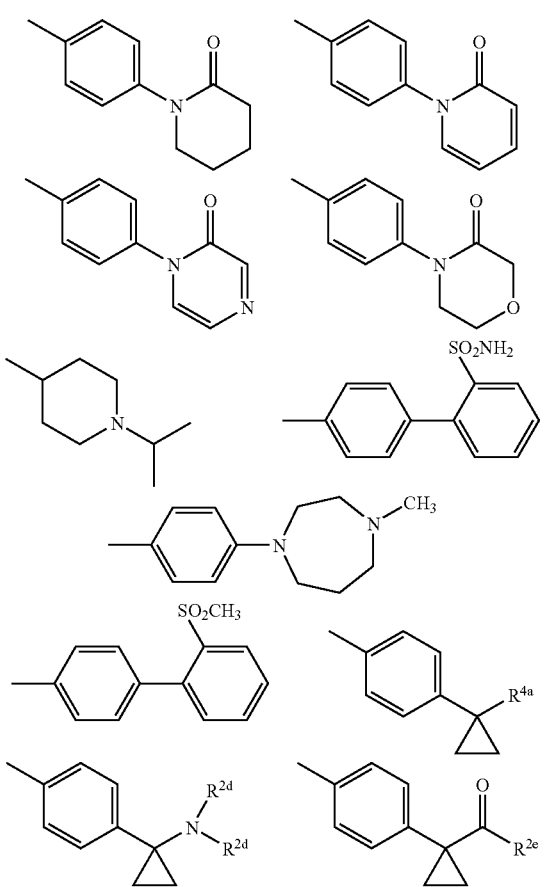

-continued
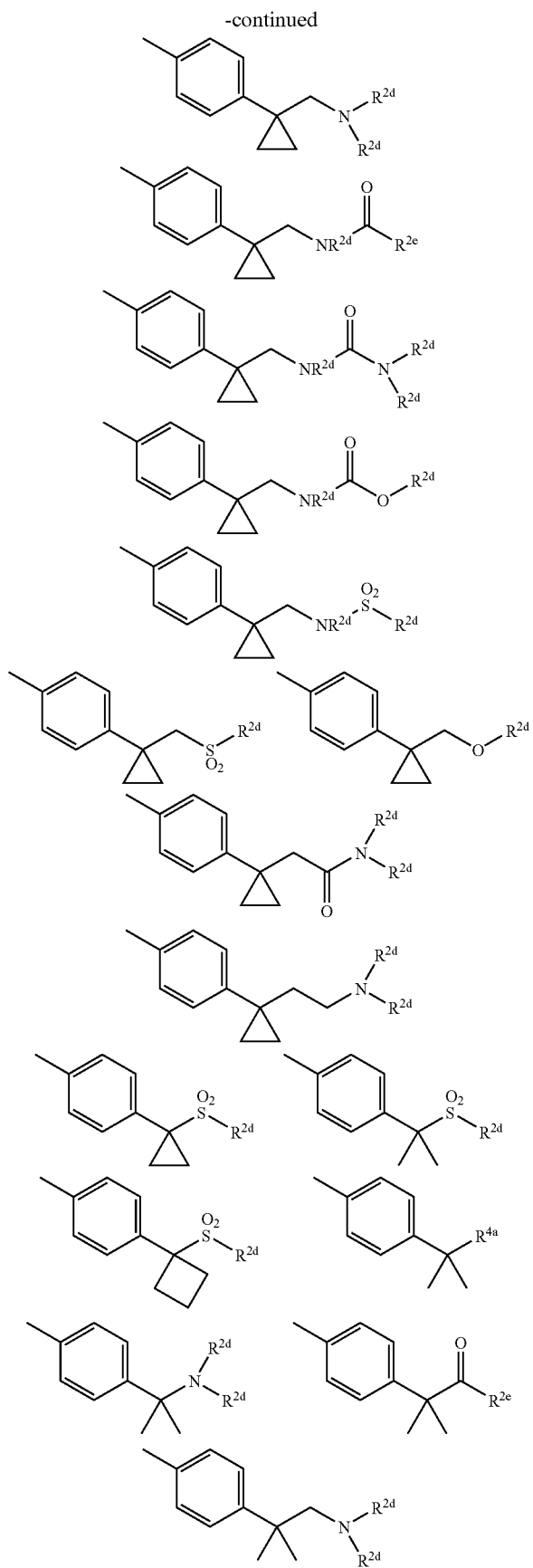
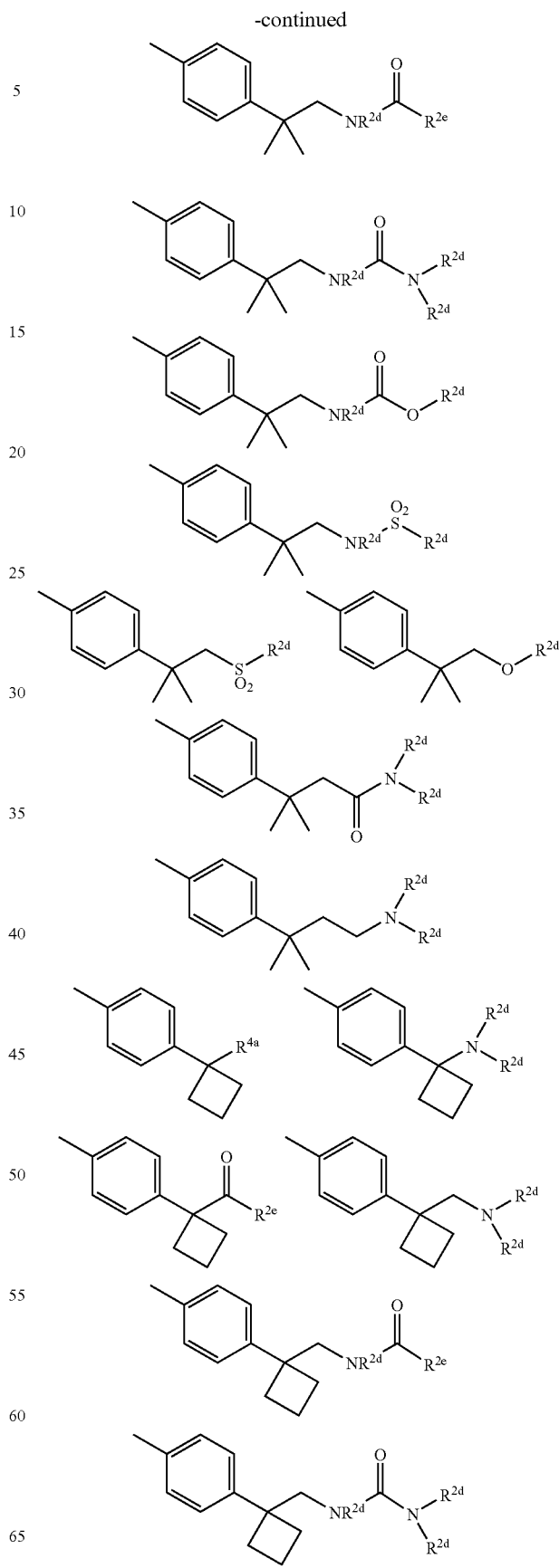

-continued
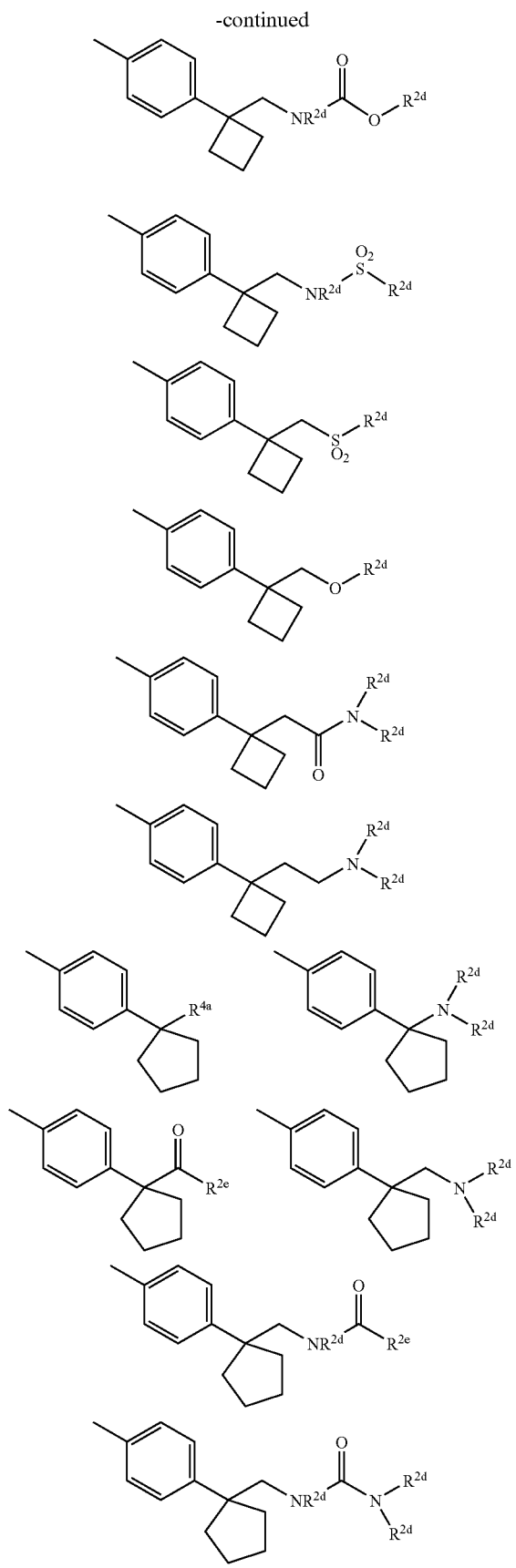
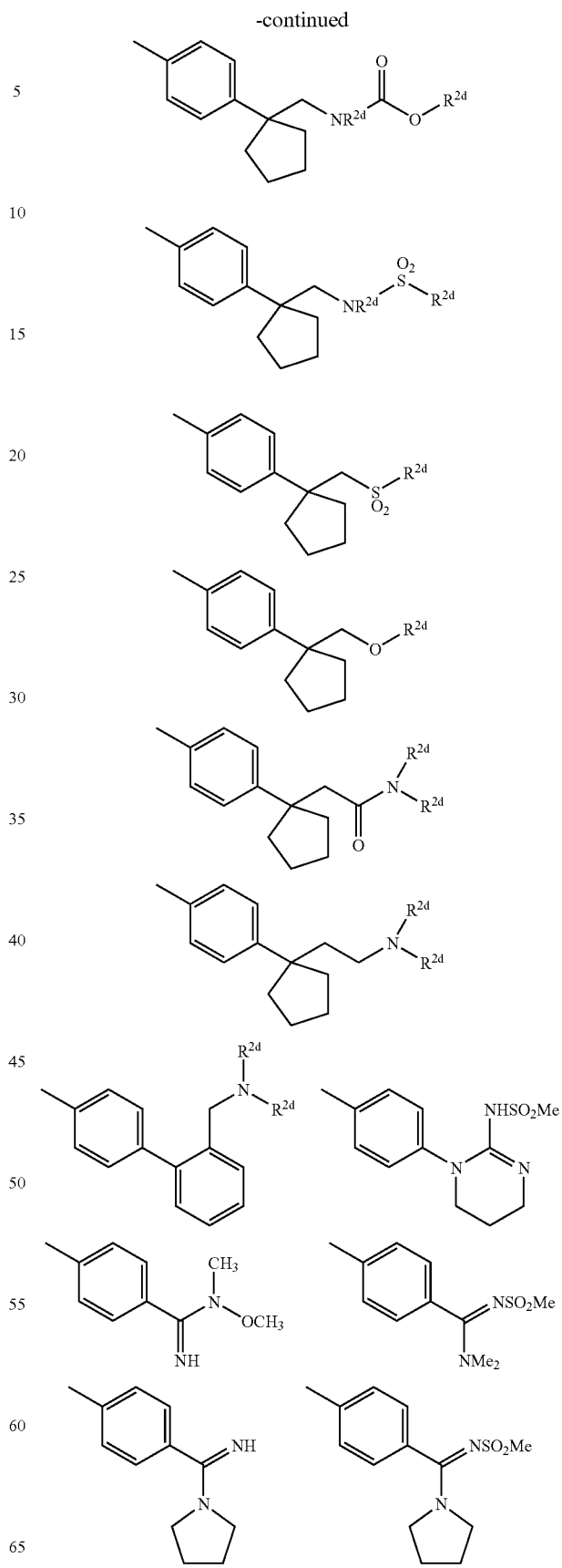

-continued

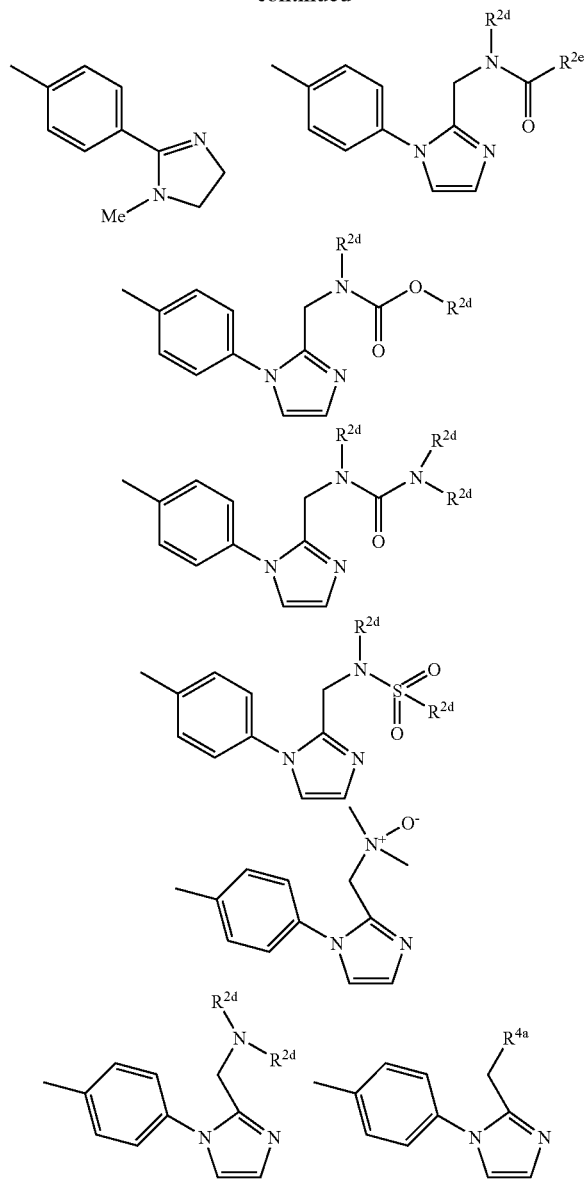

$R^{2d}$, at each occurrence, is selected from H, CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$CCH, CH$_2$CH$_2$OH, CH$_2$C(O)NR$_2$, cyclopropyl, CH$_2$-cyclopropyl, cyclobutyl, cyclopentyl, and thiazolyl;

$R^{2e}$, at each occurrence, is selected from CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$-cyclopropyl, cyclopropyl, and cyclopentyl;

$R^{4a}$ is substituted with 0–2 $R^{4c}$ and selected from morpholine, 1,1-dioxo-thiomorpholine, dihydropyridine, piperidine, piperazine, pyrrolidine, imidazole, imidazoline, imidazolidine, oxazoline, and thiazoline; and $R^{4c}$ is selected from =O, OH, OCH$_3$, and CH$_3$.

In a fifteenth embodiment, the present invention provides a novel compound selected from Examples 3–6 or a pharmaceutically acceptable salt thereof.

In a sixteenth embodiment, the present invention provides a novel compound selected from the Examples of Table 1 and Table 2 or a pharmaceutically acceptable salt thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder.

In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfmpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of a thromboembolic disorder.

In another preferred embodiment, the present invention provides a novel article of manufacture, further comprising:
(a) (d) a second container;
wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:
(d) a second container;
wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of: carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of: carbon atoms and 1, 2, 3, or 4 heteroatoms independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethane-sulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

All references cited herein are hereby incorporated in their entirety by reference.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). Examples of suitable blocking groups and their uses are also described in "The Peptides: analysis, Synthesis, Biology", Academic Press, Vol.3 (Groii, et. al. Eds., 1981). Functional group transformations and coupling reactions that can be used to prepare compounds of the present invention are described in "Advanced Organic Chemistry: Reaction, Mechanism, and Structure", (March, et. al. fourth Ed.) and "Comprehensive Organic Transformations", (Larock, second Ed.).

Compounds having the general structures of formula Ia, Ib, or Ic can be prepared as shown in schemes 1–15. For example, as shown in Scheme 1, an appropriately amine and itaconic acid 1a can be converted to 1b under refluxed condition in toluene (*J. Org. Chem.*, 1980, 45, 810). Reduction of the acid group to hydroxyl followed by a standard three-step conversion of hydroxyl to amino group, should provide amine 1d. The formation of desired target can be completed by reacting an appropriately substituted acid, or sulfonyl chloride, or isocyanide.

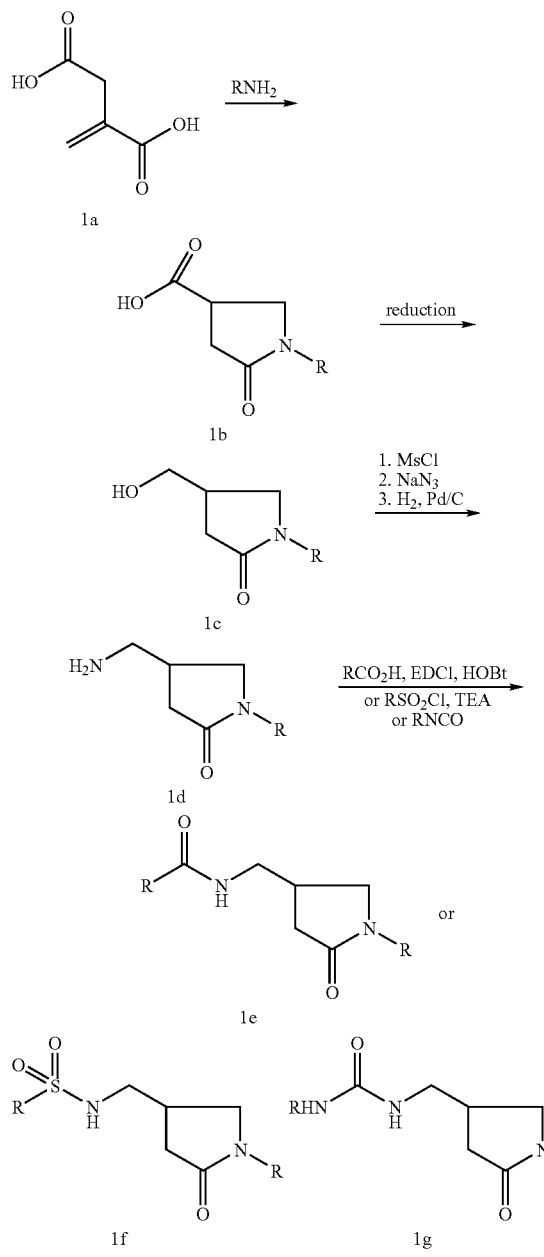

appropriate amine should provide the corresponding secondary amine, which under reflux condition in an appropriate solvent should yield 2b (*Helvetica Chimica Acta*, 2002, 85, 4046). Target compounds can be obtained via procedures known to those skilled in the art.

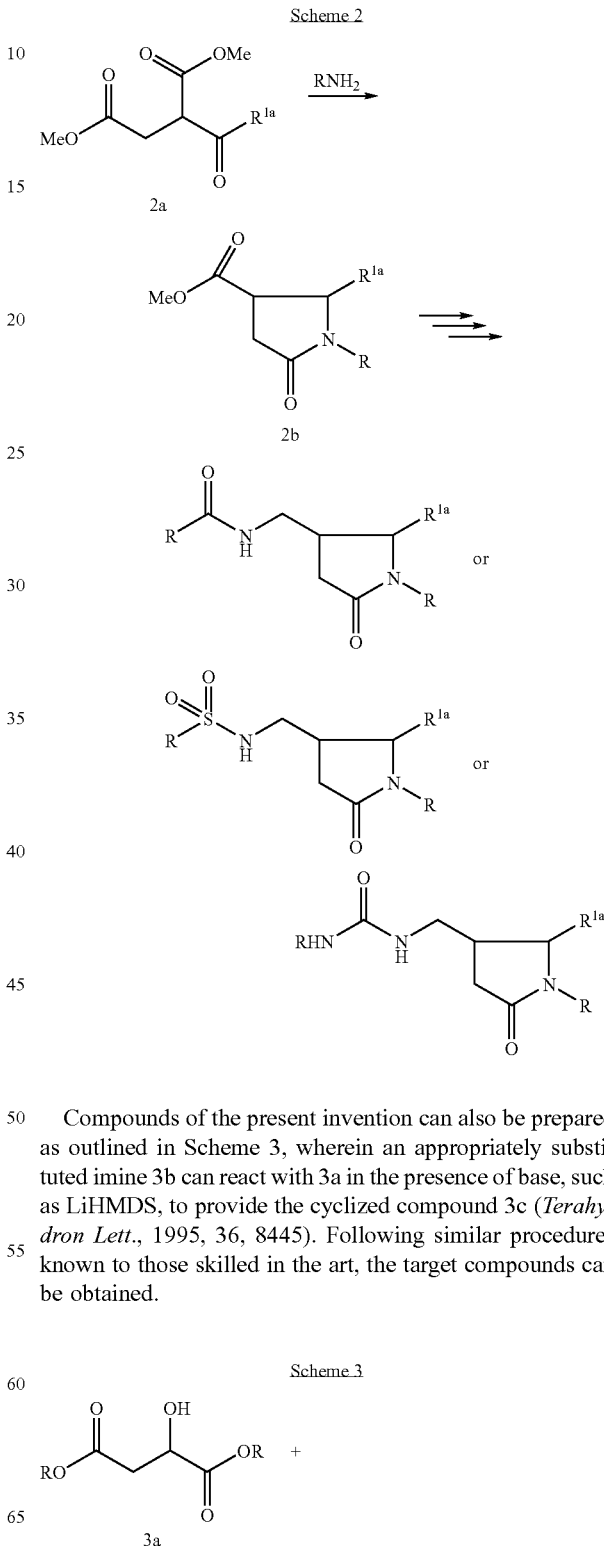

Compounds of the present invention can also be prepared as outlined in Scheme 3, wherein an appropriately substituted imine 3b can react with 3a in the presence of base, such as LiHMDS, to provide the cyclized compound 3c (*Terahydron Lett.*, 1995, 36, 8445). Following similar procedures known to those skilled in the art, the target compounds can be obtained.

Compounds of the present invention can also be prepared as outlined in Scheme 2. Reductive amination of 2a with an

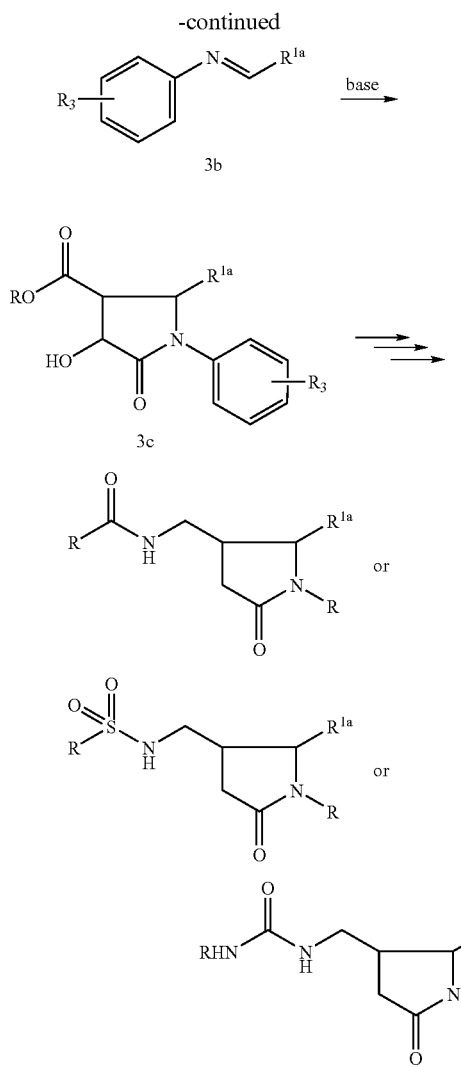

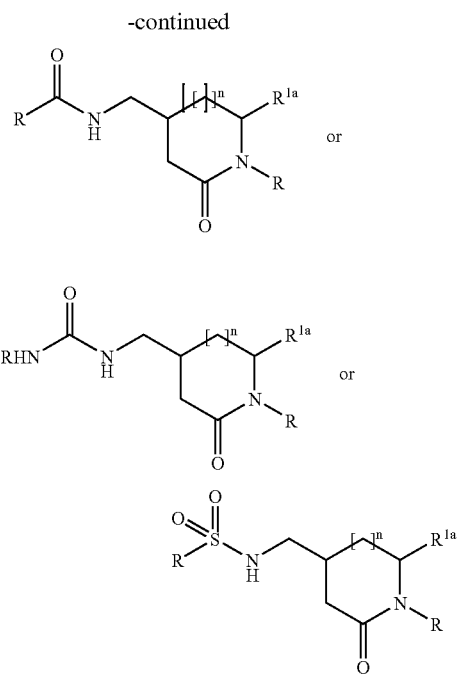

n = 0–2

Compounds of the present invention can also be prepared as outlined in Scheme 5. Compound 5a can be converted to lactam 5b under acid and base treatments. Then Ullmann or Buchwald reaction should provide 5c, which can be converted to target compounds via procedures described in the art.

Similarly, compounds of the present invention can also be prepared as outlined in Scheme 4. Reductive amination of an appropriate amine with 4a followed by cylization should provide 4b, which can follow procedures similar to those described and known to those of skill in the art to produce target compounds.

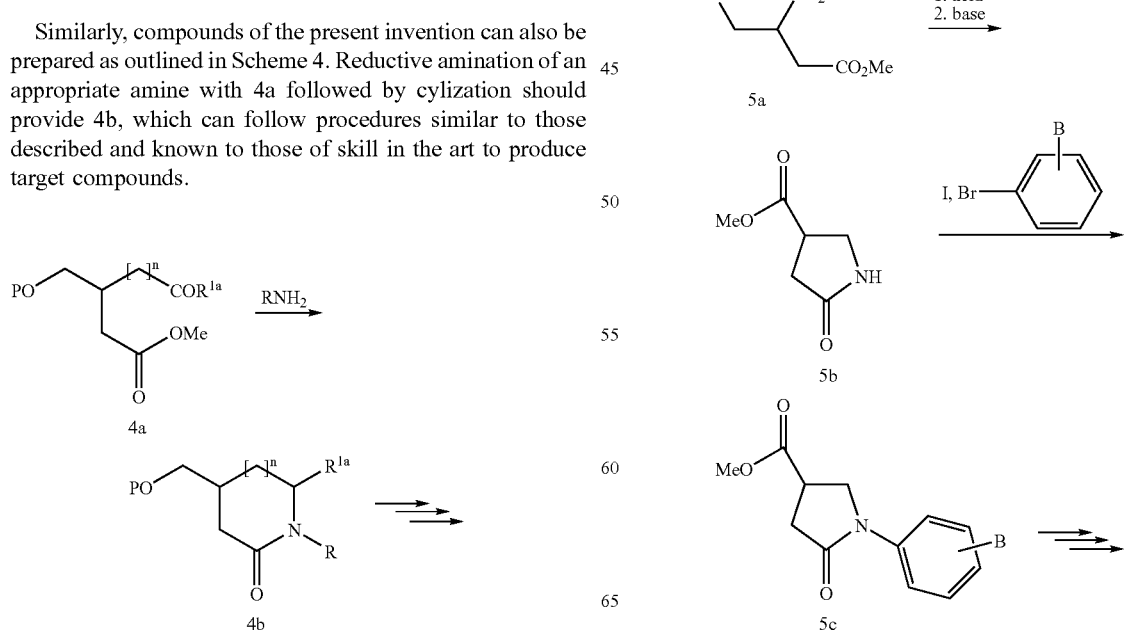

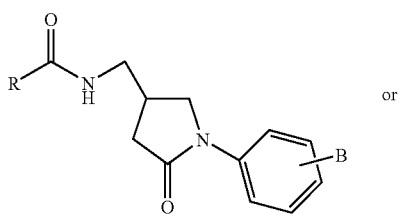

or

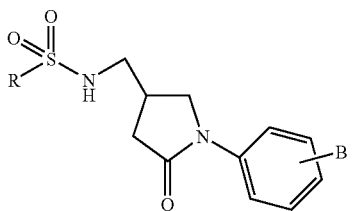

or

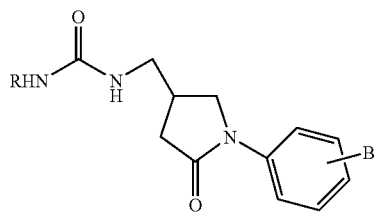

Compounds of the present invention with variable ring sizes can be prepared as outlined in Scheme 6. Dienoate 6a can be converted to hydroxyl acid 6b via procedures described by Kishi (*Tetrhedron Lett.*, 1995, 36, 4579). Functional group manipulation and cyclization can give lactam 6d, which under Ullmann or Buchwald condition should yield 6e. Deprotection and acylation or sulfonation should provide the target compounds.

Scheme 6

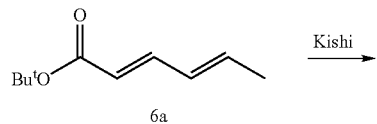

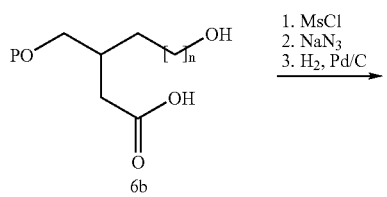

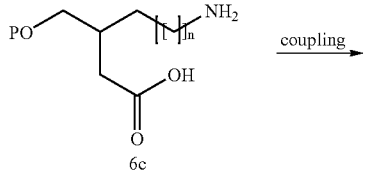

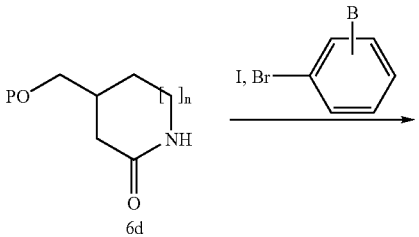

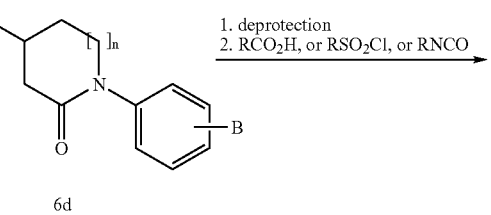

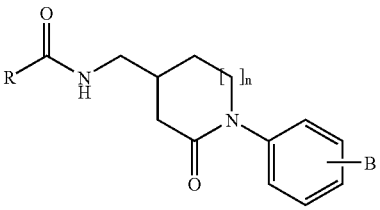

or

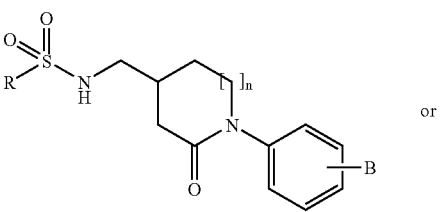

or

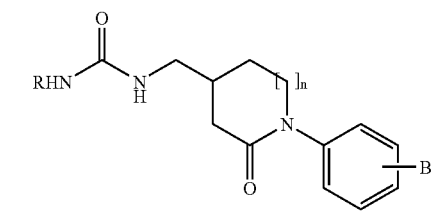

n = 0–2

Compounds of the present invention with variable ring sizes are also prepared as outlined in Scheme 7. Treatment of 7a with appropriate amine 7b under coupling conditions should yield compound 7c. Sulfide 7c can be converted to its corresponding sulfonium salt by treatment with methyl iodide, and then to lactam 7d under basic conditions such as $K_2CO_3$ or KHMDS. Following the procedures known to those skilled in the art, compounds of the present invention can be obtained. (*Tetrahedron* 1984, 40, 1433; *Organic Lett.* 2000, 2, 1101; Klapers et al. *JACS*, 2001, 123, 7727; *Tet. Lett.*, 1999, 40, 2657).

Scheme 7

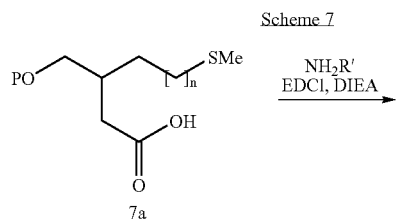
7a

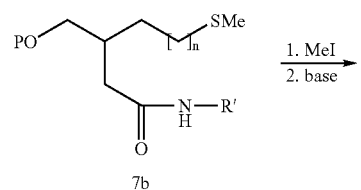
7b

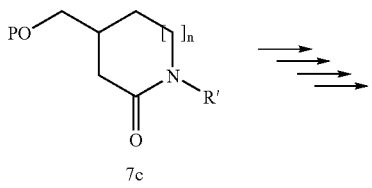
7c

Scheme 8

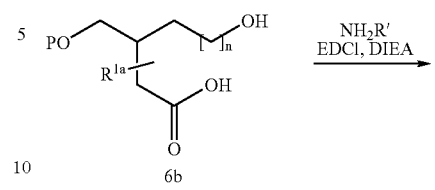
6b

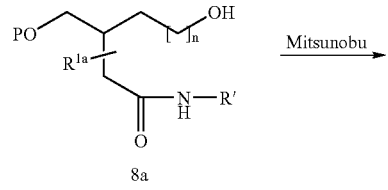
8a

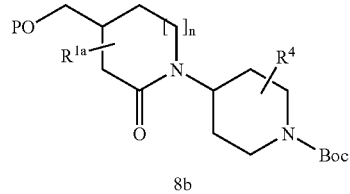
8b

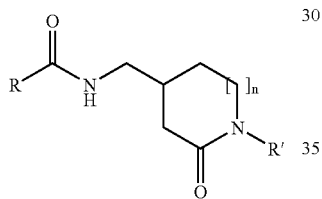

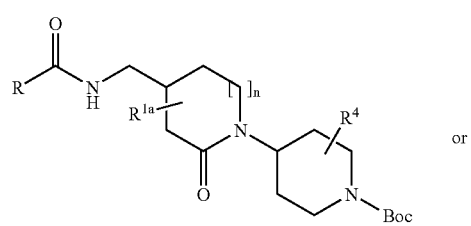

or

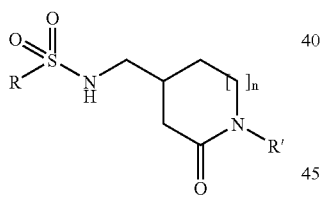

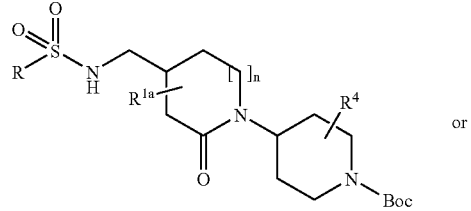

or

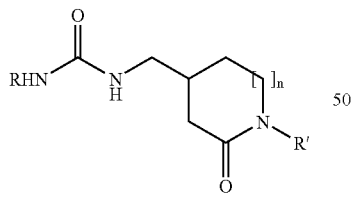

n = 0–2

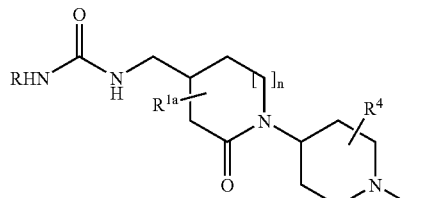

n = 0–2

Compounds of the present invention can also be prepared as outlined in Scheme 8. Acid 6b can be coupled with appropriate amine to give compound 8a. Under Mitsunobu conditions (Mitsunobu, *Synthesis*, 1981, 1), 8a can be converted to lactam 8b, which can then be converted to a compound of the present invention via procedures known to those skilled in the art.

Alternately, the fully elaborated A—B moiety can be prepared as a heterocyclic amine derivative as shown in Scheme 9. Cyclization of 9a should give heterocycle 9b, which then can be converted to compounds of the present invention via procedures known to those skilled in the art.

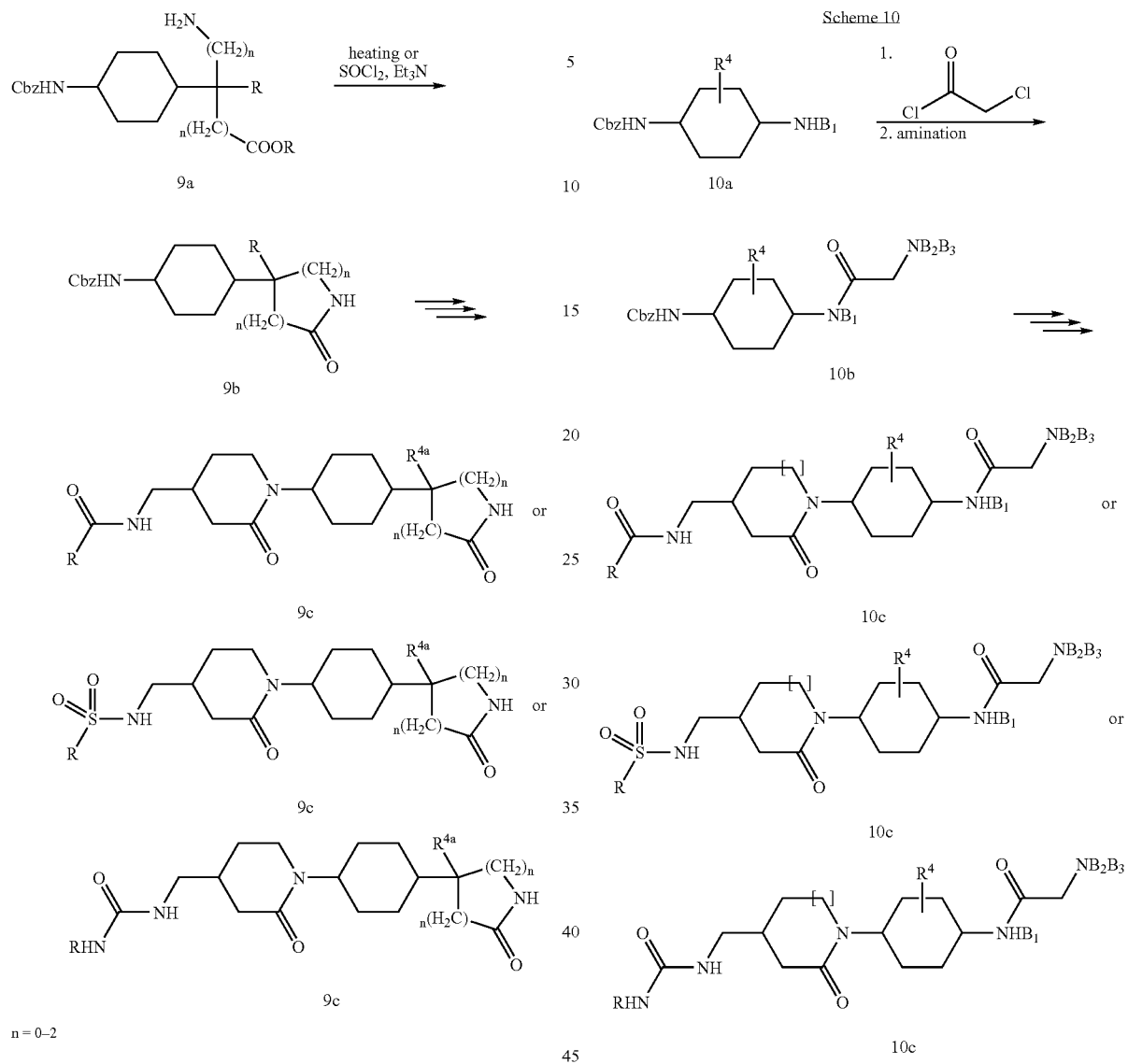
A fully elaborated A—B moiety, such as 10b, can also be prepared as shown in Scheme 10, which then can be converted to 10c via procedures known to those skilled in the art.
Ahe fully elaborated A—B moiety, such as 11b and 11c can be prepared as shown in Scheme 11, which then can be converted to 11d and 11e via procedures known to those skilled in the art.
Scheme 11
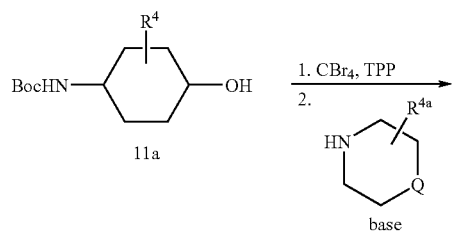

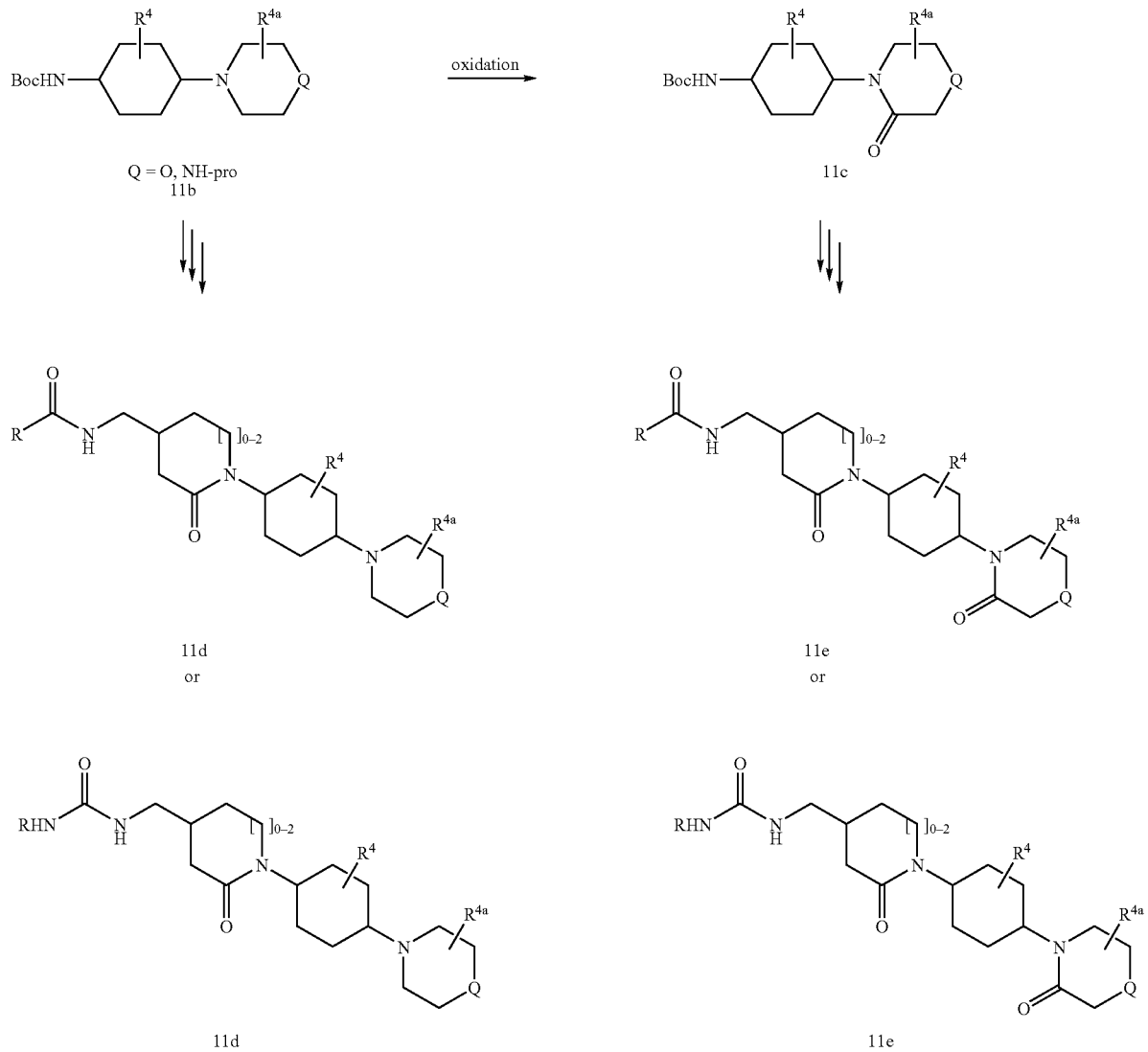
Alternately, compounds of the present invention can be prepared as described in Scheme 12. An appropriately substituted amine 12a can react with an appropriately substituted halogenated acyl chloride to give lactam 12b, which can then be converted to compounds of the present invention via procedures known to those skilled in the art.
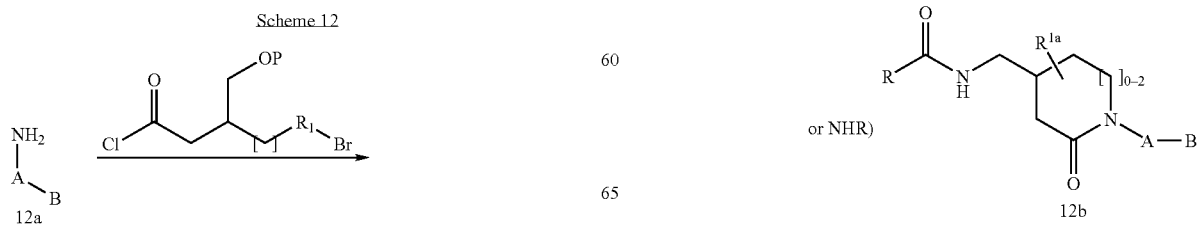

A fully elaborated A—B moiety, such as 13c, can be prepared via Ullmann or Buckwald methodology starting from 13a and 13b as shown in Scheme 13. Following similar procedures known to those skilled in the art, the target compound can be obtained.

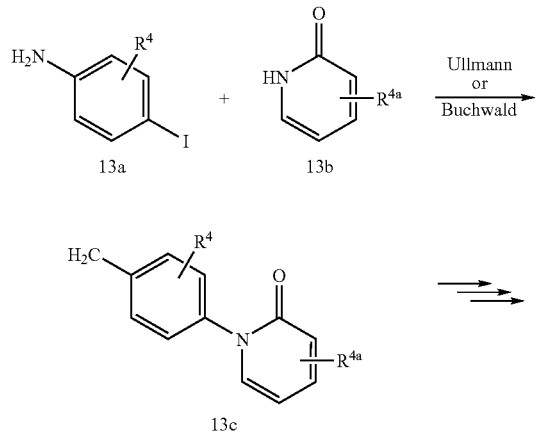

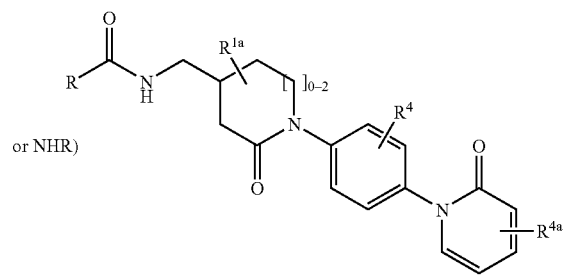

A fully elaborated A—B moiety, such as 14c, can be prepared as illustrated in Scheme 14. Iodoaniline 14a can be aminated with benzophenone imine using Wolfe method (*Tetrahydron Lett.* 1997, 38, 6367) to provide the monoprotected diaminobenzene 14b. Acylation with 5-bromovaleryl-chloride followed by cyclization in the presence of base should give aryllactam 14c, which can be converted to a compound of the present invention via procedures known to those skilled in the art.

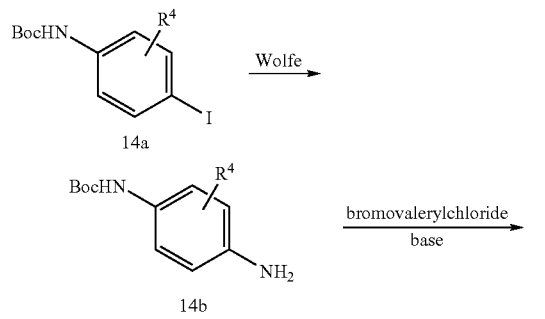

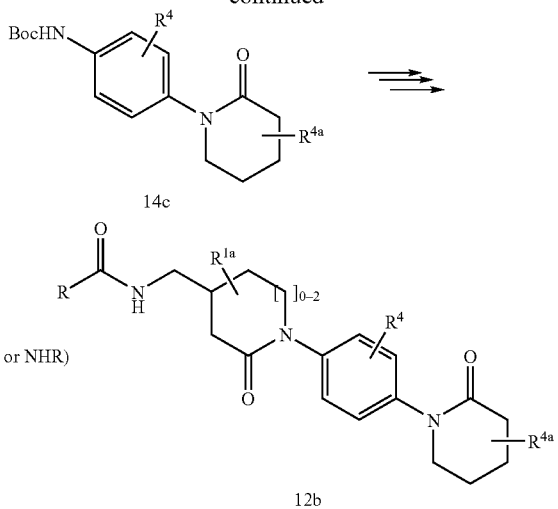

A fully elaborated A—B moiety, such as 15b, can be prepared as illustrated in Scheme 15. Ullmann or Buckwald chemistry can also applied to prepared 15b, which can be subsequentially converted to compounds of the present invention via procedures known to those skilled in the art.

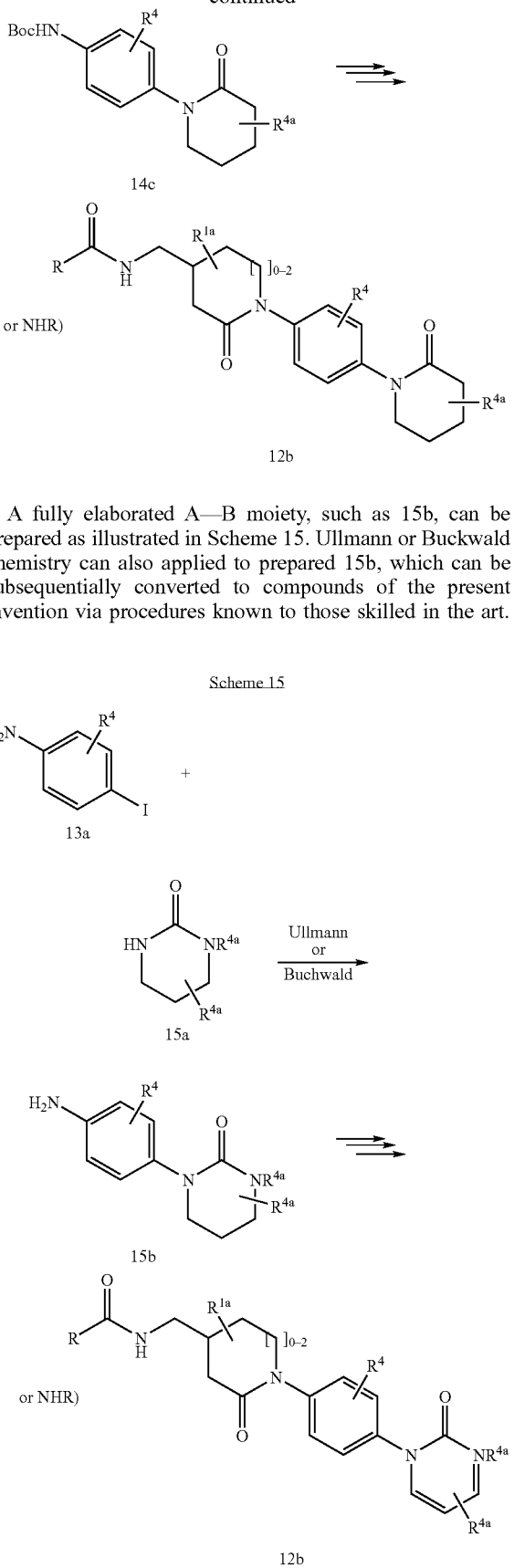

Construction of compounds with general structures of formula Id or Ie can be performed in the following direction: from W—A—B (W is $NH_2$, I, Br, etc) to compounds of formula IId or IIe where Rg is a stable group attached to the bicyclic ring during the process of preparing compounds of formula IId or IIe. The Rg group in compounds of formula IId or IIe can be transformed to the "reactive" intermediate of formula IIId or IIIe, and then reacted with compounds of formula IVd or IVe, containing G groups under standard coupling conditions known in the literature and by ones skilled in the art, to provide compounds of formula Id or Ie of the present invention. The general route that involves this type of methodology is outlined in Scheme 1.

Scheme 16

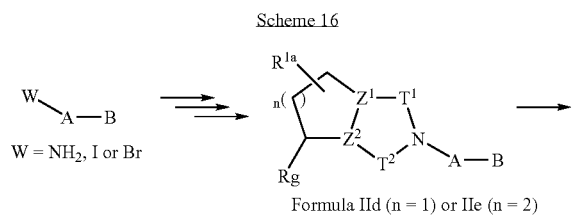

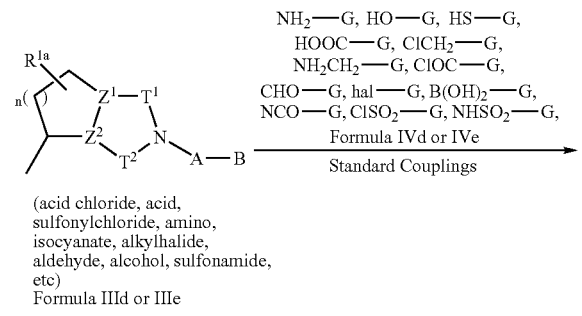

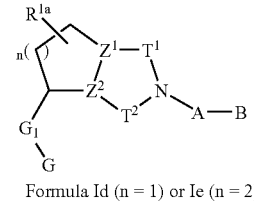

Formula Id (n = 1) or Ie (n = 2)

Intermediates of formula IId and IIe can be prepared by using the methods described in the following synthetic schemes (Scheme 17 to Scheme 21) from intermediates W—A—B, wherein W is $NH_2$, I, or Br, and by using relevant published literature procedures that are known to those skilled in the art.

As shown in Scheme 17, intermediates of formula IId and IIe ($Z^1$=N, $Z^2$=CH, $T^1$ is C=O or C=S, and $T^2$ is $CH_2$) can be prepared from appropriately protected five-membered or six-membered monocyclic intermediates 16, which can be readily prepared from commercially available materials or by using methods known in the literature and by one skilled in the art. The carboxylic acid intermediate 16 can be treated with a reducing agent, such as $BH_3$ and $LiAlH_4$, to form the alcohol 17, which can then be oxidized to form the aldehyde 18 by using an oxidizing agent, such as Dess-Martin periodinate. Reductive amination of the aldehyde 18 and the amine of formula $NH_2$—A—B in the presence of sodium triacetoxyborohydride can give the intermediate 19. Removing N-protecting group (PG) of 19 can then be achieved by methods known in the literature or by one skilled in the art to give diamino intermediate 20. Intermediate 20 can be treated with phosgene or phosgene equivalent in the presence of a base, such as triethylamine, to provide the compounds of formula IId and IIe. Alternatively, compounds of formula IId and IIe can be obtained from the methyl ester intermediate 21. Urea formation of 21 with isocyanate of formula OCN—A—B in a solvent, such as toluene, tetrahydrofuran, or methylene chloride, with a base, such as triethylamine, can provide the intermediate 22. Treatment of 22 with a reducing agent, such as $LiAlH_4$ or super hydride, can afford the alcohol intermediate 23. Treatment of 23 with an activating agent, such as mesyl chloride or tosyl chloride, in the presence of a base such as potassium tert-butoxide or an equivalent reagent, can generate the compound of formula IId or IIe.

Scheme 17

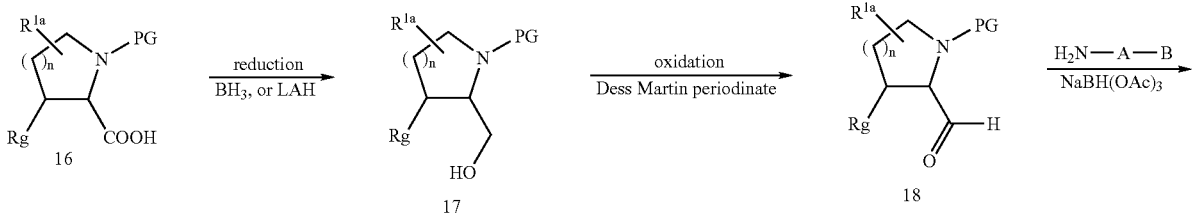

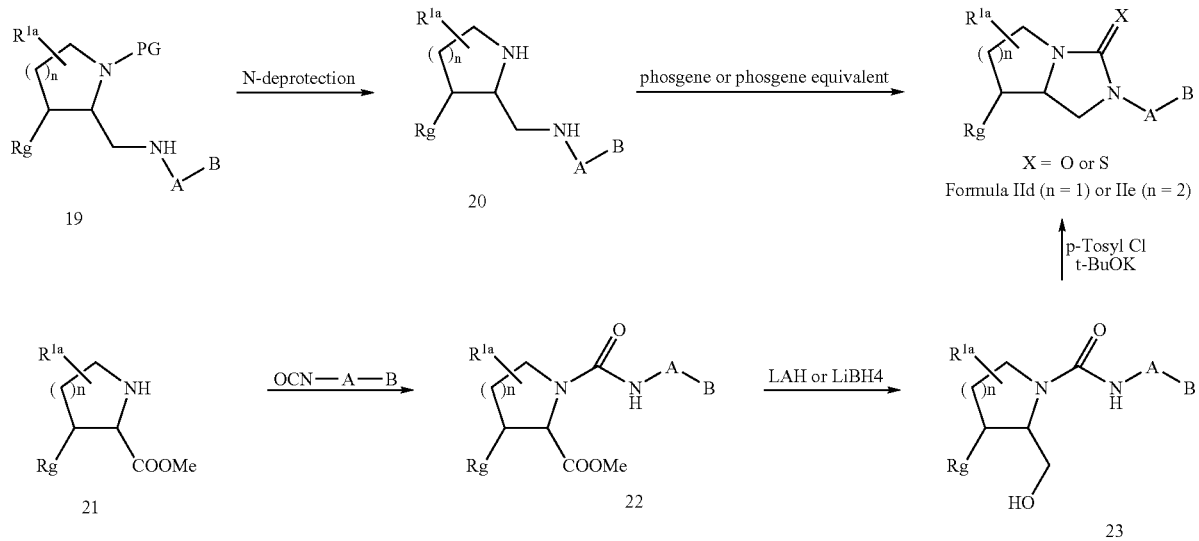

On the other hand, as illustrated in Scheme 18, intermediates of formula IId or IIe ($Z^1$=N, $Z^2$=CH, $T^1$ is C=O or C=S, and $T^2$ is $CH_2$) can also be prepared via an intermediate of formula of W—A—B (wherein W can be I, Br, TfO, etc.) via either Copper(I)-catalyzed Ullmann-type aromatic amination of aryl iodides and aryl bromides, heating in DMSO with either N-methylglycine or L-proline as a ligand (Ma, Dawei, et. al, *Organic Letters* 2003, 5, 2453–2455); or ethylene glycol as the ligand while heating in 2-propanol (Buchwald, S. L., et al., *Organic Letter* 2002, 4, 581–584); or via Pd(0)-catalyzed amination of aryl iodides in the presence of palladium (such as $Pd_2(dba)_3$), a suitable ligand (such as 1,1'-biphenyl-2-yldicyclohexylphosphine), and NaOt-Bu (Buchwald, S. L. et. al., *Journal of Organic Chemistry* 2001, 66, 2560–2565). Thus, alcohol intermediate 17 can be translated to an azide intermediate 24 by first activating the alcohol with mesyl chloride, etc , and then reacting with sodium azide. Reduction of the azide 24 to the primary amine 25 can be carried out either by hydrogenation or by using $PPh_3/THF/H_2O$ conditions.

The primary amine 25 can react with the compounds of formula W—A—B in the presence of a palladium catalyst to afford the intermediate of formula 26. N-deprotection of 26 can be achieved by methods known in the literature or by one skilled in the art to give diamino intermediate 27. The intermediate 27 can be treated with phosgene or phosgene equivalent in the presence of a base, such as triethylamine, to provide the intermediates of formula IId or IIe. Alternatively, intermediate 28 bearing a L group (such as phenyl or benzyl group) as a protecting group can be prepared as discussed previously. Deprotection of L by hydrogenation under high pressure can afford the intermediate 29, which can be reacted with compound of formula W—A—B (wherein W is I or Br) in the presence of Pd(0) or under Ullman coupling conditions to provide the intermediates of formula IId or IIe of the present invention.

-continued

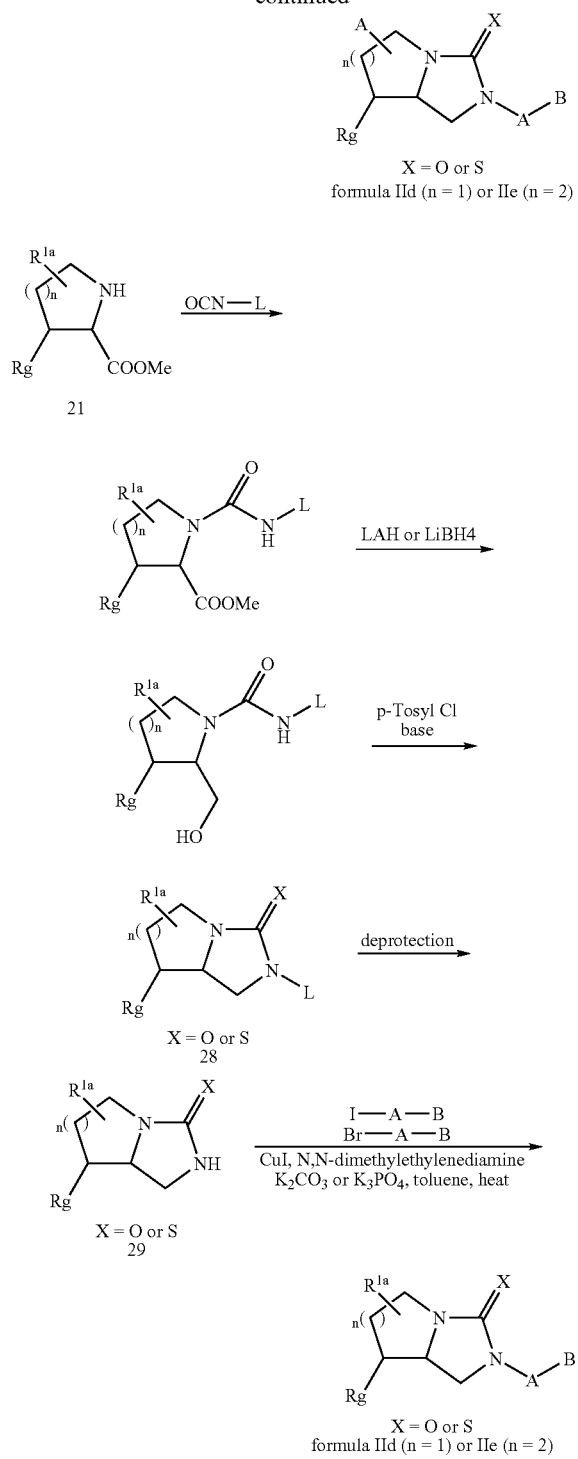

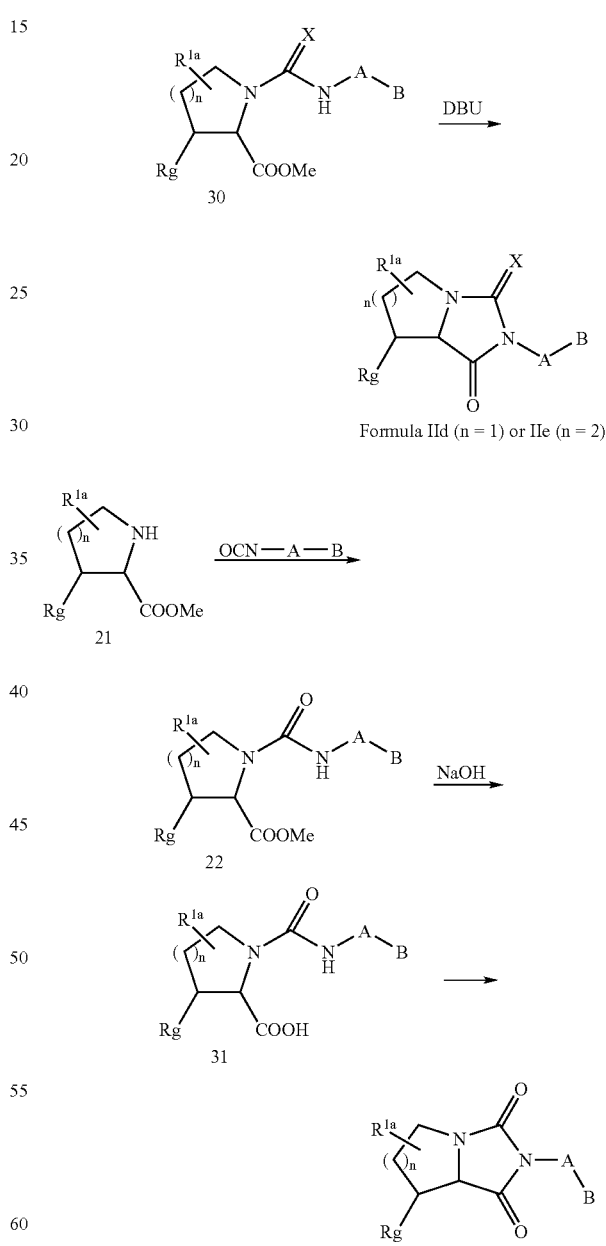

treated with a suitable coupling reagent such as DCC, can also form intermediates of formula IId or IIe of the present invention.

Scheme 19

Scheme 4 shows the preparation of intermediates of formula IId or IIe when $Z^1=N$, $Z^2=C$, $T^1$ is C=O or C=S, and $T^2$ is C=O. Treatment of methyl ester 21 with an isocyanates or thioisocyanates of formula X=C=N—A—B can afford intermediate 30, which can be treated with a base, such as DBU, to yield intermediates of formula IId or IIe. On the other hand, hydrolysis of the methyl ester in intermediate 22 using NaOH to give the acid 31, which is Scheme 20 shows the preparation of intermediates of formula IId and IIe ($Z^1=N$, $Z^2=C$, $T^1$ is $SO_2$, and $T^2$ is C=O or $CH_2$) starting from the diamine intermediate 20.

Scheme 20

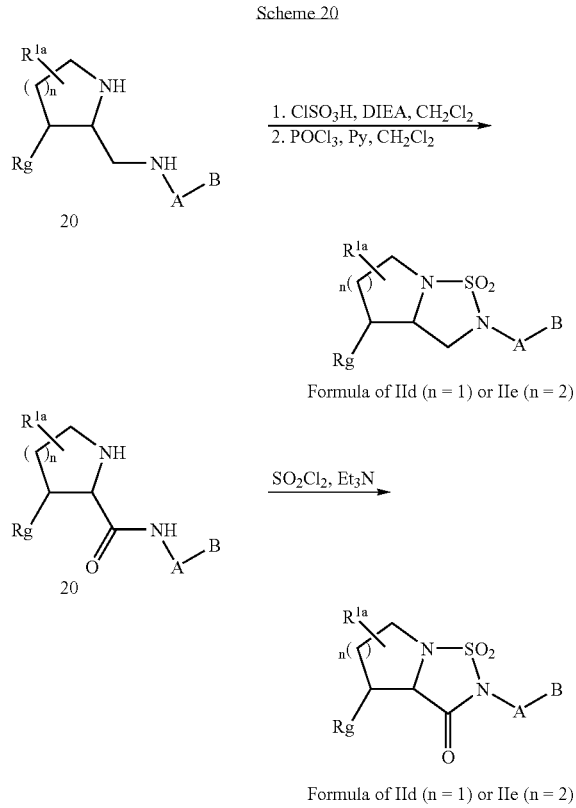

Scheme 21 also depicts the preparation of intermediates of formula IId and IIe ($Z^1$=C, $Z^2$=N, $T^1$ is $CH_2$, and $T^2$ is C=O.)

Scheme 21

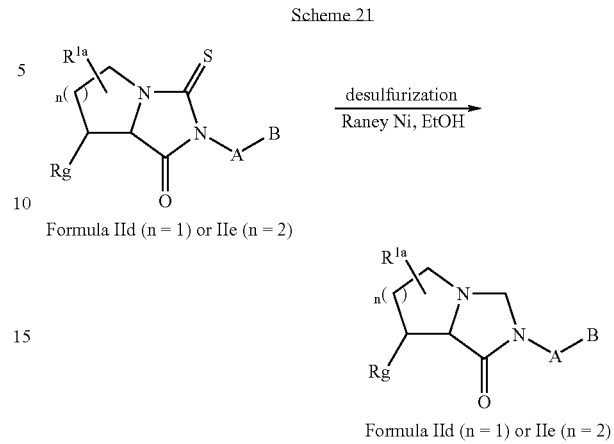

Scheme 22 describes general methods of converting the intermediate of formula IId or IIe to compounds of the present invention of formula Id or Ie wherein linker $G_1$ can be —NHCO—, —NHCOCONH—, —NHCOC(S)NH—, —NHC(S)CONH—, —NHSO$_2$—, or —NHCH$_2$—. The intermediates of formula IId or IIe where Rg is a properly protected alcohol can be obtained by the methods described in schemes 17–23 and by those skilled in the art. O-deprotection can be achieved by known literature method or by those skilled in the art. The alcohol intermediate 34 can be activated and then displaced with NaN$_3$ to afford the azide intermediate 35, which under reduction gives the amine intermediate 36. Coupling of the amine 36 with a variety of reagents containing the G group can provide a variety of compounds of formula Id or Ie.

Scheme 22

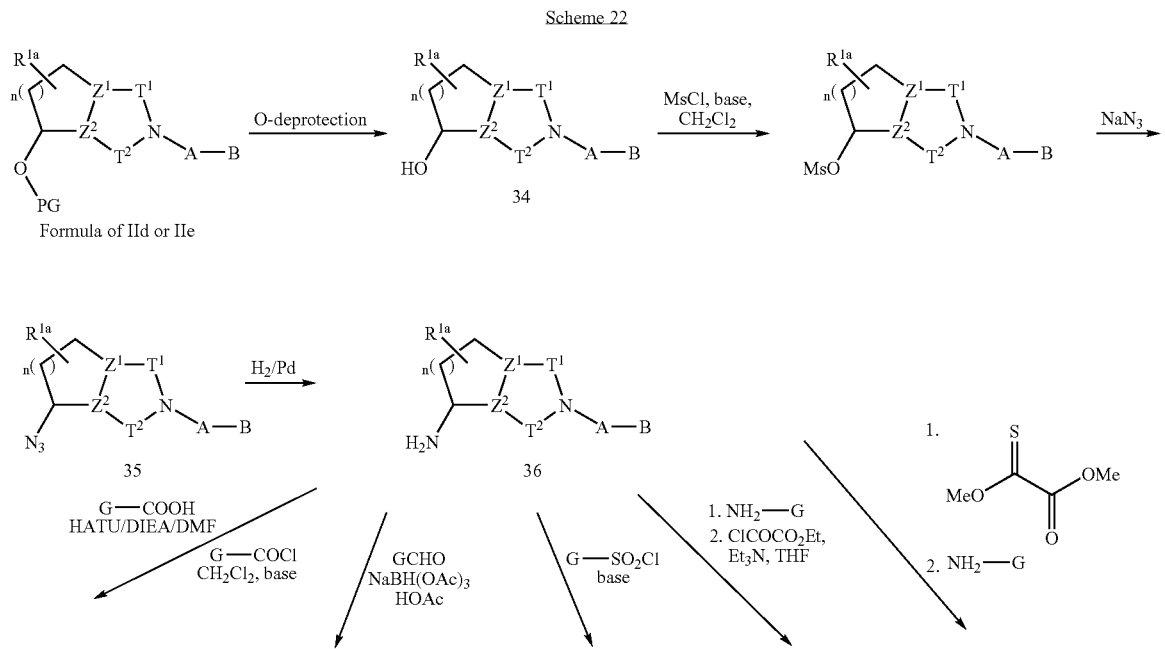

-continued

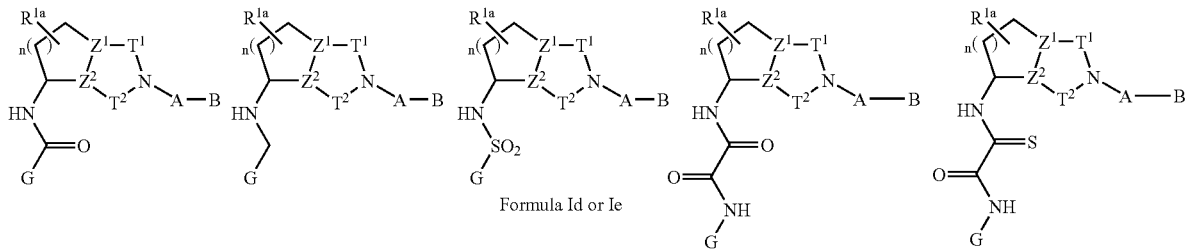

Formula Id or Ie

A series of compounds of the present invention of formula Id or Id wherein $G_1$ is 1,1-dioxo-sulfonylmethyl can be prepared following the sequence outlined in Scheme 23.

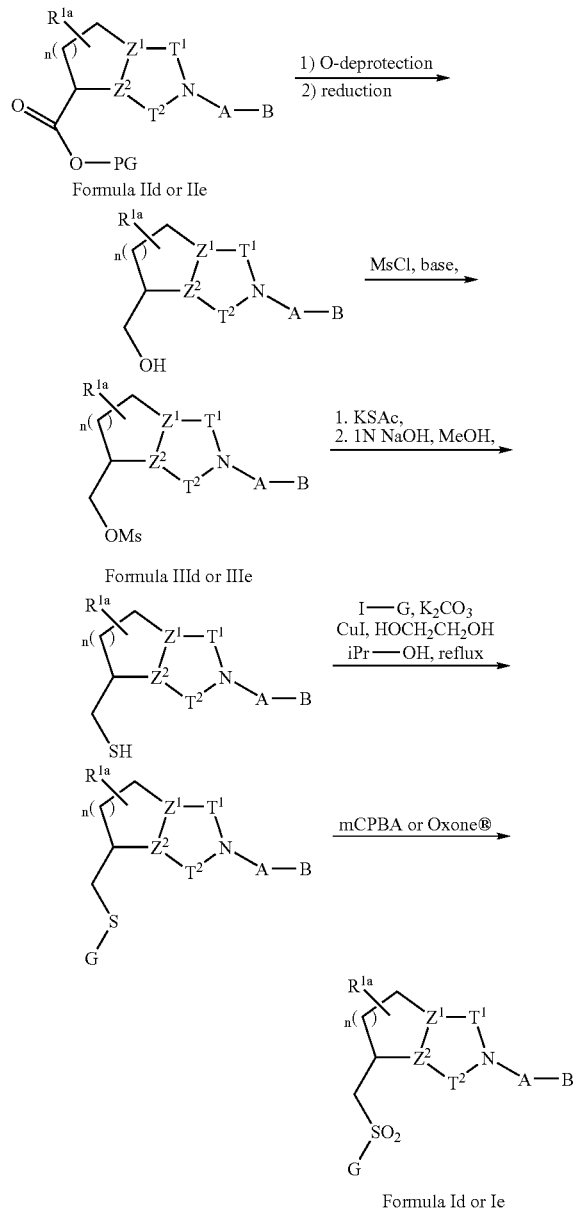

Formula Id or Ie

The functionalized G moiety of the present invention can be prepared using methods known to those of ordinary skill in the art. All of the following patents and publications are incorporated herein by reference. For compounds wherein G is a ring substituted with a basic moiety, one of ordinary skill in the art can look to U.S. Pat. Nos. 5,939,418, 5,925,635, 6,057,342, 6,187,797, 6,020,357, 6,060,491, 6,191,159, 6,339,099, 6,271,237, 6,399,644, 6,407,256, 6,413,980, WO02/00651, WO02/102380, WO02/094197, U.S. 2003/78,255, and U.S. 2003/18,023 for starting materials. For compounds wherein G is a ring substituted with a non-basic group, one of ordinary skill in the art can look to U.S. Pat. Nos. 5,998,424, 6,413,980, 6,399,644, 6,407,256, WO02/00651, WO02/102380, WO02/094197, U.S. 2003/78,255, and U.S. 2003/18,023 for starting materials. For compounds wherein G is a bicyclic moiety, one of ordinary skill in the art can look to U.S. Pat. Nos. 6,339,099, 6,369,227, 6,413,980, WO02/00651, WO02/102380, WO02/094197, U.S. 2003/78,255, and U.S. 2003/18,023 for starting materials. For compounds wherein A is an indoline or similar bicycle, one of ordinary skill in the art can look to U.S. Pat. No. 6,429,205 for starting materials and intermediates to which the present B group can be coupled or from which the present A—B groups can be formed.

The A—B intermediates of the present invention wherein A is a substituted phenyl and B is

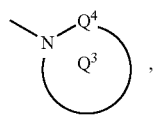

wherein $Q^4$ is CO or $SO_2$, and $Q^3$ is a 5–7 membered ring containing 0–1 hetero atom, can be prepared by methods shown in Scheme 24–29 and by those skilled in the art.

The A—B intermediates can be obtained via the Ullman reaction or Buchwald modified Ullman reaction (*J. Am. Chem. Soc.* 2001, 123, 7727) using CuI and 1,2-cyclohexyldiamine or 1,10-phenanthroline as the catalyst as outlined in Scheme 24.

Scheme 24
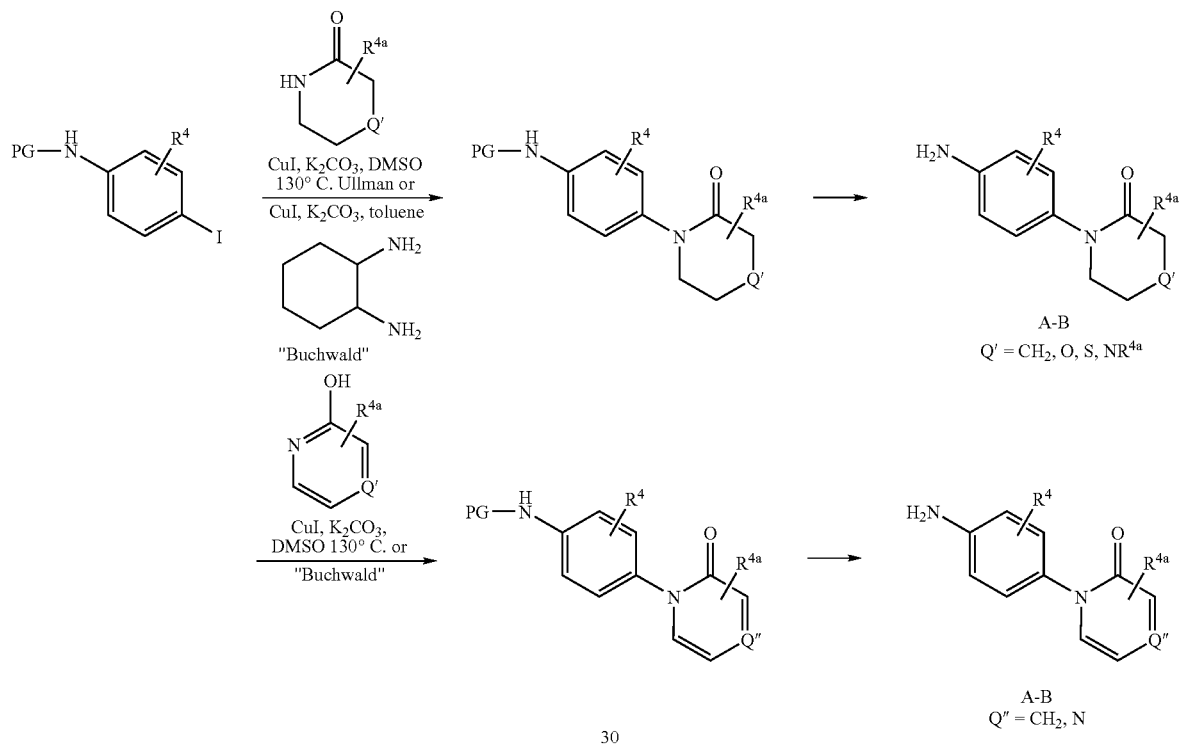
The Ullman coupling methodology can also be applied to prepare the cyclic urea or cyclic carbamate analogs shown in Scheme 25.
Scheme 25
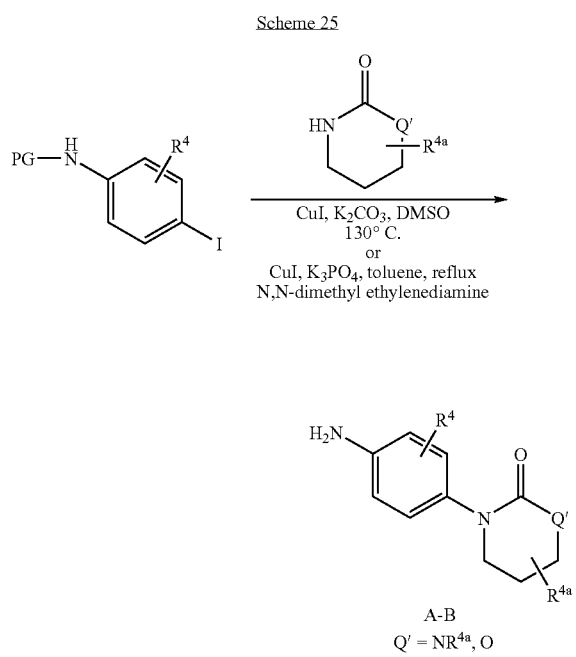
The lactam A—B group can also be prepared via aromatic nucleophile displacement of substituted halo-nitrobenzenes followed by reduction and other transformations as shown in Scheme 11.
Scheme 26
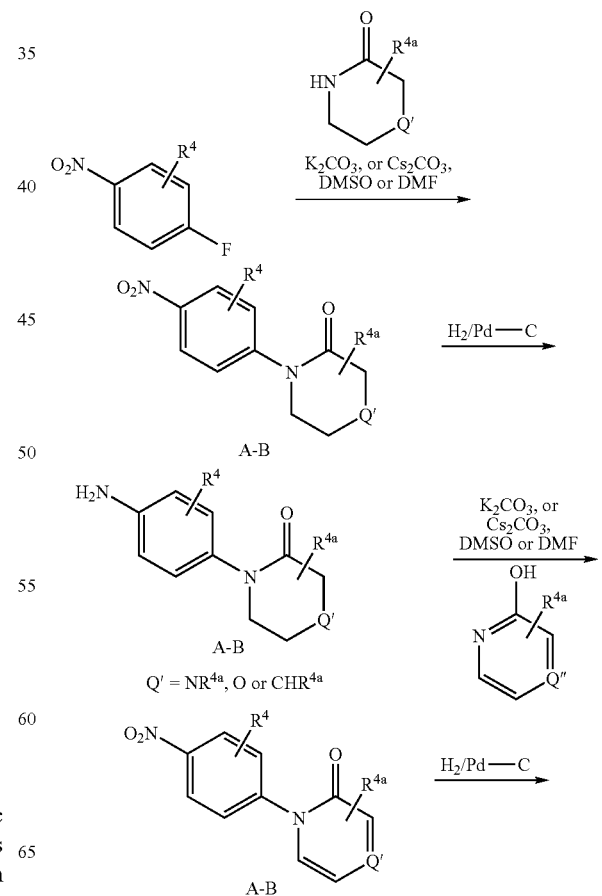

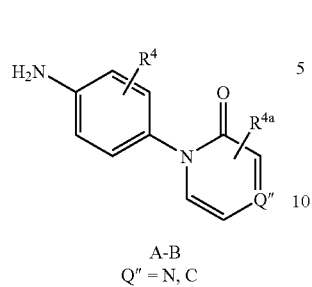
The lactam containing A—B intermediates can also be prepared via aromatic nucleophilic substitution of fluoronitrobenzenes with the 5–7 membered bases followed by α-carbon oxidation with KMnO$_4$ as shown in Scheme 27.
Scheme 27
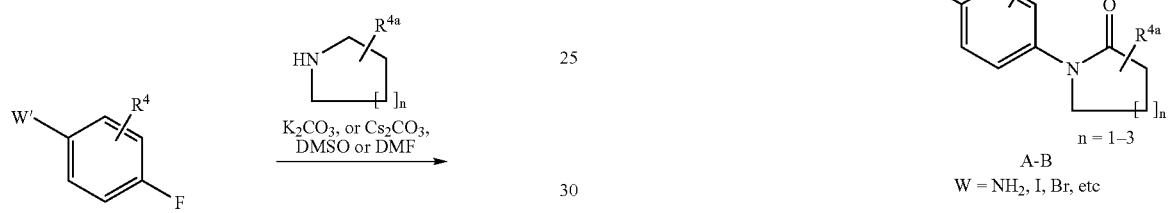
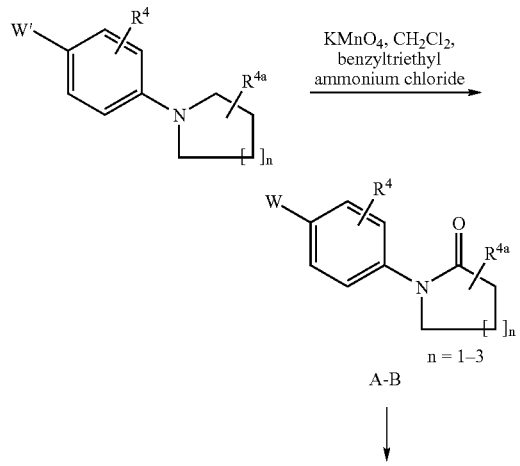
Lactam, cyclic sulfonamide, cyclic urea, and cyclic carbamate A—B analogs can be prepared via the method outlined in Scheme 28.
Scheme 28
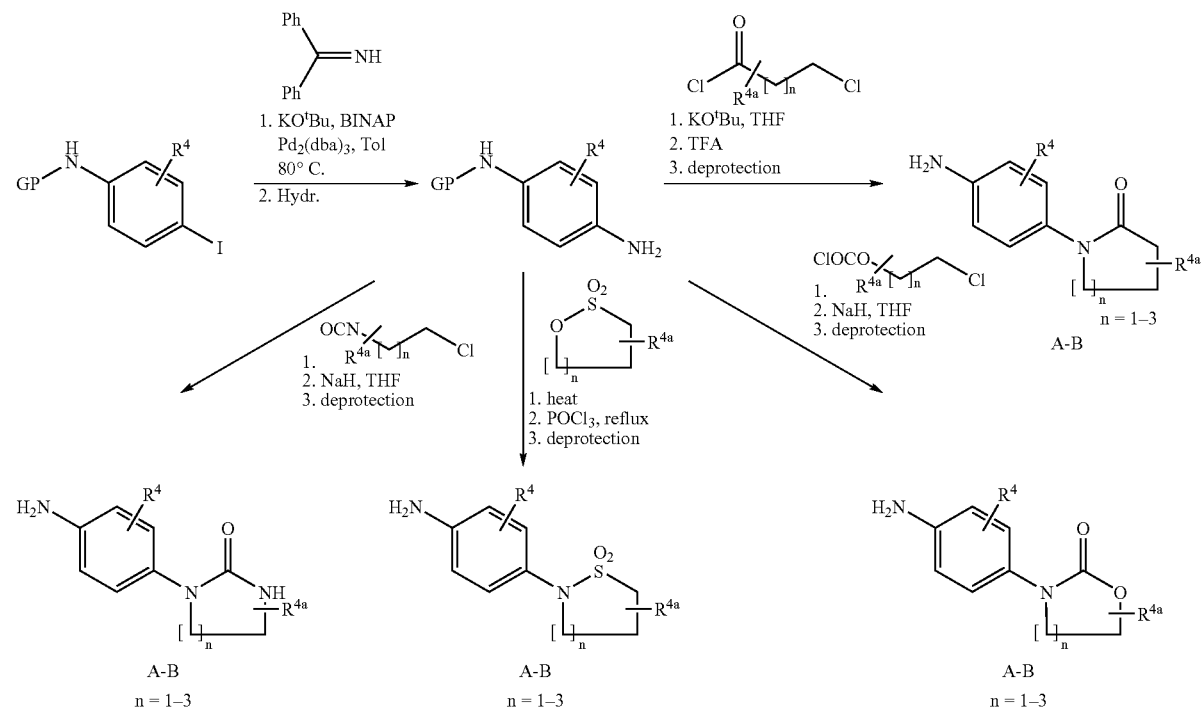

The piperidone A—B groups shown above can also be further elaborated to afford other compounds of the present invention by numerous methods known to those skilled in the art as shown in Scheme 29.

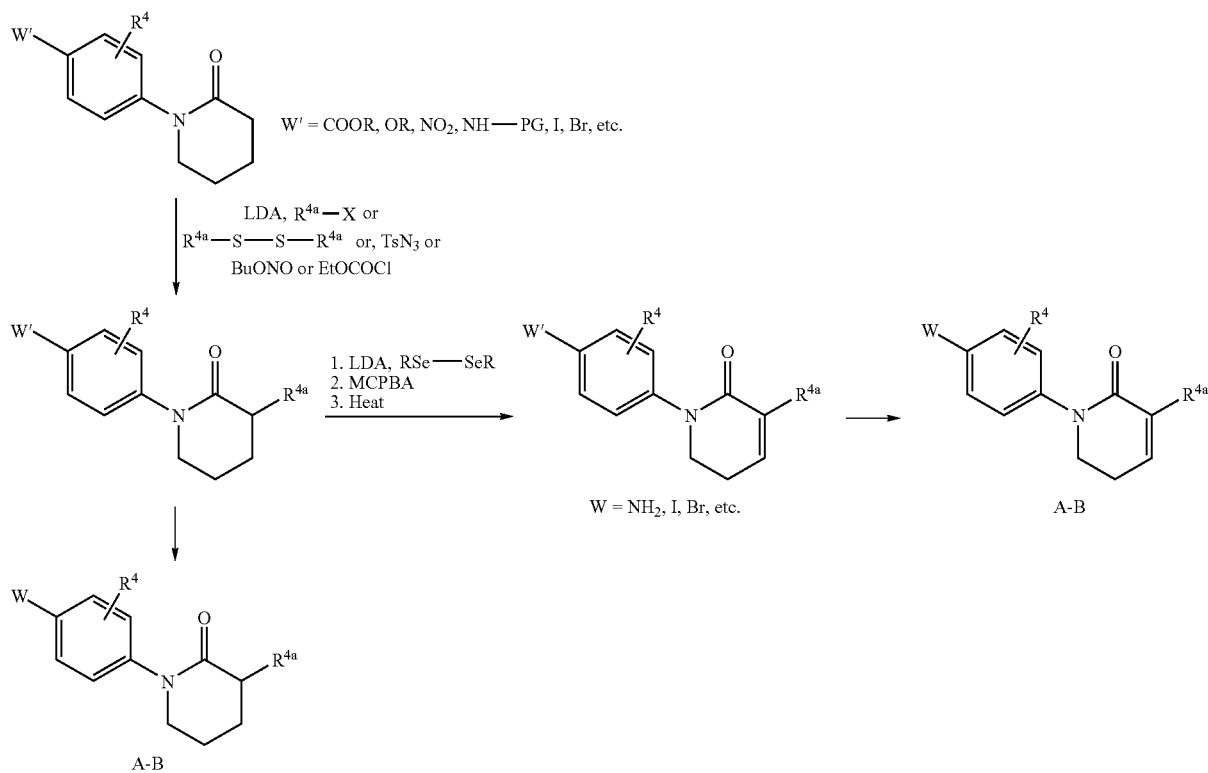

Ortho-substituted pyridyl and pyrimidyl A—B analogs wherein B is a lactam-containing group (see structures in Scheme 30), can also be prepared using routes similar to those of Schemes 24–29.

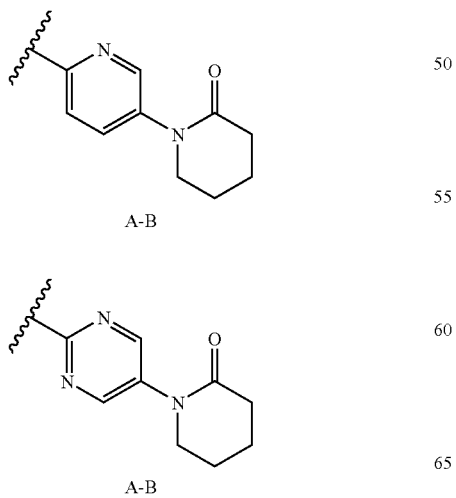

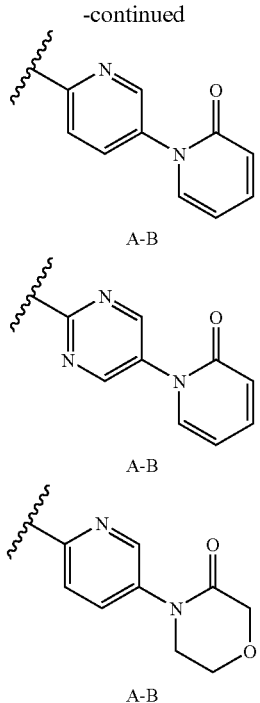

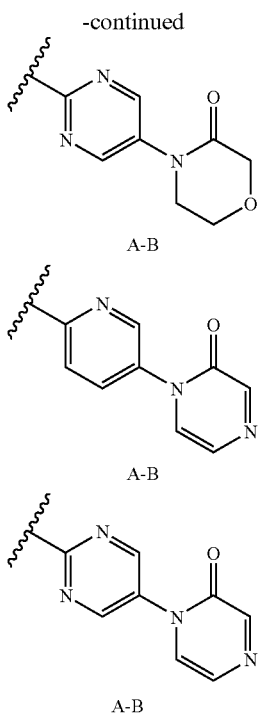

The non-aromatic A—B intermediates in Scheme 16 wherein A is a cyclohexyl ring and B is a lactam ring, can be synthesized via procedures known to those skilled in the art. These intermediates can than be further manipulated to incorporate substituent $R^4$ via procedures previously described.

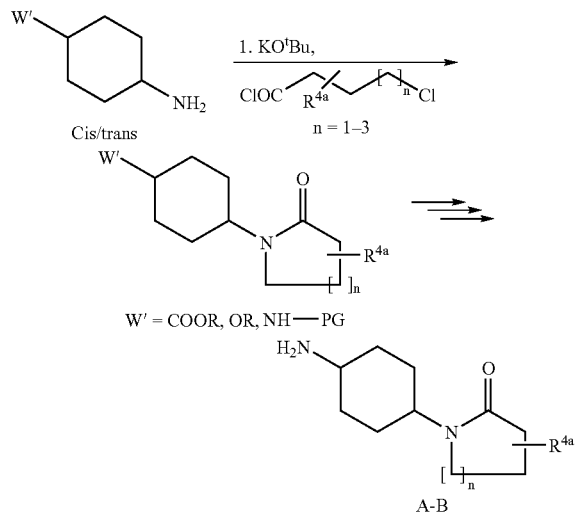

Compounds of the present invention wherein Y is $N(B^1)C(O)C(R^3R^{3g})_{2-4}NB^2B^3$ can be made as described in Schemes 32–34. Scheme 32 describes the syntheses of A—B intermediate via Buchwald Ullman coupling reaction (*J. Am. Chem. Soc.* 2001, 123, 7727) using CuI and 1,2-cyclohexyldiamine or 1,10-phenanthroline as the catalyst.

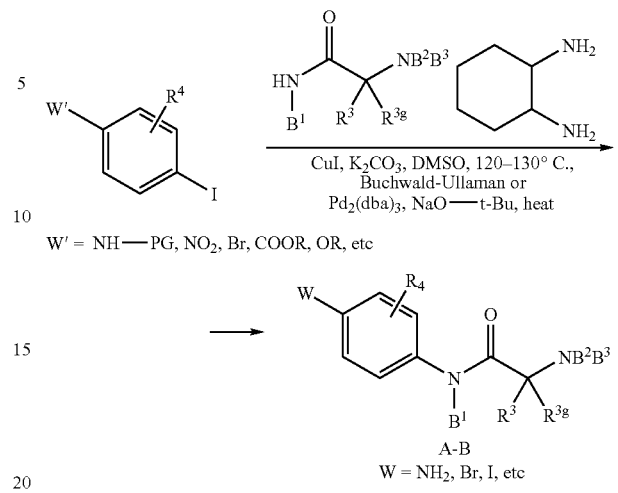

Alternatively, the A—B intermediates containing amides $NH(B^1)C(O)C(R^3R^{3g})_{2-4}NB^2B^3$ can also be prepared from readily available anilines as shown in Scheme 33.

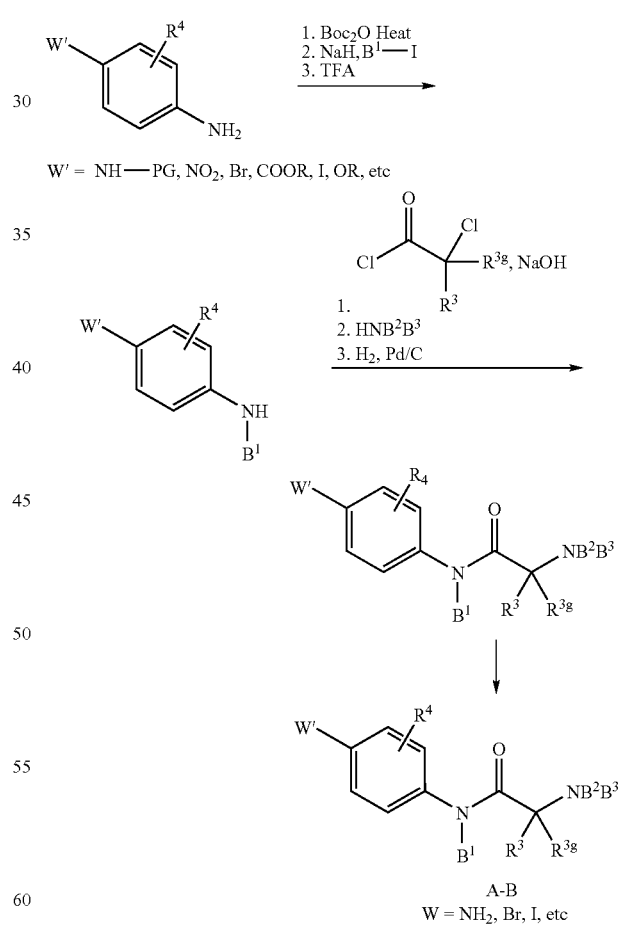

Aminopyridyl, aminopyrimidyl, indonyl, cyclohexyl, and piperidinyl A—B analogs containing $NH(B^1)C(O)C(R^3 R^{3g})_{2-4}NB^2B^3$ (see structures in Scheme 34) can be prepared using routes similar to those of Schemes 31–33 and by those known in the art.

Scheme 34

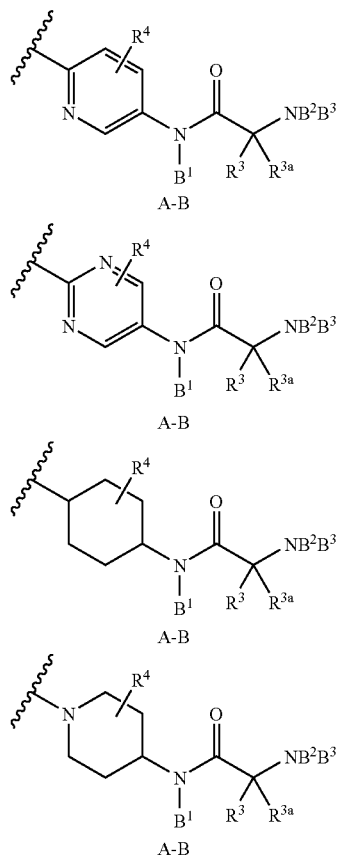

A—B intermediates of the present invention wherein B is an amidino derivative can be prepared following the general procedure outlined in Schemes 35–40. A—B intermediates of the present invention wherein B is a cyclic amidino derivative with one of the nitrogen atoms of the aminido group linked to the A ring, can be prepared as shown in Scheme 20. Boc-protection of the aniline followed by alkylation with chloro iodoalkane can provide the Boc-protected intermediate. Azide displacement followed by reduction and deprotection can afford the diamine compound. Reaction with ethylformate, etc. can generate the corresponding A—B intermediate.

Scheme 35

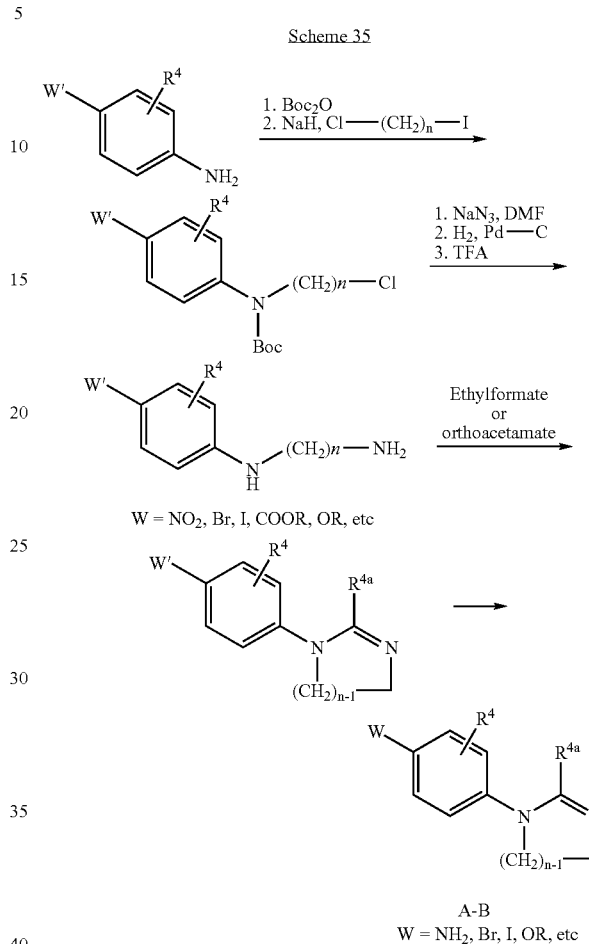

The diamino intermediate from Scheme 35 can also be transformed to an alcohol intermediate followed by treatment with $POCl_3$, $POBr_3$, $Tf_2O$, or an alkylating agent. Further manipulations of these versatile intermediates can be achieved using the methods described in Scheme 36 and by those known in the art.

Scheme 36

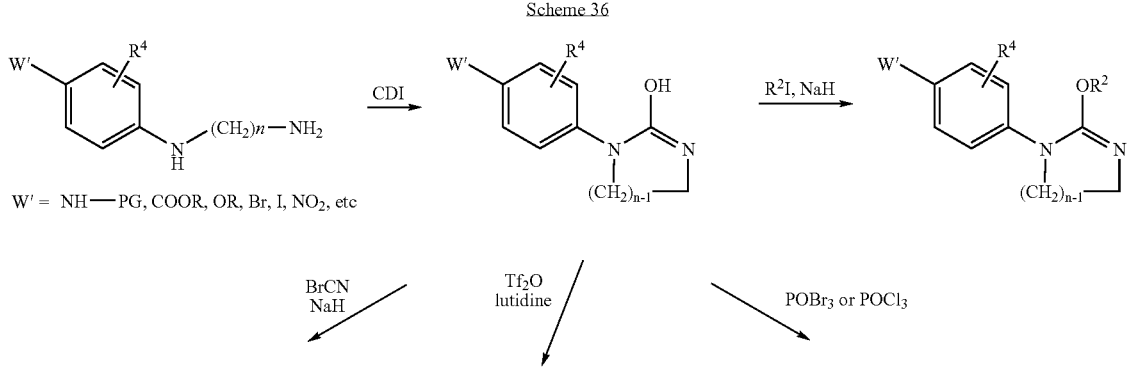

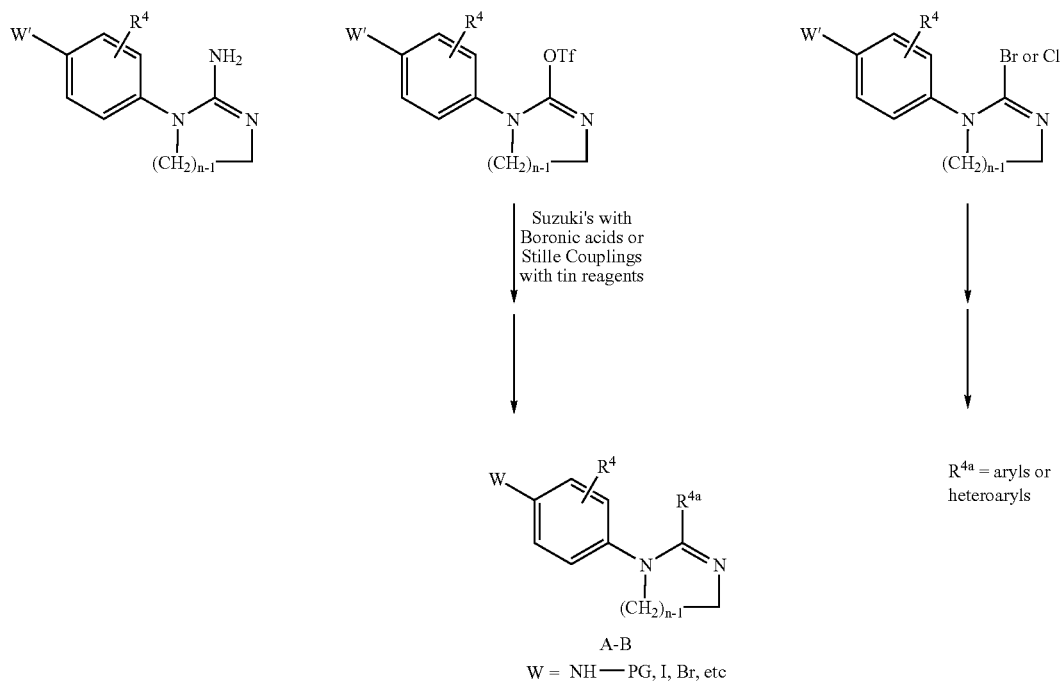
The guanidino A—B derivative from Scheme 36 can be converted to a number of A—B intermediates of the present invention by techniques known to those of skill in the art of organic synthesis, as outlined in Scheme 37.
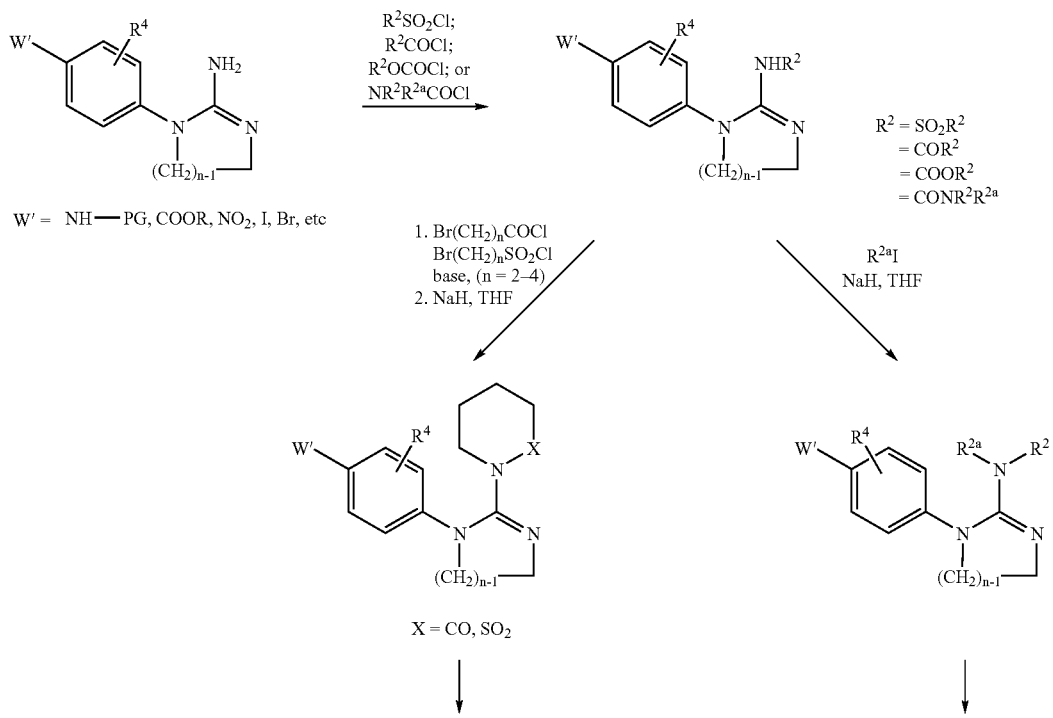

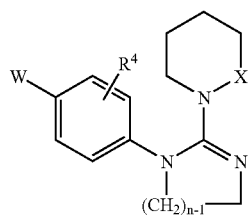

X = CO, SO₂
A-B

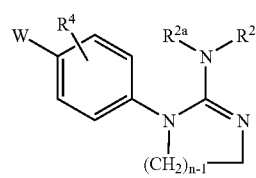

A-B
W = NH₂, I, Br, etc

Using the methodologies outlined above, other compounds of the present invention can be obtained as shown in Scheme 38 by functional manipulations and cyclization techniques known to those of skill in the art of organic synthesis.

Scheme 38

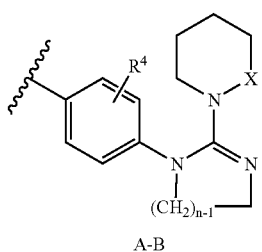

A-B

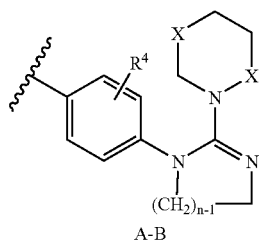

A-B
X = CH₂, O, S, CO, SO₂

Phenylamidino-sulfonyl and -carbonyl A—B intermediates of the present invention can be obtained from the readily available amidino compounds shown in Scheme 39 below.

Scheme 39

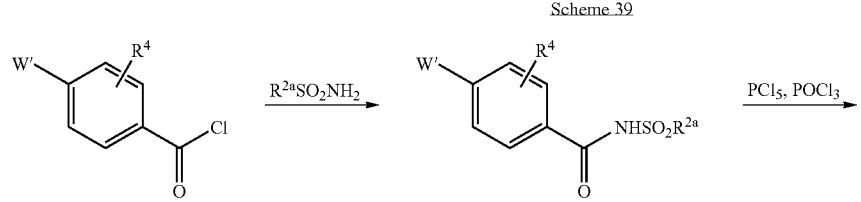

W' = NH—PG, NO2, COOR, OR, Br, I, etc

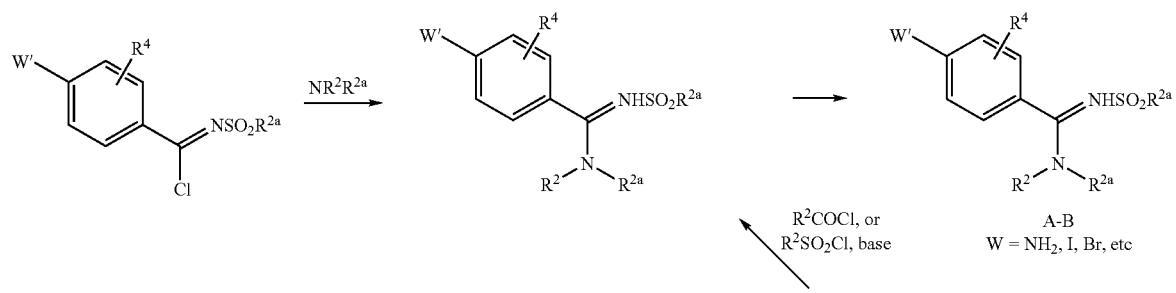

A-B
W = NH₂, I, Br, etc

-continued

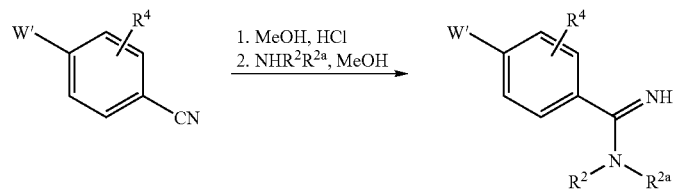

Other A—B intermediates of the present invention wherein B is a cyclic amidino derivative with the carbon atom of the amidino group linked to the A ring can be prepared using properly protected aryl nitriles as the starting material as illustrated in Scheme 40. The pinner reaction (MeOH, HCl), followed by displacement with a diamine can provide protected A—B precursor, which can be transformed to A—B intermediates of the present invention using methods described previously and by those skilled in the art. Alternatively, iodination will provide the desired para-substituted intermediate, which can in turn be transformed to the amino A—B intermediate via Buchwald palladium-catalyzed amination (*Tetrahedron Lett.* 1997, 38, 6367–6370).

Other A—B intermediates of the present invention containing a substituted biaryl or a substituted aryl-heteroaryl can be prepared as shown in Scheme 41. They can be obtained by reacting a boronic acid with a properly protected 4-bromobenzene under Suzuki coupling conditions.

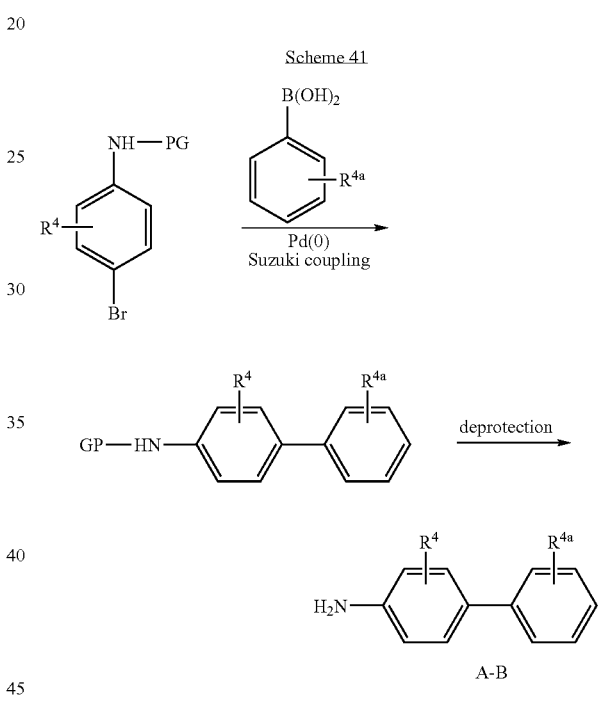

Other A—B intermediates of the present invention wherein B is an imidazole derivative can be prepared as shown in Scheme 42, using Ullman or Buchwald modified Ullman reaction conditions (*J. Am. Chem. Soc.* 2001, 123, 7727) using CuI and 1,2-cyclohexyldiamine, or N,N-dimethylethylene diamine, or 1,10-phenanthroline.

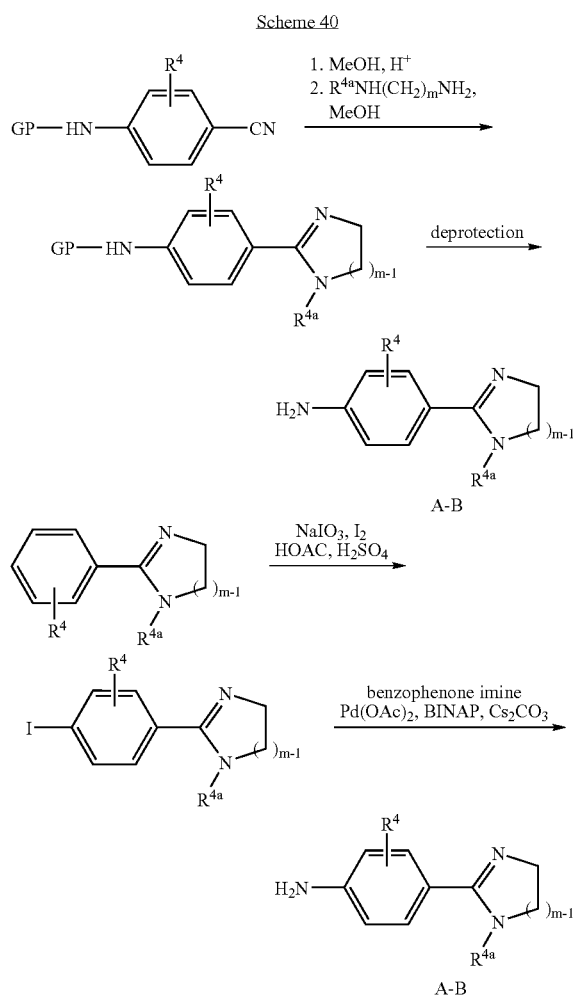

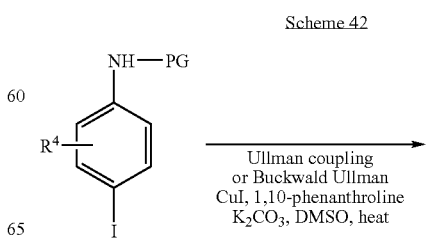

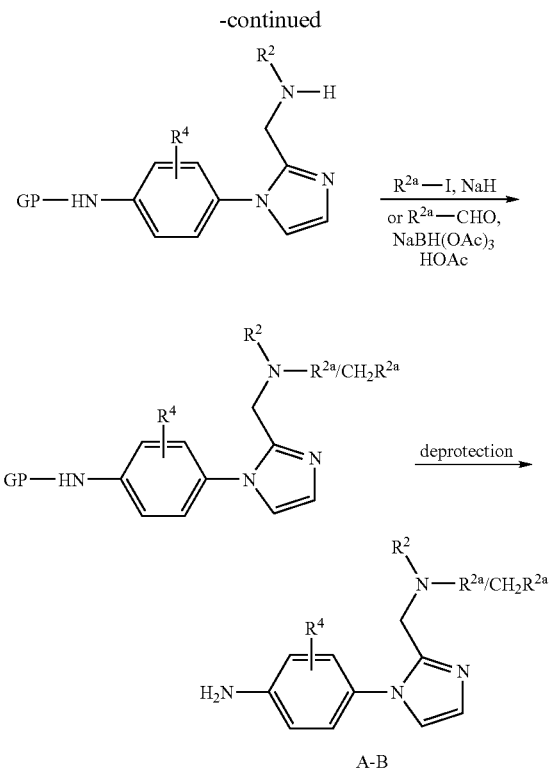

Other A—B intermediates of the present invention wherein B is a [1,4]diazepane derivative can be prepared using the procedures shown in Scheme 43. Aromatic nucleophilic displacement or C—N bond formation using Pd(0) chemistry should provide the A—B intermediate.

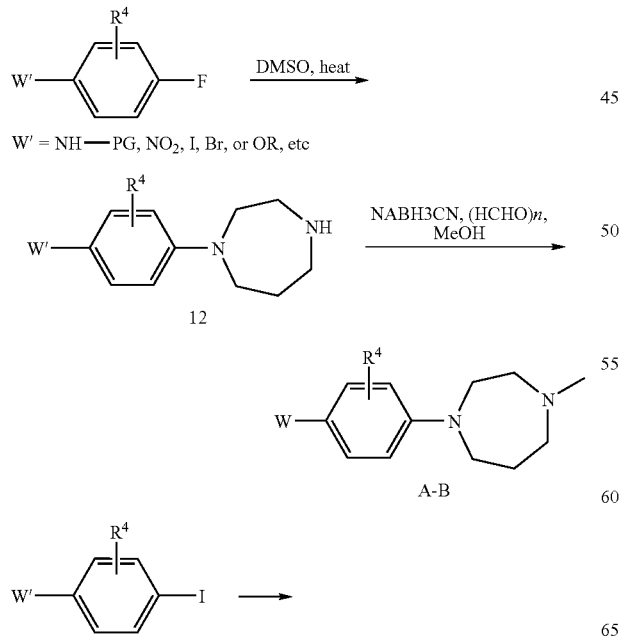

A—B intermediates wherein B is X—Y, X is a 1–3 atom linker, and Y is a heteroaryl or aryl derivative can also be prepared as described previously in WO 98/06694, U.S. Pat. No. 6,057,342, WO 98/28282, U.S. Pat. No. 6,187,797, WO 98/28269, U.S. Pat. No. 6,020,357, WO 98/57934, and U.S. Pat. No. 6,426,346 and by methods known to those skilled in the art.

Aminopyridyl and aminopyrimidyl A—B analogs (see Scheme 44) can be prepared using routes similar to those of Schemes 35–43 and also by those skilled in the art. These intermediates can then be manipulated to compounds of the present invention via procedures previously described.

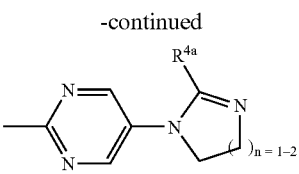

A—B intermediates of the present invention wherein B is

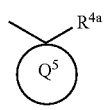

(provided that A and $R^{4a}$ are attached to the same carbon atom in $Q^5$, and $Q^5$ is $C_3$–$C_7$ cycloalkyl) can be prepared as shown in Scheme 45. Commercially available 4-nitrophenylacetonitrile (or properly protected 4-aminophenylacetonitrile) can be used as the starting material. Alkylation with NaH, KtOBu, $NaNH_2$, n-BuLi, s-BuLi, NaOEt, aq NaOH, etc. as the base, and X—$(CH_2)_n$—Y (X and Y can be Cl, Br, I, OMs, OTs, or $^+S(CH_3)_2$ and n=2–6) as the alkylating reagent can afford the cycloalkyl intermediate 37. Hydrolysis of the nitrile group, followed by reduction of the ester group can provide the alcohol 38. Oxidation of 38, then reductive amination with $NHR^2R^{2d}$ can provide 39. Reduction of the nitro group or deprotection of the amino-group can produce the A—B precursor 40. When one of the $R^2$ and $R^{2d}$ group is H, 40 can react with acid chlorides, carbamoyl chlorides, sulfonyl chlorides, and isocyanates to provide A—B intermediates of the invention with structures 41, 42, 43, and 44. Alternatively, alcohol 38 can react with alkyl halides and amines to form compounds of the invention with structures 45 and 46. Alcohol 38 can also be transferred into a halide or its equivalents (X=Cl, Br, I, OMs, or OTs), followed by alkylation with a variety of alkylating reagents to afford A—B intermediates of the present invention with structures 47, 48, and 49.

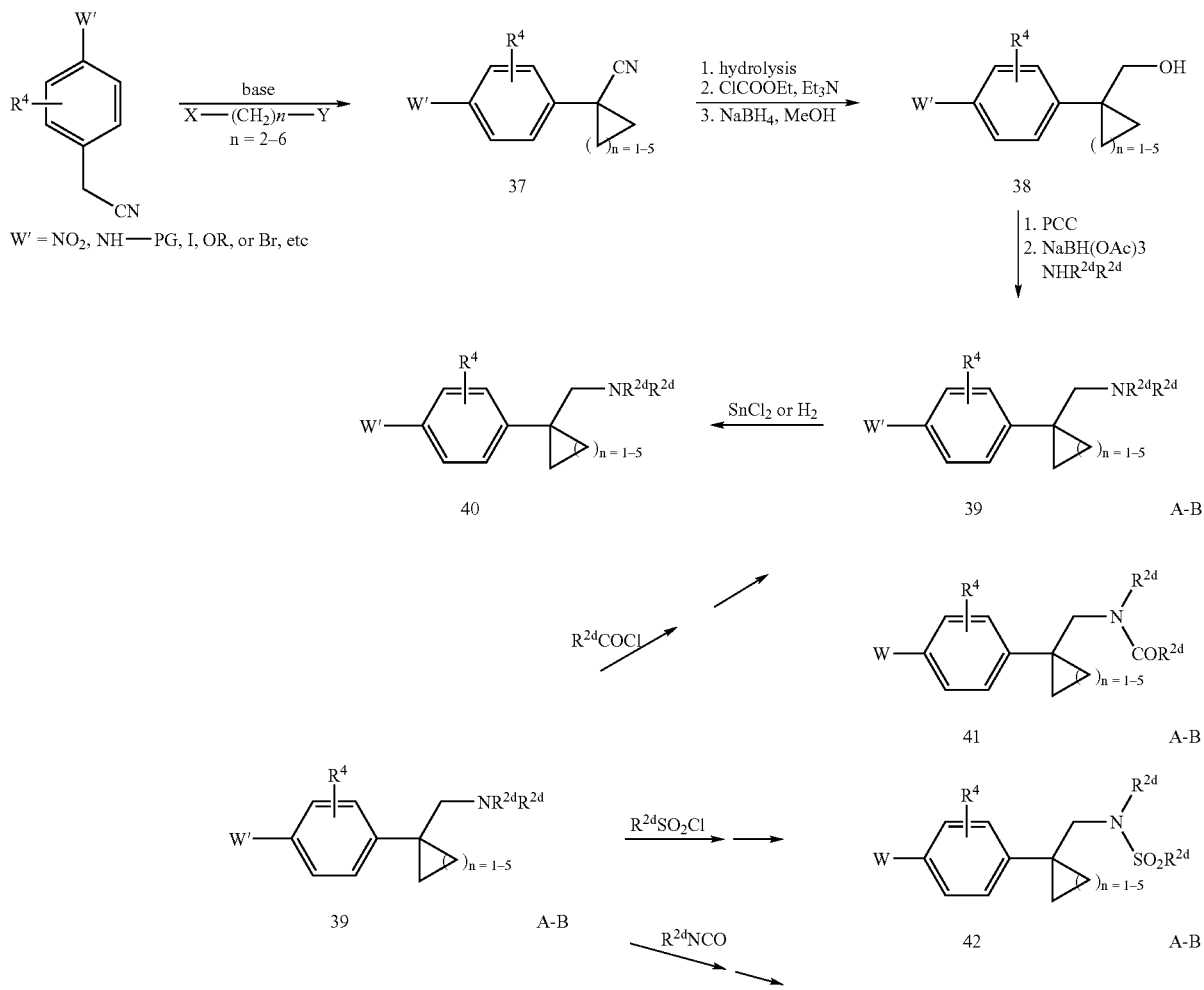

Scheme 45

-continued

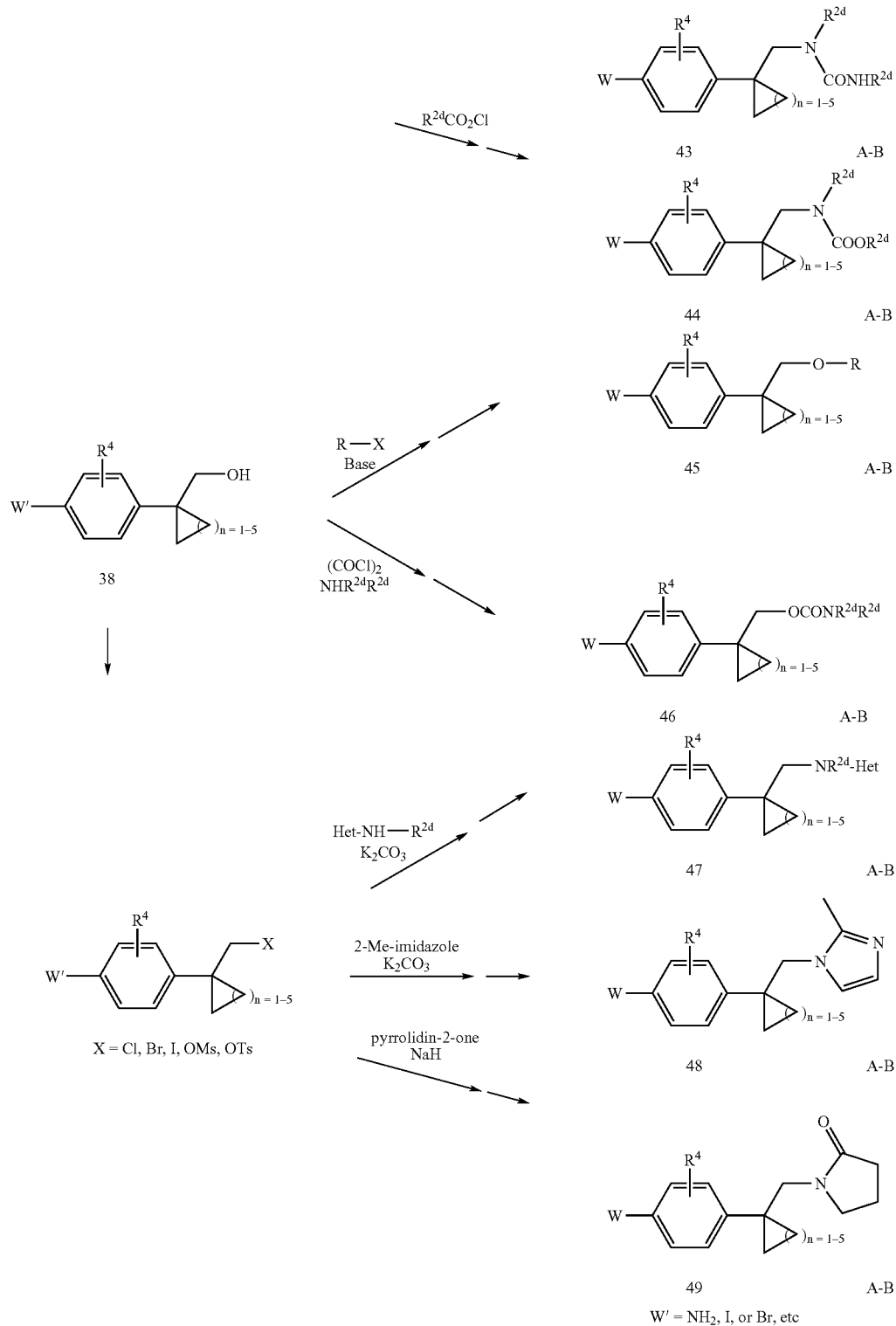

Other A—B intermediates of the present invention wherein $Q^5$ is a cycloalkyl derivative can be prepared using commercially available 1-phenylcycloalkylcarboxylic acids (or 1-phenylcycloalkylcarbonitriles) as the starting materials as illustrated in Scheme 46. Thus, nitration, followed by reduction of the $NO_2$ group and protection of the acid group can provide the A—B precursor 50.

Alternatively, iodination can provide the desired para-iodo compound 51, which can in turn be transformed to the amine 52 via Buchwald palladium-catalyzed amination (*Tet-* rahedron Lett. 1997, 38, 6367–6370) and to the acid 53 via palladium-catalyzed carboxylation (CO, Pd(OAc)$_2$, dppf). Additional A—B intermediates can be synthesized by chemical manipulation of the amino and carboxylic acid functionality in 52 and 53, respectively.

cycloalkyl halides 55 (X=Cl, Br, I, OMs, OTs, etc.) using Pd(dba)$_2$/1,2-bis(diphenylphosphino)ethane (dppe) or NiCl$_2$ (PPh$_3$)$_2$ as the catalyst system can provide intermediate 56. Alternatively, Grignard reaction of 54 with cycloalkyl

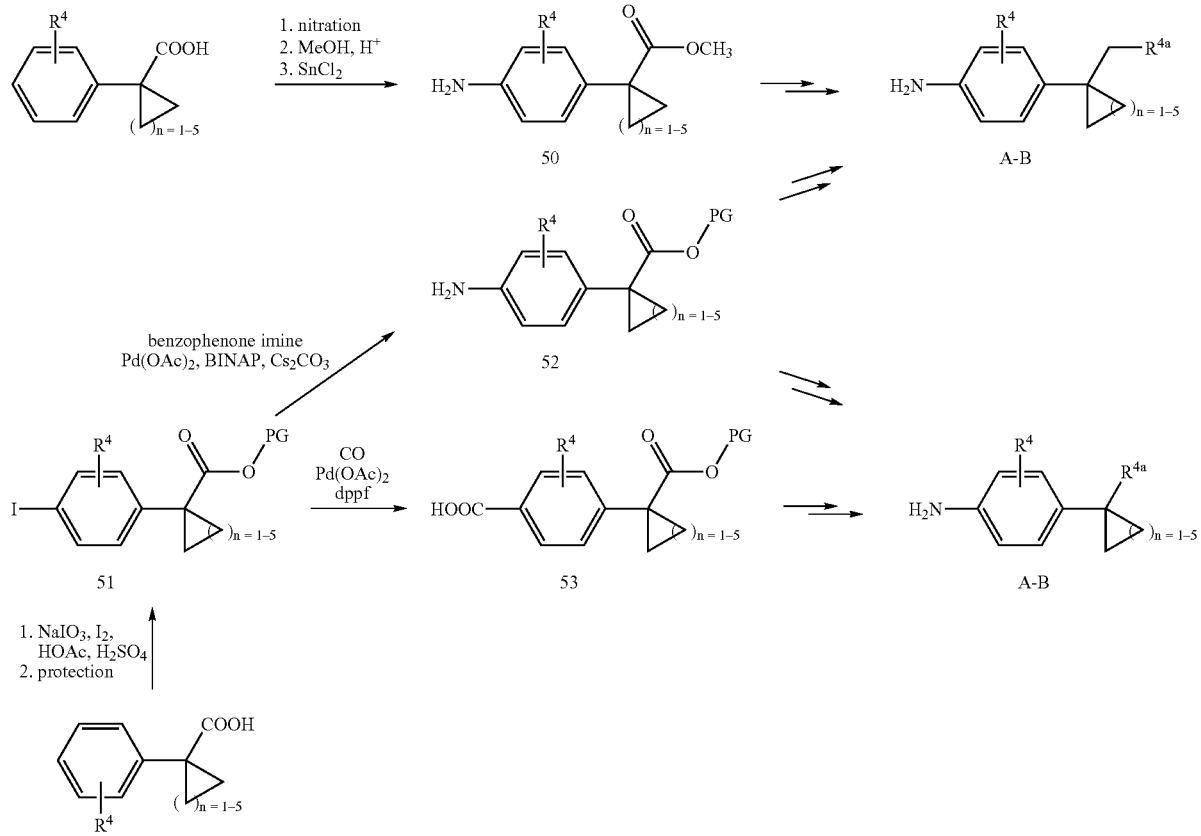

Scheme 46

Other compounds of the present invention wherein Q$^5$ is a cycloalkyl derivative can be prepared using organometalic reagents (Zn, Mg, etc) 54 as starting materials as shown in Scheme 32. Reaction of 54 with properly substituted ketones can provide intermediate 57. Further elaboration of 56 and 57 using the methods described above and by those known in the art should provide A—B intermediates of the present invention.

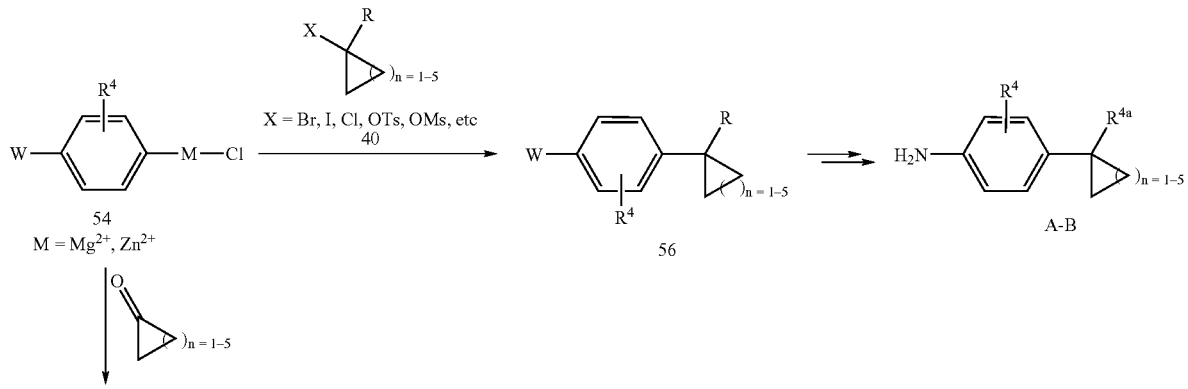

Scheme 47

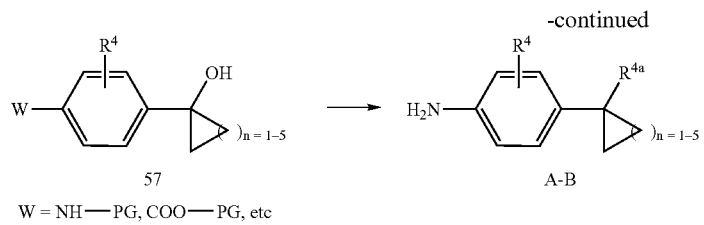

57

W = NH—PG, COO—PG, etc

A—B

A—B intermediates of the present invention wherein $Q^5$ is a pyrrolidine or piperidine derivative can be prepared as shown in Scheme 48. Thus, phenylcyanoacetate can be alkylated with X—$(CH_2)_n$—Cl (X and Y=Br, I, OMs, OTs, etc and n=2–3) to provide the chloronitrile 58, which can be reduced to the corresponding primary amine, followed by cyclization in refluxing EtOH to form 3-pyrrolidine or 3-piperdine derivatives 59. Alkylation or reductive amination can provide the N-substituted intermediate 60. Further elaboration using the methods described above and by those known in the art should provide A—B intermediates of the present invention.

A—B intermediates of the present invention wherein $Q^5$ is a 4-piperidine derivative or tetrahydropyran derivative can be prepared using 2-aryl acetonitriles 61 as starting materials as shown in Scheme 49. Dialkylation of 61 with bromoacetaldehyde dimethyl acetal, followed by hydrolysis of the acetals and reductive amination can give the 4-aryl-4-cyanopiperidine 62. Alkylation of 61 with di-2-chloroethyl ether can give the 4-aryl-4-cyanotetrahydropyran 63.

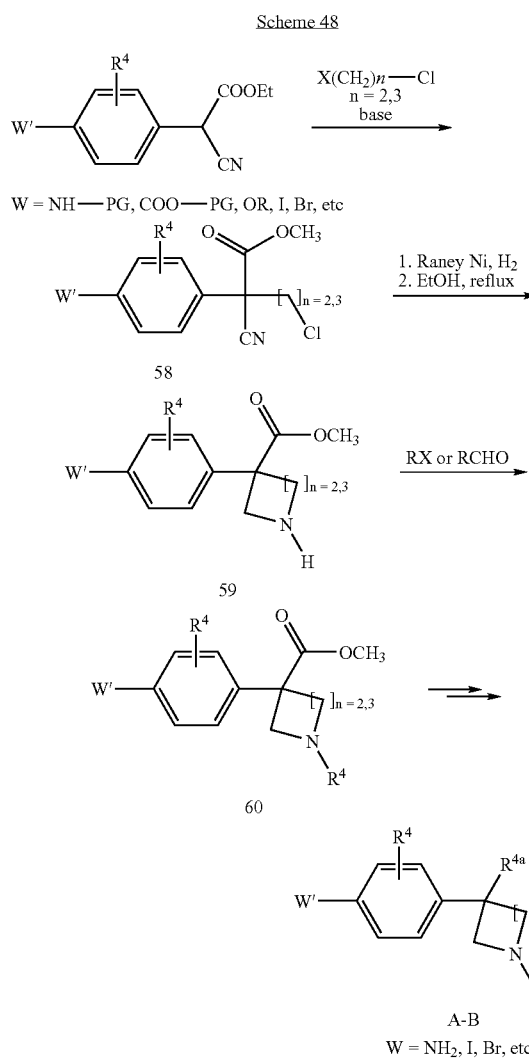

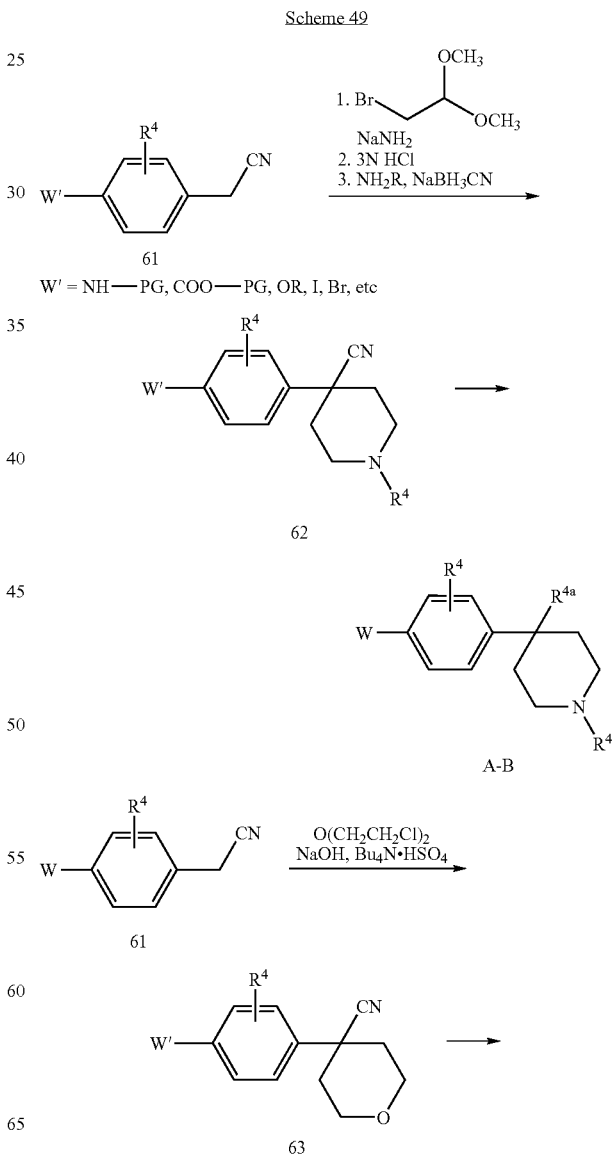

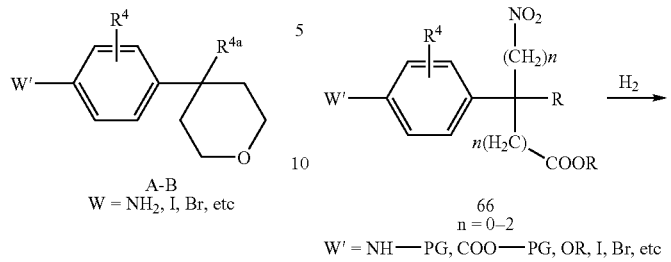

A—B intermediates of the present invention wherein $Q^5$ is a 4-tetrahydrofuran derivative can be prepared using diol 64 as the starting material as illustrated in Scheme 50. Cyclization of 64 with HBr will give the 4-aryl-4-substituted tetrahydrofuran 65. Further elaboration using the methods described above and by those known in the art should provide A—B intermediates of the present invention.

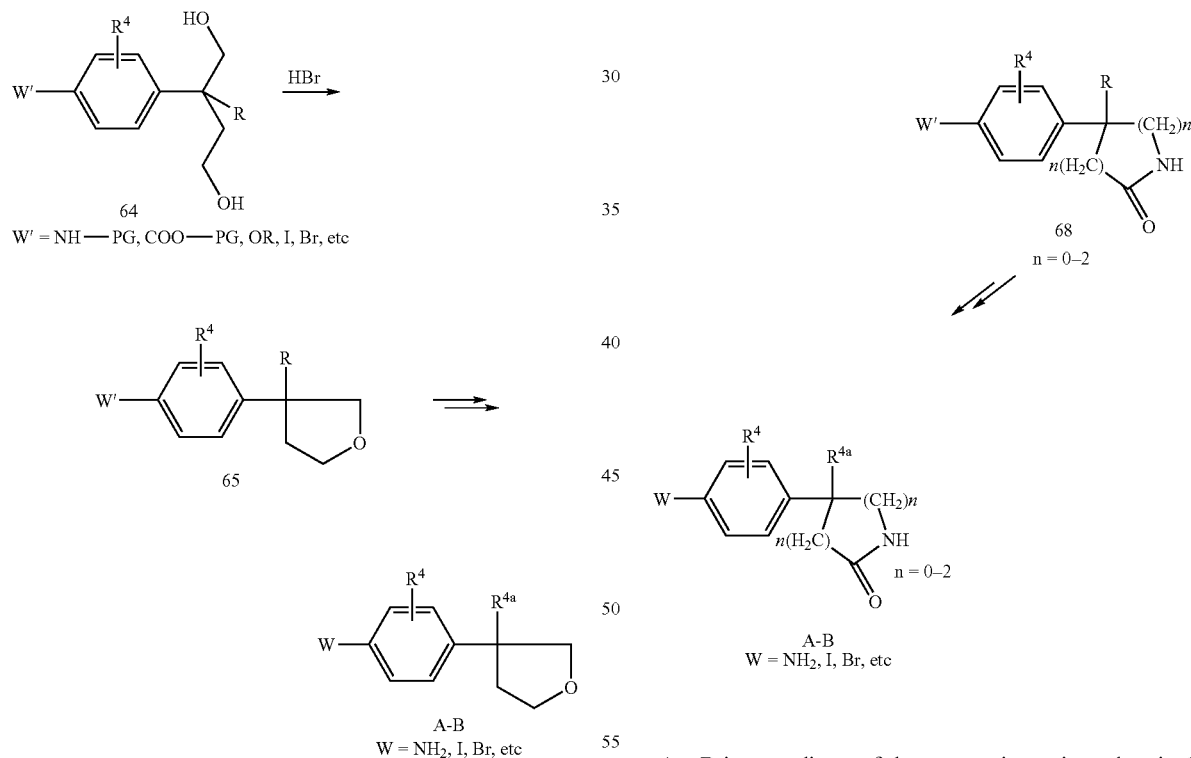

A—B intermediates of the present invention wherein $Q^5$ is a lactam derivative can be prepared using intermediate 66 as the starting material as shown in Scheme 51. Reduction of $NO_2$ group or nitrile group can provide the primary amine 67, which can be coupled intramolecularly with the acid or ester to form the lactam 68. Further elaboration using the methods described above and by those known in the art should provide A—B intermediates of the present invention.

A—B intermediates of the present invention wherein $Q^5$ is a carbocycle or heterocycle and $R^{4a}$ is $CH_2CH_2NR^{2d}R^{2d}$ or $CH_2CONR^{2d}R^{2d}$ can be prepared as outlined in Scheme 52, and via standard methods known to those skilled in the art. The ester or nitrile intermediates 69 can be subjected to alkylation conditions, followed by other manipulations as described in Schemes 45–51 to form 70. Homologation of intermediates 70 with $TMSCHN_2$ as the reagent can afford 71. Further elaboration of 71 to form 72 and A—B intermediates of the present invention can be achieved using the methods described above and by those known in the art.

Scheme 52

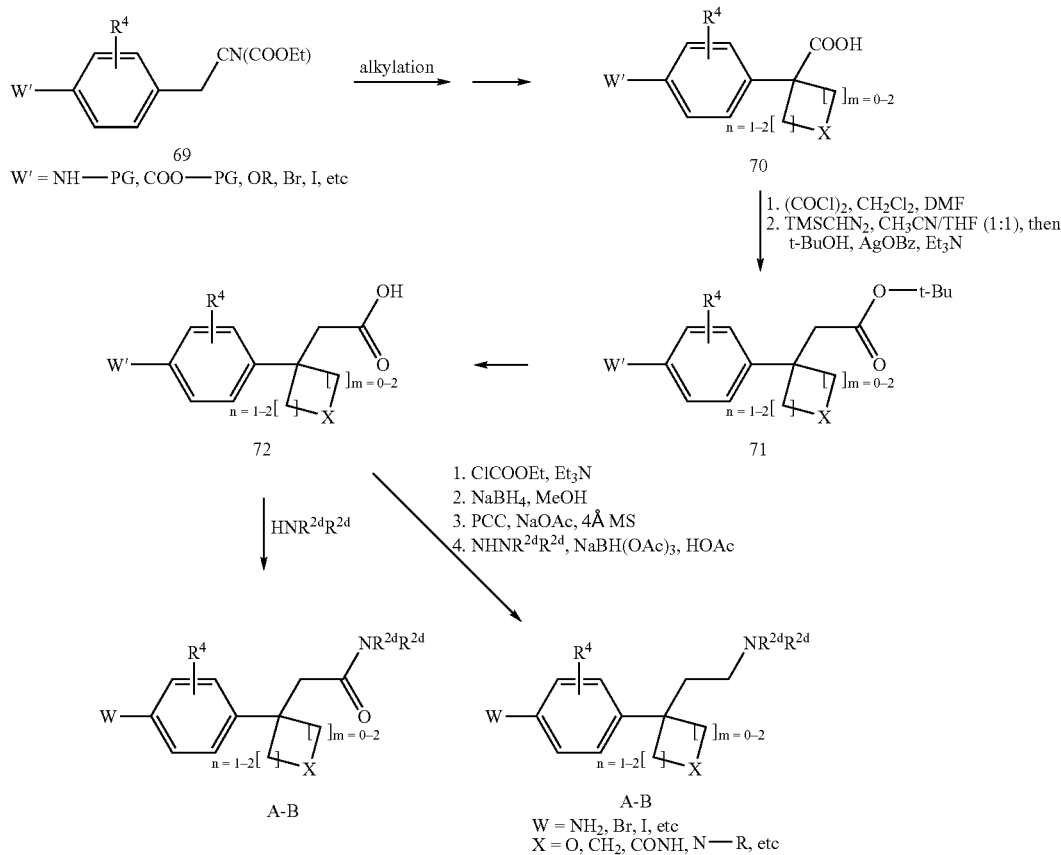

A—B intermediates of the present invention wherein $Q^5$ is a carbocycle or heterocycle and $R^{4a}$ is $NR^{2d}R^{2d}$ can be prepared as outlined in Scheme 53 and via standard methods known to those skilled in the art. The acid intermediates 70 illustrated in Scheme 52 can undergo Curtius rearrangement with DPPA in $CH_2Cl_2$ followed by heating in t-BuOH to afford Boc-protected cyclopropylamine intermediates 73.

Alkylation of 73 with $R^{2d}$—I and NaH in THF followed by manipulations described previously will give amines 74. Reductive amination of 74 with aqueous formaldehyde and $NaBH_3CN$ in $CH_3CN$ can afford the methyl alkyl amine analogues of A—B intermediates. On the other hand, alkylation of the amine 75 with a dibromide using $K_2CO_3$ as the base can afford A—B intermediates bearing tertiary or cyclic amines, respectively.

Scheme 53

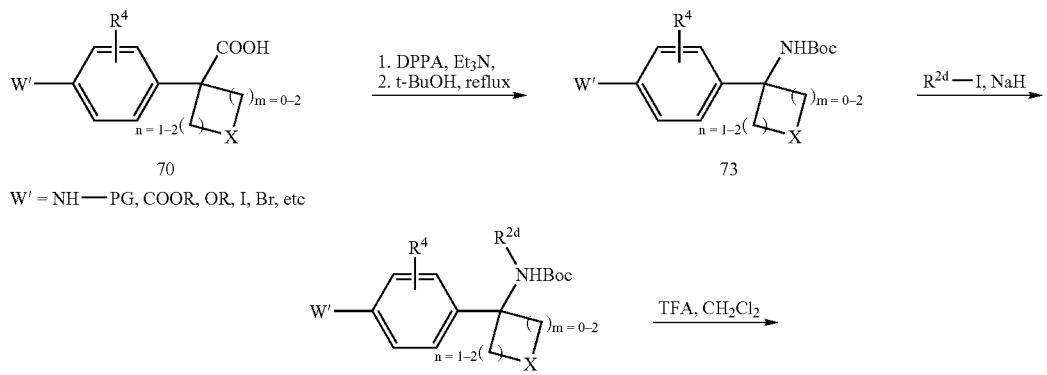

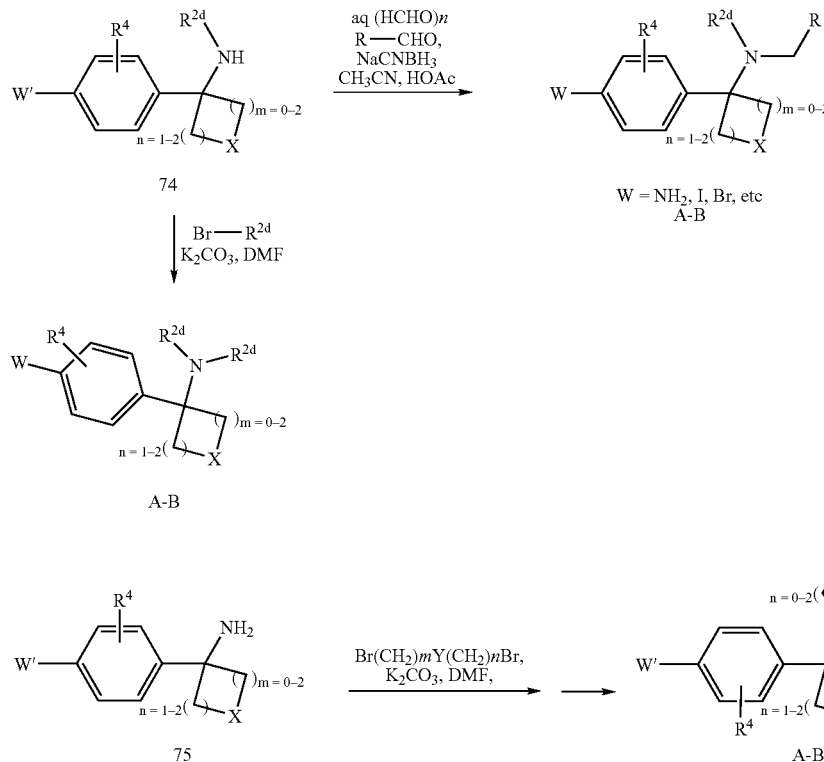

Schemes 45–53 describe how to make the A—B moieties of the present invention wherein B is

and $Q^5$ is a cycloalkyl or heterocyclyl. A—B moieties of the present invention wherein B is $YR^{4a}$ and Y is $CY^1Y^2$ can be made analogously to the cycloalkyl/heterocyclyl compounds of Schemes 45–53. For example, in Scheme 45, instead of intermediate 37 being a cycloalkyl intermediate, it can be $Y^1Y^2$ disubstituted intermediate. This intermediate could be made by a number of methods including di-substituting the starting 4-nitrophenyl-acetonitrile by reaction with a base and a $Y^1$-leaving group and a $y^2$-leaving group. One of ordinary skill in the art would recognize that other routes to the $Y^1Y^2$ disubstituted intermediate are available. In Scheme 46, instead of use the starting 1-phenylcycloalkylcarboxylic acids or 1-phenylcycloalkylcarbonitriles, one could use the corresponding $Y^1Y^2$ disubstituted intermediates. Just like in Scheme 45, these intermediates could be prepared by di-substituting a phenylcarboxylic acid or phenylcarbonitrile. One of ordinary skill in the art would recognize that other routes to these types of $Y^1Y^2$ disubstituted intermediate are also available. The remainder of the chemistry shown in Scheme 46 will then follow.

Aminopyridyl, aminopyrimidyl, cyclohexyl, and piperidinyl A—B analogs wherein B is

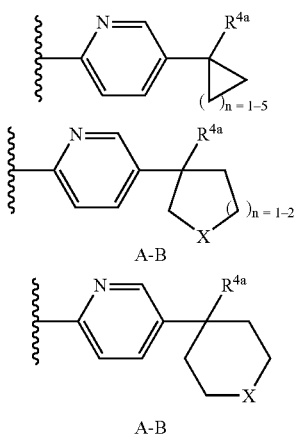

and $Q^5$ is a cycloalkyl or heterocyclic groups, as well as aminopyridyl, aminopyrimidyl, cyclohexyl, and piperidinyl A—B analogs wherein B is $Y—R^{4a}$ and Y is geminal dimethyl group (see structures in Scheme 54), can be prepared using routes similar to those of Schemes 45–53 and by those known in the art.

Scheme 54

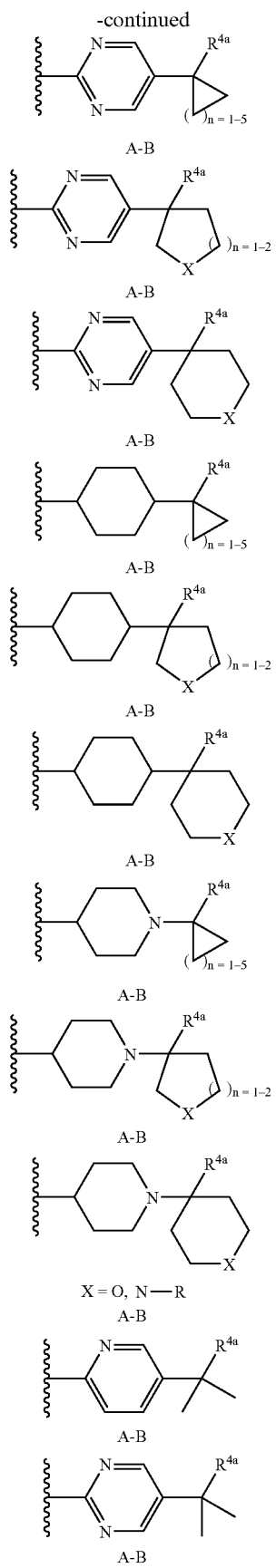

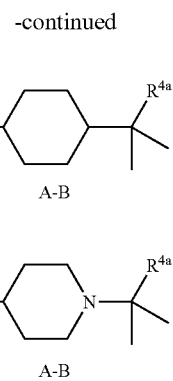

As shown in Scheme 55, additional A—B intermediates can be synthesized by chemical manipulation of the amino functionality of the compounds described in Schemes 24–53.

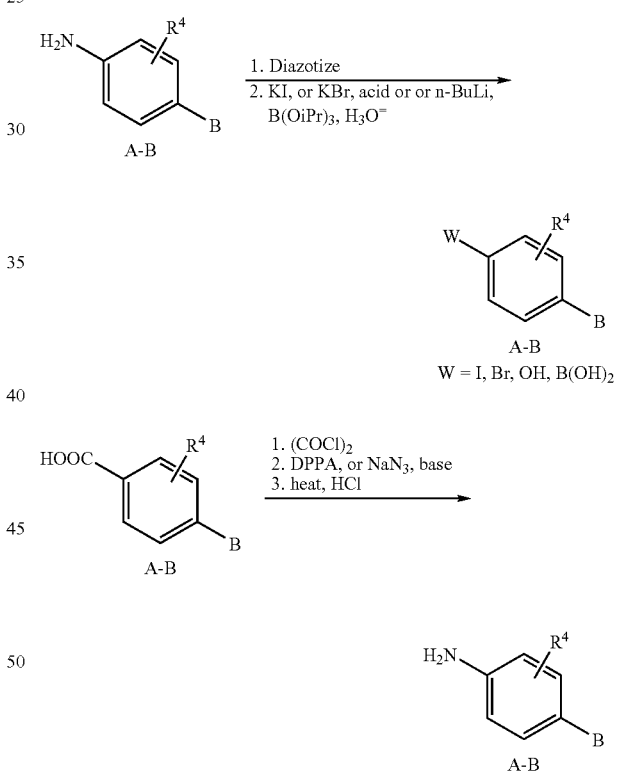

The compounds of the present invention and the intermediates described above wherein the B group contains an oxidizable group can be oxidized, e.g., N to N-oxide.

Schemes 24–55 describe how to make the A—B moieties of the present invention and schemes 1–6 describe how to incorporate them to prepare compounds of formula Id or Ie of the present invention. Scheme 56 depicts the preparation of compounds of the present invention of formula Id ($Z^1$=N, $Z^2$=CH, $T^1$=CO, $T^2$=CH$_2$, n=1) wherein A—B is a phenyl pyridone group.

Scheme 56
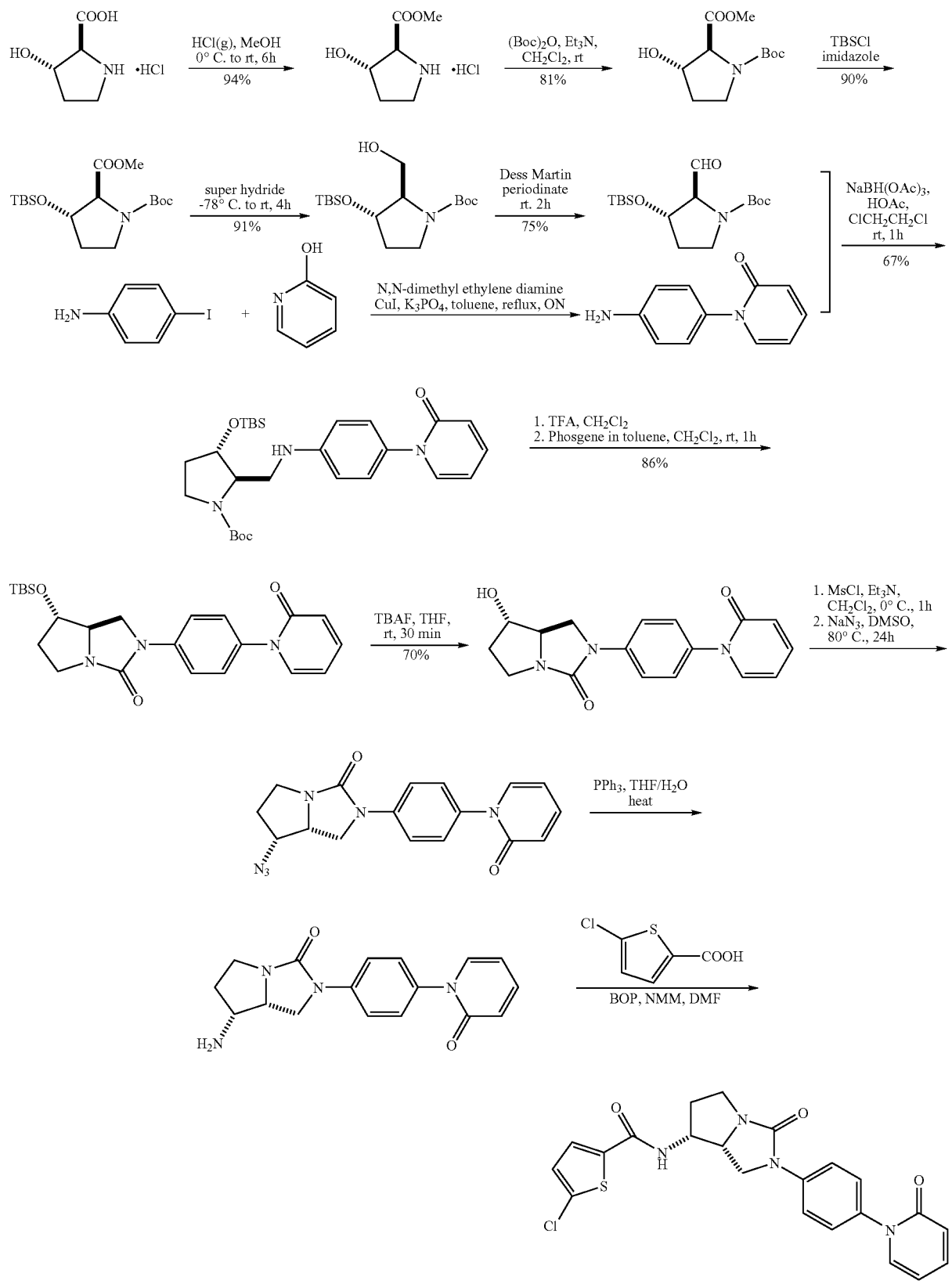

Scheme 57 shows the preparation of compounds of the present invention of formula Id ($Z^1$=N, $Z^2$=CH, $T^1$=CO, $T^2$=CO, n=1) wherein A—B is a phenyl pyridone group.
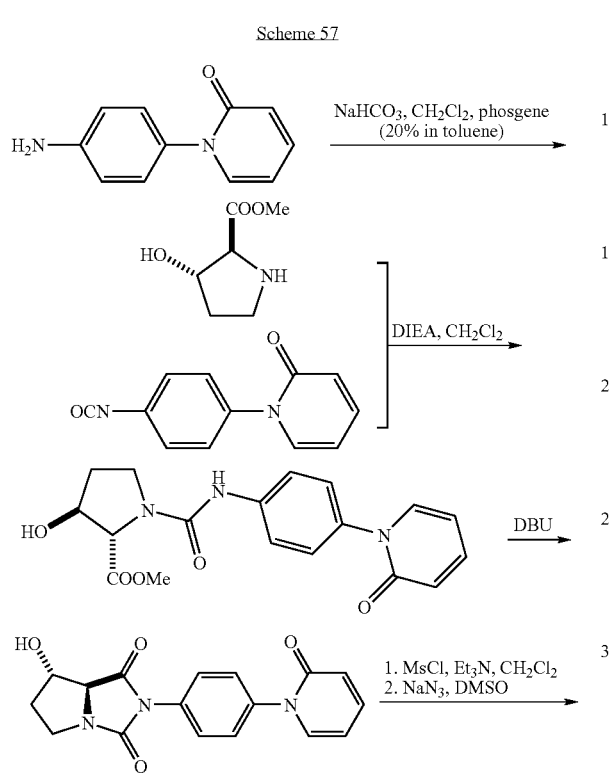
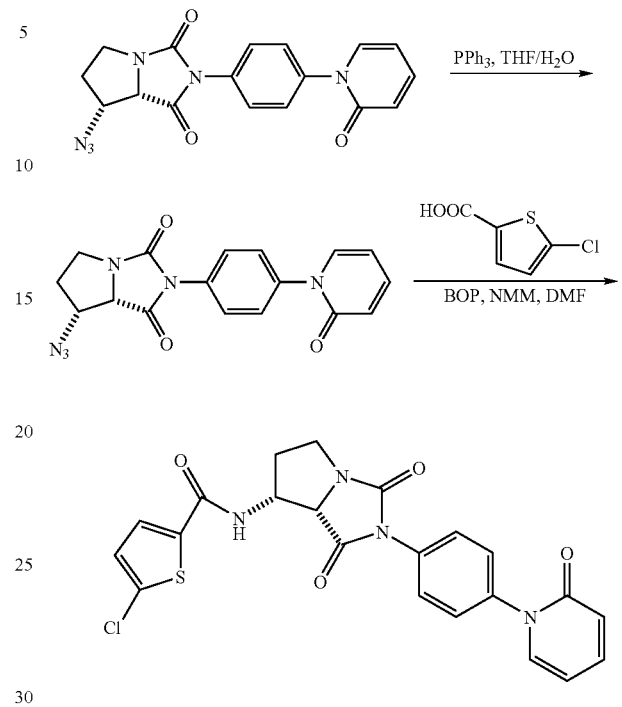
Scheme 58 depicts the preparation of compounds of the present invention of formula Id ($Z^1$=N, $Z^2$=CH, $T^1$=CO, $T^2$=$CH_2$, n=2) wherein A—B is a phenyl pyridone group.
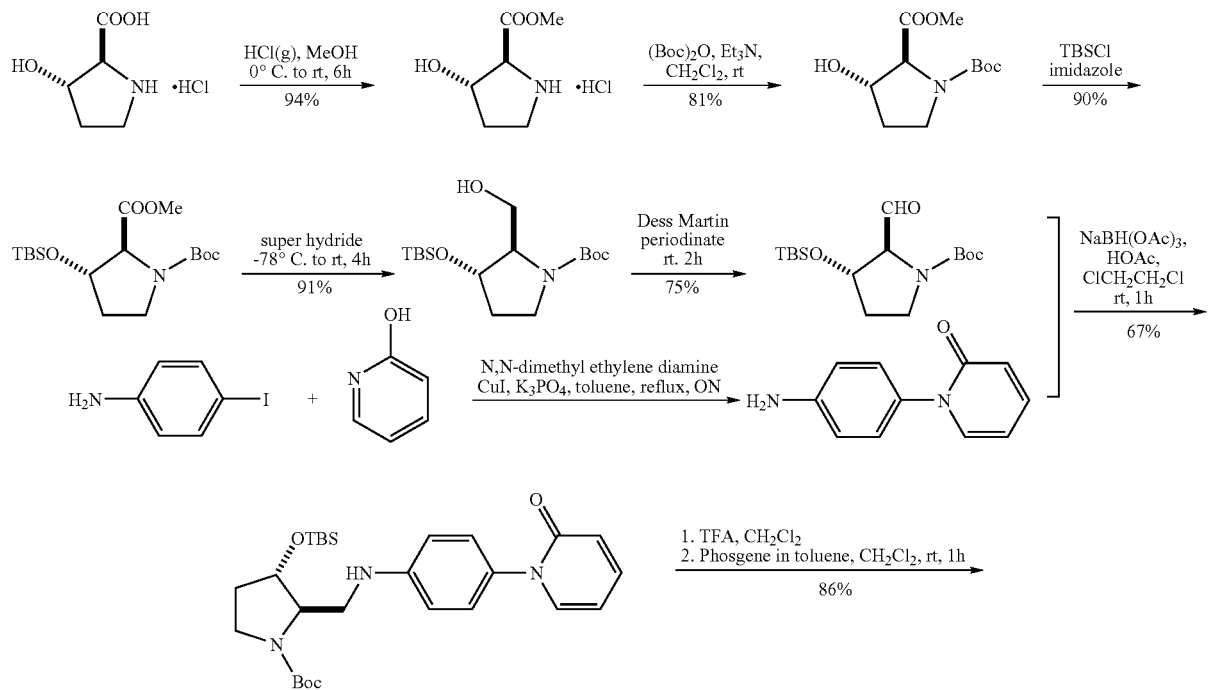

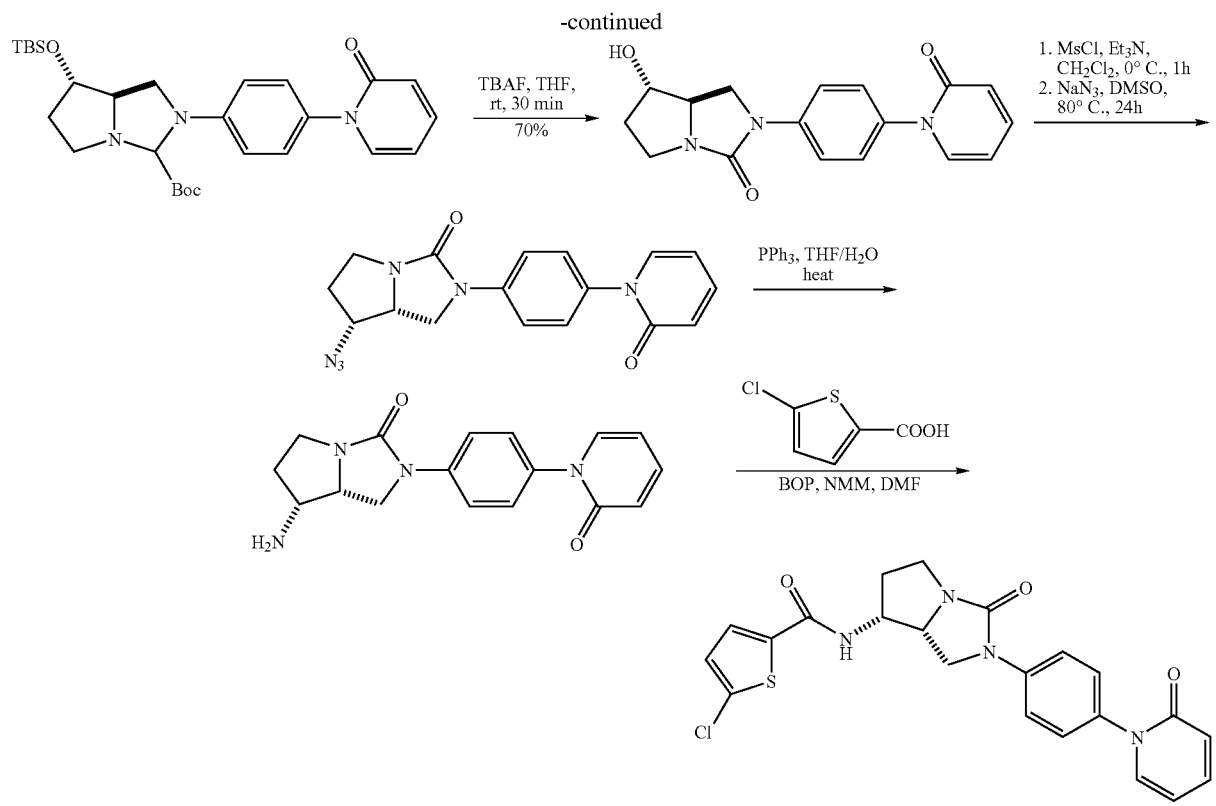

One diastereomer of a compound of Formula Id or Ie may be more potent against fXa than the others. Thus, the diastereomers shown below are considered to be part of the present invention. When required, separation of the racemic material can be achieved by HPLC using a chiral column or by a resolution using a resolving agent such as camphonic chloride (Steven D. Young, et al, *Antimicrobial Agents and Chemotheraphy* 1995, 2602–2605). A chiral compound of Formula I may also be directly synthesized using a chiral catalyst or a chiral ligand (for example, Andrew S. Thompson, et al, *Tetrahedron Lett.* 1995, 36, 8937–8940).

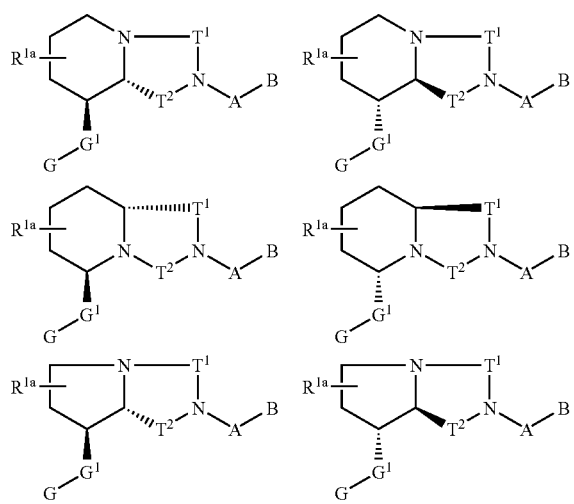

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nm. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 min and the velocities (rate of absorbance change vs. time) were measured in the time frame of 25–30 min. The following relationship was used to calculate $K_i$ values:

$$(v_O - v_S)/v_S = I/(K_i(1 + S/K_m))$$

where:
 $v_O$ is the velocity of the control in the absence of inhibitor;
 $v_S$ is the velocity in the presence of inhibitor;
 I is the concentration of inhibitor;
 $K_i$ is the dissociation constant of the enzyme:inhibitor complex;
 S is the concentration of substrate;
 $K_m$ is the Michaelis constant.

Compounds tested in the above assay are considered to be active if they exhibit a $K_i$ of ≦10 μM. Preferred compounds of the present invention have $K_i$'s of ≦1 μM. More preferred compounds of the present invention have $K_i$'s of ≦0.1 μM. Even more preferred compounds of the present invention have $K_i$'s of ≦0.01 μM. Still more preferred compounds of the present invention have $K_i$'s of ≦0.001 μM. Using the methodology described above, a number of compounds of the present invention were found to exhibit $K_i$'s of ≦10 μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After 40 min, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 min of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin, for example LOVENOX™), synthetic pentasaccharide, direct acting thrombin inhibitors including hirudin and argatrobanas, factor VIIa, IXa, XIa inhibitors, well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K+ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/min during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of The present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of The present invention and about 50 to 150 milligrams of the anti-platelet agent, preferably about 0.1 to 1 milligrams of the compound of The present invention and about 1 to 3 milligrams of antiplatelet agents, per kilogram of patient body weight.

Where the compounds of The present invention are administered in combination with thrombolytic agent, typically a daily dosage may be about 0.1 to 1 milligrams of the compound of The present invention, per kilogram of patient body weight and, in the case of the thrombolytic agents, the usual dosage of the thrombolyic agent when administered alone may be reduced by about 70–80% when administered with a compound of The present invention.

Where two or more of the foregoing second therapeutic agents are administered with the compound of The present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of The present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

5-chloro-N{[1-(2-fluoro-4-(2-N,N-dimethylaminomethylphenyl)phenyl)-5-oxopyrrolidin-3-yl]methyl}thiophene-2-carboxamide

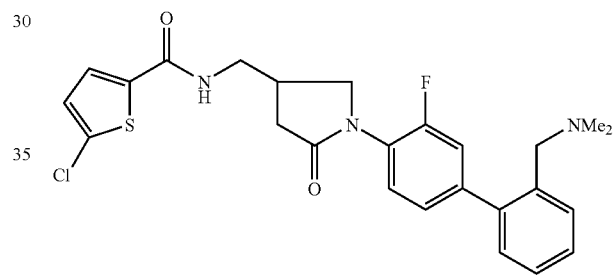

Step A: A mixture of itaconic acid (130 mg, 1.0 mmol) and 2-fluoro-4-(2-N,N-dimethylaminomethylphenyl)aniline, hydrochloride salt (317 mg, 1.0 mmol, WO 02/102380) were stirred at reflux in toluene for 18 hrs. The mixture was cooled to room temperature. Solvent was evaporated, and the residue was re-dissolved in ethyl acetate. The mixture was washed with water, brine and dried over MgSO$_4$. HPLC purification (30% to 100% acetonitrile/water gradient) gave the desired product 1-(2-fluoro-4-(2-N,N-dimethylamino-methylphenyl)phenyl-5-oxopyrrolidine-3-carboxylic acid as white solid. LC-MS found: (M+1)$^+$=357.3.

Step B: To a solution of the product obtained above (356 mg, 1.0 mmol) in THF was added BH$_3$ in THF (5.0 mL, 1 M solution) at 0° C. under N$_2$. After addition, the mixture was brought to room temperature and stirred for 8 hrs. The mixture was quenched with water and most of the THF was removed under reduced pressure. The residue was diluted with ethyl acetate, washed with water, brine, and dried over MgSO$_4$. HPLC purification (20% to 100% acetonitrile/water gradient) provided the desired product 1-[2-fluoro-4-(2-N,N-dimethylaminomethyl-phenyl)phenyl-4-(hydroxymethyl)pyrrolidin-2-one as white solid. LC-MS found: (M+1)$^+$=343.2.

Step C: At 0° C. under N$_2$, TEA was added to a mixture of the product obtained above (342 mg, 1.0 mmol) and MsCl (1.2 mmol) in dichloromethane. After addition, the resulted mixture was brought to room temperature and stirred for 2 hrs. The mixture was diluted with dichloromethane, washed with water, and dried over MgSO$_4$. Prep TLC purification (5 MeOH/CHCl$_3$) provided the desired product {1-[2-fluoro-4-(2-N,N-dimethylaminomethyl-phenyl)phenyl]-5-oxopyrrolidin-3-yl}methyl methanesulfonate as light yellow solid. LC-MS found: (M+1)$^+$=421.4.

Step D: To a solution of the product obtained above (210 mg, 0.5 mmol) in DMF was added sodium azide (65 mg, 1.0 mmol). The mixture was stirred at 80° C. under N$_2$ for 3 hrs. The mixture was cooled to room temperature and most of the DMF was removed under reduced pressure. The residue was dissolved in ethyl acetate, washed with water and brine, and dried over MgSO$_4$. Removal of solvent yielded the desired azide derivative which was dissolved in methanol, and the flask was purged with nitrogen gas. Then, Pd/C (cat.) was added. The mixture was hydrogenated under 1 atm for 2 hrs. The mixture was filtered through a pad of celite. HPLC purification (10% to 100% acetonitrile/water gradient) provided the desired amine as white solid. LC-Ms found: (M+1)$^+$=342.4.

Step E: At 0° C. under N$_2$, DIEA (diethyl-propyl-ethyl-amine) was added to a mixture of the product obtained above (34.1 mg, 0.1 mmol), 5-chlorothiophene-2-carboxylic acid (20.0 mg, 0.12 mmol), EDCI (23.0 mg, 0.12 mmol), and HOBt (16.2 mg, 0.12 mmol) in DMF (5 ml). After addition, the mixture was brought to room temperature and stirred for 3 hrs. The mixture was diluted with ethyl acetate; washed with water, 1N HCl, Sat. NaHCO$_3$, and brine; and, dried over MgSO$_4$. HPLC purification (30% to 100% acetonitrile/water gradient) provided the desired 5-chloro-N{[1-(2-fluoro-4-(2-N,N-dimethylaminomethylphenyl)phenyl)-5-oxopyrrolidin-3-yl]methyl}thiophene-2-carboxamide as a white solid. LC-Ms found: (M+1)$^+$=486.3.

Example 2

5-chloro-N-((1-(2-fluoro-4-(2-N,N-dimethylaminomethylphenyl)phenyl)-5-oxopyrrolidin-3-yl)methyl)thiophene-2-sulfonamide

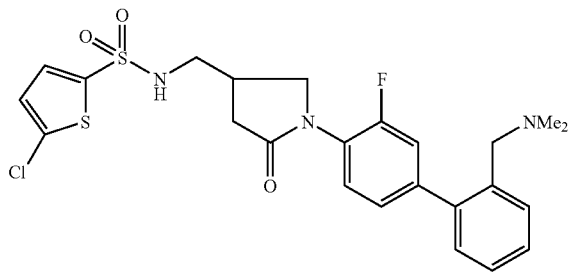

At 0° C. under N$_2$, DIEA was added to a mixture of the product obtained from Step d in Example 1 (34.1 mg, 0.1 mmol) and 5-chlorothiophene-2-sulfonyl chloride (26.0 mg, 0.12 mmol) in dichloromethane. The mixture was stirred at 0° C. for 30 min. and at room temperature for 2 hrs. The mixture was diluted with dichloromethane, washed with water and brine, and dried over MgSO$_4$. HPLC purification (30% to 100% acetonitrile/water gradient) provided the desired 5-chloro-N-((1-(2-fluoro-4-(2-N,N-dimethylaminomethylphenyl)phenyl)-5-oxopyrrolidin-3-yl)methyl) thiophene-2-sulfonamide as white solid. LC-Ms found: (M+1)$^+$=522.2.

Example 3

5-Chloro-thiophene-2-carboxylic acid {(7R,7aR)-3-oxo-2-[4-(2-oxo-2H-pyridin-1-yl)-phenyl]-hexahydro-pyrrolo[1,2-c]imidazol-7-yl}-amide

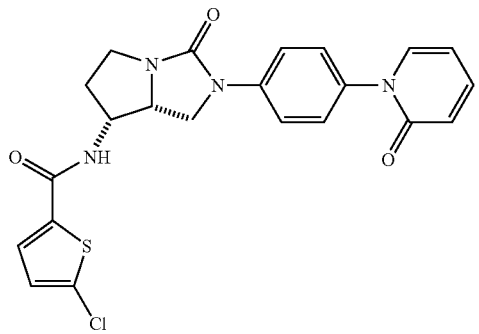

Part A. Hydrogen chloride gas was bubbled into a stirred suspension of trans-3-hydroxy-L-proline (25 g, 190 mmol) in MeOH (250 mL) at 0° C. for 10 min. The resulting clear solution was capped and stirred at room temperature for 6 h. It was concentrated under reduced pressure. The resulting white solids were triturated with either, filtered, and dried under vacuum to give (2S,3S)-3-hydroxy-pyrrolidine-2-carboxylic acid methyl ester hydrochloride salt (32.5 g, yield: 93.7%).

Part B. To a suspension of the product from Part A (15.0 g, 82.4 mmol) in CH$_2$Cl$_2$ (500 mL) was added Et$_3$N (22.7 mL, 164.8 mmol) at 0° C. under N$_2$, followed by portionwise addition of di-tert-butyldicarbonate (17.6 g, 80.8 mmol). The resulting mixture was stirred at room temperature for overnight. It was partitioned between CH$_2$Cl$_2$ and H$_2$O. The organic layer was washed with H$_2$O (2×), 20% aqueous citric acid (1×), H$_2$O, and brine; dried over Na$_2$SO$_4$; and concentrated to dryness to give an oil residue. The crude product was purified by FCC (silica gel) with 0–50% EtOAc/Hexanes to afford (2S,3S)-N-tert-butyloxycarbonyl-3-hydroxy-2-pyrrolidinecarboxylic acid methyl ester (16.4 g, yield: 81.1%) as a colorless oil.

Part C. To a solution of the product from Part B (5.0 g, 20.4 mmol) in CH$_2$Cl$_2$ (100 mL) at room temperature under N$_2$, was added imidazole (2.78 g, 40.8 mmol), followed by the addition of tert-butyldimethylsilyl chloride (3.43 g, 22.6 mmol). After stirring at room temperature overnight, the reaction mixture as partitioned between CH$_2$Cl$_2$ and H$_2$O. The organic layer was washed with 1N H$_3$PO$_4$, sat'd NaHCO$_3$, and then brine; dried over MgSO$_4$; filtered; and concentrated under reduced pressure. The residue was purified by FCC (silica gel) with 0–50% EtOAc/Hexanes as the solvents to give (2S,3S)-3-(tert-butyldimethylsilanyloxy)-pyrrolidine-1,2-dicarboxylic acid 1-tert-butyl ester 2-methyl ester (6.6 g, yield: 90.1%). LC/MS (ESI): 360 (M+H).

Part D. To the stirred solution of the product from Part C (5.0 g, 13.92 mmol) in THF (50 mL) was added dropwise super-hydride (1.0 M THF solution, 70 mL, 70 mmol) at −78° C. under N$_2$ during a 40-min period. The resulting mixture was warmed slowly to room temperature and stirred for 3 h. It was poured into crushed ice and stirred for 15 min.

It was then extracted with EtOAc (2×); washed with sat'd NaHCO₃ and brine; dried over MgSO₄; filtered; and concentrated. The residue was purified by silica gel chromatography (hexanes/EtOAc gradients) to give pure (2R,3S)-3-(tert-butyldimethylsilanyloxy)-2-hydroxymethylpyrroline-1-carboxylic acid tert-butyl ester (4.37 g, yield: 91%).

Part E. The product from Part D (4.37 g, 13.9 mmol) was stirred in dry CH₂CH₂ (100 ML) at 0° C. under N₂. Dess-Martin Periodinane (8.8 g) was added as several portions. The resulting mixture was stirred at room temperature for 4 h. TLC showed completion of the reaction. Sat'd Na₂S₂O₃ (15 ML) was added, followed by the addition of Sat'd NaHCO₃ (15 mL). The organic layer was separated and washed with sat'd Na₂S₂O₃, sat'd NaHCO₃, brine, and H₂O, sequentially. It was then dried over MgSO₄, filtered, and concentrated to dryness. The residue was purified by silica gel filtration (hexanes:EtOAc=1:0 to 10:1) to give pure (2S,3S)-3-(tert-butyldimethylsilanyloxy)-2-formylpyrroline-1-carboxylic acid tert-butyl ester (3.57 g, 75%) as colorless oil.

Part F. The product from Part E (640 mg, 1.95 mmol) was stirred in 1,2-dichloroethane (6 mL) at room temperature under N₂. The aniline (450 mg, 2.42 mmol) was added, followed by the addition of NaBH(OAc)₃ (2.1 g, 10 mmol) and HOAc (0.1 mL). The resulting mixture was stirred at room temperature for 1 h, LCMS showed completion of the reaction. Sat'd NaHCO₃ was the added. It was extracted with EtOAc; washed with H₂O and brine; dried over MgSO₄; filtered; and concentrated to dryness. The residue was purified by FCC (silica gel, hexanes:EtOAc=1:0 to 1:1) to give pure (2R,3S)-3-(tert-butyl-dimethyl-silanyloxy)-2-{[4-(2-oxo-2H-pyridin-1-yl)-phenylamino]-methyl}-pyrrolidine-1-carboxylic acid tert-butyl ester (650 mg, yield: 67%). LC/MS (ESI) 500.30 (M+H), 444.30 (M−tBu+H), 400.30 (M−Boc+H), $t_R$=4.11 min (10–90% MeOH in H₂O with 0.1% TFA in a 4 min run).

Part G. The product from Part F (550 mg, 1.1 mmol) was stirred in CH₂Cl₂ (10 mL) and TFA (4 mL) at room temperature for 1 h. It was evaporated; dissolved in CH₂Cl₂; washed with sat'd NaHCO₃ and H₂O; dried over MgSO₄; filtered; and concentrated to dryness to give crude 1-(4-{[(2R,3S)-3-(tert-butyl-dimethyl-silanyloxy)-pyrrolidin-2-ylmethyl]-amino}-phenyl)-1H-pyridin-2-one. LC/MS (ESI) 400.30 (M+H), $t_R$=3.11 min (10–90% MeOH in H₂O with 0.1% TFA in a 4 min run). This product was dissolved in CH₂Cl₂ (10 mL) and stirred at 0° C. under N₂. DIEA (1.02 mL) was added, followed by dropwise addition of phosgene (20% in toluene, 0.5 mL). The resulting mixture was warmed to r.t. and stirred for 2 h. It was evaporated and purified by FCC (hexanes:EtOAc+1:1 to 0:1) to give pure (7S,7aR)-7-(tert-butyl-dimethyl-silanyloxy)-2-[4-(2-oxo-2H-pyridin-1-yl)-phenyl]-hexahydro-pyrrolo[1,2-c]imidazol-3-one (400 mg, 85.6%). LC/MS (ESI) 426.24 (M+H), $t_R$=3.86 min (10–90% MeOH in H₂O with 0.1% TFA in a 4 min run).

Part H. The product from Part G (390 mg, 0.92 mmol) was stirred in THF (6 mL) at 0° C. under N₂. TBAF (1.0 M in THF, 1.5 mL, 1.5 mmol) was added. The resulting mixture was stirred at room temperature for 30 min. TLC showed completion of the reaction. EtOAc was added. The mixture was washed with sat'd NH₄Cl, H₂O, and brine; dried over MgSO₄; filtered; and concentrated to dryness. The residue was purified by FCC (hexanes:EtOAc=1:1 to 0:1) to give (7S,7aR)-7-hydroxy-2-[4-(2-oxo-2H-pyridin-1-yl)-phenyl]-hexahydro-pyrrolo[1,2-c]imidazol-3-one (200 mg, yield: 70%). LC-MS (ESI) 312.18 (M+H), $t_R$=1.66 min (10–90% MeOH in H₂O with 0.1% TFA in a 4-min run).

Part I. The product from Part H (200 mg, 0.64 mmol) was stirred in dry CH₂Cl₂ (6 mL) at 0° C. under N₂. Et₃N (1.7 mL) was added followed by the addition of MsCl (0.9 mL). The solution was stirred at 0° C. for 45 min. TLC showed completion of the reaction. It was washed with H₂O and brine; dried over Na₂SO₄; filtered; and concentrated to dryness. The residue was dissolved in DMSO (1 mL), and NaN₃ (200 mg) was added. The resulting mixture was heated at 80° C. for 24 h. It was cooled, partitioned between EtOAc and H₂O, washed with brine, dried over MgSO₄, filtered, and concentrated to dryness. The residue was purified by FCC (silica gel, EtOAc) to give (7R,7aR)-7-azido-2-[4-(2-oxo-2H-pyridin-1-yl)-phenyl]-hexahydro-pyrrolo[1,2-c]imidazol-3-one (156 mg, yield: 72%).

Part J. The product from Part I (230 mg, 0.68 mmol) was stirred in THF (4 mL). PPh₃ (250 mg, 0.95 mmol) was added, followed by the addition of H₂O (0.1 mL). The resulting mixture was heated at 50–70° C. for 2 days. After cooling, it was evaporated to dryness to give crude (7R,7aR)-7-amino-2-[4-(2-oxo-2H-pyridin-1-yl)-phenyl]-hexahydro-pyrrolo[1,2-c]imidazol-3-one which was used directly in the next step. LC/MS (ESI) 311.21 (M+H), $t_R$=1.29 min (10–90% MeOH in H₂O with 0.1% TFA in a 4 min run).

Part K. One quarter of the crude product of Part J (ca. 50 mg) was dissolved in DMF (0.5 mL). 5-Chlorothiophene carboxylic acid (15 mg) was added followed by the addition of NMM (0.02 mL) and BOP (35 mg). The resulting mixture was stirred at room temperature for 1 h. It was purified by reverse phase HPLC to give the desired title compound: LC/MS (ESI) 455.17, 457.18 (M+H), $t_R$=2.74 min (10–90% MeOH in H₂O with 0.1% TFA in a 4 min run).

Using a procedure similar to that of Example 3, the following Examples 4–6 were prepared.

Example 4

6-Chloro-naphthalene-2-carboxylic acid {(7R,7aR)-3-oxo-2-[4-(2-oxo-2H-pyridin-1-yl)-phenyl]-hexahydro-pyrrolo[1,2-c]imidazol-7-yl}-amide

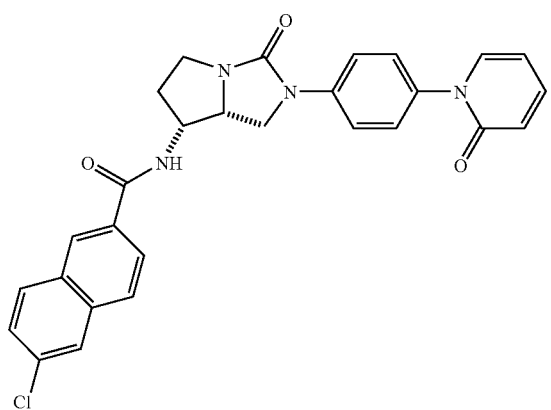

LC/MS (ESI) 500.14, 502.18 (M+H), $t_R$=2.79 min (10–90% MeOH in H₂O with 0.1% TFA in a 4 min run).

Example 5

3-Chloro-1H-indole-6-carboxylic acid {(7R,7aR)-3-oxo-2-[4-(2-oxo-2H-pyridin-1-yl)-phenyl]-hexahydro-pyrrolo[1,2-c]imidazol-7-yl}-amide

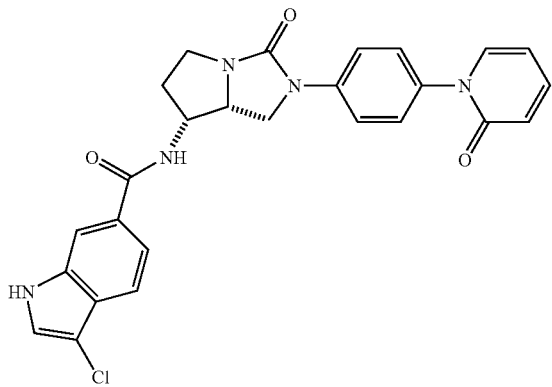

MS (ESI) 488.2 (M+H).

Example 6

4-Chloro-N-{(7R,7aR)-3-oxo-2-[4-(2-oxo-2H-pyridin-1-yl)-phenyl]-hexahydro-pyrrolo[1,2-c]imidazol-7-yl}-benzamide

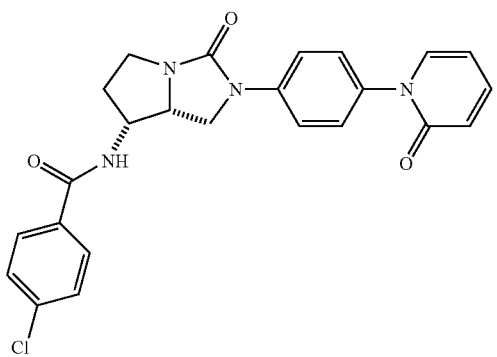

LC/MS (ESI): 449.18, 551.20 (M+H), $t_R$=2.67 min (10–90% MeOH in $H_2O$ with 0.1% TFA in a 4 min run).

The following tables list representative compounds of the present invention that can be prepared by the methods of the above examples as well as by methods known to those of skill in the art.

TABLE 1

1. N-((5-oxo-1-(4-(2-oxopiperidin-1-yl)phenyl)pyrrolidin-3-yl)methyl)benzamide
2. 4-chloro-N-((5-oxo-1-(4-(2-oxopiperidin-1-yl)phenyl)pyrrolidin-3-yl)methyl)benzamide
3. 4-methoxy-N-((5-oxo-1-(4-(2-oxopiperidin-1-yl)phenyl)pyrrolidin-3-yl)methyl)benzamide
4. 4-fluoro-N-((5-oxo-1-(4-(2-oxopiperidin-1-yl)phenyl)pyrrolidin-3-yl)methyl)benzamide
5. 3-carbamimidoyl-N-((5-oxo-1-(4-(2-oxopiperidin-1-yl)phenyl)pyrrolidin-3-yl)methyl)benzamide
6. 3-(carbamimidoyl)-N-((5-oxo-1-(4-(2-oxopiperidin-1-yl)phenyl)pyrrolidin-3-yl)methyl)benzamide
7. 3-(benzamide)-4-fluoro-N-((5-oxo-1-(4-(2-oxopiperidin-1-yl)phenyl)pyrrolidin-3-yl)methyl)benzamide
8. 3-amino-N-((5-oxo-1-(4-(2-oxopiperidin-1-yl)phenyl)pyrrolidin-3-yl)methyl)benzo[d]isoxazole-5-carboxamide
9. 3-amino-N-((5-oxo-1-(4-(2-oxopiperidin-1-yl)phenyl)pyrrolidin-3-yl)methyl)benzo[d]isoxazole-5-carboxamide
10. 4-fluoro-N1-((5-oxo-1-(4-(2-oxopiperidin-1-yl)phenyl)pyrrolidin-3-yl)methyl)isophthalamide
11. 4-chloro-N1-((5-oxo-1-(4-(2-oxopiperidin-1-yl)phenyl)pyrrolidin-3-yl)methyl)isophthalamide
12. 3-chloro-N-((5-oxo-1-(4-(2-oxopiperidin-1-yl)phenyl)pyrrolidin-3-yl)methyl)benzamide
13. 5-chloro-N1-((5-oxo-1-(4-(2-oxopiperidin-1-yl)phenyl)pyrrolidin-3-yl)methyl)phthalamide
14. 5-fluoro-N1-((5-oxo-1-(4-(2-oxopiperidin-1-yl)phenyl)pyrrolidin-3-yl)methyl)phthalamide
15. 5-methoxy-N1-((5-oxo-1-(4-(2-oxopiperidin-1-yl)phenyl)pyrrolidin-3-yl)methyl)phthalamide
16. 4-ethyl-N-((5-oxo-1-(4-(2-oxopiperidin-1-yl)phenyl)pyrrolidin-3-yl)methyl)benzamide
17. 4-(aminomethyl)-N-((5-oxo-1-(4-(2-oxopiperidin-1-yl)phenyl)pyrrolidin-3-yl)methyl)benzamide
18. N1,N1-dimethyl-N3-((5-oxo-1-(4-(2-oxopiperidin-1-yl)phenyl)pyrrolidin-3-yl)methyl)isophthalamide
19. 3-chloro-4-fluoro-N-((5-oxo-1-(4-(2-oxopiperidin-1-yl)phenyl)pyrrolidin-3-yl)methyl)benzamide
20. 6-chloro-N-((5-oxo-1-(4-(2-oxopiperidin-1-yl)phenyl)pyrrolidin-3-yl)methyl)nicotinamide
21. 6-methoxy-N-((5-oxo-1-(4-(2-oxopiperidin-1-yl)phenyl)pyrrolidin-3-yl)methyl)nicotinamide
22. 6-amino-N-((5-oxo-1-(4-(2-oxopiperidin-1-yl)phenyl)pyrrolidin-3-yl)methyl)nicotinamide
23. 2-amino-N-((5-oxo-1-(4-(2-oxopiperidin-1-yl)phenyl)pyrrolidin-3-yl)methyl)isonicotinamide
24. 2-methoxy-N-((5-oxo-1-(4-(2-oxopiperidin-1-yl)phenyl)pyrrolidin-3-yl)methyl)isonicotinamide
25. N-((5-oxo-1-(4-(2-oxopiperidin-1-yl)phenyl)pyrrolidin-3-yl)methyl)-2-naphthamide
26. 6-chloro-N-((5-oxo-1-(4-(2-oxopiperidin-1-yl)phenyl)pyrrolidin-3-yl)methyl)-2-naphthamide
27. 2-chloro-N-((5-oxo-1-(4-(2-oxopiperidin-1-yl)phenyl)pyrrolidin-3-yl)methyl)quinoline-6-carboxamide
28. 3-chloro-N-((5-oxo-1-(4-(2-oxopiperidin-1-yl)phenyl)pyrrolidin-3-yl)methyl)isoquinoline-7-carboxamide
29. 3-chloro-N-((5-oxo-1-(4-(2-oxopiperidin-1-yl)phenyl)pyrrolidin-3-yl)methyl)quinoline-7-carboxamide
30. 6-chloro-N-((5-oxo-1-(4-(2-oxopiperidin-1-yl)phenyl)pyrrolidin-3-yl)methyl)quinoline-2-carboxamide
31. 7-chloro-N-((5-oxo-1-(4-(2-oxopiperidin-1-yl)phenyl)pyrrolidin-3-yl)methyl)quinoline-3-carboxamide
32. 7-chloro-N-((5-oxo-1-(4-(2-oxopiperidin-1-yl)phenyl)pyrrolidin-3-yl)methyl)-2-naphthamide
33. N-((5-oxo-1-(4-(2-oxopiperidin-1-yl)phenyl)pyrrolidin-3-yl)methyl)quinoline-6-carboxamide
34. N-((5-oxo-1-(4-(2-oxopiperidin-1-yl)phenyl)pyrrolidin-3-yl)methyl)isoquinoline-6-carboxamide
35. 1-amino-N-((5-oxo-1-(4-(2-oxopiperidin-1-yl)phenyl)pyrrolidin-3-yl)methyl)isoquinoline-6-carboxamide
36. 3-amino-N-((5-oxo-1-(4-(2-oxopiperidin-1-yl)phenyl)pyrrolidin-3-yl)methyl)isoquinoline-6-carboxamide 37. 2-amino-N-((5-oxo-1-(4-(2-oxopiperidin-1-yl)phenyl)pyrrolidin-3-yl)methyl)quinoline-7-carboxamide
38. 1-amino-N-((5-oxo-1-(4-(2-oxopiperidin-1-yl)phenyl)pyrrolidin-3-yl)methyl)isoquinoline-6-carboxamide
39. 5-chloro-N-((5-oxo-1-(4-(2-oxopiperidin-1-yl)phenyl)pyrrolidin-3-yl)methyl)-2-naphthamide
40. 6-amino-N-((5-oxo-1-(4-(2-oxopiperidin-1-yl)phenyl)pyrrolidin-3-yl)methyl)-2-naphthamide
41. 2-amino-N-((5-oxo-1-(4-(2-oxopiperidin-1-yl)phenyl)pyrrolidin-3-yl)methyl)quinoline-6-carboxamide
42. 3-amino-N-((5-oxo-1-(4-(2-oxopiperidin-1-yl)phenyl)pyrrolidin-3-yl)methyl)isoquinoline-7-carboxamide
43. 6-methoxy-N-((5-oxo-1-(4-(2-oxopiperidin-1-yl)phenyl)pyrrolidin-3-yl)methyl)-2-naphthamide
44. 2-methoxy-N-((5-oxo-1-(4-(2-oxopiperidin-1-yl)phenyl)pyrrolidin-3-yl)methyl)quinoline-6-carboxamide
45. 6-cyano-N-((5-oxo-1-(4-(2-oxopiperidin-1-yl)phenyl)pyrrolidin-3-yl)methyl)-2-naphthamide
46. N-((5-oxo-1-(4-(2-oxopiperidin-1-yl)phenyl)pyrrolidin-3-yl)methyl)benzofuran-2-carboxamide
47. 7-chloro-N-((5-oxo-1-(4-(2-oxopiperidin-1-yl)phenyl)pyrrolidin-3-yl)methyl)benzofuran-2-carboxamide
48. 6-chloro-N-((5-oxo-1-(4-(2-oxopiperidin-1-yl)phenyl)pyrrolidin-3-yl)methyl)benzofuran-2-carboxamide
49. 5-chloro-N-((5-oxo-1-(4-(2-oxopiperidin-1-yl)phenyl)pyrrolidin-3-yl)methyl)benzofuran-2-carboxamide
50. 4-chloro-N-((5-oxo-1-(4-(2-oxopiperidin-1-yl)phenyl)pyrrolidin-3-yl)methyl)benzofuran-2-carboxamide
51. 4,6-dichloro-N-((5-oxo-1-(4-(2-oxopiperidin-1-yl)phenyl)pyrrolidin-3-yl)methyl)benzofuran-2-carboxamide
52. 6-chloro-N-((5-oxo-1-(4-(2-oxopiperidin-1-yl)phenyl)pyrrolidin-3-yl)methyl)benzo[b]thiophene-2-carboxamide
53. N-((5-oxo-1-(4-(2-oxopiperidin-1-yl)phenyl)pyrrolidin-3-yl)methyl)benzo[b]thiophene-2-carboxamide
54. 5-chloro-N-((5-oxo-1-(4-(2-oxopiperidin-1-yl)phenyl)pyrrolidin-3-yl)methyl)benzo[b]thiophene-2-carboxamide
55. 5-chloro-6-fluoro-N-((5-oxo-1-(4-(2-oxopiperidin-1-yl)phenyl)pyrrolidin-3-yl)methyl)benzo[b]thiophene-2-carboxamide
56. 4-chloro-N-((5-oxo-1-(4-(2-oxopiperidin-1-yl)phenyl)pyrrolidin-3-yl)methyl)benzo[b]thiophene-2-carboxamide
57. 7-chloro-N-((5-oxo-1-(4-(2-oxopiperidin-1-yl)phenyl)pyrrolidin-3-yl)methyl)benzo[b]thiophene-2-carboxamide
58. 3,6-dichloro-N-((5-oxo-1-(4-(2-oxopiperidin-1-yl)phenyl)pyrrolidin-3-yl)methyl)benzo[b]thiophene-2-carboxamide
59. 6-bromo-N-((5-oxo-1-(4-(2-oxopiperidin-1-yl)phenyl)pyrrolidin-3-yl)methyl)benzo[b]thiophene-2-carboxamide
60. 6-chloro-N-((5-oxo-1-(4-(2-oxopiperidin-1-yl)phenyl)pyrrolidin-3-yl)methyl)thieno[2,3-b]pyridine-2-carboxamide
61. 6-chloro-N-((5-oxo-1-(4-(2-oxopiperidin-1-yl)phenyl)pyrrolidin-3-yl)methyl)thieno[3,2-c]pyridine-2-carboxamide
62. 5-chloro-N-((5-oxo-1-(4-(2-oxopiperidin-1-yl)phenyl)pyrrolidin-3-yl)methyl)thieno[3,2-b]pyridine-2-carboxamide
63. 5-chloro-N-((5-oxo-1-(4-(2-oxopiperidin-1-yl)phenyl)pyrrolidin-3-yl)methyl)benzo[d]thiazole-2-carboxamide
64. 5-chloro-N-((5-oxo-1-(4-(2-oxopiperidin-1-yl)phenyl)pyrrolidin-3-yl)methyl)benzo[d]oxazole-2-carboxamide
65. N-((5-oxo-1-(4-(2-oxopiperidin-1-yl)phenyl)pyrrolidin-3-yl)methyl)benzo[d]oxazole-2-carboxamide
66. 6-chloro-N-((5-oxo-1-(4-(2-oxopiperidin-1-yl)phenyl)pyrrolidin-3-yl)methyl)-1H-benzo[d]imidazole-2-carboxamide
67. 6-chloro-N-((5-oxo-1-(4-(2-oxopiperidin-1-yl)phenyl)pyrrolidin-3-yl)methyl)-1H-indole-2-carboxamide
68. 5-chloro-N-((5-oxo-1-(4-(2-oxopiperidin-1-yl)phenyl)pyrrolidin-3-yl)methyl)-1H-indole-2-carboxamide
69. 7-chloro-N-((5-oxo-1-(4-(2-oxopiperidin-1-yl)phenyl)pyrrolidin-3-yl)methyl)-1H-indole-2-carboxamide
70. 7-amino-N-((5-oxo-1-(4-(2-oxopiperidin-1-yl)phenyl)pyrrolidin-3-yl)methyl)-1H-indole-2-carboxamide
71. 6-amino-N-((5-oxo-1-(4-(2-oxopiperidin-1-yl)phenyl)pyrrolidin-3-yl)methyl)-1H-indole-2-carboxamide
72. N-((5-oxo-1-(4-(2-oxopiperidin-1-yl)phenyl)pyrrolidin-3-yl)methyl)-1H-indole-5-carboxamide
73. 3-chloro-N-((5-oxo-1-(4-(2-oxopiperidin-1-yl)phenyl)pyrrolidin-3-yl)methyl)-1H-indole-5-carboxamide
74. 3-cyano-N-((5-oxo-1-(4-(2-oxopiperidin-1-yl)phenyl)pyrrolidin-3-yl)methyl)-1H-indole-5-carboxamide
75. N-((5-oxo-1-(4-(2-oxopiperidin-1-yl)phenyl)pyrrolidin-3-yl)methyl)-1H-indole-6-carboxamide
76. 3-chloro-N-((5-oxo-1-(4-(2-oxopiperidin-1-yl)phenyl)pyrrolidin-3-yl)methyl)-1H-indole-6-carboxamide
77. 3-bromo-N-((5-oxo-1-(4-(2-oxopiperidin-1-yl)phenyl)pyrrolidin-3-yl)methyl)-1H-indole-6-carboxamide
78. 2-chloro-N-((5-oxo-1-(4-(2-oxopiperidin-1-yl)phenyl)pyrrolidin-3-yl)methyl)benzo[b]thiophene-6-carboxamide
79. 5-chloro-N-((5-oxo-1-(4-(2-oxopiperidin-1-yl)phenyl)pyrrolidin-3-yl)methyl)furan-2-carboxamide
80. 5-chloro-N-((5-oxo-1-(4-(2-oxopiperidin-1-yl)phenyl)pyrrolidin-3-yl)methyl)thiophene-2-carboxamide
81. 3,5-dichloro-N-((5-oxo-1-(4-(2-oxopiperidin-1-yl)phenyl)pyrrolidin-3-yl)methyl)thiophene-2-carboxamide
82. 5-chloro-3-fluoro-N-((5-oxo-1-(4-(2-oxopiperidin-1-yl)phenyl)pyrrolidin-3-yl)methyl)thiophene-2-carboxamide
83. 5-bromo-N-((5-oxo-1-(4-(2-oxopiperidin-1-yl)phenyl)pyrrolidin-3-yl)methyl)thiophene-2-carboxamide
84. N-((5-oxo-1-(4-(2-oxopiperidin-1-yl)phenyl)pyrrolidin-3-yl)methyl)-5-phenylthiophene-2-carboxamide
85. N-((5-oxo-1-(4-(2-oxopiperidin-1-yl)phenyl)pyrrolidin-3-yl)methyl)-5-(pyridin-2-yl)thiophene-2-carboxamide
86. 5-(6-chloropyridin-2-yl)-N-((5-oxo-1-(4-(2-oxopiperidin-1-yl)phenyl)pyrrolidin-3-yl)methyl)thiophene-2-carboxamide
87. 5-cyano-N-((5-oxo-1-(4-(2-oxopiperidin-1-yl)phenyl)pyrrolidin-3-yl)methyl)thiophene-2-carboxamide
88. 5-(5-chlorothiophen-2-yl)-N-((5-oxo-1-(4-(2-oxopiperidin 1-yl)phenyl)pyrrolidin-3-yl)methyl)thiophene-2-carboxamide
89. 5-(isothiazol-5-yl)-N-((5-oxo-1-(4-(2-oxopiperidin-1-yl)phenyl)pyrrolidin-3-yl)methyl)thiophene-2-carboxamide
90. 5-(3-chloroisothiazol-5-yl)-N-((5-oxo-1-(4-(2-oxopiperidin-1-yl)phenyl)pyrrolidin-3-yl)methyl)thiophene-2-carboxamide
91. 5-(3-chloroisoxazol-5-yl)-N-((5-oxo-1-($^4$-(2-oxopiperidin-1-yl)phenyl)pyrrolidin-3-yl)methyl)thiophene-2-carboxamide
92. 5-(3-methylisoxazol-5-yl)-N-((5-oxo-1-(4-(2-oxopiperidin-1-yl)phenyl)pyrrolidin-3-yl)methyl)thiophene-2-carboxamide
93. 5-(5-methyl-2H-1,2,4-triazol-3-yl)-N-((5-oxo-1-(4-(2-oxopiperidin-1-yl)phenyl)pyrrolidin-3-yl)methyl)thiophene-2-carboxamide 94. N-((5-oxo-1-(4-(2-oxopiperidin-1-yl)phenyl)pyrrolidin-3-yl)methyl)-5-(1H-tetrazol-5-yl)thiophene-2-carboxamide
95. (E)-3-(4-chlorophenyl)-N-((5-oxo-1-(4-(2-oxopiperidin-1-yl)phenyl)pyrrolidin-3-yl)methyl)acrylamide
96. 3-(4-chlorophenyl)-N-((5-oxo-1-(4-(2-oxopiperidin-1-yl)phenyl)pyrrolidin-3-yl)methyl)propanamide
97. (E)-3-(5-chlorothiophen-2-yl)-N-((5-oxo-1-(4-(2-oxopiperidin-1-yl)phenyl)pyrrolidin-3-yl)methyl)acrylamide
98. 3-(5-chlorothiophen-2-yl)-N-((5-oxo-1-(4-(2-oxopiperidin-1-yl)phenyl)pyrrolidin-3-yl)methyl)propanamide
99. N-((5-oxo-1-(4-(2-oxopiperidin-1-yl)phenyl)pyrrolidin-3-yl)methyl)cyclohexanecarboxamide
100. N-((1-(4-(2-(dimethylamino)-N-methylacetamido)phenyl)-5-oxopyrrolidin-3-yl)methyl)benzamide
101. 4-chloro-N-((1-(4-(2-(dimethylamino)-N-methylacetamido)phenyl)-5-oxopyrrolidin-3-yl)methyl)benzamide
102. N-((1-(4-(2-(dimethylamino)-N-methylacetamido)phenyl)-5-oxopyrrolidin-3-yl)methyl)-4-methoxybenzamide
103. 3-carbamimidoyl-N-((1-(4-(2-(dimethylamino)-N-methylacetamido)phenyl)-5-oxopyrrolidin-3-yl)methyl)benzamide
104. 3-carbamimidoyl-N-((1-(4-(N-methyl-2-(pyrrolidin-1-yl)acetamido)phenyl)-5-oxopyrrolidin-3-yl)methyl)benzamide
105. 3-amino-N-((1-(4-(2-(dimethylamino)-N-methylacetamido)phenyl)-5-oxopyrrolidin-3-yl)methyl)benzo[d]isoxazole-5-carboxamide
106. 3-amino-N-((1-(4-(N-methyl-2-(pyrrolidin-1-yl)acetamido)phenyl)-5-oxopyrrolidin-3-yl)methyl)benzo[d]isoxazole-5-carboxamide
107. N1-((1-(4-(N-methyl-2-(pyrrolidin-1-yl)acetamido)phenyl)-5-oxopyrrolidin-3-yl)methyl)isophthalamide
108. 3-chloro-N-((1-(4-(N-methyl-2-(pyrrolidin-1-yl)acetamido)phenyl)-5-oxopyrrolidin-3-yl)methyl)benzamide
109. 3-(aminomethyl)-N-((1-(4-(N-methyl-2-(pyrrolidin-1-yl)acetamido)phenyl)-5-oxopyrrolidin-3-yl)methyl)benzamide
110. 3-((dimethylamino)methyl)-N-((1-(4-(N-methyl-2-(pyrrolidin-1-yl)acetamido)phenyl)-5-oxopyrrolidin-3-yl)methyl)benzamide
111. 4-chloro-N-((1-(4-(N-methyl-2-(pyrrolidin-1-yl)acetamido)phenyl)-5-oxopyrrolidin-3-yl)methyl)benzamide
112. 4-methoxy-N-((1-(4-(N-methyl-2-(pyrrolidin-1-yl)acetamido)phenyl)-5-oxopyrrolidin-3-yl)methyl)benzamide
113. 6-methoxy-N-((1-(4-(N-methyl-2-(pyrrolidin-1-yl)acetamido)phenyl)-5-oxopyrrolidin-3-yl)methyl)nicotinamide
114. 6-chloro-N-((1-(4-(N-methyl-2-(pyrrolidin-1-yl)acetamido)phenyl)-5-oxopyrrolidin-3-yl)methyl)nicotinamide
115. 6-amino-N-((1-(4-(N-methyl-2-(pyrrolidin-1-yl)acetamido)phenyl)-5-oxopyrrolidin-3-yl)methyl)nicotinamide
116. N-((1-(4-(N-methyl-2-(pyrrolidin-1-yl)acetamido)phenyl)-5-oxopyrrolidin-3-yl)methyl)-2-naphthamide
117. 6-chloro-N-((1-(4-(N-methyl-2-(pyrrolidin-1-yl)acetamido)phenyl)-5-oxopyrrolidin-3-yl)methyl)-2-naphthamide
118. 7-chloro-N-((1-(4-(N-methyl-2-(pyrrolidin-1-yl)acetamido)phenyl)-5-oxopyrrolidin-3-yl)methyl)-2-naphthamide
119. 2-chloro-N-((1-(4-(N-methyl-2-(pyrrolidin-1-yl)acetamido)phenyl)-5-oxopyrrolidin-3-yl)methyl)quinoline-7-carboxamide
120. 2-amino-N-((1-(4-(N-methyl-2-(pyrrolidin-1-yl)acetamido)phenyl)-5-oxopyrrolidin-3-yl)methyl)quinoline-7-carboxamide
121. 7-amino-N-((1-(4-(N-methyl-2-(pyrrolidin-1-yl)acetamido)phenyl)-5-oxopyrrolidin-3-yl)methyl)-2-naphthamide
122. 6-amino-N-((1-(4-(N-methyl-2-(pyrrolidin-1-yl)acetamido)phenyl)-5-oxopyrrolidin-3-yl)methyl)-2-naphthamide
123. 2-amino-N-((1-(4-(N-methyl-2-(pyrrolidin-1-yl)acetamido)phenyl)-5-oxopyrrolidin-3-yl)methyl)quinoline-6-carboxamide
124. N-((1-(4-(N-methyl-2-(pyrrolidin-1-yl)acetamido)phenyl)-5-oxopyrrolidin-3-yl)methyl)quinoline-6-carboxamide
125. N-((1-(4-(N-methyl-2-(pyrrolidin-1-yl)acetamido)phenyl)-5-oxopyrrolidin-3-yl)methyl)isoquinoline-6-carboxamide
126. N-((1-(4-(N-methyl-2-(pyrrolidin-1-yl)acetamido)phenyl)-5-oxopyrrolidin-3-yl)methyl)-2,7a-dihydrobenzofuran-2-carboxamide
127. 6-chloro-N-((1-(4-(N-methyl-2-(pyrrolidin-1-yl)acetamido)phenyl)-5-oxopyrrolidin-3-yl)methyl)-2,7a-dihydrobenzofuran-2-carboxamide
128. 6-chloro-N-((1-(4-(N-methyl-2-(pyrrolidin-1-yl)acetamido)phenyl)-5-oxopyrrolidin-3-yl)methyl)-2,7a-dihydro-1H-indole-2-carboxamide
129. 6-chloro-N-((1-(4-(N-methyl-2-(pyrrolidin-1-yl)acetamido)phenyl)-5-oxopyrrolidin-3-yl)methyl)-2,7a-dihydrobenzo[b]thiophene-2-carboxamide
130. N-((1-(4-(N-methyl-2-(pyrrolidin-1-yl)acetamido)phenyl)-5-oxopyrrolidin-3-yl)methyl)-2,7a-dihydrobenzo[b]thiophene-2-carboxamide
131. 5-chloro-N-((1-(4-(N-methyl-2-(pyrrolidin-1-yl)acetamido)phenyl)-5-oxopyrrolidin-3-yl)methyl)-2,7a-dihydrobenzo[b]thiophene-2-carboxamide
132. 5-chloro-N-((1-(4-(N-methyl-2-(pyrrolidin-1-yl)acetamido)phenyl)-5-oxopyrrolidin-3-yl)methyl)-2,7a-dihydrothieno[3,2-b]pyridine-2-carboxamide
133. 5-amino-N-((1-(4-(N-methyl-2-(pyrrolidin-1-yl)acetamido)phenyl)-5-oxopyrrolidin-3-yl)methyl)-2,7a-dihydrothieno[3,2-b]pyridine-2-carboxamide
134. 5-amino-N-((1-(4-(N-methyl-2-(pyrrolidin-1-yl)acetamido)phenyl)-5-oxopyrrolidin-3-yl)methyl)-2,7a-dihydrothieno[2,3-b]pyridine-2-carboxamide
135. 6-chloro-N-((1-(4-(N-methyl-2-(pyrrolidin-1-yl)acetamido)phenyl)-5-oxopyrrolidin-3-yl)methyl)-2,7a-dihydrothieno[2,3-b]pyridine-2-carboxamide
136. N-((1-(4-(N-methyl-2-(pyrrolidin-1-yl)acetamido)phenyl)-5-oxopyrrolidin-3-yl)methyl)-1H-indole-6-carboxamide
137. 3-chloro-N-((1-(4-(N-methyl-2-(pyrrolidin-1-yl)acetamido)phenyl)-5-oxopyrrolidin-3-yl)methyl)-1H-indole-6-carboxamide
138. N-((1-(4-(N-methyl-2-(pyrrolidin-1-yl)acetamido)phenyl)-5-oxopyrrolidin-3-yl)methyl)-3H-benzo[d]imidazole-5-carboxamide
139. 2-methyl-N-((1-(4-(N-methyl-2-(pyrrolidin-1-yl)acetamido)phenyl)-5-oxopyrrolidin-3-yl)methyl)-3H-benzo[d]imidazole-5-carboxamide
140. 2-methyl-N-((1-(4-(N-methyl-2-(pyrrolidin-1-yl)acetamido)phenyl)-5-oxopyrrolidin-3-yl)methyl)benzo[d]oxazole-6-carboxamide
141. 6-chloro-N-((1-(4-(N-methyl-2-(pyrrolidin-1-yl)acetamido)phenyl)-5-oxopyrrolidin-3-yl)methyl)benzo[d]oxazole-2-carboxamide
142. N-((1-(4-(N-methyl-2-(pyrrolidin-1-yl)acetamido)phenyl)-5-oxopyrrolidin-3-yl)methyl)benzo[d]oxazole-2-carboxamide 143. N-((1-(4-(N-methyl-2-(pyrrolidin-1-yl)acetamido)phenyl)-5-oxopyrrolidin-3-yl)methyl)-1H-benzo[d]imidazole-2-carboxamide
144. N-((1-(4-(N-methyl-2-(pyrrolidin-1-yl)acetamido)phenyl)-5-oxopyrrolidin-3-yl)methyl)benzo[d]thiazole-2-carboxamide
145. N-((1-(4-(N-methyl-2-(pyrrolidin-1-yl)acetamido)phenyl)-5-oxopyrrolidin-3-yl)methyl)thiophene-2-carboxamide
146. 5-chloro-N-((1-(4-(N-methyl-2-(pyrrolidin-1-yl)acetamido)phenyl)-5-oxopyrrolidin-3-yl)methyl)thiophene-2-carboxamide
147. 5-chloro-N-((1-(4-(N-methyl-2-(pyrrolidin-1-yl)acetamido)phenyl)-5-oxopyrrolidin-3-yl)methyl)furan-2-carboxamide
148. N-((1-(4-(N-methyl-2-(pyrrolidin-1-yl)acetamido)phenyl)-5-oxopyrrolidin-3-yl)methyl)-5-phenylthiophene-2-carboxamide
149. N-((1-(4-(N-methyl-2-(pyrrolidin-1-yl)acetamido)phenyl)-5-oxopyrrolidin-3-yl)methyl)-5-(pyridin-2-yl)thiophene-2-carboxamide
150. N-((1-(4-(N-methyl-2-(pyrrolidin-1-yl)acetamido)phenyl)-5-oxopyrrolidin-3-yl)methyl)-5-(thiophen-2-yl)thiophene-2-carboxamide
151. 5-(5-chlorothiophen-2-yl)-N-((1-(4-(N-methyl-2-(pyrrolidin-1-yl)acetamido)phenyl)-5-oxopyrrolidin-3-yl)methyl)thiophene-2-carboxamide
152. N-((1-(4-(N-methyl-2-(pyrrolidin-1-yl)acetamido)phenyl)-5-oxopyrrolidin-3-yl)methyl)cyclohexanecarboxamide
153. N-((5-oxo-1-(4-(2-oxopyridin-1(2H)-yl)phenyl)pyrrolidin-3-yl)methyl)cyclohexanecarboxamide
154. N-((5-oxo-1-(4-(2-oxopyridin-1(2H)-yl)phenyl)pyrrolidin-3-yl)methyl)benzamide
155. 4-chloro-N-((5-oxo-1-(4-(2-oxopyridin-1(2H)-yl)phenyl)pyrrolidin-3-yl)methyl)benzamide
156. 4-methoxy-N-((5-oxo-1-(4-(2-oxopyridin-1(2H)-yl)phenyl)pyrrolidin-3-yl)methyl)benzamide
157. 4-cyano-N-((5-oxo-1-(4-(2-oxopyridin-1(2H)-yl)phenyl)pyrrolidin-3-yl)methyl)benzamide
158. 4-amino-N-((5-oxo-1-(4-(2-oxopyridin-1(2H)-yl)phenyl)pyrrolidin-3-yl)methyl)benzamide
159. 4-(aminomethyl)-N-((5-oxo-1-(4-(2-oxopyridin-1(2H)-yl)phenyl)pyrrolidin-3-yl)methyl)benzamide
160. 3-chloro-N-((5-oxo-1-(4-(2-oxopyridin-1(2H)-yl)phenyl)pyrrolidin-3-yl)methyl)benzamide
161. 3-(aminomethyl)-N-((5-oxo-1-(4-(2-oxopyridin-1(2H)-yl)phenyl)pyrrolidin-3-yl)methyl)benzamide
162. N1-((5-oxo-1-(4-(2-oxopyridin-1(2H)-yl)phenyl)pyrrolidin-3-yl)methyl)isophthalamide
163. 2-amino-N-((5-oxo-1-(4-(2-oxopyridin-1(2H)-yl)phenyl)pyrrolidin-3-yl)methyl)isonicotinamide
164. 2-chloro-N-((5-oxo-1-(4-(2-oxopyridin-1(2H)-yl)phenyl)pyrrolidin-3-yl)methyl)isonicotinamide
165. N-((5-oxo-1-(4-(2-oxopyridin-1(2H)-yl)phenyl)pyrrolidin-3-yl)methyl)-2-naphthamide
166. N-((5-oxo-1-(4-(2-oxopyridin-1(2H)-yl)phenyl)pyrrolidin-3-yl)methyl)quinoline-7-carboxamide
167. 2-amino-N-((5-oxo-1-(4-(2-oxopyridin-1(2H)-yl)phenyl)pyrrolidin-3-yl)methyl)quinoline-7-carboxamide
168. 7-amino-N-((5-oxo-1-(4-(2-oxopyridin-1(2H)-yl)phenyl)pyrrolidin-3-yl)methyl)-2-naphthamide
169. 7-chloro-N-((5-oxo-1-(4-(2-oxopyridin-1(2H)-yl)phenyl)pyrrolidin-3-yl)methyl)-2-naphthamide
170. 2-chloro-N-((5-oxo-1-(4-(2-oxopyridin-1(2H)-yl)phenyl)pyrrolidin-3-yl)methyl)quinoline-7-carboxamide
171. 6-chloro-N-((5-oxo-1-(4-(2-oxopyridin-1(2H)-yl)phenyl)pyrrolidin-3-yl)methyl)-2-naphthamide
172. 6-amino-N-((5-oxo-1-(4-(2-oxopyridin-1(2H)-yl)phenyl)pyrrolidin-3-yl)methyl)-2-naphthamide
173. 3-amino-N-((5-oxo-1-(4-(2-oxopyridin-1(2H)-yl)phenyl)pyrrolidin-3-yl)methyl)isoquinoline-7-carboxamide
174. 6-amino-N-((5-oxo-1-(4-(2-oxopyridin-1(2H)-yl)phenyl)pyrrolidin-3-yl)methyl)furo[3,2-c]pyridine-2-carboxamide
175. 6-chloro-N-((5-oxo-1-(4-(2-oxopyridin-1(2H)-yl)phenyl)pyrrolidin-3-yl)methyl)furo[3,2-c]pyridine-2-carboxamide
176. 6-chloro-N-((5-oxo-1-(4-(2-oxopyridin-1(2H)-yl)phenyl)pyrrolidin-3-yl)methyl)benzofuran-2-carboxamide
177. 6-chloro-N-((5-oxo-1-(4-(2-oxopyridin-1(2H)-yl)phenyl)pyrrolidin-3-yl)methyl)benzo[b]thiophene-2-carboxamide
178. 6-chloro-N-((5-oxo-1-(4-(2-oxopyridin-1(2H)-yl)phenyl)pyrrolidin-3-yl)methyl)benzo[d]thiazole-2-carboxamide
179. 6-chloro-N-((5-oxo-1-(4-(2-oxopyridin-1(2H)-yl)phenyl)pyrrolidin-3-yl)methyl)-1H-benzo[d]imidazole-2-carboxamide
180. N-((5-oxo-1-(4-(2-oxopyridin-1(2H)-yl)phenyl)pyrrolidin-3-yl)methyl)-1H-benzo[d]imidazole-2-carboxamide
181. N-((5-oxo-1-(4-(2-oxopyridin-1(2H)-yl)phenyl)pyrrolidin-3-yl)methyl)benzo[d]thiazole-2-carboxamide
182. 5-chloro-N-((5-oxo-1-(4-(2-oxopyridin-1(2H)-yl)phenyl)pyrrolidin-3-yl)methyl)benzo[d]thiazole-2-carboxamide
183. 5-chloro-N-((5-oxo-1-(4-(2-oxopyridin-1(2H)-yl)phenyl)pyrrolidin-3-yl)methyl)benzo[b]thiophene-2-carboxamide
184. 5-chloro-N-((5-oxo-1-(4-(2-oxopyridin-1(2H)-yl)phenyl)pyrrolidin-3-yl)methyl)benzofuran-2-carboxamide
185. 5-chloro-N-((5-oxo-1-(4-(2-oxopyridin-1(2H)-yl)phenyl)pyrrolidin-3-yl)methyl)-1H-indole-2-carboxamide
186. N-((5-oxo-1-(4-(2-oxopyridin-1(2H)-yl)phenyl)pyrrolidin-3-yl)methyl)-1H-indole-2-carboxamide
187. N-((5-oxo-1-(4-(2-oxopyridin-1(2H)-yl)phenyl)pyrrolidin-3-yl)methyl)thiophene-2-carboxamide
188. 5-chloro-N-((5-oxo-1-(4-(2-oxopyridin-1(2H)-yl)phenyl)pyrrolidin-3-yl)methyl)thiophene-2-carboxamide
189. 5-methyl-N-((5-oxo-1-(4-(2-oxopyridin-1(2H)-yl)phenyl)pyrrolidin-3-yl)methyl)thiophene-2-carboxamide
190. N-((5-oxo-1-(4-(2-oxopyridin-1(2H)-yl)phenyl)pyrrolidin-3-yl)methyl)-5-phenylthiophene-2-carboxamide
191. N-((5-oxo-1-(4-(2-oxopyridin-1(2H)-yl)phenyl)pyrrolidin-3-yl)methyl)-5-(pyridin-2-yl)thiophene-2-carboxamide
192. N-((5-oxo-1-(4-(2-oxopyridin-1(2H)-yl)phenyl)pyrrolidin-3-yl)methyl)-5-(thiophen-2-yl)thiophene-2-carboxamide
193. 5-(5-chlorothiophen-2-yl)-N-((5-oxo-1-(4-(2-oxopyridin-1(2H)-yl)phenyl)pyrrolidin-3-yl)methyl)thiophene-2-carboxamide
194. N-((1-(4-(2-((dimethylamino)methyl)-1H-imidazol-1-yl)phenyl)-5-oxopyrrolidin-3-yl)methyl)benzamide
195. N-((1-(4-(2-((dimethylamino)methyl)-1H-imidazol-1-yl)phenyl)-5-oxopyrrolidin-3-yl)methyl)-4-methoxybenzamide
196. 4-chloro-N-((1-(4-(2-((dimethylamino)methyl)-1H-imidazol-1-yl)phenyl)-5-oxopyrrolidin-3-yl)methyl)benzamide
197. 3-chloro-N-((1-(4-(2-((dimethylamino)methyl)-1H-imidazol-1-yl)phenyl)-5-oxopyrrolidin-3-yl)methyl)benzamide 198. 3-(aminomethyl)-N-((1-(4-(2-((dimethylamino)methyl)-1H-imidazol-1-yl)phenyl)-5-oxopyrrolidin-3-yl)methyl)benzamide
199. 3-((dimethylamino)methyl)-N-((1-(4-(2-((dimethylamino)methyl)-1H-imidazol-1-yl)phenyl)-5-oxopyrrolidin-3-yl)methyl)benzamide
200. 3-carbamimidoyl-N-((1-(4-(2-((dimethylamino)methyl)-1H-imidazol-1-yl)phenyl)-5-oxopyrrolidin-3-yl)methyl)benzamide
201. 3-amino-N-((1-(4-(2-((dimethylamino)methyl)-1H-imidazol-1-yl)phenyl)-5-oxopyrrolidin-3-yl)methyl)benzo[d]isoxazole-5-carboxamide
202. 3-amino-N-((1-(4-(2-((methylamino)methyl)-1H-imidazol-1-yl)phenyl)-5-oxopyrrolidin-3-yl)methyl)benzo[d]isoxazole-5-carboxamide
203. 3-amino-N-((1-(2-fluoro-4-(2-((methylamino)methyl)-1H-imidazol-1-yl)phenyl)-5-oxopyrrolidin-3-yl)methyl)benzo[d]isoxazole-5-carboxamide
204. 3-amino-N-((1-(3-fluoro-4-(2-((methylamino)methyl)-1H-imidazol-1-yl)phenyl)-5-oxopyrrolidin-3-yl)methyl)benzo[d]isoxazole-5-carboxamide
205. 3-amino-N-((1-(4-(2-((dimethylamino)methyl)-1H-imidazol-1-yl)-3-fluorophenyl)-5-oxopyrrolidin-3-yl)methyl)benzo[d]isoxazole-5-carboxamide
206. 3-amino-N-((1-(5-(2-((dimethylamino)methyl)-1H-imidazol-1-yl)pyridin-2-yl)-5-oxopyrrolidin-3-yl)methyl)benzo[d]isoxazole-5-carboxamide
207. 3-amino-N-((1-(6-(2-((dimethylamino)methyl)-1H-imidazol-1-yl)pyridin-3-yl)-5-oxopyrrolidin-3-yl)methyl)benzo[d]isoxazole-5-carboxamide
208. 3-amino-N-((1-(4-(2-methyl-1H-imidazol-1-yl)phenyl)-5-oxopyrrolidin-3-yl)methyl)benzo[d]isoxazole-5-carboxamide
209. N1-((1-(4-(2-((dimethylamino)methyl)-1H-imidazol-1-yl)phenyl)-5-oxopyrrolidin-3-yl)methyl)isophthalamide
210. N-((1-(4-(2-((dimethylamino)methyl)-1H-imidazol-1-yl)phenyl)-5-oxopyrrolidin-3-yl)methyl)-2-naphthamide
211. 7-chloro-N-((1-(4-(2-((dimethylamino)methyl)-1H-imidazol-1-yl)phenyl)-5-oxopyrrolidin-3-yl)methyl)-2-naphthamide
212. 6-chloro-N-((1-(4-(2-((dimethylamino)methyl)-1H-imidazol-1-yl)phenyl)-5-oxopyrrolidin-3-yl)methyl)-2-naphthamide
213. 2-chloro-N-((1-(4-(2-((dimethylamino)methyl)-1H-imidazol-1-yl)phenyl)-5-oxopyrrolidin-3-yl)methyl)quinoline-6-carboxamide
214. 2-amino-N-((1-(4-(2-((dimethylamino)methyl)-1H-imidazol-1-yl)phenyl)-5-oxopyrrolidin-3-yl)methyl)quinoline-6-carboxamide
215. N-((1-(4-(2-((dimethylamino)methyl)-1H-imidazol-1-yl)phenyl)-5-oxopyrrolidin-3-yl)methyl)-2-methylquinoline-6-carboxamide
216. N-((1-(4-(2-((dimethylamino)methyl)-1H-imidazol-1-yl)phenyl)-5-oxopyrrolidin-3-yl)methyl)-5-methylfuro[3,2-b]pyridine-2-carboxamide
217. 5-chloro-N-((1-(4-(2-((dimethylamino)methyl)-1H-imidazol-1-yl)phenyl)-5-oxopyrrolidin-3-yl)methyl)furo[3,2-b]pyridine-2-carboxamide
218. 5-chloro-N-((1-(4-(2-((dimethylamino)methyl)-1H-imidazol-1-yl)phenyl)-5-oxopyrrolidin-3-yl)methyl)thieno[3,2-b]pyridine-2-carboxamide
219. 5-chloro-N-((1-(4-(2-((dimethylamino)methyl)-1H-imidazol-1-yl)phenyl)-5-oxopyrrolidin-3-yl)methyl)benzo[b]thiophene-2-carboxamide
220. N-((1-(4-(2-((dimethylamino)methyl)-1H-imidazol-1-yl)phenyl)-5-oxopyrrolidin-3-yl)methyl)-5-methylbenzo[b]thiophene-2-carboxamide
221. N-((1-(4-(2-((dimethylamino)methyl)-1H-imidazol-1-yl)phenyl)-5-oxopyrrolidin-3-yl)methyl)benzo[b]thiophene-2-carboxamide
222. 6-chloro-N-((1-(4-(2-((dimethylamino)methyl)-1H-imidazol-1-yl)phenyl)-5-oxopyrrolidin-3-yl)methyl)benzo[b]thiophene-2-carboxamide
223. 6-chloro-N-((1-(4-(2-((dimethylamino)methyl)-1H-imidazol-1-yl)phenyl)-5-oxopyrrolidin-3-yl)methyl)thieno[2,3-b]pyridine-2-carboxamide
224. N-((1-(4-(2-((dimethylamino)methyl)-1H-imidazol-1-yl)phenyl)-5-oxopyrrolidin-3-yl)methyl)-6-methylthieno[2,3-b]pyridine-2-carboxamide
225. N-((1-(4-(2-((dimethylamino)methyl)-1H-imidazol-1-yl)phenyl)-5-oxopyrrolidin-3-yl)methyl)-6-methylbenzo[b]thiophene-2-carboxamide
226. N-((1-(4-(2-((dimethylamino)methyl)-1H-imidazol-1-yl)phenyl)-5-oxopyrrolidin-3-yl)methyl)-6-methyl-1H-indole-2-carboxamide
227. 6-chloro-N-((1-(4-(2-((dimethylamino)methyl)-1H-imidazol-1-yl)phenyl)-5-oxopyrrolidin-3-yl)methyl)-1H-indole-2-carboxamide
228. N-((1-(4-(2-((dimethylamino)methyl)-1H-imidazol-1-yl)phenyl)-5-oxopyrrolidin-3-yl)methyl)-1H-indole-2-carboxamide
229. N-((1-(4-(2-((dimethylamino)methyl)-1H-imidazol-1-yl)phenyl)-5-oxopyrrolidin-3-yl)methyl)-5-methyl-iH-indole-2-carboxamide
230. 5-chloro-N-((1-(4-(2-((dimethylamino)methyl)-1H-imidazol-1-yl)phenyl)-5-oxopyrrolidin-3-yl)methyl)-1H-indole-2-carboxamide
231. 5-chloro-N-((1-(4-(2-((dimethylamino)methyl)-1H-imidazol-1-yl)phenyl)-5-oxopyrrolidin-3-yl)methyl)-1H-benzo[d]imidazole-2-carboxamide
232. 5-chloro-N-((1-(4-(2-((dimethylamino)methyl)-1H-imidazol-1-yl)phenyl)-5-oxopyrrolidin-3-yl)methyl)benzo[d]oxazole-2-carboxamide
233. 5-chloro-N-((1-(4-(2-((dimethylamino)methyl)-1H-imidazol-1-yl)phenyl)-5-oxopyrrolidin-3-yl)methyl)benzo[d]thiazole-2-carboxamide
234. N-((1-(4-(2-((dimethylamino)methyl)-1H-imidazol-1-yl)phenyl)-5-oxopyrrolidin-3-yl)methyl)-5-methylbenzo[d]thiazole-2-carboxamide
235. N-((1-(4-(2-((dimethylamino)methyl)-1H-imidazol-1-yl)phenyl)-5-oxopyrrolidin-3-yl)methyl)benzo[d]thiazole-2-carboxamide
236. N-((1-(4-(2-((dimethylamino)methyl)-1H-imidazol-1-yl)phenyl)-5-oxopyrrolidin-3-yl)methyl)benzo[d]oxazole-2-carboxamide
237. N-((1-(4-(2-((dimethylamino)methyl)-1H-imidazol-1-yl)phenyl)-5-oxopyrrolidin-3-yl)methyl)-5-methylthiophene-2-carboxamide
238. 5-chloro-N-((1-(4-(2-((dimethylamino)methyl)-1H-imidazol-1-yl)phenyl)-5-oxopyrrolidin-3-yl)methyl)thiophene-2-carboxamide
239. 5-chloro-N-((1-(4-(2-((dimethylamino)methyl)-1H-imidazol-1-yl)phenyl)-5-oxopyrrolidin-3-yl)methyl)furan-2-carboxamide
240. N-((1-(4-(2-((dimethylamino)methyl)-1H-imidazol-1-yl)phenyl)-5-oxopyrrolidin-3-yl)methyl)-5-(thiophen-2-yl)thiophene-2-carboxamide
241. 5-(5-chlorothiophen-2-yl)-N-((1-(4-(2-((dimethylamino)methyl)-1H-imidazol-1-yl)phenyl)-5-oxopyrrolidin-3-yl)methyl)thiophene-2-carboxamide 242. 5-chloro-N-((1-(4-(2-((dimethylamino)methyl)-1H-imidazol-1-yl)-2-fluorophenyl)-5-oxopyrrolidin-3-yl)methyl)thiophene-2-carboxamide
243. 5-chloro-N-((1-(5-(2-((dimethylamino)methyl)-1H-imidazol-1-yl)pyridin-2-yl)-5-oxopyrrolidin-3-yl)methyl)thiophene-2-carboxamide
244. 5-chloro-N-((1-(6-(2-((dimethylamino)methyl)-1H-imidazol-1-yl)pyridin-3-yl)-5-oxopyrrolidin-3-yl)methyl)thiophene-2-carboxamide
245. 5-chloro-N-((1-(4-(1-((dimethylamino)methyl)cyclopropyl)phenyl)-5-oxopyrrolidin-3-yl)methyl)thiophene-2-carboxamide
246. 5-chloro-N-((5-oxo-1-(4-(1-(pyrrolidin-1-ylmethyl)cyclopropyl)phenyl)pyrrolidin-3-yl)methyl)thiophene-2-carboxamide
247. 5-chloro-N-((1-(4-(1-((dimethylamino)methyl)cyclopropyl)phenyl)-5-oxopyrrolidin-3-yl)methyl)thiophene-2-carboxamide
248. 5-(5-chlorothiophen-2-yl)-N-((1-(4-(1-((dimethylamino)methyl)cyclopropyl)phenyl)-5-oxopyrrolidin-3-yl)methyl)thiophene-2-carboxamide
249. N-((1-(4-(1-((dimethylamino)methyl)cyclopropyl)phenyl)-5-oxopyrrolidin-3-yl)methyl)-5-(thiophen-2-yl)thiophene-2-carboxamide
250. 5-(5-chlorothiophen-2-yl)-N-((5-oxo-1-(4-(1-(pyrrolidin-1-ylmethyl)cyclopropyl)phenyl)pyrrolidin-3-yl)methyl)thiophene-2-carboxamide
251. N-((5-oxo-1-(4-(1-(pyrrolidin-1-ylmethyl)cyclopropyl)phenyl)pyrrolidin-3-yl)methyl)benzo[b]thiophene-2-carboxamide
252. N-((1-(4-(1-((dimethylamino)methyl)cyclopropyl)phenyl)-5-oxopyrrolidin-3-yl)methyl)benzo[b]thiophene-2-carboxamide
253. 6-chloro-N-((1-(4-(1-((dimethylamino)methyl)cyclopropyl)phenyl)-5-oxopyrrolidin-3-yl)methyl)benzo[b]thiophene-2-carboxamide
254. 6-chloro-N-((5-oxo-1-(4-(1-(pyrrolidin-1-ylmethyl)cyclopropyl)phenyl)pyrrolidin-3-yl)methyl)benzo[b]thiophene-2-carboxamide
255. 6-chloro-N-((5-oxo-1-(4-(1-(pyrrolidin-1-ylmethyl)cyclopropyl)phenyl)pyrrolidin-3-yl)methyl)thieno[2,3-b]pyridine-2-carboxamide
256. 6-chloro-N-((1-(4-(1-((dimethylamino)methyl)cyclopropyl)phenyl)-5-oxopyrrolidin-3-yl)methyl)thieno[2,3-b]pyridine-2-carboxamide
257. N-((1-(4-(1-((dimethylamino)methyl)cyclopropyl)phenyl)-5-oxopyrrolidin-3-yl)methyl)-1H-indole-2-carboxamide
258. N-((5-oxo-1-(4-(1-(pyrrolidin-1-ylmethyl)cyclopropyl)phenyl)pyrrolidin-3-yl)methyl)-1H-indole-2-carboxamide
259. 6-chloro-N-((5-oxo-1-(4-(1-(pyrrolidin-1-ylmethyl)cyclopropyl)phenyl)pyrrolidin-3-yl)methyl)-1H-indole-2-carboxamide
260. 6-chloro-N-((1-(4-(1-((dimethylamino)methyl)cyclopropyl)phenyl)-5-oxopyrrolidin-3-yl)methyl)-1H-indole-2-carboxamide
261. 5-chloro-N-((1-(4-(1-((dimethylamino)methyl)cyclopropyl)phenyl)-5-oxopyrrolidin-3-yl)methyl)-1H-indole-2-carboxamide
262. 5-chloro-N-((5-oxo-1-(4-(1-(pyrrolidin-1-ylmethyl)cyclopropyl)phenyl)pyrrolidin-3-yl)methyl)-1H-indole-2-carboxamide
263. 5-chloro-N-((5-oxo-1-(4-(1-(piperidin-1-ylmethyl)cyclopropyl)phenyl)pyrrolidin-3-yl)methyl)-1H-indole-2-carboxamide
264. 5-chloro-N-((1-(4-(1-(morpholinomethyl)cyclopropyl)phenyl)-5-oxopyrrolidin-3-yl)methyl)-1H-indole-2-carboxamide
265. 5-chloro-N-((1-(4-(1-(morpholinomethyl)cyclopropyl)phenyl)-5-oxopyrrolidin-3-yl)methyl)-1H-pyrrolo[3,2-b]pyridine-2-carboxamide
266. 5-chloro-N-((5-oxo-1-(4-(1-(piperidin-1-ylmethyl)cyclopropyl)phenyl)pyrrolidin-3-yl)methyl)-1H-pyrrolo[3,2-b]pyridine-2-carboxamide
267. 5-chloro-N-((1-(4-(1-((dimethylamino)methyl)cyclopropyl)phenyl)-5-oxopyrrolidin-3-yl)methyl)-1H-pyrrolo[3,2-b]pyridine-2-carboxamide
268. 5-chloro-N-((1-(4-(1-((dimethylamino)methyl)cyclopropyl)phenyl)-5-oxopyrrolidin-3-yl)methyl)thieno[3,2-b]pyridine-2-carboxamide
269. 5-chloro-N-((1-(4-(1-((dimethylamino)methyl)cyclopropyl)phenyl)-5-oxopyrrolidin-3-yl)methyl)thiazolo[4,5-b]pyridine-2-carboxamide
270. 5-chloro-N-((1-(4-(1-((dimethylamino)methyl)cyclopropyl)phenyl)-5-oxopyrrolidin-3-yl)methyl)benzo[d]thiazole-2-carboxamide
271. 5-chloro-N-((1-(4-(1-((dimethylamino)methyl)cyclopropyl)phenyl)-5-oxopyrrolidin-3-yl)methyl)benzo[b]thiophene-2-carboxamide
272. 5-chloro-N-((1-(4-(1-((dimethylamino)methyl)cyclopropyl)phenyl)-5-oxopyrrolidin-3-yl)methyl)benzofuran-2-carboxamide
273. 6-chloro-N-((1-(4-(1-((dimethylamino)methyl)cyclopropyl)phenyl)-5-oxopyrrolidin-3-yl)methyl)-2-naphthamide
274. 6-chloro-N-((1-(4-(1-((dimethylamino)methyl)cyclopropyl)phenyl)-5-oxopyrrolidin-3-yl)methyl)quinoline-2-carboxamide
275. 6-chloro-N-((5-oxo-1-(4-(1-(pyrrolidin-1-ylmethyl)cyclopropyl)phenyl)pyrrolidin-3-yl)methyl)quinoline-2-carboxamide
276. 2-chloro-N-((5-oxo-1-(4-(1-(pyrrolidin-1-ylmethyl)cyclopropyl)phenyl)pyrrolidin-3-yl)methyl)quinoline-6-carboxamide
277. 2-amino-N-((5-oxo-1-(4-(1-(pyrrolidin-1-ylmethyl)cyclopropyl)phenyl)pyrrolidin-3-yl)methyl)quinoline-6-carboxamide
278. N-((5-oxo-1-(4-(1-(pyrrolidin-1-ylmethyl)cyclopropyl)phenyl)pyrrolidin-3-yl)methyl)-2-naphthamide
279. 7-chloro-N-((5-oxo-1-(4-(1-(pyrrolidin-1-ylmethyl)cyclopropyl)phenyl)pyrrolidin-3-yl)methyl)-2-naphthamide
280. 7-chloro-N-((1-(4-(1-((dimethylamino)methyl)cyclopropyl)phenyl)-5-oxopyrrolidin-3-yl)methyl)-2-naphthamide
281. N-((1-(4-(1-((dimethylamino)methyl)cyclopropyl)phenyl)-5-oxopyrrolidin-3-yl)methyl)-1H-indole-5-carboxamide
282. 3-chloro-N-((1-(4-(1-((dimethylamino)methyl)cyclopropyl)phenyl)-5-oxopyrrolidin-3-yl)methyl)-1H-indole-5-carboxamide
283. 3-chloro-N-((5-oxo-1-(4-(1-(pyrrolidin-1-ylmethyl)cyclopropyl)phenyl)pyrrolidin-3-yl)methyl)-1H-indole-5-carboxamide
284. 4-amino-N-((5-oxo-1-(4-(1-(pyrrolidin-1-ylmethyl)cyclopropyl)phenyl)pyrrolidin-3-yl)methyl)benzamide
285. 4-chloro-N-((5-oxo-1-(4-(1-(pyrrolidin-1-ylmethyl)cyclopropyl)phenyl)pyrrolidin-3-yl)methyl)benzamide
286. 4-chloro-N-((1-(4-(1-((diethylamino)methyl)cyclopropyl)phenyl)-5-oxopyrrolidin-3-yl)methyl)benzamide
287. N-((1-(4-(1-((diethylamino)methyl)cyclopropyl)phenyl)-5-oxopyrrolidin-3-yl)methyl)-4-methoxybenzamide 288. N-((1-(4-(1-((dimethylamino)methyl)cyclopropyl)phenyl)-5-oxopyrrolidin-3-yl)methyl)-4-methoxybenzamide
289. 3-chloro-N-((1-(4-(1-((dimethylamino)methyl)cyclopropyl)phenyl)-5-oxopyrrolidin-3-yl)methyl)benzamide
290. 3-chloro-N-((5-oxo-1-(4-(1-(pyrrolidin-1-ylmethyl)cyclopropyl)phenyl)pyrrolidin-3-yl)methyl)benzamide
291. 3-amino-N-((5-oxo-1-(4-(1-(pyrrolidin-1-ylmethyl)cyclopropyl)phenyl)pyrrolidin-3-yl)methyl)benzo[d]isoxazole-5-carboxamide
292. 3-amino-N-((1-(4-(1-((diethylamino)methyl)cyclopropyl)phenyl)-5-oxopyrrolidin-3-yl)methyl)benzo[d]isoxazole-5-carboxamide
293. 3-amino-N-((1-(4-(1-((dimethylamino)methyl)cyclopropyl)phenyl)-5-oxopyrrolidin-3-yl)methyl)benzo[d]isoxazole-5-carboxamide
294. 3-amino-N-((1-(4-(1-((methylamino)methyl)cyclopropyl)phenyl)-5-oxopyrrolidin-3-yl)methyl)benzo[d]isoxazole-5-carboxamide
295. 3-amino-N-((1-(4-(1-(dimethylamino)-2-methylpropan-2-yl)phenyl)-5-oxopyrrolidin-3-yl)methyl)benzo[d]isoxazole-5-carboxamide
296. 3-carbamimidoyl-N-((1-(4-(1-(dimethylamino)-2-methylpropan-2-yl)phenyl)-5-oxopyrrolidin-3-yl)methyl)-4-hydroxybenzamide
297. 3-carbamimidoyl-N-((1-(4-(1-(dimethylamino)-2-methylpropan-2-yl)phenyl)-5-oxopyrrolidin-3-yl)methyl)benzamide
298. 3-carbamimidoyl-N-((1-(4-(2-methyl-1-(pyrrolidin-1-yl)propan-2-yl)phenyl)-5-oxopyrrolidin-3-yl)methyl)benzamide
299. 3-carbamimidoyl-N-((1-(4-(2-methyl-1-(piperidin-1-yl)propan-2-yl)phenyl)-5-oxopyrrolidin-3-yl)methyl)benzamide
300. 3-carbamimidoyl-N-((1-(4-(2-methyl-1-morpholinopropan-2-yl)phenyl)-5-oxopyrrolidin-3-yl)methyl)benzamide
301. N1-((1-(4-(2-methyl-1-morpholinopropan-2-yl)phenyl)-5-oxopyrrolidin-3-yl)methyl)isophthalamide
302. 3-(aminomethyl)-N-((1-(4-(2-methyl-1-morpholinopropan-2-yl)phenyl)-5-oxopyrrolidin-3-yl)methyl)benzamide
303. 3-chloro-N-((1-(4-(2-methyl-1-morpholinopropan-2-yl)phenyl)-5-oxopyrrolidin-3-yl)methyl)benzamide
304. 4-methoxy-N-((1-(4-(2-methyl-1-morpholinopropan-2-yl)phenyl)-5-oxopyrrolidin-3-yl)methyl)benzamide
305. 4-methoxy-N-((1-(4-(2-methyl-1-(piperidin-1-yl)propan-2-yl)phenyl)-5-oxopyrrolidin-3-yl)methyl)benzamide
306. N-((1-(4-(1-(diethylamino)-2-methylpropan-2-yl)phenyl)-5-oxopyrrolidin-3-yl)methyl)-4-methoxybenzamide
307. N-((1-(4-(1-(dimethylamino)-2-methylpropan-2-yl)phenyl)-5-oxopyrrolidin-3-yl)methyl)-4-methoxybenzamide
308. N-((1-(4-(1-(dimethylamino)-2-methylpropan-2-yl)phenyl)-5-oxopyrrolidin-3-yl)methyl)benzamide
309. N-((1-(4-(1-(dimethylamino)-2-methylpropan-2-yl)phenyl)-5-oxopyrrolidin-3-yl)methyl)-2-naphthamide
310. 7-chloro-N-((1-(4-(1-(dimethylamino)-2-methylpropan-2-yl)phenyl)-5-oxopyrrolidin-3-yl)methyl)-2-naphthamide
311. N-((1-(4-(2-methyl-1-(pyrrolidin-1-yl)propan-2-yl)phenyl)-5-oxopyrrolidin-3-yl)methyl)-2-naphthamide
312. 6-chloro-N-((1-(4-(2-methyl-1-(pyrrolidin-1-yl)propan-2-yl)phenyl)-5-oxopyrrolidin-3-yl)methyl)-2-naphthamide
313. 6-chloro-N-((1-(4-(1-(dimethylamino)-2-methylpropan-2-yl)phenyl)-5-oxopyrrolidin-3-yl)methyl)-2-naphthamide
314. 3-chloro-N-((1-(4-(1-(dimethylamino)-2-methylpropan-2-yl)phenyl)-5-oxopyrrolidin-3-yl)methyl)-1H-indole-6-carboxamide
315. 3-chloro-N-((1-(4-(2-methyl-1-(pyrrolidin-1-yl)propan-2-yl)phenyl)-5-oxopyrrolidin-3-yl)methyl)-1H-indole-6-carboxamide
316. (E)-N-((1-(4-(2-methyl-1-(pyrrolidin-1-yl)propan-2-yl)phenyl)-5-oxopyrrolidin-3-yl)methyl)-3-(thiophen-2-yl)acrylamide
317. (E)-3-(5-chlorothiophen-2-yl)-N-((1-(4-(2-methyl-1-(pyrrolidin-1-yl)propan-2-yl)phenyl)-5-oxopyrrolidin-3-yl)methyl)acrylamide
318. N-((1-(4-(2-methyl 1-(pyrrolidin-1-yl)propan-2-yl)phenyl)-5-oxopyrrolidin-3-yl)methyl)benzofuran-2-carboxamide
319. N-((1-(4-(2-methyl-1-(pyrrolidin-1-yl)propan-2-yl)phenyl)-5-oxopyrrolidin-3-yl)methyl)-1H-indole-2-carboxamide
320. N-((1-(4-(2-methyl-1-(pyrrolidin-1-yl)propan-2-yl)phenyl)-5-oxopyrrolidin-3-yl)methyl)benzo[b]thiophene-2-carboxamide
321. N-((1-(4-(1-(diethylamino)-2-methylpropan-2-yl)phenyl)-5-oxopyrrolidin-3-yl)methyl)benzo[b]thiophene-2-carboxamide
322. 6-chloro-N-((1-(4-(1-(diethylamino)-2-methylpropan-2-yl)phenyl)-5-oxopyrrolidin-3-yl)methyl)benzo[b]thiophene-2-carboxamide
323. 5-chloro-N-((1-(4-(1-(diethylamino)-2-methylpropan-2-yl)phenyl)-5-oxopyrrolidin-3-yl)methyl)benzo[b]thiophene-2-carboxamide
324. 5-chloro-N-((1-(4-(1-(diethylamino)-2-methylpropan-2-yl)phenyl)-5-oxopyrrolidin-3-yl)methyl)benzo[d]thiazole-2-carboxamide
325. 5-chloro-N-((1-(4-(1-(diethylamino)-2-methylpropan-2-yl)phenyl)-5-oxopyrrolidin-3-yl)methyl)thiophene-2-carboxamide
326. 5-chloro-N-((1-(4-(1-(dimethylamino)-2-methylpropan-2-yl)phenyl)-5-oxopyrrolidin-3-yl)methyl)thiophene-2-carboxamide
327. 5-chloro-N-((1-(4-(2-methyl-1-(pyrrolidin-1-yl)propan-2-yl)phenyl)-5-oxopyrrolidin-3-yl)methyl)thiophene-2-carboxamide
328. N-((1-(4-carbamimidoylphenyl)-5-oxopyrrolidin-3-yl)methyl)-5-chlorothiophene-2-carboxamide
329. (Z)—N-((1-(4-(N'-(methylsulfonyl)carbamimidoyl)phenyl)-5-oxopyrrolidin-3-yl)methyl)-5-chlorothiophene-2-carboxamide
330. (Z)—N-((1-(4-(N,N-dimethyl-N'-(methylsulfonyl)carbamimidoyl)phenyl)-5-oxopyrrolidin-3-yl)methyl)-5-chlorothiophene-2-carboxamide
331. (Z)—N-((1-(4-(N,N-dimethyl-N'-(methylsulfonyl)carbamimidoyl)phenyl)-5-oxopyrrolidin-3-yl)methyl)benzo[b]thiophene-2-carboxamide
332. (Z)—N-((1-(4-(N,N-dimethyl-N'-(methylsulfonyl)carbamimidoyl)phenyl)-5-oxopyrrolidin-3-yl)methyl)-6-chlorobenzo[b]thiophene-2-carboxamide
333. (Z)—N-((1-(4-(N,N-dimethyl-N'-(methylsulfonyl)carbamimidoyl)phenyl)-5-oxopyrrolidin-3-yl)methyl)-1H-indole-2-carboxamide
334. (Z)—N-((1-(4-(N,N-dimethyl-N'-(methylsulfonyl)carbamimidoyl)phenyl)-5-oxopyrrolidin-3-yl)methyl)-6-chloro-1H-indole-2-carboxamide 335. (E)—N-((1-(4-(N,N-dimethyl-N'-(methylsulfonyl)carbamimidoyl)phenyl)-5-oxopyrrolidin-3-yl)methyl)-6-chloro-1H-indole-2-carboxamide
336. (E)—N-((1-(4-(N,N-dimethyl-N'-(methylsulfonyl)carbamimidoyl)phenyl)-5-oxopyrrolidin-3-yl)methyl)-7-chloro-2-naphthamide
337. (E)—N-((1-(4-(N,N-dimethyl-N'-(methylsulfonyl)carbamimidoyl)phenyl)-5-oxopyrrolidin-3-yl)methyl)-4-chlorobenzamide
338. (E)—N-((1-(4-(N,N-dimethyl-N'-(methylsulfonyl)carbamimidoyl)phenyl)-5-oxopyrrolidin-3-yl)methyl)-4-methoxybenzamide
339. (E)—N-((1-(4-(N,N-dimethyl-N'-(methylsulfonyl)carbamimidoyl)phenyl)-5-oxopyrrolidin-3-yl)methyl)-3-chlorobenzamide
340. (E)—N-((1-(4-(N,N-dimethyl-N'-(methylsulfonyl)carbamimidoyl)phenyl)-5-oxopyrrolidin-3-yl)methyl)-3-aminobenzo[d]isoxazole-5-carboxamide
341. (E)—N-((1-(4-(N,N-dimethyl-N'-(methylsulfonyl)carbamimidoyl)phenyl)-5-oxopyrrolidin-3-yl)methyl)-3-carbamimidoyl-4-hydroxybenzamide
342. (E)—N-((1-(4-(N,N-dimethyl-N'-(methylsulfonyl)carbamimidoyl)phenyl)-5-oxopyrrolidin-3-yl)methyl)-3-carbamimidoylbenzamide

TABLE 2

1. 5-Chloro-thiophene-2-carboxylic acid {(7R,7aR)-3-oxo-2-[4-(2-oxo-2H-pyridin-1-yl)-phenyl]-hexahydro-pyrrolo[1,2-c]imidazol-7-yl}-amide
2. 6-Chloro-naphthalene-2-carboxylic acid {(7R,7aR)-3-oxo-2-[4-(2-oxo-2H-pyridin-1-yl)-phenyl]-hexahydro-pyrrolo[1,2-c]imidazol-7-yl}-amide
3. 3-Chloro-1H-indole-6-carboxylic acid {(7R,7aR)-3-oxo-2-[4-(2-oxo-2H-pyridin-1-yl)-phenyl]-hexahydro-pyrrolo[1,2-c]imidazol-7-yl}-amide
4. 4-Chloro-N-{(7R,7aR)-3-oxo-2-[4-(2-oxo-2H-pyridin-1-yl)-phenyl]-hexahydro-pyrrolo[1,2-c]imidazol-7-yl}-benzamide
5. 5-Chloro-thiophene-2-carboxylic acid {(7R,7aR)-3-oxo-2-[4-(2-oxo-piperidin-1-yl)-phenyl]-hexahydro-pyrrolo[1,2-c]imidazol-7-yl}-amide
6. 5-Chloro-thiophene-2-carboxylic acid {(7R,7aR)-3-oxo-2-[4-(2-oxo-2H-pyrazin-1-yl)-phenyl]-hexahydro-pyrrolo[1,2-c]imidazol-7-yl}-amide
7. 5-Chloro-thiophene-2-carboxylic acid {(7R,7aR)-3-oxo-2-[4-(3-oxo-morpholin-4-yl)-phenyl]-hexahydro-pyrrolo[1,2-c]imidazol7-yl}-amide
8. 5-Chloro-thiophene-2-carboxylic acid {(7R,7aR)-3-oxo-2-[4-(3-oxo-2-aza-bicyclo[2.2.1]hept-2-yl)-phenyl]-hexahydro-pyrrolo[1,2-c]imidazol-7-yl}-amide
9. 5-Chloro-thiophene-2-carboxylic acid {(7R,7aR)-3-oxo-2-[4-(2-oxo-[1,3]oxazinan-3-yl)-phenyl]-hexahydro-pyrrolo[1,2-c]imidazol-7-yl}-amide
10. 5-Chloro-thiophene-2-carboxylic acid {(7R,7aS)-1,3-dioxo-2-[4-(2-oxo-2H-pyridin-1-yl)-phenyl]-hexahydro-pyrrolo[1,2-c]imidazol-7-yl}-amide
11. 5-Chloro-thiophene-2-carboxylic acid {(7R,7aS)-1,3-dioxo-2-[4-(2-oxo-piperidin-1-yl)-phenyl]-hexahydro-pyrrolo[1,2-c]imidazol-7-yl}-amide
12. 5-Chloro-thiophene-2-carboxylic acid {(7R,7aS)-1,3-dioxo-2-[4-(3-oxo-2-aza-bicyclo[2.2.1]hept-2-yl)-phenyl]-hexahydro-pyrrolo[1,2-c]imidazol-7-yl}-amide
13. 5-Chloro-thiophene-2-carboxylic acid {(7R,7aS)-1,3-dioxo-2-[4-(3-oxo-morpholin-4-yl)-phenyl]-hexahydro-pyrrolo[1,2-c]imidazol-7-yl}-amide
14. 5-Chloro-thiophene-2-carboxylic acid {(3aR,4R)-1,1-dioxo-2-[4-(2-oxo-2H-pyridin-1-yl)-phenyl]-hexahydro-1$\lambda^6$-thia-2,6a-diaza-pentalen-4-yl}-amide
15. 5-Chloro-thiophene-2-carboxylic acid {(3aR,4R)-1,1-dioxo-2-[4-(2-oxo-piperidin-1-yl)-phenyl]-hexahydro-1$\lambda^6$-thia-2,6a-diaza-pentalen-4-yl}-amide
16. 5-Chloro-thiophene-2-carboxylic acid {(3aR,4R)-1,1-dioxo-2-[4-(2-oxo-2H-pyrazin-1-yl)-phenyl]-hexahydro-1$\lambda^6$-thia-2,6a-diaza-pentalen-4-yl}-amide
17. 5-Chloro-thiophene-2-carboxylic acid {(3aR,4R)-1,1-dioxo-2-[4-(3-oxo-morpholin-4-yl)-phenyl]-hexahydro-1$\lambda^6$-thia-2,6a-diaza-pentalen-4-yl}-amide
18. 5-Chloro-thiophene-2-carboxylic acid {(7R,7aS)-1-oxo-2-[4-(2-oxo-2H-pyridin-1-yl)-phenyl]-hexahydro-pyrrolo[1,2-c]imidazol-7-yl}-amide
19. 5-Chloro-thiophene-2-carboxylic acid {(7R,7aS)-1-oxo-2-[4-(2-oxo-piperidin-1-yl)-phenyl]-hexahydro-pyrrolo[1,2-c]imidazol-7-yl}-amide
20. 5-Chloro-thiophene-2-carboxylic acid {(3 aS,4R)-1,1,3-trioxo-2-[4-(2-oxo-2H-pyridin-1-yl)-phenyl]-hexahydro-1$\lambda^6$-thia-2,6a-diaza-pentalen-4-yl}-amide
21. 3-Chloro-1H-indole-6-carboxylic acid {(7R,7aS)-1,3-dioxo-2-[4-(2-oxo-2H-pyridin-1-yl)-phenyl]-hexahydro-pyrrolo[1,2-c]imidazol-7-yl}-amide
22. 3-Chloro-1H-indole-6-carboxylic acid {(7R,7aS)-1-oxo-2-[4-(2-oxo-2H-pyridin-1-yl)-phenyl]-hexahydro-pyrrolo[1,2-c]imidazol-7-yl}-amide
23. 3-Chloro-1H-indole-6-carboxylic acid {(7R,7aS)-1-oxo-2-[4-(3-oxo-morpholin-4-yl)-phenyl]-hexahydro-pyrrolo[1,2-c]imidazol-7-yl}-amide
24. 3-Chloro-1H-indole-6-carboxylic acid {(3aR,4R)-1,1-dioxo-2-[4-(2-oxo-2H-pyridin-1-yl)-phenyl]-hexahydro-1$\lambda^6$-thia-2,6a-diaza-pentalen-4-yl}-amide
25. 5-Chloro-1H-indole-2-carboxylic acid {(7R,7aR)-3-oxo-2-[4-(2-oxo-2H-pyridin-1-yl)-phenyl]-hexahydro-pyrrolo[1,2-c]imidazol-7-yl}-amide
26. 5-Chloro-1H-indole-2-carboxylic acid {(7R,7aS)-1,3-dioxo-2-[4-(2-oxo-2H-pyridin-1-yl)-phenyl]-hexahydro-pyrrolo[1,2-c]imidazol-7-yl}-amide
27. 5-Chloro-1H-indole-2-carboxylic acid {(3aR,4R)-1,1-dioxo-2-[4-(2-oxo-2H-pyridin-1-yl)-phenyl]-hexahydro-1$\lambda^6$-thia-2,6a-diaza-pentalen-4-yl}-amide
28. 5-Chloro-thiophene-2-carboxylic acid {(8R,8aR)-3-oxo-2-[4-(2-oxo-2H-pyridin-1-yl)-phenyl]-octahydro-imidazo[1,5-a]pyridin-8-yl}-amide
29. 5-Chloro-thiophene-2-carboxylic acid {(8R,8aR)-3-oxo-2-[4-(3-oxo-morpholin-4-yl)-phenyl]-octahydro-imidazo[1,5-a]pyridin-8-yl}-amide
30. 5-Chloro-thiophene-2-carboxylic acid {(8R,8aS)-1,3-dioxo-2-[4-(2-oxo-2H-pyridin-1-yl)-phenyl]-octahydro-imidazo[1,5-a]pyridin-8-yl}-amide
31. 5-Chloro-thiophene-2-carboxylic acid {(8R,8aR)-3-oxo-2-[4-(2-oxo-piperidin-1-yl)-phenyl]-octahydro-imidazo[1,5-a]pyridin-8-yl}-amide
32. 5-Chloro-thiophene-2-carboxylic acid {(8R,8aS)-1,3-dioxo-2-[4-(2-oxo-piperidin-1-yl)-phenyl]-octahydro-imidazo[1,5-a]pyridin-8-yl}-amide
33. 5-Chloro-thiophene-2-carboxylic acid {(8R,8aS)-1,3-dioxo-2-[4-(3-oxo-2-aza-bicyclo[2.2.1]hept-2-yl)-phenyl]-octahydro-imidazo[1,5-a]pyridin-8-yl}-amide
34. 5-Chloro-thiophene-2-carboxylic acid {(8R,8aR)-3-oxo-2-[4-(2-oxo-2H-pyrazin-1-yl)-phenyl]-octahydro-imidazo[1,5-a]pyridin-8-yl}-amide
35. 5-Chloro-thiophene-2-carboxylic acid {(8R,8aS)-1-oxo-2-[4-(2-oxo-2H-pyridin-1-yl)-phenyl]-octahydro-imidazo[1,5-a]pyridin-8-yl}-amide 36. 5-Chloro-1H-indole-2-carboxylic acid {(3aR,4S)-1,1-dioxo-2-[4-(2-oxo-2H-pyridin-1-yl)-phenyl]-octahydro-1λ⁶-[1,2,5]thiadiazolo[2,3-a]pyridin-4-yl}-amide
37. 3-Chloro-1H-indole-6-carboxylic acid {(8R,8aS)-1-oxo-2-[4-(2-oxo-2H-pyridin-1-yl)-phenyl]-octahydro-imidazo[1,5-a]pyridin-8-yl}-amide
38. 5-Chloro-1H-indole-2-carboxylic acid {(8R,8aR)-3-oxo-2-[4-(2-oxo-2H-pyridin-1-yl)-phenyl]-octahydro-imidazo[1,5-a]pyridin-8-yl}-amide
39. 5-Chloro-1H-indole-2-carboxylic acid {(8R,8aS)-1,3-dioxo-2-[4-(2-oxo-2H-pyridin-1-yl)-phenyl]-octahydro-imidazo[1,5-a]pyridin-8-yl}-amide
40. 5-Chloro-thiophene-2-carboxylic acid ((7R,7aR)-2-{4-[(2-dimethylamino-acetyl)-methyl-amino]-phenyl}-3-oxo-hexahydro-pyrrolo[1,2-c]imidazol-7-yl)-amide
41. 5-Chloro-thiophene-2-carboxylic acid ((7R,7aR)-2-{4-[(2-diethylamino-acetyl)-methyl-amino]-phenyl}-3-oxo-hexahydro-pyrrolo[1,2-c]imidazol-7-yl)-amide
42. 5-Chloro-thiophene-2-carboxylic acid ((7R,7aR)-2-{4-[methyl-(2-piperidin-1-yl-acetyl)-amino]-phenyl}-3-oxo-hexahydro-pyrrolo[1,2-c]imidazol-7-yl)-amide
43. 5-Chloro-thiophene-2-carboxylic acid ((7R,7aR)-2-{4-[methyl-(2-pyrrolidin-1-yl-acetyl)-amino]-phenyl}-3-oxo-hexahydro-pyrrolo[1,2-c]imidazol-7-yl)-amide
44. 5-Chloro-thiophene-2-carboxylic acid ((7R,7aS)-2-{4-[(2-dimethylamino-acetyl)-methyl-amino]-phenyl}-1,3-dioxo-hexahydro-pyrrolo[1,2-c]imidazol-7-yl)-amide
45. 5-Chloro-thiophene-2-carboxylic acid ((7R,7aS)-2-{4-[methyl-(2-pyrrolidin-1-yl-acetyl)-amino]-phenyl}-1,3-dioxo-hexahydro-pyrrolo[1,2-c]imidazol-7-yl)-amide
46. 3-Chloro-1H-indole-6-carboxylic acid ((8R,8aR)-2-{4-[(2-dimethylamino-acetyl)-methyl-amino]-phenyl}-3-oxo-octahydro-imidazo[1,5-a]pyridin-8-yl)-amide
47. 3-Chloro-1H-indole-6-carboxylic acid ((8R,8aR)-2-{4-[methyl-(2-pyrrolidin-1-yl-acetyl)-amino]-phenyl}-3-oxo-octahydro-imidazo[1,5-a]pyridin-8-yl)-amide
48. 3-Chloro-1H-indole-6-carboxylic acid ((8R,8aS)-2-{4-[(2-dimethylamino-acetyl)-methyl-amino]-phenyl}-1,3-dioxo-octahydro-imidazo[1,5-a]pyridin-8-yl)-amide
49. 3-Chloro-1H-indole-6-carboxylic acid ((8R,8aS)-2-{4-[methyl-(2-pyrrolidin-1-yl-acetyl)-amino]-phenyl}-1,3-dioxo-octahydro-imidazo[1,5-a]pyridin-8-yl)-amide
50. 3-Chloro-1H-indole-6-carboxylic acid ((3aR,4S)-2-{4-[(2-dimethylamino-acetyl)-methyl-amino]-phenyl}-1,1-dioxo-octahydro-1λ⁶-[1,2,5]thiadiazolo[2,3-a]pyridin-4-yl)-amide
51. 5-Chloro-thiophene-2-carboxylic acid [(7R,7aR)-2-(1-isopropyl-piperidin-4-yl)-3-oxo-hexahydro-pyrrolo[1,2-c]imidazol-7-yl]-amide
52. 5-Chloro-thiophene-2-carboxylic acid [(7R,7aR)-2-(1-cyclopropyl-piperidin-4-yl)-3-oxo-hexahydro-pyrrolo[1,2-c]imidazol-7-yl]-amide
53. 5-Chloro-thiophene-2-carboxylic acid [(7R,7aR)-2-(1-cyclohexyl-piperidin-4-yl)-3-oxo-hexahydro-pyrrolo[1,2-c]imidazol-7-yl]-amide
54. 5-Chloro-thiophene-2-carboxylic acid [(7R,7aR)-2-(1'-methyl-[1,4']bipiperidinyl-4-yl)-3-oxo-hexahydro-pyrrolo[1,2-c]imidazol-7-yl]-amide
55. 5-Chloro-thiophene-2-carboxylic acid [(7R,7aS)-2-(1-isopropyl-piperidin-4-yl)-1,3-dioxo-hexahydro-pyrrolo[1,2-c]imidazol-7-yl]-amide
56. 3-Chloro-1H-indole-6-carboxylic acid [(8R,8aS)-2-(1-isopropyl-piperidin-4-yl)-1,3-dioxo-octahydro-imidazo[1,5-a]pyridin-8-yl]-amide
57. 3-Chloro-1H-indole-6-carboxylic acid [(3aR,4S)-2-(1-isopropyl-piperidin-4-yl)-1,1-dioxo-octahydro-1λ⁶-[1,2,5]thiadiazolo[2,3-a]pyridin-4-yl]-amide
58. 5-Chloro-thiophene-2-carboxylic acid [(7R,7aR)-2-(2'-methanesulfonyl-biphenyl-4-yl)-3-oxo-hexahydro-pyrrolo[1,2-c]imidazol-7-yl]-amide
59. 5-Chloro-thiophene-2-carboxylic acid [(7R,7aR)-3-oxo-2-(2'-sulfamoyl-biphenyl-4-yl)-hexahydro-pyrrolo[1,2-c]imidazol-7-yl]-amide
60. 5-Chloro-thiophene-2-carboxylic acid [(7R,7aR)-2-(2'-dimethylaminomethyl-biphenyl-4-yl)-3-oxo-hexahydro-pyrrolo[1,2-c]imidazol-7-yl]-amide
61. 5-Chloro-thiophene-2-carboxylic acid [(7R,7aR)-2-(4-dimethylamino-phenyl)-3-oxo-hexahydro-pyrrolo[1,2-c]imidazol-7-yl]-amide
62. 5-Chloro-thiophene-2-carboxylic acid {(7R,7aR)-2-[4-(4-methyl-[1,4]diazepan-1-yl)-phenyl]-3-oxo-hexahydro-pyrrolo[1,2-c]imidazol-7-yl}-amide
63. 5-Chloro-thiophene-2-carboxylic acid [(7R,7aR)-2-(4-morpholin-4-yl-phenyl)-3-oxo-hexahydro-pyrrolo[1,2-c]imidazol-7-yl]-amide
64. 5-Chloro-thiophene-2-carboxylic acid [(7R,7aR)-2-(4-dimethylcarbamoyl-phenyl)-3-oxo-hexahydro-pyrrolo[1,2-c]imidazol-7-yl]-amide
65. 5-Chloro-thiophene-2-carboxylic acid {(7R,7aR)-3-oxo-2-[4-(pyrrolidine-1-carbonyl)-phenyl]-hexahydro-pyrrolo[1,2-c]imidazol-7-yl}-amide
66. 3-Chloro-1H-indole-6-carboxylic acid [(8R,8aR)-2-(2'-methanesulfonyl-biphenyl-4-yl)-3-oxo-octahydro-imidazo[1,5-a]pyridin-8-yl]-amide
67. 3-Chloro-1H-indole-6-carboxylic acid [(8R,8aR)-3-oxo-2-(2'-sulfamoyl-biphenyl-4-yl)-octahydro-imidazo[1,5-a]pyridin-8-yl]-amide
68. 3-Chloro-1H-indole-6-carboxylic acid [(8R,8aR)-2-(2'-dimethylaminomethyl-biphenyl-4-yl)-3-oxo-octahydro-imidazo[1,5-a]pyridin-8-yl]-amide
69. 3-Chloro-1H-indole-6-carboxylic acid {(8R,8aR)-2-[4-(4-methyl-[1,4]diazepan-1-yl)-phenyl]-3-oxo-octahydro-imidazo[1,5-a]imidazol-8-yl}-amide
70. 3-Chloro-1H-indole-6-carboxylic acid {(8R,8aR)-2-[4-(1-methyl-4,5-dihydro-1H-imidazol-2-yl)-phenyl]-3-oxo-octahydro-imidazo[1,5-a]pyridin-8-yl}-amide
71. 5-Chloro-thiophene-2-carboxylic acid [(7R,7aS)-2-(4-{[methanesulfonylimino]-pyrrolidin-1-yl-methyl}-phenyl)-1,3-dioxo-hexahydro-pyrrolo[1,2-c]imidazol-7-yl]-amide
72. 5-Chloro-thiophene-2-carboxylic acid {(7R,7aS)-2-[4-(imino-pyrrolidin-1-yl-methyl)-phenyl]-1,3-dioxo-hexahydro-pyrrolo[1,2-c]imidazol-7-yl}-amide
73. 5-Chloro-thiophene-2-carboxylic acid {(7R,7aS)-2-[4-(2-isopropyl-5,6-dihydro-4H-pyrimidin-1-yl)-phenyl]-1,3-dioxo-hexahydro-pyrrolo[1,2-c]imidazol-7-yl}-amide
74. 5-Chloro-thiophene-2-carboxylic acid {(7R,7aR)-2-[4-(5,6-dihydro-4H-pyrimidin-1-yl)-phenyl]-3-oxo-hexahydro-pyrrolo[1,2-c]imidazol-7-yl}-amide
75. 5-Chloro-thiophene-2-carboxylic acid {(7R,7aR)-2-[4-(2-methyl-5,6-dihydro-4H-pyrimidin-1-yl)-phenyl]-3-oxo-hexahydro-pyrrolo[1,2-c]imidazol-7-yl}-amide
76. 5-Chloro-thiophene-2-carboxylic acid {(7R,7aR)-2-[4-(2-ethyl-5,6-dihydro-4H-pyrimidin-1-yl)-phenyl]-3-oxo-hexahydro-pyrrolo[1,2-c]imidazol-7-yl}-amide
77. 5-Chloro-thiophene-2-carboxylic acid {(7R,7aR)-3-oxo-2-[4-(2-phenyl-5,6-dihydro-4H-pyrimidin-1-yl)-phenyl]-hexahydro-pyrrolo[1,2-c]imidazol-7-yl}-amide
78. 5-Chloro-thiophene-2-carboxylic acid {(7R,7aR)-2-[4-(2-isopropyl-5,6-dihydro-4H-pyrimidin-1-yl)-phenyl]-3-oxo-hexahydro-pyrrolo[1,2-c]imidazol-7-yl}-amide
79. 5-Chloro-thiophene-2-carboxylic acid {(7R,7aR)-2-[4-(2-acetylamino-5,6-dihydro-4H-pyrimidin-1-yl)-phenyl]-3-oxo-hexahydro-pyrrolo[1,2-c]imidazol-7-yl}-amide 80. 5-Chloro-thiophene-2-carboxylic acid {(7R,7aR)-2-[4-(2-methanesulfonylamino-5,6-dihydro-4H-pyrimidin-1-yl)-phenyl]-3-oxo-hexahydro-pyrrolo[1,2-c]imidazol-7-yl}-amide 81. 5-Chloro-thiophene-2-carboxylic acid {(7R,7aR)-2-[4-(2-methoxy-5,6-dihydro-4H-pyrimidin-1-yl)-phenyl]-3-oxo-hexahydro-pyrrolo[1,2-c]imidazol-7-yl}-amide 82. 5-Chloro-thiophene-2-carboxylic acid [(7R,7aR)-2-(4-{dimethylamino-[methanesulfonylimino]-methyl}-phenyl)-3-oxo-hexahydro-pyrrolo[1,2-c]imidazol-7-yl]-amide 83. 5-Chloro-thiophene-2-carboxylic acid [(7R,7aR)-2-(4-{[methanesulfonylimino]-pyrrolidin-1-yl-methyl}-phenyl)-3-oxo-hexahydro-pyrrolo[1,2-c]imidazol-7-yl]-amide 84. 5-Chloro-thiophene-2-carboxylic acid {(7R,7aR)-2-[4-(imino-pyrrolidin-1-yl-methyl)-phenyl]-3-oxo-hexahydro-pyrrolo[1,2-c]imidazol-7-yl}-amide 85. 5-Chloro-thiophene-2-carboxylic acid {(7R,7aR)-2-[4-(N,N-dimethyl-carbamimidoyl)-phenyl]-3-oxo-hexahydro-pyrrolo[1,2-c]imidazol-7-yl}-amide 86. 5-Chloro-thiophene-2-carboxylic acid {(7R,7aR)-2-[4-(N'-methoxy-N,N-dimethyl-carbamimidoyl)-phenyl]-3-oxo-hexahydro-pyrrolo[1,2-c]imidazol-7-yl}-amide 87. 3-Chloro-1H-indole-6-carboxylic acid {(8R,8aR)-2-[4-(2-isopropyl-5,6-dihydro-4H-pyrimidin-1-yl)-phenyl]-3-oxo-octahydro-imidazo[1,5-a]pyridin-8-yl}-amide 88. 3-Chloro-1H-indole-6-carboxylic acid {(8R,8aR)-2-[4-(N'-methoxy-N,N-dimethyl-carbamimidoyl)-phenyl]-3-oxo-octahydro-imidazo[1,5-a]pyridin-8-yl}-amide 89. 3-Chloro-1H-indole-6-carboxylic acid [(8R,8aR)-2-(4-{dimethylamino-[methanesulfonylimino]-phenyl)-3-oxo-octahydro-imidazo[1,5-a]pyridin-8-yl]-amide 90. 3-Chloro-1H-indole-6-carboxylic acid [(8R,8aR)-2-(4-{[methanesulfonylimino]-pyrrolidin-1-yl-methyl}-phenyl)-3-oxo-octahydro-imidazo[1,5-a]pyridin-8-yl]-amide 91. 3-Chloro-1H-indole-6-carboxylic acid {(8R,8aR)-2-[4-(imino-pyrrolidin-1-yl-methyl)-phenyl]-3-oxo-octahydro-imidazo[1,5-a]pyridin-8-yl}-amide 92. 3-Chloro-1H-indole-6-carboxylic acid {(8R,8aR)-2-[4-(N,N-dimethyl-carbamimidoyl)-phenyl]-3-oxo-octahydro-imidazo[1,5-a]pyridin-8-yl}-amide 93. 3-Chloro-1H-indole-6-carboxylic acid {(8R,8aS)-2-[4-(2-isopropyl-5,6-dihydro-4H-pyrimidin-1-yl)-phenyl]-1,3-dioxo-octahydro-imidazo[1,5-a]pyridin-8-yl}-amide 94. 3-Chloro-1H-indole-6-carboxylic acid {(8R,8aS)-2-[4-(N'-methoxy-N,N-dimethyl-carbamimidoyl)-phenyl]-1,3-dioxo-octahydro-imidazo[1,5-a]pyridin-8-yl}-amide 95. 3-Chloro-1H-indole-6-carboxylic acid {(8R,8aS)-2-[4-(N,N-dimethyl-carbamimidoyl)-phenyl]-1,3-dioxo-octahydro-imidazo[1,5-a]pyridin-8-yl}-amide 96. 3-Chloro-1H-indole-6-carboxylic acid [(8R,8aS)-2-(4-{[methanesulfonylimino]-pyrrolidin-1-yl-methyl}-phenyl)-1,3-dioxo-octahydro-imidazo[1,5-a]pyridin-8-yl]-amide 97. 3-Chloro-1H-indole-6-carboxylic acid {(3aR,4R)-2-[4-(2-isopropyl-5,6-dihydro-4H-pyrimidin-1-yl)-phenyl]-1,1-dioxo-octahydro-1$\lambda^6$-[1,2,5]thiadiazolo[2,3-a]pyridin-4-yl}-amide 98. 3-Chloro-1H-indole-6-carboxylic acid {(3aR,4S)-2-[4-(N,N-dimethyl-carbamimidoyl)-phenyl]-1,1-dioxo-octahydro-1$\lambda^6$-[1,2,5]thiadiazolo[2,3-a]pyridin-4-yl}-amide 99. 5-Chloro-thiophene-2-carboxylic acid {(7R,7aR)-2-[4-(2-dimethylaminomethyl-imidazol-1-yl)-phenyl]-3-oxo-hexahydro-pyrrolo[1,2-c]imidazol-7-yl}-amide 100. 5-Chloro-thiophene-2-carboxylic acid {(7R,7aR)-3-oxo-2-[4-(2-pyrrolidin-1-ylmethyl-imidazol-1-yl)-phenyl]-hexahydro-pyrrolo[1,2-c]imidazol-7-yl}-amide 101. 5-Chloro-thiophene-2-carboxylic acid [(7R,7aR)-2-(4-{2-[(methanesulfonyl-methyl-amino)-methyl]-imidazol-1-yl}-phenyl)-3-oxo-hexahydro-pyrrolo[1,2-c]imidazol-7-yl]-amide 102. 5-Chloro-thiophene-2-carboxylic acid [(7R,7aR)-2-(4-{2-[(acetyl-methyl-amino)-methyl]-imidazol-1-yl}-phenyl)-3-oxo-hexahydro-pyrrolo[1,2-c]imidazol-7-yl]-amide 103. [1-(4-{(7R,7aR)-7-[(5-Chloro-thiophene-2-carbonyl)-amino]-3-oxo-tetrahydro-pyrrolo[1,2-c]imidazol-2-yl}-phenyl)-1H-imidazol-2-ylmethyl]-methyl-carbamic acid methyl ester 104. 5-Chloro-thiophene-2-carboxylic acid ((7R,7aR)-2-{4-[2-(isopropylamino-methyl)-imidazol-1-yl]-phenyl}-3-oxo-hexahydro-pyrrolo[1,2-c]imidazol-7-yl)-amide 105. 5-Chloro-thiophene-2-carboxylic acid {(7R,7aS)-2-[4-(2-dimethylaminomethyl-imidazol-1-yl)-phenyl]-1,3-dioxo-hexahydro-pyrrolo[1,2-c]imidazol-7-yl}-amide 106. 5-Chloro-thiophene-2-carboxylic acid {(8R,8aR)-2-[4-(2-dimethylaminomethyl-imidazol-1-yl)-phenyl]-3-oxo-octahydro-imidazo[1,5-a]pyridin-8-yl}-amide 107. 5-Chloro-thiophene-2-carboxylic acid {(8R,8aS)-2-[4-(2-dimethylaminomethyl-imidazol-1-yl)-phenyl]-1,3-dioxo-octahydro-imidazo[1,5-a]pyridin-8-yl}-amide 108. 3-Chloro-1H-indole-6-carboxylic acid {(3aS,4R)-2-[4-(2-dimethylaminomethyl-imidazol-1-yl)-phenyl]-1,1,3-trioxo-octahydro-1$\lambda^6$-[1,2,5]thiadiazolo[2,3-a]pyridin-4-yl}-amide 109. 3-Chloro-1H-indole-6-carboxylic acid {(3aR,4R)-2-[4-(2-dimethylaminomethyl-imidazol-1-yl)-phenyl]-1,1-dioxo-octahydro-1$\lambda^6$-[1,2,5]thiadiazolo[2,3-a]pyridin-4-yl}-amide 110. 3-Chloro-1H-indole-6-carboxylic acid {(8R,8aS)-2-[4-(2-dimethylaminomethyl-imidazol-1-yl)-phenyl]-1,3-dioxo-octahydro-imidazo[1,5-a]pyridin-8-yl}-amide 111. 3-Chloro-1H-indole-6-carboxylic acid {(8R,8aS)-2-[4-(2-dimethylaminomethyl-imidazol-1-yl)-phenyl]-1-oxo-octahydro-imidazo[1,5-a]pyridin-8-yl}-amide 112. 5-Chloro-thiophene-2-carboxylic acid {(7R,7aR)-3-oxo-2-[4-(1-pyrrolidin-1-ylmethyl-cyclobutyl)-phenyl]-hexahydro-pyrrolo[1,2-c]imidazol-7-yl}-amide 113. 5-Chloro-thiophene-2-carboxylic acid {(7R,7aR)-2-[4-(1-morpholin-4-ylmethyl-cyclobutyl)-phenyl]-3-oxo-hexahydro-pyrrolo[1,2-c]imidazol-7-yl}-amide 114. 5-Chloro-thiophene-2-carboxylic acid [(7R,7aR)-2-(4-{1-[(5-methyl-thiazol-2-ylamino)-methyl]-cyclobutyl}-phenyl)-3-oxo-hexahydro-pyrrolo[1,2-c]imidazol-7-yl]-amide 115. 5-Chloro-thiophene-2-carboxylic acid ((7R,7aR)-3-oxo-2-{4-[1-(2-pyrrolidin-1-yl-ethyl)-cyclobutyl]-phenyl}-hexahydro-pyrrolo[1,2-c]imidazol-7-yl)-amide 116. 5-Chloro-thiophene-2-carboxylic acid ((7R,7aR)-2-{4-[1-(2-morpholin-4-yl-ethyl)-cyclobutyl]-phenyl}-3-oxo-hexahydro-pyrrolo[1,2-c]imidazol-7-yl)-amide 117. 5-Chloro-thiophene-2-carboxylic acid ((7R,7aR)-2-{4-[1-(2-dimethylamino-ethyl)-cyclopentyl]-phenyl}-3-oxo-hexahydro-pyrrolo[1,2-c]imidazol-7-yl)-amide 118. 5-Chloro-thiophene-2-carboxylic acid ((7R,7aR)-3-oxo-2-{4-[1-(2-pyrrolidin-1-yl-ethyl)-cyclopropyl]-phenyl}-hexahydro-pyrrolo[1,2-c]imidazol-7-yl)-amide 119. 5-Chloro-thiophene-2-carboxylic acid ((7R,7aR)-2-{4-[1-(2-morpholin-4-yl-ethyl)-cyclopropyl]-phenyl}-3-oxo-hexahydro-pyrrolo[1,2-c]imidazol-7-yl)-amide 120. 5-Chloro-thiophene-2-carboxylic acid {(7R,7aR)-2-[4-(1,1-dimethyl-3-morpholin-4-yl-propyl)-phenyl]-3-oxo-hexahydro-pyrrolo[1,2-c]imidazol-7-yl}-amide
121. 5-Chloro-thiophene-2-carboxylic acid {(7R,7aR)-2-[4-(1-methoxymethyl-cyclopropyl)-phenyl]-3-oxo-hexahydro-pyrrolo[1,2-c]imidazol-7-yl}-amide
122. 5-Chloro-thiophene-2-carboxylic acid {(7R,7aR)-2-[4-(1-methoxymethyl-cyclobutyl)-phenyl]-3-oxo-hexahydro-pyrrolo[1,2-c]imidazol-7-yl}-amide
123. 5-Chloro-thiophene-2-carboxylic acid ((7R,7aS)-1-oxo-2-{4-[1-(2-pyrrolidin-1-yl-ethyl)-cyclobutyl]-phenyl}-hexahydro-pyrrolo[1,2-c]imidazol-7-yl)-amide
124. 5-Chloro-thiophene-2-carboxylic acid {(7R,7aS)-2-[4-(1-morpholin-4-ylmethyl-cyclobutyl)-phenyl]-1-oxo-hexahydro-pyrrolo[1,2-c]imidazol-7-yl}-amide
125. 5-Chloro-thiophene-2-carboxylic acid ((7R,7aS)-2-{4-[1-(2-morpholin-4-yl-ethyl)-cyclobutyl]-phenyl}-1-oxo-hexahydro-pyrrolo[1,2-c]imidazol-7-yl)-amide
126. 5-Chloro-thiophene-2-carboxylic acid ((7R,7aS)-2-{4-[1-(2-dimethylamino-ethyl)-cyclopentyl]-phenyl}-1-oxo-hexahydro-pyrrolo[1,2-c]imidazol-7-yl)-amide
127. 5-Chloro-thiophene-2-carboxylic acid ((7R,7aS)-1-oxo-2-{4-[1-(2-pyrrolidin-1-yl-ethyl)-cyclopropyl]-phenyl}-hexahydro-pyrrolo[1,2-c]imidazol-7-yl)-amide
128. 5-Chloro-thiophene-2-carboxylic acid ((7R,7aS)-2-{4-[1-(2-morpholin-4-yl-ethyl)-cyclopropyl]-phenyl}-1-oxo-hexahydro-pyrrolo[1,2-c]imidazol-7-yl)-amide
129. 5-Chloro-thiophene-2-carboxylic acid {(7R,7aS)-2-[4-(1,1-dimethyl-3-pyrrolidin-1-yl-propyl)-phenyl]-1-oxo-hexahydro-pyrrolo[1,2-c]imidazol-7-yl}-amide
130. 5-Chloro-thiophene-2-carboxylic acid {(7R,7aS)-2-[4-(1,1-dimethyl-3-morpholin-4-yl-propyl)-phenyl]-1-oxo-hexahydro-pyrrolo[1,2-c]imidazol-7-yl}-amide
131. 5-Chloro-thiophene-2-carboxylic acid {(7R,7aS)-2-[4-(1-methoxymethyl-cyclopropyl)-phenyl]-1-oxo-hexahydro-pyrrolo[1,2-c]imidazol-7-yl}-amide
132. 5-Chloro-thiophene-2-carboxylic acid {(7R,7aS)-2-[4-(1-methoxymethyl-cyclobutyl)-phenyl]-1-oxo-hexahydro-pyrrolo[1,2-c]imidazol-7-yl}-amide
133. 5-Chloro-thiophene-2-carboxylic acid {(7R,7aS)-1,3-dioxo-2-[4-(1-pyrrolidin-1-ylmethyl-cyclobutyl)-phenyl]-hexahydro-pyrrolo[1,2-c]imidazol-7-yl}-amide
134. 5-Chloro-thiophene-2-carboxylic acid {(7R,7aS)-2-[4-(1-morpholin-4-ylmethyl-cyclobutyl)-phenyl]-1,3-dioxo-hexahydro-pyrrolo[1,2-c]imidazol-7-yl}-amide
135. 5-Chloro-thiophene-2-carboxylic acid [(7R,7aS)-2-(4-{1-[(5-methyl-thiazol-2-ylamino)-methyl]-cyclobutyl}-phenyl)-1,3-dioxo-hexahydro-pyrrolo[1,2-c]imidazol-7-yl]-amide
136. 5-Chloro-thiophene-2-carboxylic acid ((7R,7aS)-1,3-dioxo-2-{4-[1-(2-pyrrolidin-1-yl-ethyl)-cyclobutyl]-phenyl}-hexahydro-pyrrolo[1,2-c]imidazol-7-yl)-amide
137. 5-Chloro-thiophene-2-carboxylic acid ((7R,7aS)-2-{4-[1-(2-morpholin-4-yl-ethyl)-cyclobutyl]-phenyl}-1,3-dioxo-hexahydro-pyrrolo[1,2-c]imidazol-7-yl)-amide
138. 5-Chloro-thiophene-2-carboxylic acid ((7R,7aS)-2-{4-[1-(2-dimethylamino-ethyl)-cyclopentyl]-phenyl}-1,3-dioxo-hexahydro-pyrrolo[1,2-c]imidazol-7-yl)-amide
139. 5-Chloro-thiophene-2-carboxylic acid ((7R,7aS)-1,3-dioxo-2-{4-[1-(2-pyrrolidin-1-yl-ethyl)-cyclopropyl]-phenyl}-hexahydro-pyrrolo[1,2-c]imidazol-7-yl)-amide
140. 5-Chloro-thiophene-2-carboxylic acid ((7R,7aS)-2-{4-[1-(2-morpholin-4-yl-ethyl)-cyclopropyl]-phenyl}-1,3-dioxo-hexahydro-pyrrolo[1,2-c]imidazol-7-yl)-amide
141. 5-Chloro-thiophene-2-carboxylic acid {(7R,7aS)-2-[4-(1-methoxymethyl-cyclopropyl)-phenyl]-1,3-dioxo-hexahydro-pyrrolo[1,2-c]imidazol-7-yl}-amide
142. 5-Chloro-thiophene-2-carboxylic acid {(7R,7aS)-2-[4-(1,1-dimethyl-3-morpholin-4-yl-propyl)-phenyl]-1,3-dioxo-hexahydro-pyrrolo[1,2-c]imidazol-7-yl}-amide
143. 5-Chloro-thiophene-2-carboxylic acid {(7R,7aR)-2-[4-(1-dimethylamino-cyclopropyl)-phenyl]-3-oxo-hexahydro-pyrrolo[1,2-c]imidazol-7-yl}-amide
144. 5-Chloro-thiophene-2-carboxylic acid {(7R,7aR)-2-[4-(1-dimethylaminomethyl-cyclopropyl)-phenyl]-3-oxo-hexahydro-pyrrolo[1,2-c]imidazol-7-yl}-amide
145. 5-Chloro-thiophene-2-carboxylic acid ((7R,7aR)-2-{4-[1-(2-dimethylamino-ethyl)-cyclopropyl]-phenyl}-3-oxo-hexahydro-pyrrolo[1,2-c]imidazol-7-yl)-amide
146. 5-Chloro-thiophene-2-carboxylic acid {(7R,7aR)-2-[4-(1-carbamoylmethyl-cyclopropyl)-phenyl]-3-oxo-hexahydro-pyrrolo[1,2-c]imidazol-7-yl}-amide
147. 5-Chloro-thiophene-2-carboxylic acid {(7R,7aR)-2-[4-(1-dimethylamino-cyclobutyl)-phenyl]-3-oxo-hexahydro-pyrrolo[1,2-c]imidazol-7-yl}-amide
148. 5-Chloro-thiophene-2-carboxylic acid {(7R,7aR)-2-[4-(1-dimethylaminomethyl-cyclobutyl)-phenyl]-3-oxo-hexahydro-pyrrolo[1,2-c]imidazol-7-yl}-amide
149. 5-Chloro-thiophene-2-carboxylic acid ((7R,7aR)-2-{4-[1-(2-dimethylamino-ethyl)-cyclobutyl]-phenyl}-3-oxo-hexahydro-pyrrolo[1,2-c]imidazol-7-yl)-amide
150. 5-Chloro-thiophene-2-carboxylic acid {(7R,7aR)-2-[4-(1-carbamoylmethyl-cyclobutyl)-phenyl]-3-oxo-hexahydro-pyrrolo[1,2-c]imidazol-7-yl}-amide
151. 5-Chloro-thiophene-2-carboxylic acid {(7R,7aR)-2-[4-(1-dimethylamino-cyclopentyl)-phenyl]-3-oxo-hexahydro-pyrrolo[1,2-c]imidazol-7-yl}-amide
152. 5-Chloro-thiophene-2-carboxylic acid {(7R,7aR)-2-[4-(1-dimethylaminomethyl-cyclopentyl)-phenyl]-3-oxo-hexahydro-pyrrolo[1,2-c]imidazol-7-yl}-amide
153. 5-Chloro-thiophene-2-carboxylic acid ((7R,7aR)-2-{4-[1-(2-dimethylamino-ethyl)-cyclopentyl]-phenyl}-3-oxo-hexahydro-pyrrolo[1,2-c]imidazol-7-yl)-amide
154. 5-Chloro-thiophene-2-carboxylic acid {(7R,7aR)-2-[4-(1-carbamoylmethyl-cyclopentyl)-phenyl]-3-oxo-hexahydro-pyrrolo[1,2-c]imidazol-7-yl}-amide
155. 5-Chloro-thiophene-2-carboxylic acid {(7R,7aR)-2-[4-(2-dimethylamino-1,1-dimethyl-ethyl)-phenyl]-3-oxo-hexahydro-pyrrolo[1,2-c]imidazol-7-yl}-amide
156. 5-Chloro-thiophene-2-carboxylic acid {(7R,7aR)-2-[4-(3-dimethylamino-1,1-dimethyl-propyl)-phenyl]-3-oxo-hexahydro-pyrrolo[1,2-c]imidazol-7-yl}-amide
157. 5-Chloro-thiophene-2-carboxylic acid {(7R,7aR)-2-[4-(2-carbamoyl-1,1-dimethyl-ethyl)-phenyl]-3-oxo-hexahydro-pyrrolo[1,2-c]imidazol-7-yl}-amide
158. 5-Chloro-thiophene-2-carboxylic acid {(7R,7aR)-2-[4-(1-methanesulfonyl-1-methyl-ethyl)-phenyl]-3-oxo-hexahydro-pyrrolo[1,2-c]imidazol-7-yl}-amide
159. 5-Chloro-thiophene-2-carboxylic acid {(7R,7aR)-2-[4-(1-methanesulfonyl-cyclopropyl)-phenyl]-3-oxo-hexahydro-pyrrolo[1,2-c]imidazol-7-yl}-amide
160. 5-Chloro-thiophene-2-carboxylic acid {(7R,7aR)-2-[4-(1-methanesulfonylmethyl-cyclopropyl)-phenyl]-3-oxo-hexahydro-pyrrolo[1,2-c]imidazol-7-yl}-amide
161. 5-Chloro-thiophene-2-carboxylic acid {(7R,7aR)-3-oxo-2-[4-(1-pyrrolidin-1-ylmethyl-cyclopropyl)-phenyl]-hexahydro-pyrrolo[1,2-c]imidazol-7-yl}-amide
162. 5-Chloro-thiophene-2-carboxylic acid ((7R,7aR)-2-{4-[1-(3-hydroxy-pyrrolidin-1-ylmethyl)-cyclopropyl]-phenyl}-3-oxo-hexahydro-pyrrolo[1,2-c]imidazol-7-yl)-amide
163. 5-Chloro-thiophene-2-carboxylic acid {(7R,7aR)-2-[4-(1-morpholin-4-ylmethyl-cyclopropyl)-phenyl]-3-oxo-hexahydro-pyrrolo[1,2-c]imidazol-7-yl}-amide 164. 5-Chloro-thiophene-2-carboxylic acid [(7R,7aR)-2-(4-{1-[(5-methyl-thiazol-2-ylamino)-methyl]-cyclopropyl}-phenyl)-3-oxo-hexahydro-pyrrolo[1,2-c]imidazol-7-yl]-amide 165. 5-Chloro-thiophene-2-carboxylic acid {(7R,7aS)-2-[4-(1-dimethylamino-cyclopropyl)-phenyl]-1-oxo-hexahydro-pyrrolo[1,2-c]imidazol-7-yl}-amide 166. 5-Chloro-thiophene-2-carboxylic acid {(7R,7aS)-2-[4-(1-dimethylaminomethyl-cyclopropyl)-phenyl]-1-oxo-hexahydro-pyrrolo[1,2-c]imidazol-7-yl}-amide 167. 5-Chloro-thiophene-2-carboxylic acid ((7R,7aS)-2-{4-[1-(2-dimethylamino-ethyl)-cyclopropyl]-phenyl}-1-oxo-hexahydro-pyrrolo[1,2-c]imidazol-7-yl)-amide 168. 5-Chloro-thiophene-2-carboxylic acid {(7R,7aS)-2-[4-(1-carbamoylmethyl-cyclopropyl)-phenyl]-1-oxo-hexahydro-pyrrolo[1,2-c]imidazol-7-yl}-amide 169. 5-Chloro-thiophene-2-carboxylic acid {(7R,7aS)-2-[4-(1-dimethylamino-cyclobutyl)-phenyl]-1-oxo-hexahydro-pyrrolo[1,2-c]imidazol-7-yl}-amide 170. 5-Chloro-thiophene-2-carboxylic acid {(7R,7aS)-2-[4-(1-dimethylaminomethyl-cyclobutyl)-phenyl]-1-oxo-hexahydro-pyrrolo[1,2-c]imidazol-7-yl}-amide 171. 5-Chloro-thiophene-2-carboxylic acid ((7R,7aS)-2-{4-[1-(2-dimethylamino-ethyl)-cyclobutyl]-phenyl}-1-oxo-hexahydro-pyrrolo[1,2-c]imidazol-7-yl)-amide 172. 5-Chloro-thiophene-2-carboxylic acid {(7R,7aS)-2-[4-(1-carbamoylmethyl-cyclobutyl)-phenyl]-1-oxo-hexahydro-pyrrolo[1,2-c]imidazol-7-yl}-amide 173. 5-Chloro-thiophene-2-carboxylic acid {(7R,7aS)-2-[4-(2-dimethylamino-1,1-dimethyl-ethyl)-phenyl]-1-oxo-hexahydro-pyrrolo[1,2-c]imidazol-7-yl}-amide 174. 5-Chloro-thiophene-2-carboxylic acid {(7R,7aS)-1-oxo-2-[4-(1-pyrrolidin-1-ylmethyl-cyclopropyl)-phenyl]-hexahydro-pyrrolo[1,2-c]imidazol-7-yl}-amide 175. 5-Chloro-thiophene-2-carboxylic acid {(7R,7aS)-2-[4-(1-morpholin-4-ylmethyl-cyclopropyl)-phenyl]-1-oxo-hexahydro-pyrrolo[1,2-c]imidazol-7-yl}-amide 176. 5-Chloro-thiophene-2-carboxylic acid [(7R,7aS)-2-(4-{1-[(5-methyl-thiazol-2-ylamino)-methyl]-cyclopropyl}-phenyl)-1-oxo-hexahydro-pyrrolo[1,2-c]imidazol-7-yl]-amide 177. 3-Chloro-1H-indole-6-carboxylic acid {(3aR,4S)-1,1-dioxo-2-[4-(1-pyrrolidin-1-ylmethyl-cyclobutyl)-phenyl]-octahydro-1λ$^6$-[1,2,5]thiadiazolo[2,3-a]pyridin-4-yl}-amide 178. 3-Chloro-1H-indole-6-carboxylic acid ((3aR,4R)-1,1-dioxo-2-{4-[1-(2-pyrrolidin-1-yl-ethyl)-cyclobutyl]-phenyl}-octahydro-1λ$^6$-1,2,5]thiadiazolo[2,3-a]pyridin-4-yl)-amide 179. 3-Chloro-1H-indole-6-carboxylic acid ((3aR,4R)-2-{4-[1-(2-morpholin-4-yl-ethyl)-cyclobutyl]-phenyl}-1,1-dioxo-octahydro-1λ$^6$-[1,2,5]thiadiazolo[2,3-a]pyridin-4-yl)-amide 180. 3-Chloro-1H-indole-6-carboxylic acid ((3aR,4R)-2-{4-[1-(2-dimethylamino-ethyl)-cyclopentyl]-phenyl}-1,1-dioxo-octahydro-1λ$^6$-[1,2,5]thiadiazolo[2,3-a]pyridin-4-yl)-amide 181. 3-Chloro-1H-indole-6-carboxylic acid ((3 aR,4R)-1,1-dioxo-2-{4-[1-(2-pyrrolidin-1-yl-ethyl)-cyclopropyl]-phenyl}-octahydro-1λ$^6$-[1,2,5]thiadiazolo[2,3-a]pyridin-4-yl)-amide 182. 3-Chloro-1H-indole-6-carboxylic acid {(3aR,4R)-2-[4-(1,1-dimethyl-3-morpholin-4-yl-propyl)-phenyl]-1,1-dioxo-octahydro-1λ$^6$-[1,2,5]thiadiazolo[2,3-a]pyridin-4-yl}-amide 183. 3-Chloro-1H-indole-6-carboxylic acid ((3aR,4R)-2-{4-[1-(2-morpholin-4-yl-ethyl)-cyclopropyl]-phenyl}-1,1-dioxo-octahydro-1λ$^6$-[1,2,5]thiadiazolo[2,3-a]pyridin-4-yl)-amide 184. 3-Chloro-1H-indole-6-carboxylic acid {(3aR,4S)-2-[4-(1-methoxymethyl-cyclopropyl)-phenyl]-1,1-dioxo-octahydro-1λ$^6$-[1,2,5]thiadiazolo[2,3-a]pyridin-4-yl}-amide 185. 3-Chloro-1H-indole-6-carboxylic acid {(8R,8aS)-1,3-dioxo-2-[4-(1-pyrrolidin-1-ylmethyl-cyclobutyl)-phenyl]-octahydro-imidazo[1,5-a]pyridin-8-yl}-amide 186. 3-Chloro-1H-indole-6-carboxylic acid [(8R,8aS)-2-(4-{1-[(5-methyl-thiazol-2-ylamino)-methyl]-cyclobutyl}-phenyl)-1,3-dioxo-octahydro-imidazo[1,5-a]pyridin-8-yl]-amide 187. 3-Chloro-1H-indole-6-carboxylic acid ((8R,8aS)-1,3-dioxo-2-{4-[1-(2-pyrrolidin-1-yl-ethyl)-cyclobutyl]-phenyl}-octahydro-imidazo[1,5-a]pyridin-8-yl)-amide 188. 3-Chloro-1H-indole-6-carboxylic acid {(8R,8aS)-2-[4-(1-methoxymethyl-cyclopropyl)-phenyl]-1,3-dioxo-octahydro-imidazo[1,5-a]pyridin-8-yl}-amide 189. 3-Chloro-1H-indole-6-carboxylic acid ((8R,8aS)-2-{4-[1-(2-morpholin-4-yl-ethyl)-cyclobutyl]-phenyl}-1,3-dioxo-octahydro-imidazo[1,5-a]pyridin-8-yl)-amide 190. 3-Chloro-1H-indole-6-carboxylic acid ((8R,8aS)-2-{4-[1-(2-dimethylamino-ethyl)-cyclopentyl]-phenyl}-1,3-dioxo-octahydro-imidazo[1,5-a]pyridin-8-yl)-amide 191. 3-Chloro-1H-indole-6-carboxylic acid ((8R,8aS)-2-{4-[1-(2-dimethylamino-ethyl)-cyclopropyl]-phenyl}-1,3-dioxo-octahydro-imidazo[1,5-a]pyridin-8-yl)-amide 192. 3-Chloro-1H-indole-6-carboxylic acid {(8R,8aS)-2-[4-(1,1-dimethyl-3-pyrrolidin-1-yl-propyl)-phenyl]-1,3-dioxo-octahydro-imidazo[1,5-a]pyridin-8-yl}-amide 193. 3-Chloro-1H-indole-6-carboxylic acid ((8R,8aS)-2-{4-[1-(2-morpholin-4-yl-ethyl)-cyclopropyl]-phenyl}-1,3-dioxo-octahydro-imidazo[1,5-a]pyridin-8-yl)-amide 194. 3-Chloro-1H-indole-6-carboxylic acid {(3aR,4S)-2-[4-(1-dimethylamino-cyclopropyl)-phenyl]-1,1-dioxo-octahydro-1λ$^6$-[1,2,5]thiadiazolo[2,3-a]pyridin-4-yl}-amide 195. 3-Chloro-1H-indole-6-carboxylic acid {(3aR,4R)-2-[4-(1-dimethylaminomethyl-cyclopropyl)-phenyl]-1,1-dioxo-octahydro-1λ$^6$-[1,2,5]thiadiazolo[2,3-a]pyridin-4-yl}-amide 196. 3-Chloro-1H-indole-6-carboxylic acid ((3aR,4R)-2-{4-[1-(2-dimethylamino-ethyl)-cyclopropyl]-phenyl}-1,1-dioxo-octahydro-1λ$^6$-[1,2,5]thiadiazolo[2,3-a]pyridin-4-yl)-amide 197. 3-Chloro-1H-indole-6-carboxylic acid {(3aR,4R)-2-[4-(1-carbamoylmethyl-cyclopropyl)-phenyl]-1,1-dioxo-octahydro-1λ$^6$-[1,2,5]thiadiazolo[2,3-a]pyridin-4-yl}-amide 198. 3-Chloro-1H-indole-6-carboxylic acid {(8R,8aS)-2-[4-(1-dimethylamino-cyclopropyl)-phenyl]-1,3-dioxo-octahydro-imidazo[1,5-a]pyridin-8-yl}-amide 199. 3-Chloro-1H-indole-6-carboxylic acid {(8R,8aS)-2-[4-(1-dimethylaminomethyl-cyclopropyl)-phenyl]-1,3-dioxo-octahydro-imidazo[1,5-a]pyridin-8-yl}-amide 200. 3-Chloro-1H-indole-6-carboxylic acid ((8R,8aS)-2-{4-[1-(2-dimethylamino-ethyl)-cyclopropyl]-phenyl}-1,3-dioxo-octahydro-imidazo[1,5-a]pyridin-8-yl)-amide 201. 3-Chloro-1H-indole-6-carboxylic acid {(8R,8aS)-1,3-dioxo-2-[4-(1-pyrrolidin-1-ylmethyl-cyclopropyl)-phenyl]-octahydro-imidazo[1,5-a]pyridin-8-yl}-amide 202. 3-Chloro-1H-indole-6-carboxylic acid {(8R,8aR)-2-[4-(1-dimethylamino-cyclopropyl)-phenyl]-3-oxo-octahydro-imidazo[1,5-a]pyridin-8-yl}-amide 203. 3-Chloro-1H-indole-6-carboxylic acid {(8R,8aR)-2-[4-(1-dimethylaminomethyl-cyclopropyl)-phenyl]-3-oxo-octahydro-imidazo[1,5-a]pyridin-8-yl}-amide
204. 3-Chloro-1H-indole-6-carboxylic acid ((8R,8aR)-2-{4-[1-(2-dimethylamino-ethyl)-cyclopropyl]-phenyl}-3-oxo-octahydro-imidazo[1,5-a]pyridin-8-yl)-amide
205. 3-Chloro-1H-indole-6-carboxylic acid {(8R,8aR)-2-[4-(1-carbamoylmethyl-cyclopropyl)-phenyl]-3-oxo-octahydro-imidazo[1,5-a]pyridin-8-yl}-amide
206. 3-Chloro-1H-indole-6-carboxylic acid {(8R,8aR)-3-oxo-2-[4-(1-pyrrolidin-1-ylmethyl-cyclopropyl)-phenyl]-octahydro-imidazo[1,5-a]pyridin-8-yl}-amide
207. 3-Chloro-1H-indole-6-carboxylic acid {(8S,8aR)-2-[4-(1-methanesulfonylmethyl-cyclopropyl)-phenyl]-3-oxo-octahydro-imidazo[1,5-a]pyridin-8-yl}-amide
208. 3-Chloro-1H-indole-6-carboxylic acid [(8R,8aR)-2-(4-{1-[(5-methyl-thiazol-2-ylamino)-methyl]-cyclopropyl}-phenyl)-3-oxo-octahydro-imidazo[1,5-a]pyridin-8-yl]-amide
209. 3-Chloro-1H-indole-6-carboxylic acid {(8R,8aR)-2-[4-(1-morpholin-4-ylmethyl-cyclopropyl)-phenyl]-3-oxo-octahydro-imidazo[1,5-a]pyridin-8-yl}-amide
210. 5-Chloro-thiophene-2-carboxylic acid {(7R,7aS)-2-[4-(1-dimethylamino-cyclopropyl)-phenyl]-1,3-dioxo-hexahydro-pyrrolo[1,2-c]imidazol-7-yl}-amide
211. 5-Chloro-thiophene-2-carboxylic acid {(7R,7aS)-2-[4-(1-dimethylaminomethyl-cyclopropyl)-phenyl]-1,3-dioxo-hexahydro-pyrrolo[1,2-c]imidazol-7-yl}-amide
212. 5-Chloro-thiophene-2-carboxylic acid ((7R,7aS)-2-{4-[1-(2-dimethylamino-ethyl)-cyclopropyl]-phenyl}-1,3-dioxo-hexahydro-pyrrolo[1,2-c]imidazol-7-yl)-amide
213. 5-Chloro-thiophene-2-carboxylic acid {(7R,7aS)-2-[4-(1-morpholin-4-ylmethyl-cyclopropyl)-phenyl]-1,3-dioxo-hexahydro-pyrrolo[1,2-c]imidazol-7-yl}-amide
214. 5-Chloro-thiophene-2-carboxylic acid {(7R,7aS)-1,3-dioxo-2-[4-(1-pyrrolidin-1-ylmethyl-cyclopropyl)-phenyl]-hexahydro-pyrrolo[1,2-c]imidazol-7-yl}-amide
215. 3-Chloro-1H-indole-6-carboxylic acid ((8R,8aR)-2-{4-[1-(2-morpholin-4-yl-ethyl)-cyclopropyl]-phenyl}-3-oxo-octahydro-imidazo[1,5-a]pyridin-8-yl)-amide
216. 3-Chloro-1H-indole-6-carboxylic acid {(8R,8aR)-2-[4-(1-methoxymethyl-cyclopropyl)-phenyl]-3-oxo-octahydro-imidazo[1,5-a]pyridin-8-yl}-amide
217. 5-Chloro-thiophene-2-carboxylic acid {(8R,8aR)-2-[4-(1-dimethylaminomethyl-cyclopropyl)-phenyl]-3-oxo-octahydro-imidazo[1,5-a]pyridin-8-yl}-amide
218. 5-Chloro-thiophene-2-carboxylic acid {(8R,8aR)-3-oxo-2-[4-(1-pyrrolidin-1-ylmethyl-cyclopropyl)-phenyl]-octahydro-imidazo[1,5-a]pyridin-8-yl}-amide Numerous modifications and variations of the present invention are possible in light of the above teachings. It is therefore to be understood that within the scope of the appended claims, the invention may be practiced otherwise that as specifically described herein.

What is claimed is:
1. A compound selected from formula I:

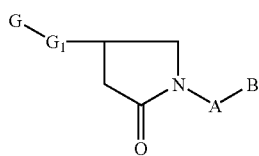

I or a stereoisomer or pharmaceutically acceptable salt thereof, wherein;

G is thienyl substituted with 1–3 R;

R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, $C(=NR^8)NR^7R^9$, $NHC(=NR^8)NR^7R^9$, $ONHC(=NR^8)NR^7R^9$, $NR^8CH(=NR^7)$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$, provided that $S(O)_pR^7$ and $S(O)_2R^3$ form other than $S(O)_2H$ or $S(O)H$;

$G_1$ is selected from $(CR^3R^{3a})_uNR^{3b}(CR^3R^{3a})_w$, $(CR^3R^{3a})_u NR^{3b}C(O)(CR^3R^{3a})_w$, $(CR^3R^{3a})_uNR^{3b}C(O)O(CR^3R^{3a})_w$, $(CR^3R^{3a})_uNR^{3b}C(O)NR^{3b(CR3}R^{3a})_w$, $(CR^3R^{3a})_uNR^{3b}C(S)NR^{3b}(CR^3R^{3a})_w$, $(CR^3R^{3a})_uNR^{3b}S(O)_2(CR^3R^{3a})_w$, $(CR^3R^{3a})_uNR^{3b}S(O)_2NR^{3b}(CR^3R^{3a})_w$, $(CR^3R^{3a})_uNRR^{3e}(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uNR^{3b}C(O)(CR^3R^{3a})_uC(S)NR^{3b}(CR^3R^{3a})_w$, and $(CR^3R^{3a})_uNR^{3b}C(S)(CR^3R^{3a})_uC(O)NR^{3b}(CR^3R^{3a})_w$, wherein u is 1 and w is selected from 0, 1, 2, and 3, and the right side of $G_1$ is attached to ring G;

A is phenyl substituted with 0–2 $R^4$ $^4$;

B is Y;

Y is $C_{3-10}$ carbocycle substituted 0–2 $R^4$ and 0–1 $R^{4a}$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$(CR^3R^{3a})_r$—$NR^2$—$(CR^3R^{3a})_r$—$R^{1b}$, —$(CR^3R^{3a})_r$—$S(O)_p$—$(CR^3R^{3a})_r$—$R^{1b}$, —$(CR^3R^{3a})_r$—$CO_2$—$(CR^3R^{3a})_r$—$R^{1b}$, —$(CR^3R^{3a})_r$—$C(O)NR^2$—$(CR^3R^{3a})_r$—$R^{1b}$, —$(CR^3R^{3a})_r$—$C(O)$—$(CR^3R^{3a})_r$—$R^{1b}$, —$C_{2-6}$ alkenylene-$R^{1b}$, —$C_{2-6}$ alkynylene—$R^{1b}$, and —$(CR^3R^{3a})_r$—$C(=NR^{1b})NR^3R^{1b}$, provided that $R^{1a}$ forms other than an N-halo, N—S, O—O, or N—CN bond;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR^2)_2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, and $C_{3-6}$ carbocycle substituted with 0–2 $R^{4b}$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_r$-5–10 membered heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5–10 membered saturated, partially saturated or unsaturated ring substituted with 0–2 $R^{4b}$ and consisting of: 0–1 additional heteroatoms selected from the group consisting of N, O, and $S(O)_p$;

$R^{2e}$, at each occurrence, is selected from H, $R^{4c}$, $C_{1-6}$ alkyl substituted with 0–2 $R^{4c}$, —$(CR^3R^{3a})_r$—$C_{3-10}$ carbocycle substituted with 0–2 $R^{4c}$, and —$(CR^3R^{3a})_r$-5–10 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^3$ at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)CH_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, and —$(C_{0-4}$ alkyl)—5–10 membered carbocycle substituted with 0–3 $R^{1a}$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)—5–10 membered carbocycle substituted with 0–3 $R^{1a}$, and —$(C_{0-4}$ alkyl)—5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)—5–10 membered carbocycle substituted with 0–3 $R^{1a}$, and —$(C_{0-4}$ alkyl)—5–10 membered heterocycle substituted with 0–3 $R^{1a}$ and consisting of: carbon atoms and 1–4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_r$-3–6 membered carbocycle, and —$(CH_2)_r$-5–6 membered heterocycle consisting of: carbon atoms and 1–4 heteroatoms selected from the group consisting of N, O, and $S(O)_p$;

alternatively, $CR^3R^{3g}$ forms a cyclopropyl group;

at each occurrence, is selected from =O, CHO, $(CR^3R^{3a})_r$ $OR^2$, $(CR^3R^{3a})_r$F, $(CR^3R^{3a})_r$Cl, $(CR^3R^{3a})_r$Br, $(CR^3R^{3a})_r$I, $C_{1-4}$ alkyl, $(CR^3R^{3a})_r$CN, $(CR^3R^{3a})_r$NO_2$, $(CR^3R^{3a})_r$NR^2R^{2a}$, $(CR^3R^{3a})_r$C(O)R^{2c}$, $(CR^3R^{3a})_r$ $NR^2C(O)$ $R^{2b}$, $(CR^3R^{3a})_r$C(O)NR^2R^{2a}$, $(CR^3R^{3a})_r$ $NR^2C(O)NR^2R^{2a}$, $(CR^3R^{3a})_r$C(=NR^2)$ $NR^2R^{2a}$, $(CR^3R^{3a})_r$C(=NS(O)_2R^5)NR^2R^{2a}$, $(CR^3R^{3a})_r$ $NR^2C(=NR^2)NR^2R^{2a}$, $(CR^3R^{3a})_r$C(O) $NR^2C(=NR^2)$ $NR^2R^{2a}$, $(CR^3R^{3a})_r$SO_2NR^2R^{2a}$, $(CR^3R^{3a})_r$ $NR^2SO_2NR^2R^{2a}$, $(CR^3R^{3a})_r$NR^2SO_2$—$C_{1-4}$ alkyl, $(CR^3R^{3a})_r$NR^2SO_2R^5$, $(CR^3R^{3a})_r$S(O)_pR^{5a}$, $(CR^3R^{3a})_r(CF_2)_rCF_3$, $NHCH_2R^{1b}$, $OCH_2R^{1b, SCH_2}R^{1b}$, $NH(CH_2)_2(CH_2)_rR^{1b}$, $O(CH_2)_2(CH_2)_rR^{1b}$, $S(CH_2)_2(CH_2)_rR^{1b}$, and $(CR^3R^{3a})_r$-5–6 membered carbocycle substituted with 0–1 $R^5$;

$R^{4a}$ is selected from $C_{1-6}$ alkyl substituted with 0–2 $R^{4c}$, $C_{2-6}$ alkenyl substituted with 0–2 $R^{4c}$, $C_{2-6}$ alkynyl substituted with 0–2 $R^{4c}$, —$(CR^3R^{3g})_r$—$C_{5-10}$ membered carbocycle substituted with 0–3 $R^{4c}$, $(CR^3R^{3g})_r$CN, $(CR^3R^{3g})_rC(=NR^{2d})NR^{2d}R^{2d}$, $(CR^3R^{3g})_rNR^{2d}C(=NR^{2d})NR^{2d}R^{2d}$, $(CR^3R^{3g})_rNR^{2d}C(R^{2e})(=NR^{2d})$, $(CR^3R^{3g})_rNR^{2d}R^{2d}$, $(CR^3R^{3g})_rN(\rightarrow O)R^{2d}R^{2d}$, $(CR^3R^{3g})_rOR^{2d}$, $(CR^3R^{3g})$ —$NR^{2d}C(O)R^{2e}$, $(CR^3R^{3g})_r$—$C(O)R^{2e}$, $(CR^3R^{3g})_r$—$OC(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)NR^{2d}R^{2d}$, $(CR^3R^{3g})_r$—$OC(O)NR^{2d}R^{2d}$, $(CR^3R^{3g})_r$$NR^{2d}C(O)OR^{2d}$, $(CR^3R^{3g})_r$—$SO_2NR^{2d}R^{2d}$, $(CR^3R^{3g})_r$—$NR^{2d}SO_2NR^{2d}R^{2d}$, $(CR^3R^{3g})_r$—$C(O)NR^{2d}SO_2R^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$ and further provided that $R^{4a}$ is other than a hydroxamic acid;

$R^{4b}$, at each occurrence, is selected from H, =O, $(CH_2)_r$ $OR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_r$—$C(O)NR^3R^{3a}$, $(CH_2)_rNR^3C(O)NR^3R^{3a}$, $(CH_2)_r$—$C(=NR^3)NR^3R^{3a}$, $(CH_2)_rNR^3C(=NR^3)NR^3R^{3a}$, $(CH_2)_r$ $SO_2NR^3R^{3a}$, $(CH_2)_rNR^3SO_2NR^3R^{3a}$, $(CH_2)_r$ $NR^3SO_2$—$C_{1-4}$ alkyl, $(CH_2)_rNR^3SO_2CF_3$, $(CH_2)_r$ $NR^3SO_2$-phenyl, $(CH_2)_rS(O)_pCF_3$, $(CH_2)_rS(O)_p$—$C_{1-4}$ alkyl, $(CH_2)_rS(O)_p$-phenyl, and $(CH_2)_r(CF_2)_rCF_3$;

$R_{4c}$, at each occurrence, is selected from =O, $(CR_3R_{3a})r$ $OR_2$, $(CR_3R_{3a})_rF$, $(CR^3R^{3a})_rBr$, $(CR^3R^{3a})_rCl$, $(CR^3R^{3a})_rCF_3$, $C_{1-4}$ alkyl, $C_{2-6}$ alkenyl, $C_{2-6}$ alkynyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NR^2(CH_2)_2$ $NR^2R^{2a}$, $(CR^3R^{3a})_rNR^2C(O)NR^{2a}$, $(CR^3R^{3a})_rC(=NR^2)NR^2R^{2a}$, $(CR^3R^{3a})_rNR^2C(=NR^2)NR^2R^{2a}$, $(CR^3R^{3a})_rSO_2NR^2R^{2a}$, $(CR^3R^{3a})_rNR^2SO_2NR^2R^{2a}$, $(CR_3R^{3a})_rC(O)NR^2SO_2$—$C_{1-4}$ alkyl, $(CR^3R^{3a})_r$ $NR^2SO_2R^{5a}$, $(CR^3R^{3a})_rC(O)NR^2SO_2R^{5a}$, $(CR^3R^{3a})_rS$ $(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$4–10 membered heterocycle substituted with 0–2 $R^{4b}$ and consisting of carbon atoms and from 1–4 heteroatoms selected from the group consisting of N, O, and $S(O)_p$;

$R^5$, at each occurrence, is selected from H, $C_{1-6}$ alkyl, =O, $(CH_2)_rOR^3$, F, Cl, Br, I, —CN, $NO_2$, $(CH_2)_r$ $NR^3R^{3a}$, $(CH_2)_rC(O)R^3$, $(CH_2)_rC(O)OR^{3c}$, $(CH_2)_r$ $NR^3C(O)R^{3a}$, $(CH_2)_rC(O)NR^3R^{3a}$, $(CH_2)_rNR^3C(O)$ $NR^3R^{3a}$, $(CH^2)_rCH(=NOR^{3d})$, $(CH^2)_rC(=NR^3)$ $NR^3R^{3a}$, $(CH^2)_rNR^3C(=NR^3)NR^3R^{3a}$, $(CH_2)_r$ $SO_2NR^3R^{3a}$, $(CH_2)_rNR^3SO_2NR^3R^{3a}$, $(CH_2)_r$ $NR^3SO_2$—$C_{1-4}$ alkyl, $(CH_2)_r$ $NR^3SO_2CF_3$, $(CH_2)_r$ $NR^3SO_2$-phenyl, $(CH_2)_rS(O)_pCF_3$, $(CH_2)_rS(O)_p$—$C_{1-4}$ alkyl, $(CH_2)_rS(O)_p$phenyl, $(CF_2)_rCF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_rOR^3$, $(CH_2)_rNR^3R^{3a}$, $(CH_2)_rC(O)R^3$, $(CH_2)_rC$ $(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

$R^6$, at each occurrence, is selected from H, OH, $(CH_2)_r$ $OR^2$, halo, $C_{1-4}$ alkyl, CN, $NO_2$, $(CH_2)_rNR^2R^{2a}$, $(CH_2)_r$ $C(O)R^{2b}$, $NR^2C(O)R^{2b}$, $NR^2C(O)NR^2R^{2a}$, $C(=NH)$ $NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl—C(O)—, $C_{1-6}$ alkyl-O—, $(CH_2)_n$-phenyl, $C_{1-4}$ alkyl-OC(O)—, $C_{6-10}$ aryl-O—, $C_{6-10}$ aryl-OC (O)—, $C_{6-10}$ aryl-$CH_2$—C(O)—, $C_{14}$ alkyl-C(O)O— $C_{1-4}$ alkyl-OC(O)—, $C_{6-10}$ aryl-C(O)O—$C_{1-4}$ alkyl-OC (O)—, $C_{1-6}$ alkyl-$NH_2$—C(O)—, phenyl-$NH_2$—C (O)—, and phenyl-C $_{1-4}$ alkyl-C(O)—;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and t, at each occurrence, is selected from 0, 1, 2, and 3.

2. A compound according to claim 1, wherein:

G is thienyl substituted with 1–2 R;

R is selected from H, $C_{1-4}$ alkyl, F, Cl, OH, $OCH_3$, $OCH_2CH_3$, $OCH(CH_3)_2$, CN, $C(=NH)NH_2$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $(CR^8R^9)_tNR^7R^8$, $C(O)NR^7R^8$, $CH_2C(O)NR^7R^8$, $S(O)_p$ $NR^7R^8$, $CH_2S(O)_pNR^7R^8$, and $OCF_3$;

$G_1$ is selected from $(CR^3R^{3a})_uNR^{3b}(CR^3R^{3a})_w$, $(CR^3R^{3a})_u$ $NR^{3b}C(O)(CR^3R^{3a})_w$, $(CR^3R^{3a})_uNR^{3b}S$ $(O)_2$ $(CR^3R^{3a})_w$, and $(CR^3R^{3a})_uNR^{3e}(CR^3R^{3a})_w$, wherein u is 1 and w is selected from 0, 1 and 2,and the right side of $G_1$ is attached to ring G;

Y is selected from one of the following carbocycl that are substituted with 1 $R^{4a}$ and 0–2 $R^4$: cyclopropyl, cyclopentyl, cyclohexyl, and phenyl $R^{1a}$, at each occurrence, is selected from H, —$(CH_2)_r$— $R^{1b}$, —$(CH(CH_3))_r$—$R^{1b}$, —$(C(CH_3)_2)_r$—$R^{1b}$, —O— $(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$forms other than an N-halo, N—S, O—O, or N—CN bond;

$R^{1b}$is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_p$ $R^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)$ $NR^2(CH_2)_rOR^2$, $SO_2NR^2R^{2a}$, $NR^2SO_2R^2$, and $C_{5-6}$ carbocycle substituted with 0–2 $R^{4b}$, provided that $R^{1b}$forms other than an O—O, N-halo, N—S, or N—CN bond;

$R^2$, at each occurrence, is selected from H, $CF_3$, $CH_3$, $CH_2CH^3$, $CH_2CH_2CH^3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, a $C_{5-6}$ carbocyclic-$CH_2$-group substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH^3$, $CH_2CH_2CH^3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated or unsaturated ring substituted with 0–2 $R^{4b}$and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $CH_3$, $CH_2CH^3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$, and substituted with 0–2 $R^{4b}$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle substituted with 0–2 $R^{4c}$and consisting of: carbon atoms and 1–4 heteroatoms selected from the group consisting of N, O, and $S(O)_p$, provided that $R^{2d}$forms other than a N-halo, N—C-halo, $S(O)_p$—halo, O-halo, N—S, S—N, $S(O)_p$ —$S(O)_p$, S—O, O—N, O—S, or O—O moiety;

alternatively, $NR^{2d}R^{2d}$forms a 5 or 6 membered saturated, partially saturated or unsaturated ring substituted with 0–2 $R^{4b}$and consisting of: 0–1 additional heteroatoms selected from the group consisting of N, O, and $S(O)_p$;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with $^{0-2}$ $R^{4c}$, and —$(CR^3R^{3a})_r$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

$R^{3b}$, at each occurrence, is selected from H, $CF_3$, $CH_3$, $CH_2CH_3$, $CH_2CH_2CH_3$, $CH(CH_3)_2$, and —$(C_{0-1}$ alkyl)—5–6 membered carbocycle substituted with 0–1 $R^{1a}$;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $NR^2SO_2NR^2R^{2a}$, $S(O)_pR^{5a}$, $NR^2SO_2$—$C_{1-4}$ alkyl, $NR^2SO_2R^5$, $CF_3$, $CF_2CF_3$, and 5–6 membered carbocycle substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH^2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2$—$CF_3$;

$R^{4C}$, at each occurrence, is selected from =O, $(CR^3R^{3a})_r$ $OR^2$, $(CR^3R^{3a})_r$F, $(CR^3R^{3a})_r$Br, $(CR^3R^{3a})_r$Cl, $(CR^3R^{3a})_r$CF_3$, $C_{1-4}$ alkyl, $C_{2-3}$ alkenyl, $C_{2-3}$ alkynyl, $(CR^3R^{3a})_r$CN, $(CR^3R^{3a})_r$NO_2$, $(CR^3R^{3a})_r$NR^2R^{2a}$, $(CR^3R^{3a})_r$N(\rightarrow O)R^2R^{2a}$, $(CR^3R^{3a})_r$C(O)R^{2c}$, $(CR^3R^{3a})_r$NR^2C(O)R^{2b}$, $(CR^3R^{3a})_r$C(O)NR^2R^{2a}$, $(CR^3R^{3a})_r$NR^2C(O)NR^2R^{2a}$, $(CR^3R^{3a})_r$SO_2NR^2R^{2a}$, $(CR^3R^{3a})_r$NR^2SO_2NR^2R^{2a}$, $(CR^3R^{3a})_r$NR^2SO_2R^{5a}$, $(CR^3R^{3a})_r$C(O)NR^2SO_2R^{5a}$, $(CR^3R^{3a})_r$S(O)_pR^{5a}$, $(CF_2)_rCF_3$, $(CR^3R^{3a})_r$C_{3-10}$ carbocycle substituted with 0–2 $R^{4b}$, and $(CR^3R^{3a})_r$5–10 membered heterocycle consisting of carbon atoms and from 1–4 heteroatoms selected from the group consisting of N, O, and $S(O)_p$ and substituted with 0–2 $R^{4b}$; $R^5$, at each occurrence, is selected from H, O, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)$ $R^3$, $C(O)OR^{3c}$, $CH_2C(O)OR^{3c}$, $NR^3C(O)R^{3a}$, $NR^3C(O)NR^3R^{3a}$, $CH(=NOR^{3d})$, $C(=NR^3)$ $NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$;

$NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R_6$; and, $R^{5a}$, at each occurrence, is selected from $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, $OR^3$, $CH_2OR^3$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)$ $R^{3a}$, $C(O)NR^3R^{3a}$, $CH_2C(O)NR^3R^{3a}$, $CF_3$, $CF_2CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

3. A compound according to claim 2, wherein:

G is selected from:

Y is selected from one of the following carbocycles that are substituted with $^1$ $R^{4a}$ and 0–1 $R^4$: cyclopentyl, cyclohexyl, and phenyl:

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)$ $R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, and phenyl substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and a 5–6 membered aromatic heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_{2b}$, enzyl substituted with 0–2 $R_{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle containing from 1–4 heteroatoms selected from the group consisting of N, O, and $S(O)_p$, and substituted with 0–2 $R^{4b}$;

$R^{2d}$, at each occurrence, is selected from H, $R^4C$, $C_{1-4}$ alkyl substituted with 0–2 $R^4$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^4$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, $C_{5-6}$ membered heterocycle substituted with 0–2 $R^{4c}$ and consisting of: carbon atoms and 1–4 heteroatoms selected from the group consisting of N, O, and $S(O)_p$, and —$(CR^3R^{3a})$-5–6 membered heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{3b}$, at each occurrence, is selected from H, $CF_3$, $CH_3$, $CH_2CH_3$, $CH_2CH_2CH_3$, and $CH(CH_3)_2$;

$R^4$, at each occurrence, is selected from H, =O, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, $CF_3$, and $CF_2CF_3$;

$R^{4a}$ is selected from —$(CR^3R^{3g})_r$-5–6 membered carbocycle substituted with 0–3 $R^{4c}$, —$(CR^3R^{3g})_r$ $NR^{2d}R^{2d}$, $(CR^3R^{3g})_r$N(→O)$R^{2d}R^{2d}$, $(CR^3R^{3g})_r$ $OR^{2d}$, $(CR^3R^{3g})_r$—$NR^{2d}C(O)R^{2e}$, $(CR^3R^{3g})_r$—$C(O)R^{2e}$, $(CR^3R^{3g})_r$—$OC(O)R^{2e}$, $(CR^3R^{3g})_r$—$C(O)NR^{2d}R^{2d}$, $(CR^3R^{3g})_r$—$C(O)OR^{2d}$, $(CR^3R^{3g})_r$—$NR^{2d}C(O)$ $NR^{2d}R^{2d}$, $(CR^3R^{3g})_r$—$NR^{2d}C(O)OR^{2d}$, $(CR^3R^{3g})_r$— $SO_2NR^{2d}R^{2d}$, $(CR^3R^{3g})_r$—$NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)$ $R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$— $C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})$F, Br, $(CR^3R^{3a})$Br, Cl, $(CR^3R^{3a})$Cl, $CF_3$, $(CR^3R^{3a})CF_3$, $C_{2-3}$ alkenyl, $C_{2-3}$ alkynyl, $C_{1-4}$ alkyl, —CN, $(CR^3R^{3a})$CN, $NO_2$, $(CR^3R^{3a})NO_2$, $NR^2R^{2a}$, $(CR^3R^{3a})NR^2R^{2a}$, N(→O) $R^2R^{2a}$, $(CR^3R^{3a})$N(→O)$R^2R^{2a}$, $C(O)R^{2c}$, $(CR^3R^{3a})C$ $(O)R^{2c}$, $NR^2C(O)R^{2b}$, $(CR^3R^{3a})NR^2C(O)R^{2b}$, $C(O)$ $NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})$ $SO_2NR^2R^{2a}$, $NR^2SO_2NR^2R^{2a}$, $(CR^3R^{3a})$ $NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$—5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C$ $(O)R^3$, $C(O)OR^{3c}$, $CH_2C(O)OR^{3c}$, $NR^3C(O)R^{3a}$, $C(O)$ $NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

4. A compound according to claim 3, wherein:

$G_1$ is selected from $CH_2NR^{3b}CH_2$, $CH_2NR^{3b}C(O)$, and $CH_2NR^{3b}S(O)_2$, wherein the right side of $G_1$ is attached to ring G;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, and $NR^2SO_2R^2$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

alternatively, $NR^2R^{2a}$ forms a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$, and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle containing from 1–4 heteroatoms selected from the group consisting of N, O, and $S(O)_p$, and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —($CH_2$)—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —($CH_2$)—$C_{3-6}$ carbocycle substituted with 0–2 $R^{4c}$, 5–6 membered heterocycle substituted with 0–2 $R^{4c}$ and consisting of: carbon atoms and 1–4 heteroatoms selected from the group consisting of N, O, and $S(O)_p$, and —($CH_2$)-5–6 membered heterocycle and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{3b}$, at each occurrence, is selected from H and $CH_3$;

$R^4$, at each occurrence, is selected from H, =O, OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from —$(CR^3R^{3g})_r$—5–6 membered carbocycle substituted with 0–3 $R^{4c}$, —$(CR^3R^{3g})_r$ $NR^{2d}R^{2d}$, $(CR^3R^{3g})_rN(\rightarrow O)R^{2d}R^{2d}$, $(CR^3R^{3g})_rOR^{2d}$, $(CR^3R^{3g})_r$—$C(O)NR^{2d}R^{2d}$, $(CR^3R^{3g})_r$—$NR^{2d}C(O)$ $R^{2e}$, $(CR^3R^{3g})_r$—$C(O)R^{2e}$, $(CR^3R^{3g})_r$—$NR^{2d}C(O)$ $NR^{2d}R^{2d}$, $(CR^3R^{3g})_r$—$NR^{2d}C(O)OR^{2d}$, $(CR^3R^{3g})_r$— $NR^{2d}SO_2R^{2d}$, and $(CR^3R^{3g})_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)$ $R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $CH_2CH_2CH_3$, $CH_2$, $CH(CH_3)_2$, $CH(CH_3)CH_2CH_3$, $C(CH_3)_3$, $C_{2-3}$ alkenyl, $C_{2-3}$ alkynyl, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)$ $R^{2b}$, $CH_2NR^2C(O)R^{2b}$, $C(O)NR^2R^{2a}$, $CH_2C(O)$ $NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, $(CH_2)C_{3-6}$ carbocycle substituted with 0–2 $R^{4b}$, 5–6 membered heterocycle consisting of carbon atoms and from 1–4 heteroatoms selected from the group consisting of N, O, and $S(O)_p$ and substituted with 0–2 $R^{4b}$, and ($CH_2$)—5–6 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)$ $OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

5. A compound according to claim 3, wherein:

$G_1$ is $CH_2NHC(O)$, wherein the right side of $G_1$ is attached to ring G;

A is selected from the group: phenyl, 2-Cl-phenyl, 3-Cl-phenyl, 2-F-phenyl, 3-F-phenyl, 2-methylphenyl, 2-aminophenyl, and 2-methoxyphenyl;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, and $CH_2NHSO_2CH_3$ provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$ phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$, and substituted with 0–1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle substituted with 0–2 $R^{4c}$ and consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^4$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^{4a}$ is selected from —$(CH_2)_r$—5–6 membered carbocycle substituted with 0–3 $R^{4c}$, —$(CH_2)_rNR^{2d}R^{2d}$, $(CH_2)_rN(\rightarrow O)R^{2d}R^{2d}$, $(CH_2)_rOR^{2d}$, $(CH_2)_r$—$C(O)$ $NR^{2d}R^{2d}$, $(CH_2)_r$—$NR^{2d}C(O)R^{2e}$, $(CH_2)_r$—$C(O)R^{2e}$, $(CH_2)_r$—$NR^{2d}C(O)NR^{2d}R^{2d}$, $(CH_2)_r$—$NR^{2d}C(O)$ $OR^{2d}$, $(CH_2)_r$—$NR^{2d}SO_2R^{2d}$, and $(CH_2)_r$—$S(O)_pR^{2d}$, provided that $S(O)_pR^{2d}$ forms other than $S(O)_2H$ or $S(O)H$;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $C_{2-3}$ alkenyl, $C_{2-3}$ alkynyl, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl subsubstituted with 0–1 $R^{4b}$, —$CH_2$-cyclopropyl substituted with 0–1 $R^{4b}$, —$CH_2$-cyclobutyl substituted with 0–1 $R^{4b}$, —$CH_2$-cyclopentyl substituted with 0–1 $R^{4b}$, benzyl substituted with 0–2 $R^{4b}$, 5–6 membered aromatic heterocycle consisting of carbon atoms and from 1–4 heteroatoms selected from the group consisting of N, O, and $S(O)_p$ and substituted with 0–2 $R^{4b}$, and ($CH_2$)-5–6 membered aromatic heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

6. A compound according to claim 5, wherein:

A is selected from the group: phenyl, and 2-F-phenyl, wherein B is substituted at the 4-position of A;

B is selected from:

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $NR^{2d}R^{2d}$, $CH_2NR^{2d}R^{2d}$, $CH_2CH_2NR^{2d}R^{2d}$, $N(\rightarrow O)R^{2d}R^{2d}$, $CH_2N(\rightarrow O)R^{2d}R^{2d}$, $CH_2OR^{2d}$, $C(O)R^{2e}$, $C(O)NR^{2d}R^{2d}$, $CH_2C(O)NR^{2d}R^{2d}$, $NR^{2d}C(O)R^{2e}$, $CH_2NR^{2d}C(O)R^{2e}$, $NR^{2d}C(O)NR^{2d}R^{2d}$, $CH_2NR^{2d}C(O)NR^{2d}R^{2d}$, $NR^{2d}C(O)OR^{2d}$, $CH_2NR^{2d}C(O)OR^{2d}$, $NR^{2d}SO_2R^{2d}$, $CH_2NR^{2d}SO_2R^{2d}$, $S(O)_pR^{2d}$, $CH_2S(O)_pR^{2d}$, 5–6 membered carbocycle substituted with 0–2 $R^{4c}$, and —($CH_2$)—5–6 membered carbocycle substituted with 0–2 $R^{4c}$, provided that $S(O)_pR^{2d}$ forms other than $S(O)_2H$ or $S(O)H$; and $R^{4c}$ is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH=CH_2$, $CH\equiv CH$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

7. A compound according to claim 6, wherein:

A—B is selected from:

$R^{2d}$, at each occurrence, is selected from H, $CH_3$, $CH_2CH_3$, $CH_2CH_2CH_3$, $CH(CH_3)_2$, $CH_2CH(CH_3)_2$, $CH_2CH_2CH(CH_3)_2$, $CH_2CCH$, $CH_2CH_2OH$, $CH_2C(O)NH_2$, cyclopropyl, $CH_2$-cyclopropyl, cyclobutyl, cyclopentyl, and thiazolyl;

$R^{2e}$, at each occurrence, is selected from $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl;

$R^{4c}$ is selected from =O, OH, $OCH_3$, and $CH_3$.

8. A compound according to claim 1, wherein the compound is selected from the group:

5-chloro-N{[1-(2-fluoro-4-(2-N,N-dimethylaminomethylphenyl)phenyl)-5-oxopyrrolidin-3-yl]methyl}thiophene-2-carboxamide;

5-chloro-N-((1-(2-fluoro-4-(2-N,N-dimethylaminomethylphenyl)phenyl)-5-oxopyrrolidin-3-yl)methyl)thiophene-2-sulfonamide;

5-chloro-N-((1-(4-(1-((dimethylamino)methyl)cyclopropyl)phenyl)-5-oxopyrrolidin-3-yl)methyl)thiophene-2-carboxamide;

5-chloro-N-((5-oxo- 1-(4-(1-(pyrrolidin- 1-ylmethyl)cyclopropyl)phenyl)pyrrolidin-3-yl)methyl)thiophene-2-carboxamide;

5-chloro-N-((1-(4-(1-((dimethylamino)methyl)cyclopropyl)phenyl)-5-oxopyrrolidin-3-yl)methyl)thiophene-2-carboxamide; and 5-(5-chlorothiophen-2-yl)-N-((5-oxo- 1-(4-(1-(pyrrolidin- 1-ylmethyl)cyclopropyl)phenyl)pyrrolidin-3-yl)methyl)thiophene-2-carboxamide;

or a pharmaceutically acceptable salt form thereof.

9. A pharmaceutical composition, comprising: a pharmaceutically acceptable carrier and a therapeutically effective amount of a compound of claim 1 or a pharmaceutically acceptable salt form thereof.

10. A method for treating a thromboembolic disorder, comprising:

administering to a patient in need thereof a therapeutically effective amount of a compound of claim 1 or a pharmaceutically acceptable salt form thereof.

11. A method according to claim 10, wherein the thromboembolic disorder is selected from the group consisting of arterial cardiovascular thromboembolic disorders, venous cardiovascular thromboembolic disorders, and thromboembolic disorders in the chambers of the heart.

12. A method according to claim 10, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

13. A pharmaceutical composition, comprising: a pharmaceutically acceptable carrier and a therapeutically effective amount of a compound of claim 2 or a pharmaceutically acceptable salt form thereof.

14. A pharmaceutical composition, comprising: a pharmaceutically acceptable carrier and a therapeutically effective amount of a compound of claim 3 or a pharmaceutically acceptable salt form thereof.

15. A pharmaceutical composition, comprising: a pharmaceutically acceptable carrier and a therapeutically effective amount of a compound of claim 4 or a pharmaceutically acceptable salt form thereof.

16. A pharmaceutical composition, comprising: a pharmaceutically acceptable carrier and a therapeutically effective amount of a compound of claim 5 or a pharmaceutically acceptable salt form thereof.

17. A pharmaceutical composition, comprising: a pharmaceutically acceptable carrier and a therapeutically effective amount of a compound of claim 6 or a pharmaceutically acceptable salt form thereof.

18. A pharmaceutical composition, comprising: a pharmaceutically acceptable carrier and a therapeutically effective amount of a compound of claim 7 or a pharmaceutically acceptable salt form thereof.

19. A pharmaceutical composition, comprising: a pharmaceutically acceptable carrier and a therapeutically effective amount of a compound of claim 8 or a pharmaceutically acceptable salt form thereof.

20. A method for treating a thromboembolic disorder, comprising:
    administering to a patient in need thereof a therapeutically effective amount of a compound of claim 2 or a pharmaceutically acceptable salt form thereof.

21. A method for treating a thromboembolic disorder, comprising:
    administering to a patient in need thereof a therapeutically effective amount of a compound of claim 3 or a pharmaceutically acceptable salt form thereof.

22. A method for treating a thromboembolic disorder, comprising:
    administering to a patient in need thereof a therapeutically effective amount of a compound of claim 4 or a pharmaceutically acceptable salt form thereof.

23. A method for treating a thromboembolic disorder, comprising:
    administering to a patient in need thereof a therapeutically effective amount of a compound of claim 5 or a pharmaceutically acceptable salt form thereof.

24. A method for treating a thromboembolic disorder, comprising:
    administering to a patient in need thereof a therapeutically effective amount of a compound of claim 6 or a pharmaceutically acceptable salt form thereof.

25. A method for treating a thromboembolic disorder, comprising:
    administering to a patient in need thereof a therapeutically effective amount of a compound of claim 7 or a pharmaceutically acceptable salt form thereof.

26. A method for treating a thromboembolic disorder, comprising:
    administering to a patient in need thereof a therapeutically effective amount of a compound of claim 8 or a pharmaceutically acceptable salt form thereof.

* * * * *